US009949956B2

(12) United States Patent
Shalwitz et al.

(10) Patent No.: US 9,949,956 B2
(45) Date of Patent: *Apr. 24, 2018

(54) COMPOUNDS, COMPOSITIONS, AND METHODS FOR PREVENTING METASTASIS OF CANCER CELLS

(71) Applicant: Aerpio Therapeutics, Inc., Cincinnati, OH (US)

(72) Inventors: Robert Shalwitz, Bexley, OH (US); Kevin Gene Peters, Cincinnati, OH (US)

(73) Assignee: Aerpio Therapeutics, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/864,462

(22) Filed: Sep. 24, 2015

(65) Prior Publication Data

US 2016/0008327 A1    Jan. 14, 2016

Related U.S. Application Data

(63) Continuation of application No. 14/272,689, filed on May 8, 2014, now Pat. No. 9,174,950, which is a continuation of application No. 13/783,311, filed on Mar. 3, 2013, now Pat. No. 8,883,832, which is a continuation of application No. 12/677,550, filed as application No. PCT/US2010/020822 on Jan. 12, 2010, now Pat. No. 8,569,348.

(60) Provisional application No. 61/223,260, filed on Jul. 6, 2009.

(51) Int. Cl.

| A61K 31/426 | (2006.01) |
|---|---|
| A61K 31/41 | (2006.01) |
| A61K 31/4155 | (2006.01) |
| A61K 31/4192 | (2006.01) |
| A61K 31/427 | (2006.01) |
| A61K 45/06 | (2006.01) |
| A61K 31/337 | (2006.01) |
| A61K 31/428 | (2006.01) |
| A61K 31/4375 | (2006.01) |
| A61K 31/4439 | (2006.01) |
| A61K 31/497 | (2006.01) |
| A61K 31/517 | (2006.01) |
| A61K 31/538 | (2006.01) |
| A61K 31/65 | (2006.01) |
| A61K 31/7068 | (2006.01) |
| A61K 38/20 | (2006.01) |
| A61K 39/395 | (2006.01) |
| C07D 277/28 | (2006.01) |
| C07D 277/64 | (2006.01) |
| C07D 417/04 | (2006.01) |
| C07D 417/12 | (2006.01) |
| C07D 417/14 | (2006.01) |
| A61K 31/425 | (2006.01) |

(52) U.S. Cl.
CPC .......... *A61K 31/426* (2013.01); *A61K 31/337* (2013.01); *A61K 31/41* (2013.01); *A61K 31/4155* (2013.01); *A61K 31/4192* (2013.01); *A61K 31/427* (2013.01); *A61K 31/428* (2013.01); *A61K 31/4375* (2013.01); *A61K 31/4439* (2013.01); *A61K 31/497* (2013.01); *A61K 31/517* (2013.01); *A61K 31/538* (2013.01); *A61K 31/65* (2013.01); *A61K 31/7068* (2013.01); *A61K 38/2013* (2013.01); *A61K 39/39558* (2013.01); *A61K 45/06* (2013.01); *C07D 277/28* (2013.01); *C07D 277/64* (2013.01); *C07D 417/04* (2013.01); *C07D 417/12* (2013.01); *C07D 417/14* (2013.01); *A61K 31/425* (2013.01)

(58) Field of Classification Search
None
See application file for complete search history.

(56) References Cited

U.S. PATENT DOCUMENTS

| 4,673,641 | A | 6/1987 | George et al. |
|---|---|---|---|
| 5,424,398 | A | 6/1995 | Middeldorp et al. |
| 5,585,089 | A | 12/1996 | Queen et al. |
| 5,688,781 | A | 11/1997 | Siegall et al. |
| 5,807,819 | A | 9/1998 | Cheng et al. |
| 5,919,813 | A | 7/1999 | De Juan, Jr. et al. |
| 5,980,929 | A | 11/1999 | De Juan, Jr. |
| 5,994,128 | A | 11/1999 | Fallaux et al. |
| 6,033,908 | A | 3/2000 | Bout et al. |
| 6,342,219 | B1 | 1/2002 | Thorpe et al. |
| 6,343,219 | B1 | 1/2002 | Thorpe et al. |
| 6,455,035 | B1 | 9/2002 | Suri et al. |
| 6,589,758 | B1 | 7/2003 | Zhu |
| 6,596,722 | B2 | 7/2003 | Huang et al. |
| 7,052,695 | B2 | 5/2006 | Kalish |
| 7,226,755 | B1 | 6/2007 | Peters et al. |
| 7,309,483 | B2 | 12/2007 | Wiegand et al. |
| 7,354,579 | B2 | 4/2008 | Holash et al. |
| 7,507,568 | B2 | 3/2009 | Evdokimov et al. |
| 7,588,924 | B2 | 9/2009 | Evdokiov et al. |
| 7,589,212 | B2 | 9/2009 | Gray et al. |
| 7,622,593 | B2 | 11/2009 | Gray et al. |
| 7,632,862 | B2 | 12/2009 | Peters et al. |

(Continued)

FOREIGN PATENT DOCUMENTS

| EP | 1292335 B1 | 5/2007 |
|---|---|---|
| EP | 2004697 A2 | 12/2008 |
| EP | 2371865 A2 | 10/2011 |
| EP | 2385763 A1 | 11/2011 |
| EP | 2451279 A1 | 5/2012 |

(Continued)

OTHER PUBLICATIONS

Abel et al. Social Science & Medicine (2008), vol. 66, pp. 1863-1869.*

(Continued)

*Primary Examiner* — Patrick T Lewis
(74) *Attorney, Agent, or Firm* — Wilson Sonsini Goodrich & Rosati

(57) ABSTRACT

Disclosed are methods for preventing metastasis of cancer cells. The disclosed compounds can be used to prevent the spread of tumor or other types of cancer cells.

18 Claims, 5 Drawing Sheets

(56) References Cited

U.S. PATENT DOCUMENTS

| | | |
|---|---|---|
| 7,740,846 B2 | 6/2010 | Gerber et al. |
| 7,769,575 B2 | 8/2010 | Evdokimov et al. |
| 7,795,444 B2 | 9/2010 | Gray et al. |
| 7,973,142 B2 | 7/2011 | Rotello et al. |
| 8,106,078 B2 | 1/2012 | Gray et al. |
| 8,188,125 B2 | 5/2012 | Gray et al. |
| 8,258,311 B2 | 9/2012 | Gray et al. |
| 8,329,916 B2 | 12/2012 | Gray et al. |
| 8,338,615 B2 | 12/2012 | Gray et al. |
| 8,524,235 B2 | 9/2013 | Rotello et al. |
| 8,569,348 B2 | 10/2013 | Shalwitz et al. |
| 8,846,685 B2 | 9/2014 | Gray et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 8,968,766 B2 | 3/2015 | Hughes et al. |
| 8,999,325 B2 | 4/2015 | Peters et al. |
| 8,999,953 B2 | 4/2015 | Loftsson et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 9,248,172 B2 | 2/2016 | Srivastava et al. |
| 9,284,285 B2 | 3/2016 | Gray et al. |
| 9,403,789 B2 | 8/2016 | Eissenstat et al. |
| 9,440,963 B2 | 9/2016 | Peters et al. |
| 9,539,245 B2 | 1/2017 | Peters et al. |
| 9,795,594 B2 | 10/2017 | Gray et al. |
| 2003/0040463 A1 | 2/2003 | Wiegand et al. |
| 2003/0055006 A1 | 3/2003 | Siemeister et al. |
| 2004/0077065 A1 | 4/2004 | Evdokimov et al. |
| 2004/0167183 A1 | 8/2004 | Klopfenstein et al. |
| 2004/0204863 A1 | 10/2004 | Kim et al. |
| 2005/0158320 A1* | 7/2005 | Nichols ............... A61K 31/225 424/146.1 |
| 2006/0241076 A1 | 10/2006 | Uhlman et al. |
| 2006/0246071 A1 | 11/2006 | Green et al. |
| 2007/0154482 A1 | 7/2007 | Sukhatme et al. |
| 2007/0299116 A1 | 12/2007 | Gray et al. |
| 2008/0004267 A1 | 1/2008 | Gray et al. |
| 2008/0076764 A1 | 3/2008 | Peters et al. |
| 2008/0108631 A1 | 5/2008 | Gray et al. |
| 2008/0268051 A1 | 10/2008 | Hughes et al. |
| 2009/0022715 A1 | 1/2009 | Rotello et al. |
| 2009/0227639 A1 | 9/2009 | Gray et al. |
| 2010/0016336 A1 | 1/2010 | Gray et al. |
| 2010/0030487 A1 | 2/2010 | Evdokimov et al. |
| 2010/0056610 A1 | 3/2010 | Peters et al. |
| 2010/0069448 A1 | 3/2010 | Gray et al. |
| 2010/0226992 A1 | 9/2010 | Kabra |
| 2011/0212951 A1 | 9/2011 | Gray et al. |
| 2011/0268694 A1 | 11/2011 | Shalwitz et al. |
| 2011/0274699 A1 | 11/2011 | Rotello et al. |
| 2012/0077853 A1 | 3/2012 | Gray et al. |
| 2012/0077975 A1 | 3/2012 | Gray et al. |
| 2012/0128625 A1 | 5/2012 | Shalwitz et al. |
| 2012/0129847 A1 | 5/2012 | Peters et al. |
| 2013/0023542 A1 | 1/2013 | Gray et al. |
| 2013/0023543 A1 | 1/2013 | Gray et al. |
| 2013/0095065 A1 | 4/2013 | Peters et al. |
| 2013/0095105 A1 | 4/2013 | Peters et al. |
| 2013/0096140 A1 | 4/2013 | Gray et al. |
| 2013/0137741 A1 | 5/2013 | Kabra et al. |
| 2013/0190324 A1 | 7/2013 | Kompella et al. |
| 2013/0324558 A1 | 12/2013 | Gray et al. |
| 2013/0331386 A1 | 12/2013 | Shalwitz et al. |
| 2014/0010805 A1 | 1/2014 | Hart et al. |
| 2014/0044707 A1 | 2/2014 | Rotello et al. |
| 2014/0066458 A1 | 3/2014 | Shalwitz et al. |
| 2014/0073566 A1 | 3/2014 | Koh et al. |
| 2014/0179693 A1 | 6/2014 | Gray et al. |
| 2014/0221666 A1 | 8/2014 | Gray et al. |
| 2014/0242026 A1 | 8/2014 | Shalwitz et al. |
| 2014/0249100 A1 | 9/2014 | Shalwitz et al. |
| 2014/0275103 A1 | 9/2014 | Peters et al. |
| 2014/0288134 A1 | 9/2014 | Peters et al. |
| 2015/0030603 A1 | 1/2015 | Kim et al. |
| 2015/0050277 A1 | 2/2015 | Peters et al. |
| 2015/0065781 A1 | 3/2015 | Bais et al. |
| 2015/0071941 A1 | 3/2015 | Sodhi et al. |
| 2015/0125455 A1 | 5/2015 | Green et al. |
| 2015/0125542 A1 | 5/2015 | Ohto et al. |
| 2015/0175676 A1 | 6/2015 | Fandl et al. |
| 2015/0190432 A1 | 7/2015 | Doiron et al. |
| 2015/0232425 A1 | 8/2015 | Alberico |
| 2015/0232575 A1 | 8/2015 | Peters et al. |
| 2015/0258120 A1 | 9/2015 | Zarnitsyn et al. |
| 2015/0259335 A1 | 9/2015 | Janusz et al. |
| 2015/0290235 A1 | 10/2015 | Gros et al. |
| 2015/0297740 A1 | 10/2015 | Rau et al. |
| 2016/0000871 A1 | 1/2016 | Quaggin |
| 2016/0030393 A1 | 2/2016 | Breslin et al. |
| 2016/0038467 A1 | 2/2016 | Peters |
| 2016/0045566 A1 | 2/2016 | Purcell et al. |
| 2016/0058828 A1 | 3/2016 | Dumont et al. |
| 2016/0082129 A1 | 3/2016 | Peters |
| 2016/0130321 A1 | 5/2016 | Burian |
| 2016/0130337 A1 | 5/2016 | Gekkieva et al. |
| 2016/0137717 A1 | 5/2016 | Burian |
| 2016/0144025 A1 | 5/2016 | Vitti et al. |
| 2016/0151410 A1 | 6/2016 | Ma et al. |
| 2016/0151448 A1 | 6/2016 | Van et al. |
| 2016/0159893 A1 | 6/2016 | Burian et al. |
| 2016/0168240 A1 | 6/2016 | Burian et al. |
| 2016/0220540 A1 | 8/2016 | Peters et al. |
| 2016/0220541 A1 | 8/2016 | Kevin et al. |
| 2016/0251421 A1 | 9/2016 | Brown et al. |
| 2016/0252526 A1 | 9/2016 | Bergmann et al. |
| 2016/0374996 A1 | 12/2016 | Gray et al. |
| 2017/0079959 A1 | 3/2017 | Peters |

FOREIGN PATENT DOCUMENTS

| | | |
|---|---|---|
| EP | 2142189 B1 | 2/2013 |
| EP | 2592072 A2 | 5/2013 |
| EP | 2592073 A2 | 5/2013 |
| EP | 2624916 A2 | 8/2013 |
| EP | 2766043 A1 | 8/2014 |
| EP | 2041129 B1 | 9/2014 |
| EP | 2041102 B1 | 11/2014 |
| EP | 2803663 A1 | 11/2014 |
| EP | 2038265 B1 | 3/2015 |
| EP | 2967066 A1 | 1/2016 |
| WO | WO-9818914 A1 | 5/1998 |
| WO | WO 00/57901 A1 | 10/2000 |
| WO | WO 00/65085 A1 | 11/2000 |
| WO | WO 00/65088 A2 | 11/2000 |
| WO | WO 02/26774 A2 | 4/2002 |
| WO | WO-03084565 A2 | 10/2003 |
| WO | WO-2006068953 A2 | 6/2006 |
| WO | WO 2006/116713 A1 | 11/2006 |
| WO | WO-2006116713 A1 | 11/2006 |
| WO | WO-2007033216 A2 | 3/2007 |
| WO | WO 2007/116360 A2 | 10/2007 |
| WO | WO 2008/002569 A2 | 1/2008 |
| WO | WO 2008/002570 A2 | 1/2008 |
| WO | WO 2008/002571 A2 | 1/2008 |
| WO | WO-2008002570 B1 | 4/2008 |
| WO | WO-2008002571 B1 | 4/2008 |
| WO | WO 2010/081172 A1 | 7/2010 |
| WO | WO 2011/005330 A1 | 1/2011 |
| WO | WO 2012/047966 A2 | 4/2012 |
| WO | WO 2013/056233 A1 | 4/2013 |
| WO | WO 2013/056240 A1 | 4/2013 |
| WO | WO 2014/145068 A1 | 9/2014 |
| WO | WO 2015/126860 A1 | 8/2015 |
| WO | WO 2015/138882 A1 | 9/2015 |
| WO | WO-2015152416 A1 | 10/2015 |
| WO | WO 2016/022813 A1 | 2/2016 |
| WO | WO-2016022813 A1 | 2/2016 |

(56) References Cited

FOREIGN PATENT DOCUMENTS

| WO | WO 2016/049183 A1 | 3/2016 |
|---|---|---|
| WO | WO-2016049183 A1 | 3/2016 |

OTHER PUBLICATIONS

U.S. Appl. No. 14/819,871, filed Aug. 6, 2015, Peters.
U.S. Appl. No. 14/862,948, filed Sep. 23, 2015, Peters.
Altschul, et al. Gapped Blast and Psi-Blast: a new generation of protein database search programs. Nucleic Acids Res. Sep. 1, 1997;25(17):3389-402.
Annex, et al. Growth factor-induced therapeutic angiogenesis in the heart: protein therapy. Cardiovasc Res. Feb. 15, 2005;65(3):649-55.
Ardelt, et al. Estradiol regulates angiopoietin-1 mRNA expression through estrogen receptor-alpha in a rodent experimental stroke model. Stroke. Feb. 2005;36(2):337-41. Epub Jan. 6, 2005.
Auerbach, et al. Angiogenesis assays: a critical overview. Clin Chem. Jan. 2003;49(1):32-40.
Barany, et al. Solid-phase peptide synthesis: a silver anniversary report. Int J Pept Protein Res. Dec. 1987;30(6):705-39.
Bartlett, et al. Molecular Recognition in Chemical and Biological Problems; Cavet: A Program to Facilitate the Structure-Derived Design of Biologically Active Molecules. Special Pub., Royal Chem. Soc. 1989; 78:182-196.
Bohm. The computer program LUDI: a new method for the de novo design of enzyme inhibitors. J Comput Aided Mol Des. Feb. 1992;6(1):61-78.
Brindle, et al. Signaling and functions of angiopoietin-1 in vascular protection. Circ Res. Apr. 28, 2006;98(8):1014-23.
Bussolino, et al. Molecular mechanisms of blood vessel formation. Trends Biochem Sci. Jul. 1997;22(7):251-6.
Carano, et al. Angiogenesis and bone repair. Drug Discov Today. Nov. 1, 2003;8(21):980-9.
Carvalho, et al. The role of angiogenesis in a murine tibial model of distraction osteogenesis. Bone. May 2004;34(5):849-61.
Chanteau, et al. Synthesis of anthropomorphic molecules: the NanoPutians J Org. Chem. Nov. 14, 2003;68(23):8750-66.
Cohen, et al. Molecular modeling software and methods for medicinal chemistry. J Med Chem. Mar. 1990;33(3):883-94.
Collaborative Computational Project, No. 4. The CCP4 suite: programs for protein crystallography. Acta Crystallogr D Biol Crystallogr. Sep. 1, 1994;50(Pt 5):760-3.
Daar. Emerging resistance profiles of newly approved antiretroviral drugs. Top HIV Med. Oct.-Nov. 2008;16(4):110-6.
Dean. Recent advances in drug design methods: where will they lead? Bioessays. Sep. 1994;16(9):683-7.
European search report and opinion dated Feb. 22, 2013 for EP Application No. 10797461.
Fachinger, et al. Functional interaction of vascular endothelial-protein-tyrosine phosphatase with the angiopoietin receptor Tie-2. Oncogene. Oct. 21, 1999;18(43):5948-53.
Flower. Modelling G-protein-coupled receptors for drug design. Biochim Biophys Acta. Nov. 16, 1999;1422(3):207-34.
Folkman. Tumor angiogenesis. The Molecular Basis of Cancer (eds. Mendelsohn, J., Howley, P. M., Israel, M. A. & Liotta, L. A.) 206-232 (1995).
Gaits, et al. Increase in receptor-like protein tyrosine phosphatase activity and expression level on density-dependent growth arrest of endothelial cells. Biochem J. Oct. 1, 1995;311 ( Pt 1):97-103.
Goodford. A computational procedure for determining energetically favorable binding sites on biologically important macromolecules. J Med Chem. Jul. 1985;28(7):849-57.
Goodsell, et al. Automated docking of substrates to proteins by simulated annealing. Proteins. 1990;8(3):195-202.
Harder, et al. Characterization and kinetic analysis of the intracellular domain of human protein tyrosine phosphatase 13 (HPTP(3) using synthetic phosphopeptides. Biochem J. 1994; 296:395-401.
Henikoff, et al. Amino acid substitution matrices from protein blocks. Proc Natl Acad Sci U S A. Nov. 15, 1992;89(22):10915-9.

Hopkins, et al. Inhibitors of kinesin activity from structure-based computer screening. Biochemistry. Mar. 14, 2000;39(10):2805-14.
Huang, et al. HCPTPA, a Protein Tyrosine Phosphatase that Regulates Vascular Endothelial Growth Factor Receptor-Mediated Signal Transduction and Biological Activity. J Biol. Chem. 1999; 53:38183-38188.
International search report and written opinion dated Mar. 30, 2010 for PCT/US2010/020822.
Itoh, et al. Purification and characterization of the catalytic domains of the human receptor-linked protein tyrosine phosphatases HPTP beta, leukocyte common antigen (LCA), and leukocyte common antigen-related molecule (LAR). J Biol Chem. Jun. 15, 1992;267(17):12356-63.
Jain, et al. Normalization of tumor vasculature: an emerging concept in antiangiogenic therapy. Science. 2005; 307:58-62.
Jones, et al. Development and validation of a genetic algorithm for flexible docking. J Mol Biol. Apr. 4, 1997;267(3):727-48.
Jones, et al. Molecular recognition of receptor sites using a genetic algorithm with a description of desolvation. J Mol Biol. Jan. 6, 1995;245(1):43-53.
Keen. Radioligand Binding Methods for Membrane Preparations and Intact cells, Methods in Molecular Biology, 83:Receptor Signal Transduction Protocols, edited Humana Press Inc., Totoway N.J. (1997).
Kohler, et al. Continuous cultures of fused cells secreting antibody of predefined specificity. 1975. Biotechnology. 1992;24:524-6.
Krueger, et al. Structural diversity and evolution of human receptor-like protein tyrosine phosphatases. EMBO J. Oct. 1990;9(10):3241-52.
Kugathasan, et al. Role of angiopoietin-1 in experimental and human pulmonary arterial hypertension. Chest. Dec. 2005;128(6 Suppl):6335-6425.
Kumpers, et al. Excess circulating angiopoietin-2 is a strong predictor of mortality in critically ill medical patients. Crit Care. 2008;12(6):R147. doi: 10.1186/cc7130. Epub Nov. 21, 2008.
Kumpers, et al. The Tie2 receptor antagonist angiopoietin 2 facilitates vascular inflammation in systemic lupus erythematosus. Ann Rheum Dis. Oct. 2009;68(10):1638-43. doi: 10.1136/ard.2008. 094664. Epub Oct. 17, 2008.
Kuntz, et al. A geometric approach to macromolecule-ligand interactions. J Mol Biol. Oct. 25, 1982;161(2):269-88.
Lin, et al. Inhibition of tumor angiogenesis using a soluble receptor establishes a role for Tie2 in pathologic vascular growth. J Clin Invest. Oct. 15, 1997;100(8):2072-8.
Ma, et al. RNase Protection Assay. Methods. Dec. 1996;10(3):273-8.
Martin. 3D database searching in drug design. J Med Chem. Jun. 1992 12;35(12):2145-54.
Meadows. "Keeping Up with Drug Safety Information," 2006: *FDA Consumer Magazine*: http://www.fda.gov/fdac/features/2006/306_drugsafety.html accessed Mar. 17, 2008.
Merrifield. Solid Phase Peptide Synthesism. I. The Synthesis of a Tetrapeptide. J Am. Chem. Soc. 1963; 85:2149-2154.
Milner, et al. Roles of the receptor tyrosine kinases Tie1 and Tie2 in mediating the effects of angiopoietin-1 on endothelial permeability and apoptosis. Microvasc Res. Mar. 2009;77(2):187-91. doi: 10.1016/j.mvr.2008.09.003. Epub Sep. 20, 2008.
Miranker, et al. Functionality maps of binding sites: a multiple copy simultaneous search method. Proteins. 1991;11(1):29-34.
Nathan. Points of control in inflammation. Nature 2002; 420:846-852.
Navaza. AMoRe: An Automated Package for Molecular Replacement. Acta Cryst. 1994; A50:157-163.
Nguyen, et al. Cellular interactions in vascular growth and differentiation. Int Rev Cytol. 2001;204:1-48.
Nishibata, et al. Automatic Creation of Drug Candidate Structures Based on Receptor Structure. Starting Point for Artificial Lead Generation. Tetrahedron. 1991; 47(43):8985-8990.
Notice of allowance dated Jul. 28, 2014 for U.S. Appl. No. 13/783,311.
Notice of allowance dated Aug. 13, 2013 for U.S. Appl. No. 12/677,550.

(56) References Cited

OTHER PUBLICATIONS

Notice of allowance dated Sep. 12, 2014 for U.S. Appl. No. 13/783,311.
Notice of allowance dated Sep. 17, 2015 for U.S. Appl. No. 14/272,689.
Office action dated Jan. 3, 2013 for U.S. Appl. No. 12/677,550.
Office action dated Apr. 10, 2014 for U.S. Appl. No. 13/783,311.
Office action dated Jun. 24, 2015 for U.S. Appl. No. 14/272,689.
O'Reilly, et al. Angiostatin: a novel angiogenesis inhibitor that mediates the suppression of metastases by a Lewis lung carcinoma. Cell. Oct. 21, 1994;79(2):315-28.
O'Reilly, et al. Endostatin: an endogenous inhibitor of angiogenesis and tumor growth. Cell. Jan. 24, 1997;88(2):277-85.
Rarey, et al. A fast flexible docking method using an incremental construction algorithm. J Mol Biol. Aug. 23, 1996;261(3):470-89.
Riechmann, et al. Reshaping human antibodies for therapy. Nature. Mar. 24, 1988;332(6162):323-7.
Roviezzo, et al. Angiopoetin-2 causes inflammation in vivo by promoting vascular leakage. J Pharmacol Exp Ther. Aug. 2005;314(2):738-44. Epub May 3, 2005.
Saliba. Heparin in the treatment of burns: a review. Burns. Jun. 2001;27(4):349-58.
Schoneberg, et al. Structural basis of G protein-coupled receptor function. Mol Cell Endocrinol. May 25, 1999;151(1-2):181-93.
Sexton. Recent advances in our understanding of peptide hormone receptors and Ramps. Curr Opin Drug Discov Devel. Sep. 1999;2(5):440-8.
Shiojima, et al. Disruption of coordinated cardiac hypertrophy and angiogenesis contributes to the transition to heart failure. J Clin Invest. Aug. 2005;115(8):2108-18.
Shoichet, et al. Lead discovery using molecular docking. Curr Opin Chem Biol. Aug. 2002;6(4):439-46.
Siddiqui, et al. Combination of angiopoietin-1 and vascular endothelial growth factor gene therapy enhances arteriogenesis in the ischemic myocardium. Biochem Biophys Res Commun. Oct. 24, 2003;310(3):1002-9.
Simons, et al. Clinical trials in coronary angiogenesis: issues, problems, consensus: An expert panel summary. Circulation. Sep. 12, 2000;102(11):E73-86.
Simons. Angiogenesis: where do we stand now? Circulation. Mar. 29, 2005;111(12):1556-66.
Stahl, et al. Detailed analysis of scoring functions for virtual screening. J Med Chem. Mar. 29, 2001;44(7):1035-42.
Stetler-Stevenson. The role of matrix metalloproteinases in tumor invasion, metastasis, and angiogenesis. Surg Oncol Clin N Am. Apr. 2001;10(2):383-92, x.
Suggitt, et al. 50 years of preclinical anticancer drug screening: empirical to target-driven approaches. Clin Cancer Res. Feb. 1, 2005;11(3):971-81.
Suri, et al. Increased vascularization in mice overexpressing angiopoietin-1. Science. Oct. 16, 1998;282(5388):468-71.
Takahashi, et al. Adenoviral-Delivered Angiopoietin-1 Reduces the Infarction and Attenuates the Progression of Cardiace Dysfunction in the Rate Model of Acute Myocardial Infarction. Molecular Therapy. 2003; 8(4):584-592.
Teischer, et al. Potentiation of cytotoxic cancer therapies by TNP-470 alone and with other anti-angiogenic agents. Int J Cancer. Jun. 15, 1994;57(6):920-5.
Thurston, et al. Angiopoietin-1 protects the adult vasculature against plasma leakage. Nat Med. Apr. 2000;6(4):460-3.
Thurston. Complementary actions of VEGF and angiopoietin-1 on blood vessel growth and leakage. J Anat. Jun. 2002;200(6):575-80.
Vailhe, et al. In vitro models of vasculogenesis and angiogenesis. Lab Invest. Apr. 2001;81(4):439-52.
Van Hijsduijnen, et al. Protein tyrosine phosphatases as drug targets: PTP1B and beyond. Expert Opin Ther Targets. Dec. 2002;6(6):637-47.
Wang, et al. Expression and characterization of wild type, truncated, and mutant forms of the intracellular region of the receptor-like protein tyrosine phosphatase HPTP beta. J Biol Chem. Aug. 15, 1992;267(23):16696-702.
Weidner, et al. Tumor angiogenesis and metastasis—correlation in invasive breast carcinoma. N Engl J Med. Jan. 3, 1991;324(1):1-8.
Whitaker, et al. Vascular endothelial growth factor receptor-2 and neuropilin-1 form a receptor complex that is responsible for the differential signaling potency of VEGF(165) and VEGF(121). J Biol Chem. Jul. 6, 2001;276(27):25520-31. Epub May 1, 2001.
Wright, et al. Protein-tyrosine phosphatases in the vessel wall: differential expression after acute arterial injury. Arterioscler Thromb Vasc Biol. May 2000;20(5):1189-98.
Yacyshyn, et al. Tyrosine phosphatase beta regulates angiopoietin-Tie2 signaling in human endothelial cells. Angiogenesis. 2009;12(1):25-33. doi: 10.1007/s10456-008-9126-0. Epub Jan. 1, 2009.
Yancopoulos, et al. Vascular-specific growth factors and blood vessel formation. Nature. Sep. 14, 2000;407(6801):242-8.
Zetter. Angiogenesis and tumor metastasis. Annu Rev. Med. 1989; 49:407-24.
Zhang, et al. Vascular endothelial growth factor and angiopoietins in focal cerebral ischemia. Trends Cardiovasc Med. Feb. 2002;12(2):62-6.
U.S. Appl. No. 15/016,599, filed Feb. 5, 2016, Gray et al.
U.S. Appl. No. 15/273,068, filed Sep. 22, 2016, Peters.
Co-pending U.S. Appl. No. 14/938526, filed Nov. 11, 2015.
Co-pending U.S. Appl. No. 15/016,599, filed Feb. 5, 2016.
Co-pending U.S. Appl. No. 15/355,910, filed Nov. 18, 2016.
Co-pending U.S. Appl. No. 15/438,218, filed Feb. 21, 2017.
Co-pending U.S. Appl. No. 15/443,353, filed Feb. 27, 2017.
Co-pending U.S. Appl. No. 15/443,622, filed Feb. 27, 2017.
Shintei, et al., Newly Revised Disease and Drugs, Yakuji Nippo Limited, 1986 (Third print), p. 504-510. (English Translation).
Co-pending U.S. Appl. No. 15/430,100, filed Feb. 10, 2017.
Co-Pending U.S. Appl. No. 15/705,639, filed Sep. 15, 2017.
Gallagher et al., "Angiopoietin 2 is a Potential Mediator of High-Dose Interleutkin 2-Induced Vascular Leak," Clin Cancer REs (2007);13:2115-2120.
Teicher; et al., ""Antiangiogenic Agents Potentiate Cytotoxic Cancer Therapies against Primary and Metastatic Disease," Cancer Research 52, 6702-6704 (1992)."

\* cited by examiner

COMPOUNDS, COMPOSITIONS, AND METHODS FOR PREVENTING METASTASIS OF CANCER CELLS

CROSS REFERENCE TO RELATED APPLICATIONS

This application is a continuation of U.S. application Ser. No. 14/272,689, filed May 8, 2014, which is a continuation of U.S. application Ser. No. 13/783,311, filed Mar. 3, 2013, now U.S. Pat. No. 8,883,832, which is a continuation of U.S. application Ser. No. 12/677,550, filed Dec. 1, 2010, now U.S. Pat. No. 8,569,348, which is a national stage entry of International Application No. PCT/US2010/020822, filed Jan. 12, 2010, which claims the benefit of U.S. Provisional Patent Application No. 61/223,260, filed Jul. 6, 2009, the content of each of which is incorporated herein by reference in its entirety.

FIELD

Disclosed are compounds that can prevent the metastasis of cancerous tumors and/or reduce tumor growth. Further disclosed are compositions, especially pharmaceutical compositions for preventing metastasis of malignant tumors and reducing tumor growth. Included within the compositions are combined therapy compositions for use in treating cancer. Still further disclosed are methods for preventing metastasis of cancerous tumors and other cancer cells. As such, the disclosed compounds can be used to aid in the prevention of cancerous growth in a subject having cancer or diagnosed with cancer.

BACKGROUND

One of the most frightening aspects of cancer is its ability to spread, or metastasize. Initially, cancer cells are found grouped together thereby forming one or more tumors. After formation of the primary tumor, cancer cells can gain the ability to separate from the original tumor and travel to other areas of the body. Lung cancer cells that take up in the liver and form tumors are still lung cancer cells. Thus, the propensity for one particular form of cancer to metastasize is dependent on many factors, including type of cancer; however, the overall process of how cells begin the process of metastasis is still not completely under stood.

If a single localized tumor is discovered before it has had a chance to metastasize, then the prognosis of patient survival is higher. This is because the tumor can be effectively excised or destroyed by radiation or chemotherapy. There is, therefore, a difference between tumor growth and metastasis of the tumor cells; the first does not always lead to the other. Cancers that have metastasized, however, are difficult to cure because the extent to which they have spread throughout the body is sometimes not discernable.

In order to metastasize, a cancer cell must break away from its tumor and invade either the circulatory or lymph system. The free cells are then carried to a new location where they establish themselves. Although the body has natural safeguards that prevent cell from surviving after being detached from their natural location, some cancer cells have the ability to over come these safeguards. Therefore, if metastasis is stopped or significantly reduced, the extent of cancer can be determined and subsequently treated. As such, a follow up treatment to cancer therapy wherein a tumor has been excised or radiation/chemotherapy has been used, would be the treatment of the patient to an anti-metastasizing agent. There is a long felt need for methods of preventing cancer cell metastasis.

The growth of primary tumors also presents a challenge to treatment. If the growth of a primary tumor goes unchecked, the initial tumor can grow to a size that adversely effects organ function at the primary site and in nearby tissues. Metastases of the primary tumor are also more likely if the primary tumor's growth is uncontrolled. There is a need for methods of slowing or preventing tumor growth.

SUMMARY

Disclosed herein are compounds, compositions, and methods for preventing metastasis of cancer cells. Further disclosed are compounds, compositions, and methods that can be used for treating cancer, including combination therapy compositions wherein the disclosed compounds are combined with one or more cancer treatment drugs or other chemotherapeutic agents.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
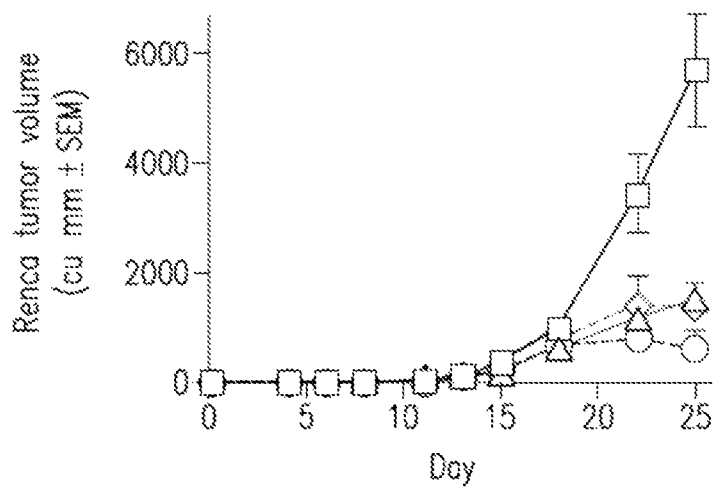
FIG. 1 depicts a graph showing the increase in tumor volume with time of renal cell carcinoma tumors (Renca) in mice; vehicle control (□); 100,000 IU/dose of IL-2 twice daily (◇); 40 mg/kg of D91 twice daily (Δ); 100,000 IU/dose of IL-2 and 40 mg/kg of D91 twice daily (○).

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a phenylsulfamic acid" includes mixtures of two or more such phenylsulfamic acids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the terms "manage," "managing" and "management" refer to the beneficial effects that a subject derives from administration of a prophylactic or therapeutic agent, which does not result in a cure of the disease or diseases. In certain embodiments, a subject is administered one or more prophylactic or therapeutic agents to "manage" a disease so as to prevent the progression or worsening of the disease or diseases.

As used herein, the terms "prevent", "preventing" and "prevention" refer to the methods to avert or avoid a disease or disorder or delay the recurrence or onset of one or more symptoms of a disorder in a subject resulting from the administration of a prophylactic agent.

As used herein, the term "in combination" refers to the use of more than one prophylactic and/or therapeutic agents. The use of the term "in combination" does not restrict the order in which prophylactic and/or therapeutic agents are administered to a subject with a disorder, e.g., hyperproliferative cell disorder, especially cancer. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a disorder. The prophylactic or therapeutic agents are administered to a subject in a sequence and within a time interval such that the agent of the present disclosure can act together with the other agent to provide an increased benefit than if they were administered otherwise. Any additional prophylactic or therapeutic agent can be administered in any order with the other additional prophylactic or therapeutic agents As used herein, the terms "administer" when used to describe the dosage of a compound, means a single dose or multiple doses of the compound.

As used herein, the term "cancer treatment" means any treatment for cancer known in the art including, but not limited to, chemotherapy and radiation therapy.

As used herein, "tumor cells" means both cells derived from tumors, including malignant tumors, and cells immortalized in vitro. "Normal" cells refer to cells with normal growth characteristics that do not show abnormal proliferation.

As used herein, the terms "an individual identified as having cancer" and "cancer patient" are used interchangeably and are meant to refer to an individual who has been diagnosed as having cancer. There are numerous well known means for identifying an individual who has cancer. In some embodiments, a cancer diagnosis is made or confirmed using PET imaging. Some embodiments of the present disclosure comprise the step of identifying individuals who have cancer.

As used herein, the term "therapeutically effective amount" is meant to refer to an amount of an active agent or combination of agents effective to ameliorate or prevent the symptoms, shrink tumor size, or prolong the survival of the patient being treated. Determination of a therapeutically effective amount is well within the capabilities of those skilled in the art, especially in light of the detailed disclosure provided herein.

As used herein the term "inhibit" or "inhibiting" refers to a statistically significant and measurable reduction in activity, preferably a reduction of at least about 10% versus control, more preferably a reduction of about 50% or more, still more preferably a reduction of about 80% or more.

As used herein the term "increase" or "enhancing" refers to a statistically significant and measurable increase in activity, preferably an increase of at least about 10% versus control, more preferably an increase of about 50% or more, still more preferably an increase of about 80% or more.

The term "prevent" or "preventing" when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a receptor modulator that can provide for enhanced or desirable effects in the subject (e.g., reduction of pathogen load, beneficial increase in a physiological parameter of the subject, reduction of disease symptoms, etc.).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon The following chemical hierarchy is used throughout the specification to describe and enable the scope of the present disclosure and to particularly point out and distinctly claim the units which comprise the compounds of the present disclosure, however, unless otherwise specifically defined, the terms used herein are the same as those of the artisan of ordinary skill. The term "hydrocarbyl" stands for any carbon atom-based unit (organic molecule), said units optionally containing one or more organic functional group, including inorganic atom comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units can comprise only carbon atoms in the ring (i.e., carbocyclic and aryl rings) or can comprise one or more heteroatoms in the ring (i.e., heterocyclic and heteroaryl rings). For "carbocyclic" rings the lowest number of carbon atoms in a ring are 3 carbon atoms; cyclopropyl. For "aryl" rings the lowest number of carbon atoms in a ring are 6 carbon atoms; phenyl. For "heterocyclic" rings the lowest number of carbon atoms in a ring is 1 carbon atom; diazirinyl. Ethylene oxide comprises 2 carbon atoms and is a $C_2$ heterocycle. For "heteroaryl" rings the lowest number of carbon atoms in a ring is 1 carbon atom; 1,2,3,4-tetrazolyl. The following is a non-limiting description of the terms "acyclic hydrocarbyl" and "cyclic hydrocarbyl" as used herein.

A. Substituted and unsubstituted acyclic hydrocarbyl:
  For the purposes of the present disclosure the term "substituted and unsubstituted acyclic hydrocarbyl" encompasses 3 categories of units:
1) linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.
2) linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.
3) linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and unsubstituted cyclic hydrocarbyl:
  For the purposes of the present disclosure the term "substituted and unsubstituted cyclic hydrocarbyl" encompasses 5 categories of units:
1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted carbocyclic rings" which encompass the following categories of units:

i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).

ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$).

iii) carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted aryl rings" which encompass the following categories of units:

i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).

ii) $C_6$ or $C_{10}$ aryl rings fused with 1 or 2 saturated rings to afford $C_8$-$C_{20}$ ring systems, non-limiting examples of which include, bicyclo[4.2.0]octa-1,3,5-trienyl ($C_8$), and indanyl ($C_9$).

3) The terms "heterocyclic" and/or "heterocycle" are defined herein as "units comprising one or more rings having from 3 to 20 atoms wherein at least one atom in at least one ring is a heteroatom chosen from nitrogen (N), oxygen (O), or sulfur (S), or mixtures of N, O, and S, and wherein further the ring which contains the heteroatom is also not an aromatic ring." The following are non-limiting examples of "substituted and unsubstituted heterocyclic rings" which encompass the following categories of units:

i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), thiazolidinyl ($C_3$), isothiazolinyl ($C_3$), oxathiazolidinyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydroquinoline ($C_9$).

ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted heterocyclic rings" which encompass the following categories of units:

i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), isoxazolyl ($C_3$), isothiazolyl ($C_3$), furanyl ($C_4$), thiophenyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$)

ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether carbocyclic units, $C_6$ or $C_{10}$ aryl units, heterocyclic units, or heteroaryl units) which connected to another moiety, unit, or core of the molecule by way of a $C_1$-$C_6$ alkylene unit. Non-limiting examples of tethered cyclic hydrocarbyl units include benzyl $C_1$—($C_6$) having the formula:

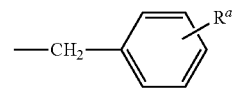

wherein $R^a$ is optionally one or more independently chosen substitutions for hydrogen. Further examples include other aryl units, inter alia, (2-hydroxyphenyl) hexyl $C_6$—($C_6$); naphthalen-2-ylmethyl $C_1$—($C_{10}$), 4-fluorobenzyl $C_1$—($C_6$), 2-(3-hydroxyphenyl)ethyl $C_2$—($C_6$), as well as substituted and unsubstituted $C_3$-$C_{10}$ alkylenecarbocyclic units, for example, cyclopropylmethyl $C_1$—($C_3$), cyclopentylethyl $C_2$—($C_5$), cyclohexylmethyl $C_1$—($C_6$). Included within this category are substituted and unsubstituted $C_1$-$C_{10}$ alkylene-heteroaryl units, for example a 2-picolyl $C_1$—($C_6$) unit having the formula:

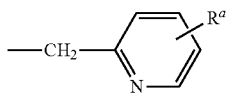

wherein $R^a$ is the same as defined above. In addition, $C_1$-$C_{12}$ tethered cyclic hydrocarbyl units include $C_1$-$C_{10}$alkyleneheterocyclic units and alkylene-heteroaryl units, non-limiting examples of which include, aziridinylmethyl $C_1$—($C_2$) and oxazol-2-ylmethyl $C_1$—($C_3$).

For the purposes of the present disclosure carbocyclic rings are from $C_3$ to $C_{20}$; aryl rings are $C_6$ or $C_{10}$; heterocyclic rings are from $C_1$ to $C_9$; and heteroaryl rings are from $C_1$ to $C_9$.

For the purposes of the present disclosure, and to provide consistency in defining the present disclosure, fused ring units, as well as spirocyclic rings, bicyclic rings and the like, which comprise a single heteroatom will be characterized and referred to herein as being encompassed by the cyclic family corresponding to the heteroatom containing ring, although the artisan may have alternative characterizations. For example, 1,2,3,4-tetrahydroquinoline having the formula:

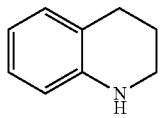

is, for the purposes of the present disclosure, considered a heterocyclic unit. 6,7-Dihydro-5H-cyclopentapyrimidine having the formula:

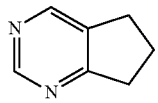

is, for the purposes of the present disclosure, considered a heteroaryl unit. When a fused ring unit contains heteroatoms in both a saturated ring (heterocyclic ring) and an aryl ring (heteroaryl ring), the aryl ring will predominate and determine the type of category to which the ring is assigned herein for the purposes of describing the present disclosure. For example, 1,2,3,4-tetrahydro-[1,8]naphthpyridine having the formula:

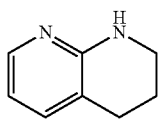

is, for the purposes of the present disclosure, considered a heteroaryl unit.

The term "substituted" is used throughout the specification. The term "substituted" is applied to the units described herein as "substituted unit or moiety is a hydrocarbyl unit or moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring (aryl ring)", (N,N-dimethyl-5-amino)octanyl is a "substituted $C_8$ linear alkyl unit, 3-guanidinopropyl is a "substituted $C_3$ linear alkyl unit," and 2-carboxypyridinyl is a "substituted heteroaryl unit."

The following are non-limiting examples of units which can substitute for hydrogen atoms on a carbocyclic, aryl, heterocyclic, or heteroaryl unit:

i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_6$ or $C_{10}$ alkylenearyl; for example, benzyl, 2-phenylethyl, naphthylen-2-ylmethyl;

iv) substituted or unsubstituted $C_1$-$C_9$ heterocyclic rings; as described herein below;

v) substituted or unsubstituted $C_1$-$C_9$ heteroaryl rings; as described herein below;

vi) —$(CR^{102a}R^{102b})_aOR^{101}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vii) —$(CR^{102a}R^{102b})_aC(O)R^{101}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;

viii) —$(CR^{102a}R^{102b})_aC(O)OR^{101}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

ix) —$(CR^{102a}R^{102b})_aC(O)N(R^{101})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

x) —$(CR^{102a}R^{102b})_aN(R^{101})_2$; for example, —$NH_2$, —$CH_2NH_2$, —$NHCH_3$, —$CH_2NHCH_3$, —$N(CH_3)_2$, and —$CH_2N(CH_3)_2$;

xi) halogen; —F, —Cl, —Br, and —I;

xii) —$(CR^{102a}R^{102b})_aCN$;

xiii) —$(CR^{102a}R^{102b})_aNO_2$;

xiv) —CH$_j$X$_k$; wherein X is halogen, the index j is an integer from 0 to 2, j+k=3; for example, —CH$_2$F, —CHF$_2$, —CF$_3$, —CCl$_3$, or —CBr$_3$;

xv) —(CR$^{102a}$R$^{102b}$)$_a$SR$^{101}$; —SH, —CH$_2$SH, —SCH$_3$, —CH$_2$SCH$_3$, —SC$_6$H$_5$, and —CH$_2$SC$_6$H$_5$;

xvi) —(CR$^{102a}$R$^{102b}$)$_a$SO$_2$R$^{101}$; for example, —SO$_2$H, —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and xvii) —(CR$^{102a}$R$^{102b}$)$_a$SO$_3$R$^{101}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each R$^{101}$ is independently hydrogen, substituted or unsubstituted C$_1$-C$_6$ linear, branched, or cyclic alkyl, phenyl, benzyl, heterocyclic, or heteroaryl; or two R$^{101}$ units can be taken together to form a ring comprising 3-7 atoms; R$^{102a}$ and R$^{102b}$ are each independently hydrogen or C$_1$-C$_4$ linear or branched alkyl; the index "a" is from 0 to 4.

For the purposes of the present disclosure the terms "compound," "analog," and "composition of matter" stand equally well for each other and are used interchangeably throughout the specification. The disclosed compounds include all enantiomeric forms, diastereomeric forms, salts, and the like.

The compounds disclosed herein include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The disclosed compounds have Formula (I):

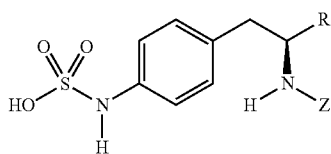

(I)

wherein the carbon atom having the amino unit has the (S) stereochemistry as indicated in the following formula:

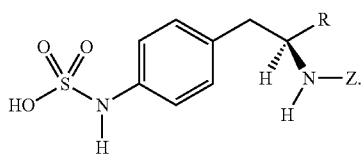

The units which comprise R and Z can comprise units having any configuration, and, as such, the disclosed compounds can be single enantiomers, diastereomeric pairs, or combinations thereof. In addition, the compounds can be isolated as salts or hydrates. In the case of salts, the compounds can comprises more than one cation or anion. In the case of hydrates, any number of water molecules, or fractional part thereof (for example, less than 1 water molecule present for each molecule of analog) can be present.

R Units

R is a substituted or unsubstituted thiazolyl unit having the formula:

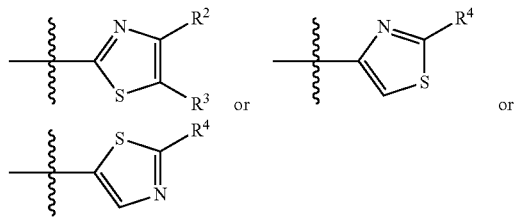

R$^2$, R$^3$, and R$^4$ are substituent groups that can be independently chosen from a wide variety of non-carbon atom containing units (for example, hydrogen, hydroxyl, amino, halogen, nitro, and the like) or organic substituent units, such as substituted and unsubstituted acyclic hydrocarbyl and cyclic hydrocarbyl units as described herein. The carbon comprising units can comprise from 1 to 12 carbon atoms, or 1 to 10 carbon atoms, or 1 to 6 carbon atoms.

An example of compounds of Formula (I) include compounds wherein R units are thiazol-2-yl units having the formula:

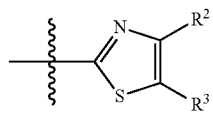

wherein R$^2$ and R$^3$ are each independently chosen from:
  i) hydrogen;
  ii) substituted or unsubstituted C$_1$-C$_6$ linear, branched, or cyclic alkyl;
  iii) substituted or unsubstituted C$_2$-C$_6$ linear, branched, or cyclic alkenyl;
  iv) substituted or unsubstituted C$_2$-C$_6$ linear or branched alkynyl;
  v) substituted or unsubstituted C$_6$ or C$_{10}$ aryl;
  vi) substituted or unsubstituted C$_1$-C$_9$ heteroaryl;
  vii) substituted or unsubstituted C$_1$-C$_9$ heterocyclic; or
  viii) R$^2$ and R$^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the R$^2$ and R$^3$ units. The following substituents, as well as others not herein described, are each independently chosen:
  i) C$_1$-C$_{12}$ linear, branched, or cyclic alkyl, alkenyl, and alkynyl; methyl (C$_1$), ethyl (C$_2$), ethenyl (C$_2$), ethynyl (C$_2$), n-propyl (C$_3$), iso-propyl (C$_3$), cyclopropyl (C$_3$), 3-propenyl (C$_3$), 1-propenyl (also 2-methylethenyl) (C$_3$), isopropenyl (also 2-methylethen-2-yl) (C$_3$), prop-2-ynyl (also propargyl) (C$_3$), propyn-1-yl (C$_3$), n-butyl (C$_4$), sec-butyl (C$_4$), iso-butyl (C$_4$), tert-butyl (C$_4$), cyclobutyl (C$_4$), buten-4-yl (C$_4$), cyclopentyl (C$_5$), cyclohexyl (C$_6$);
  ii) substituted or unsubstituted C$_6$ or C$_{10}$ aryl; for example, phenyl, naphthyl (also referred to herein as naphthylen-1-yl (C$_{10}$) or naphthylen-2-yl (C$_{10}$));
  iii) substituted or unsubstituted C$_6$ or C$_{10}$ alkylenearyl; for example, benzyl, 2-phenylethyl, naphthylen-2-ylmethyl;

iv) substituted or unsubstituted $C_1$-$C_9$ heterocyclic rings; as described herein;
v) substituted or unsubstituted $C_1$-$C_9$ heteroaryl rings; as described herein;
vi) —$(CR^{21a}R^{21b})_p OR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{21a}R^{21b})_p C(O)R^{20}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{21a}R^{21b})_p C(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
x) —$(CR^{21a}R^{21b})_p C(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{21a}R^{21b})_p N(R^{20})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{21a}R^{21b})_p CN$;
xiii) —$(CR^{21a}R^{21b})_p NO_2$;
xiv) —$(CH_jX_k)_{h}CH_{j'}X_{k'}$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;
xv) —$(CR^{21a}R^{21b})_p SR^{20}$; —SH, —$CH_2SH$, —$SCH_3$, —$CH_2SCH_3$, —$SC_6H_5$, and —$CH_2SC_6H_5$;
xvi) —$(CR^{21a}R^{21b})_p SO_2R^{20}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and
xvii) —$(CR^{21a}R^{21b})_p SO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;
wherein each $R^{20}$ is independently hydrogen, substituted or unsubstituted $C_1$-$C_4$ linear, branched, or cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or branched alkyl; the index p is from 0 to 4.

An example of compounds of Formula (I) includes R units having the formula:

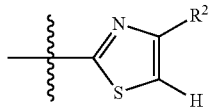

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), n-pentyl ($C_5$), 1-methylbutyl ($C_5$), 2-methylbutyl ($C_5$), 3-methylbutyl ($C_5$), cyclopropyl ($C_3$), n-hexyl ($C_6$), 4-methylpentyl ($C_6$), and cyclohexyl ($C_6$).

Another example of compounds of Formula (I) include R units having the formula:

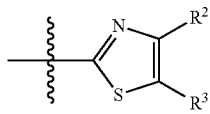

wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethylthiazol-2-yl, 4-ethyl-5-methylthiazol-2-yl, 4-methyl-5-ethylthiazol-2-yl, and 4,5-diethylthiazol-2-yl.

A further example of compounds of Formula (I) includes R units wherein $R^3$ is hydrogen and $R^2$ is a substituted alkyl unit, said substitutions chosen from:
i) halogen: —F, —Cl, —Br, and —I;
ii) —$N(R^{11})_2$; and
iii) —$OR^{11}$;
wherein each $R^{11}$ is independently hydrogen or $C_1$-$C_4$ linear or branched alkyl. Non-limiting examples of units that can be a substitute for a $R^2$ or $R^3$ hydrogen atom on R units include —$CH_2F$, —$CHF_2$, —$CF_3$, —$CH_2CF_3$, —$CH_2CH_2CF_3$, —$CH_2Cl$, —$CH_2OH$, —$CH_2OCH_3$, —$CH_2CH_2OH$, —$CH_2CH_2OCH_3$, —$CH_2NH_2$, —$CH_2NHCH_3$, —$CH_2N(CH_3)_2$, and —$CH_2NH(CH_2CH_3)$.

Further non-limiting examples of units that can be a substitute for a $R^2$ or $R^3$ hydrogen atom on R units include 2,2-difluorocyclopropyl, 2-methoxycyclohexyl, and 4-chlorocyclohexyl.

A yet further example of compounds of Formula (I), R units include units wherein $R^3$ is hydrogen and $R^2$ is phenyl or substituted phenyl, wherein non-limiting examples of $R^2$ units include phenyl, 3,4-dimethylphenyl, 4-tert-butylphenyl, 4-cyclopropylphenyl, 4-diethylaminophenyl, 4-(trifluoromethyl)phenyl, 4-methoxyphenyl, 4-(difluoromethoxy)phenyl, 4-(trifluoromethoxy)phenyl, 3-chloropheny, 4-chlorophenyl, and 3,4-dichlorophenyl, which when incorporated into the definition of R affords the following R units 4-phenylthiazol-2-yl, 3,4-dimethylphenylthiazol-2-yl, 4-tert-butylphenylthiazol-2-yl, 4-cyclopropylphenylthiazol-2-yl, 4-diethylaminophenylthiazol-2-yl, 4-(trifluoromethyl)phenylthiazol-2-yl, 4-methoxyphenylthiazol-2-yl, 4-(difluoromethoxy)phenylthiazol-2-yl, 4-(trifluoromethoxy)phenylthiazol-2-yl, 3-chlorophenylthiazol-2-yl, 4-chlorophenylthiazol-2-yl, and 3,4-dichlorophenylthiazol-2-yl.

A still further example of compounds of Formula (I) includes R units wherein $R^2$ is chosen from hydrogen, methyl, ethyl, n-propyl, and iso-propyl and $R^3$ is phenyl or substituted phenyl. A non-limiting example of a R unit according to the fifth aspect of the first category of R units includes 4-methyl-5-phenylthiazol-2-yl and 4-ethyl-5-phenylthiazol-2-yl.

Another further example of compounds of Formula (I) includes R units wherein $R^3$ is hydrogen and $R^2$ is a substituted or unsubstituted heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Further non-limiting example of compounds of Formula (I) includes R units wherein $R^2$ is substituted or unsubstituted thiophen-2-yl, for example thiophen-2-yl, 5-chlorothiophen-2-yl, and 5-methylthiophen-2-yl.

A still further example of compounds of Formula (I) includes R units wherein $R^2$ is substituted or unsubstituted thiophen-3-yl, for example thiophen-3-yl, 5-chlorothiophen-3-yl, and 5-methylthiophen-3-yl.

Another example of compounds of Formula (I) includes R units wherein $R^2$ and $R^3$ are taken together to form a saturated or unsaturated ring having from 5 to 7 atoms. Non-limiting examples of the sixth aspect of the first category of R units include 5,6-dihydro-4H-cyclopenta[d]thiazol-2-yl and 4,5,6,7-tetrahydrobenzo[d]thiazol-2-yl.

Further examples of compounds of Formula (I) include R units that are thiazol-4-yl units having the formula:

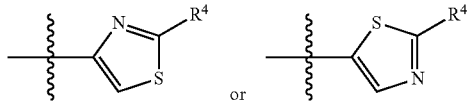

wherein $R^4$ is a unit chosen from:
i) hydrogen;
ii) substituted or unsubstituted $C_1$-$C_6$ linear, branched, or cyclic alkyl;
iii) substituted or unsubstituted $C_2$-$C_6$ linear, branched, or cyclic alkenyl;
iv) substituted or unsubstituted $C_2$-$C_6$ linear or branched alkynyl;
v) substituted or unsubstituted $C_6$ or $C_{10}$ aryl;
vi) substituted or unsubstituted $C_1$-$C_9$ heteroaryl; or
vii) substituted or unsubstituted $C_1$-$C_9$ heterocyclic.

The following are non-limiting examples of units that can substitute for one or more hydrogen atoms on the $R^4$ units. The following substituents, as well as others not herein described, are each independently chosen:
i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein below;
v) substituted or unsubstituted $C_1$-$C_9$ heteroaryl rings; as described herein below;
vi) —$(CR^{21a}R^{21b})_p OR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{21a}R^{21b})_p C(O)R^{20}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{21a}R^{21b})_p C(O)OR^{20}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
xi) —$(CR^{21a}R^{21b})_p C(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{21a}R^{21b})_p N(R^{20})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{21a}R^{21b})_p CN$;
xiii) —$(CR^{21a}R^{21b})_p NO_2$;
xiv) —$(CH_j X_k)_h CH_j X_k$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;
xv) —$(CR^{21a}R^{21b})_p SR^{20}$; —SH, —$CH_2SH$, —$SCH_3$, —$CH_2SCH_3$, —$SC_6H_5$, and —$CH_2SC_6H_5$;
xvi) —$(CR^{21a}R^{21b})_p SO_2R^{20}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and
xvii) —$(CR^{21a}R^{21b})_p SO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{20}$ is independently hydrogen, substituted or unsubstituted $C_1$-$C_4$ linear, branched, or cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or branched alkyl; the index p is from 0 to 4.

An example of compounds of Formula (I) includes R units wherein $R^4$ is hydrogen.

A further example of compounds of Formula (I) includes R units wherein $R^4$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect of R includes 2-methylthiazol-4-yl, 2-ethylthiazol-4-yl, 2-(n-propyl)thiazol-4-yl, and 2-(iso-propyl)thiazol-4-yl.

A still further example of compounds of Formula (I) includes R units wherein $R^4$ is substituted or unsubstituted phenyl, non-limiting examples of which include phenyl, 2-fluorophenyl, 2-chlorophenyl, 2-methylphenyl, 2-methoxyphenyl, 3-fluorophenyl, 3-chlorophenyl, 3-methylphenyl, 3-methoxyphenyl, 4-fluorophenyl, 4-chlorophenyl, 4-methylphenyl, and 4-methoxyphenyl.

Yet further example of compounds of Formula (I) includes R units wherein $R^4$ is substituted or unsubstituted heteroaryl, non-limiting examples of which include thiophen-2-yl, thiophen-3-yl, thiazol-2-yl, thiazol-4-yl, thiazol-5-yl, 2,5-dimethylthiazol-4-yl, 2,4-dimethylthiazol-5-yl, 4-ethylthiazol-2-yl, oxazol-2-yl, oxazol-4-yl, oxazol-5-yl, and 3-methyl-1,2,4-oxadiazol-5-yl.

Another example of 5-member ring R units includes substituted or unsubstituted imidazolyl units having the formula:

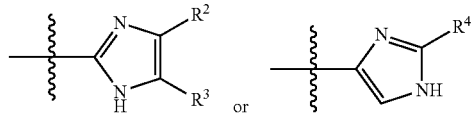

One example of imidazolyl R units includes imidazol-2-yl units having the formula:

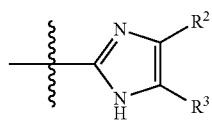

wherein $R^2$ and $R^3$ are each independently chosen from:
i) hydrogen;
ii) substituted or unsubstituted $C_1$-$C_6$ linear, branched, or cyclic alkyl;

iii) substituted or unsubstituted $C_2$-$C_6$ linear, branched, or cyclic alkenyl;
iv) substituted or unsubstituted $C_2$-$C_6$ linear or branched alkynyl;
v) substituted or unsubstituted $C_6$ or $C_{10}$ aryl;
vi) substituted or unsubstituted $C_1$-$C_9$ heteroaryl;
vii) substituted or unsubstituted $C_1$-$C_9$ heterocyclic; or
viii) $R^2$ and $R^3$ can be taken together to form a saturated or unsaturated ring having from 5 to 7 atoms; wherein from 1 to 3 atoms can optionally be heteroatoms chosen from oxygen, nitrogen, and sulfur.

The following are non-limiting examples of units that can substitute for one or more hydrogen atoms on the $R^2$ and $R^3$ units. The following substituents, as well as others not herein described, are each independently chosen:

i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein;
v) substituted or unsubstituted $C_1$-$C_9$ heteroaryl rings; as described herein;
vi) —$(CR^{21a}R^{21b})_z OR^{20}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{21a}R^{21b})_z C(O)R^{20}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{21a}R^{21b})_z C(O)OR^2$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
xii) —$(CR^{21a}R^{2b})_z C(O)N(R^{20})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{21a}R^{21b})_z N(R^{20})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{21a}R^{21b})_z CN$;
xiii) —$(CR^{21a}R^{21b})_z NO_2$;
xiv) —$(CH_j X_k)_h CH_{j'}X_{k'}$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;
xv) —$(CR^{21a}R^{21b})_z SR^{20}$; —SH, —$CH_2SH$, —$SCH_3$, —$CH_2SCH_3$, —$SC_6H_5$, and —$CH_2SC_6H_5$;
xvi) —$(CR^{21a}R^{21b})_z SO_2R^{20}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and
xvii) —$(CR^{21a}R^{21b})_z SO_3R^{20}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{20}$ is independently hydrogen, substituted or unsubstituted $C_1$-$C_4$ linear, branched, or cyclic alkyl, phenyl, benzyl, heterocyclic, or heteroaryl; or two $R^{20}$ units can be taken together to form a ring comprising 3-7 atoms; $R^{21a}$ and $R^{21b}$ are each independently hydrogen or $C_1$-$C_4$ linear or branched alkyl; the index p is from 0 to 4.

One example of R units includes compounds wherein R units have the formula:

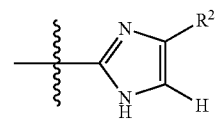

wherein $R^3$ is hydrogen and $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$).

Another example of R units includes compounds wherein $R^2$ is a unit chosen from methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); and $R^3$ is a unit chosen from methyl ($C_1$) or ethyl ($C_2$). Non-limiting examples of this aspect of R includes 4,5-dimethylimidazol-2-yl, 4-ethyl-5-methylimidazol-2-yl, 4-methyl-5-ethylimidazol-2-yl, and 4,5-diethyl-imidazol-2-yl.

An example of R units includes compounds wherein $R^3$ is hydrogen and $R^2$ is a substituted alkyl unit chosen, said substitutions chosen from:
  i) halogen: —F, —Cl, —Br, and —I;
  ii) —$N(R^{11})_2$; and
  iii) —$OR^{11}$;
wherein each $R^{11}$ is independently hydrogen or $C_1$-$C_4$ linear or branched alkyl.

Non-limiting examples of units comprising this embodiment of R includes: —$CH_2F$, —$CHF_2$, —$CF_3$, —$CH_2CF_3$, —$CH_2Cl$, —$CH_2OH$, —$CH_2OCH_3$, —$CH_2CH_2OH$, —$CH_2CH_2OCH_3$, —$CH_2NH_2$, —$CH_2NHCH_3$, —$CH_2N(CH_3)_2$, and —$CH_2NH(CH_2CH_3)$.

A yet further example of R units include units wherein $R^3$ is hydrogen and $R^2$ is phenyl.

A still further example of R units include units wherein $R^3$ is hydrogen and $R^2$ is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

Z Units

Z is a unit having the formula:

$R^1$ is chosen from:
  i) hydrogen;
  ii) hydroxyl;
  iii) amino;
  iv) substituted or unsubstituted $C_1$-$C_6$ linear, branched or cyclic alkyl;
  v) substituted or unsubstituted $C_1$-$C_6$ linear, branched or cyclic alkoxy;
  vi) substituted or unsubstituted $C_6$ or $C_{10}$ aryl;

vii) substituted or unsubstituted $C_1$-$C_9$ heterocyclic rings; or
viii) substituted or unsubstituted $C_1$-$C_9$ heteroaryl rings.

The following are non-limiting examples of units that can substitute for one or more hydrogen atoms on the $R^1$ units. The following substituents, as well as others not herein described, are each independently chosen:

i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_6$ or $C_{10}$ alkylenearyl; for example, benzyl, 2-phenylethyl, naphthylen-2-ylmethyl;

iv) substituted or unsubstituted $C_1$-$C_9$ heterocyclic rings; as described herein;

v) substituted or unsubstituted $C_1$-$C_9$ heteroaryl rings; as described herein;

vi) —$(CR^{31a}R^{31b})_q OR^{30}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;

vii) —$(CR^{31a}R^{31b})_q C(O)R^{30}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;

viii) —$(CR^{31a}R^{31b})_q C(O)OR^{30}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

xiii) —$(CR^{31a}R^{31b})_q C(O)N(R^{30})_2$; for example, —$CONH_2$, —$CH_2CONH_2$, —$CONHCH_3$, —$CH_2CONHCH_3$, —$CON(CH_3)_2$, and —$CH_2CON(CH_3)_2$;

x) —$(CR^{31a}R^{31b})_q N(R^{30})_2$; for example, —$NH_2$, —$CH_2NH_2$, —$NHCH_3$, —$CH_2NHCH_3$, —$N(CH_3)_2$, and —$CH_2N(CH_3)_2$;

xi) halogen; —F, —Cl, —Br, and —I;

xii) —$(CR^{31a}R^{31b})_q CN$;

xiii) —$(CR^{31a}R^{31b})_q NO_2$;

xiv) —$(CH_jX_k)_h CH_{j'}X_{k'}$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;

xv) —$(CR^{31a}R^{31b})_q SR^{30}$; —SH, —$CH_2SH$, —$SCH_3$, —$CH_2SCH_3$, —$SC_6H_5$, and —$CH_2SC_6H_5$;

xvi) —$(CR^{31a}R^{31b})_q SO_2R^{30}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and xvii) —$(CR^{31a}R^{31b})_q SO_3R^{30}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{30}$ is independently hydrogen, substituted or unsubstituted $C_1$-$C_6$ linear, branched, or cyclic alkyl, phenyl, benzyl, heterocyclic, or heteroaryl; or two $R^{30}$ units can be taken together to form a ring comprising 3-7 atoms; $R^{31a}$ and $R^{31b}$ are each independently hydrogen or $C_1$-$C_4$ linear or branched alkyl; the index q is from 0 to 4.

One example of $R^1$ units includes substituted or unsubstituted phenyl ($C_6$ aryl) units, wherein each substitution is independently chosen from: halogen, $C_1$-$C_4$ linear, branched alkyl, or cyclic alkyl, —$OR^1$, —CN, —$N(R^1)_2$, —$CO_2R^{11}$, —$C(O)N(R^1)_2$, —$NR^{11}C(O)R^{11}$, —$NO_2$, and —$SO_2R^{11}$; each $R^{11}$ is independently hydrogen; substituted or unsubstituted $C_1$-$C_4$ linear, branched, cyclic alkyl, alkenyl, or alkynyl; substituted or unsubstituted phenyl or benzyl; or two $R^{11}$ units can be taken together to form a ring comprising from 3-7 atoms.

Another example of $R^1$ units includes substituted $C_6$ aryl units chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl.

A further example of $R^1$ units includes substituted or unsubstituted $C_6$ aryl units chosen from 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, and 2,4,6-trichlorophenyl.

A yet further example of $R^1$ units includes substituted $C_6$ aryl units chosen from 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Another still further example of $R^1$ units includes substituted $C_6$ aryl units chosen from 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

$R^1$ can comprise heteroaryl units. Non-limiting examples of heteroaryl units include:

i)

ii)

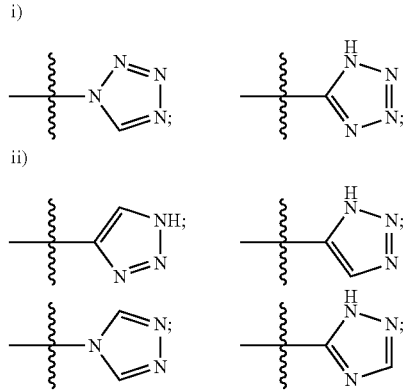

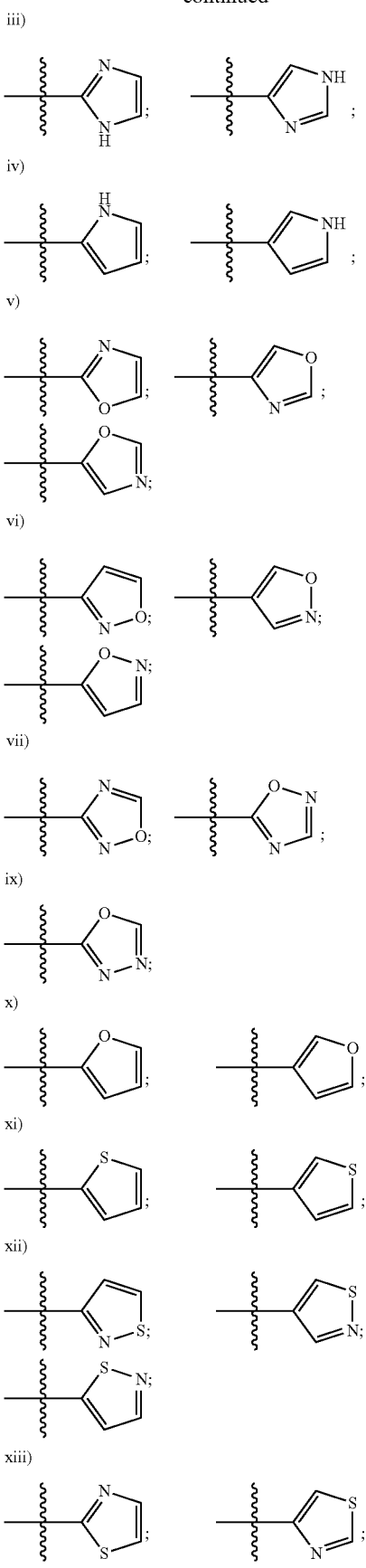

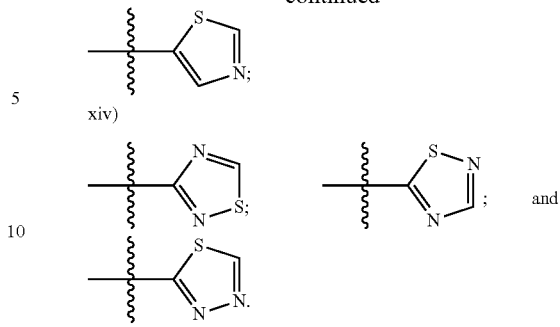

$R^1$ heteroaryl units can be substituted or unsubstituted. Non-limiting examples of units that can substitute for hydrogen include units chosen from:
  i) $C_1$-$C_6$ linear, branched, and cyclic alkyl;
  ii) substituted or unsubstituted phenyl and benzyl;
  iii) substituted of unsubstituted $C_1$-$C_9$ heteroaryl;
  iv) —C(O)$R^9$; and
  v) —NHC(O)$R^9$;
wherein $R^9$ is $C_1$-$C_6$ linear and branched alkyl; $C_1$-$C_6$ linear and branched alkoxy; or —NHCH$_2$C(O)$R^{10}$; $R^{10}$ is chosen from hydrogen, methyl, ethyl, and tert-butyl.

An example of $R^1$ relates to units substituted by an alkyl unit chosen from methyl, ethyl, n-propyl, iso-propyl, n-butyl, iso-butyl, sec-butyl, and tert-butyl.

Another example of $R^1$ includes units that are substituted by substituted or unsubstituted phenyl and benzyl, wherein the phenyl and benzyl substitutions are chosen from one or more:
  i) halogen;
  ii) $C_1$-$C_3$ alkyl;
  iii) $C_1$-$C_3$ alkoxy;
  iv) —CO$_2$$R^{11}$; and
  v) —NHCOR$^{16}$;
wherein $R^{11}$ and $R^{16}$ are each independently hydrogen, methyl, or ethyl.

Another example of $R^1$ relates to phenyl and benzyl units substituted by a carboxy unit having the formula —C(O)$R^9$; $R^9$ is chosen from methyl, methoxy, ethyl, and ethoxy.

A further example of $R^1$ includes phenyl and benzyl units substituted by an amide unit having the formula —NHC(O)$R^9$; $R^9$ is chosen from methyl, methoxy, ethyl, ethoxy, tert-butyl, and tert-butoxy.

A yet further example of $R^1$ includes phenyl and benzyl units substituted by one or more fluoro or chloro units.

L Units

L is a linking unit which is present when the index n is equal to 1, but is absent when the index n is equal to 0. L units have the formula:

$$-[Q]_y[C(R^{5a}R^{5b})]_x[Q^1]_z[C(R^{6a}R^{6b})]_w-$$

wherein Q and $Q^1$ are each independently:
  i) —C(O)—;
  ii) —NH—;
  iii) —C(O)NH—;
  iv) —NHC(O)—;
  v) —NHC(O)NH—;
  vi) —NHC(O)O—;
  vii) —C(O)O—;
  viii) —C(O)NHC(O)—;
  ix) —O—;
  x) —S—;
  xi) —SO$_2$—;

xii) —C(=NH)—;
xiii) —C(=NH)NH—;
xiv) —NHC(=NH)—; or
xv) —NHC(=NH)NH—.

When the index y is equal to 1, Q is present. When the index y is equal to 0, Q is absent.

When the index z is equal to 1, $Q^1$ is present. When the index z is equal to 0, $Q^1$ is absent.

$R^{5a}$ and $R^{5b}$ are each independently:
i) hydrogen;
ii) hydroxy;
iii) halogen;
iv) $C_1$-$C_6$ substituted or unsubstituted linear or branched alkyl; or
v) a unit having the formula:

wherein $R^{7a}$ and $R^{7b}$ are each independently:
i) hydrogen; or
ii) substituted or unsubstituted $C_1$-$C_6$ linear, branched, or cyclic alkyl.

$R^8$ is:
i) hydrogen;
ii) substituted or unsubstituted $C_1$-$C_6$ linear, branched, or cyclic alkyl;
iii) substituted or unsubstituted $C_6$ or $C_{10}$ aryl;
iv) substituted or unsubstituted $C_1$-$C_9$ heteroaryl; or
v) substituted or unsubstituted $C_1$-$C_9$ heterocyclic.

$R^{6a}$ and $R^{6b}$ are each independently:
i) hydrogen; or
ii) $C_1$-$C_4$ linear or branched alkyl.

The indices t, w and x are each independently from 0 to 4.

The following are non-limiting examples of units that can substitute for one or more hydrogen atoms on $R^{5a}$, $R^{5b}$, $R^{7a}$, $R^{7b}$, and $R^8$ units. The following substituents, as well as others not herein described, are each independently chosen:
i) $C_1$-$C_{12}$ linear, branched, or cyclic alkyl, alkenyl, and alkynyl; methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);
ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));
iii) substituted or unsubstituted $C_6$ or $C_{10}$ alkylenearyl; for example, benzyl, 2-phenylethyl, naphthylen-2-ylmethyl;
iv) substituted or unsubstituted $C_1$-$C_9$ heterocyclic rings; as described herein below;
v) substituted or unsubstituted $C_1$-$C_9$ heteroaryl rings; as described herein below;
vi) —$(CR^{41a}R^{41b})_rOR^{40}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH_2CH_3$;
vii) —$(CR^{41a}R^{41b})_rC(O)R^{40}$; for example, —$COCH_3$, —$CH_2COCH_3$, —$COCH_2CH_3$, —$CH_2COCH_2CH_3$, —$COCH_2CH_2CH_3$, and —$CH_2COCH_2CH_2CH_3$;
viii) —$(CR^{41a}R^{41b})_rC(O)OR^{40}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;
xiv) —$(CR^{41a}R^{41b})_rC(O)N(R^{40})_2$; for example, —$CONH_2$, —$CH_2CONH_2$, —$CONHCH_3$, —$CH_2CONHCH_3$, —$CON(CH_3)_2$, and —$CH_2CON(CH_3)_2$;
x) —$(CR^{41a}R^{41b})_rN(R^{40})_2$; for example, —$NH_2$, —$CH_2NH_2$, —$NHCH_3$, —$CH_2NHCH_3$, —$N(CH_3)_2$, and —$CH_2N(CH_3)_2$;
xi) halogen; —F, —Cl, —Br, and —I;
xii) —$(CR^{41a}R^{41b})_rCN$;
xiii) —$(CR^{41a}R^{41b})_rNO_2$;
xiv) —$(CH_jX_k)_hCH_{j'}X_{k'}$; wherein X is halogen, the index j is an integer from 0 to 2, j+k=3, the index j' is an integer from 0 to 2, j'+k'=2, the index h is from 0 to 6; for example, —$CH_2F$, —$CHF_2$, —$CF_3$, —$CH_2CF_3$, —$CHFCF_3$, —$CCl_3$, or —$CBr_3$;
xv) —$(CR^{41a}R^{41b})_rSR^{40}$; —SH, —$CH_2SH$, —$SCH_3$, —$CH_2SCH_3$, —$SC_6H_5$, and —$CH_2SC_6H_5$;
xvi) —$(CR^{41a}R^{41b})_rSO_2R^{40}$; for example, —$SO_2H$, —$CH_2SO_2H$, —$SO_2CH_3$, —$CH_2SO_2CH_3$, —$SO_2C_6H_5$, and —$CH_2SO_2C_6H_5$; and
xvii) —$(CR^{41a}R^{41b})_rSO_3R^{40}$; for example, —$SO_3H$, —$CH_2SO_3H$, —$SO_3CH_3$, —$CH_2SO_3CH_3$, —$SO_3C_6H_5$, and —$CH_2SO_3C_6H_5$;

wherein each $R^{40}$ is independently hydrogen, substituted or unsubstituted $C_1$-$C_6$ linear, branched, or cyclic alkyl, phenyl, benzyl, heterocyclic, or heteroaryl; or two $R^{40}$ units can be taken together to form a ring comprising 3-7 atoms; $R^{41a}$ and $R^{41b}$ are each independently hydrogen or $C_1$-$C_4$ linear or branched alkyl; the index r is from 0 to 4.

One aspect of L units relates to units having the formula:

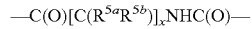

wherein $R^{5a}$ is hydrogen, substituted or unsubstituted $C_1$-$C_4$ alkyl, substituted or unsubstituted phenyl, and substituted or unsubstituted heteroaryl; and the index x is 1 or 2. One embodiment relates to linking units having the formula:
i) —C(O)[C($R^{5a}$H)]NHC(O)O—;
ii) —C(O)[C($R^{5a}$H)][$CH_2$]NHC(O)O—;
iii) —C(O)[$CH_2$][C($R^{5a}$H)]NHC(O)O—;
iv) —C(O)[C($R^{5a}$H)]NHC(O)—;
v) —C(O)[C($R^{5a}$H)][$CH_2$]NHC(O)—; or
vi) —C(O)[$CH_2$][C($R^{5a}$H)]NHC(O)—;
wherein $R^{5a}$ is:
i) hydrogen;
ii) methyl;
iii) ethyl;
iv) isopropyl;
v) phenyl;
vi) benzyl;
vii) 4-hydroxybenzyl;
viii) hydroxymethyl; or
ix) 1-hydroxyethyl.

When the index x is equal to 1, this embodiment provides the following non-limiting examples of L units:

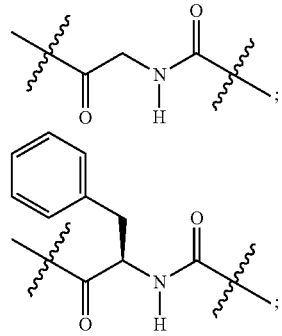

-continued

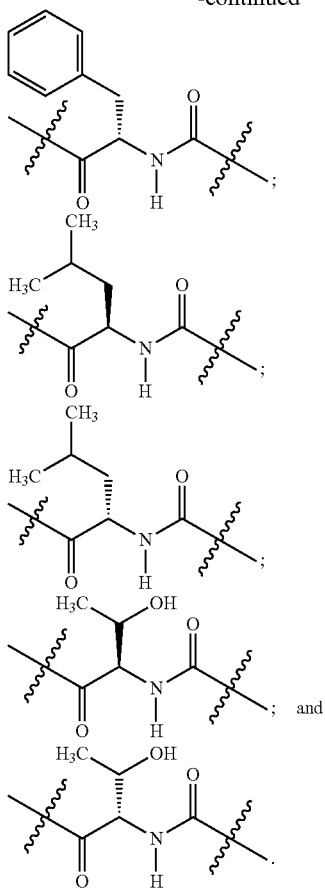

When the index x is equal to 2, this embodiment provides the following non-limiting examples of L units:

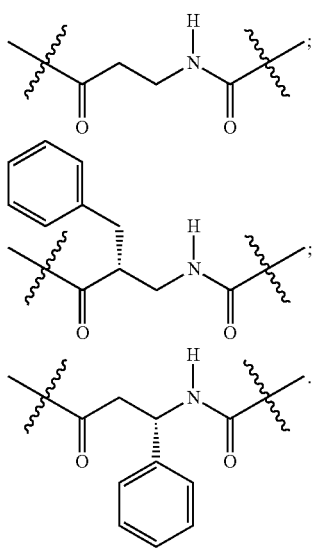

Another embodiment of L units includes units wherein Q is —C(O)—, the indices x and z are equal to 0, w is equal to 1 or 2, a first $R^{6a}$ unit chosen from phenyl, 2-fluorophenyl, 3-fluorophenyl, 4-fluorophenyl, 2,3-difluorophenyl, 3,4-difluorophenyl, 3,5-difluorophenyl, 2-chlorophenyl, 3-chlorophenyl, 4-chlorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, and 3,5-dimethoxyphenyl; a second $R^{6a}$ unit is hydrogen and $R^{6b}$ units are hydrogen. For example a linking unit having the formula:

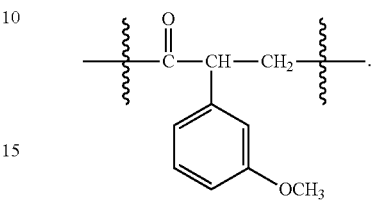

A further example of this embodiment of L includes a first $R^{6a}$ unit as depicted herein above that is a substituted or unsubstituted heteroaryl unit as described herein above.

A yet further example of this embodiment of L includes units having the formula:

—C(O)[C($R^{6a}R^{6b}$)]$_w$—;

wherein $R^{6a}$ and $R^{6b}$ are hydrogen and the index w is equal to 1 or 2; said units chosen from:
i) —C(O)CH$_2$—; and
ii) —C(O)CH$_2$CH$_2$—.

Another embodiment of L units includes units having the formula:

—C(O)[C($R^{5a}R^{5b}$)]$_x$C(O)—;

wherein $R^{5a}$ and $R^{5b}$ are hydrogen and the index x is equal to 1 or 2; said units chosen from:
i) —C(O)CH$_2$C(O)—; and
ii) —C(O)CH$_2$CH$_2$C(O)—.

A still further embodiment of L units includes units having the formula:

—C(O)NH[C($R^{5a}R^{5b}$)]$_x$—;

wherein $R^{5a}$ and $R^{5b}$ are hydrogen and the index w is equal to 0, 1 or 2; said units chosen from:
ii) —C(O)NH—;
ii) —C(O)NHCH$_2$—; and
iii) —C(O)NHCH$_2$CH$_2$—.

A yet still further example of L units includes units having the formula:

—SO$_2$[C($R^{6a}R^{6b}$)]$_w$—;

wherein $R^{8a}$ and $R^{8b}$ are hydrogen or methyl and the index w is equal to 0, 1 or 2; said units chosen from:
i) —SO$_2$—;
ii) —SO$_2$CH$_2$—; and
iii) —SO$_2$CH$_2$CH$_2$—.

Vascular Leakage Control

The disclosed compounds (analogs) are arranged into several Categories to assist the formulator in applying a rational synthetic strategy for the preparation of analogs which are not expressly exampled herein. The arrangement into categories does not imply increased or decreased efficacy for any of the compositions of matter described herein.

A described herein above the disclosed compounds include all pharmaceutically acceptable salt forms. A compound having the formula:

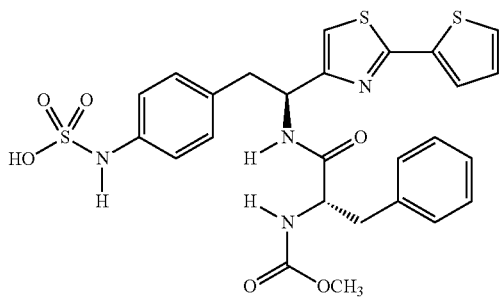 [SMILES: COC(=O)N[C@@H](Cc1ccccc1)C(=O)N[C@@H](Cc1ccc(NS(=O)(=O)O)cc1)c1csc(-c2cccs2)n1]

can form salts, for example, a salt of the sulfamic acid:

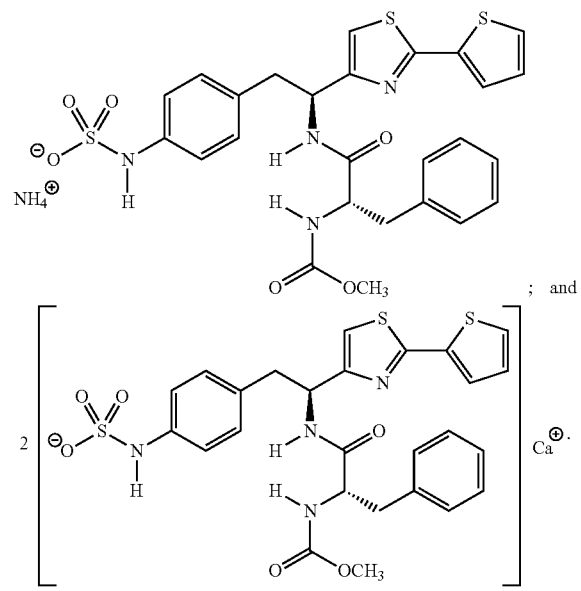

The compounds can also exist in a zwitterionic form, for example:

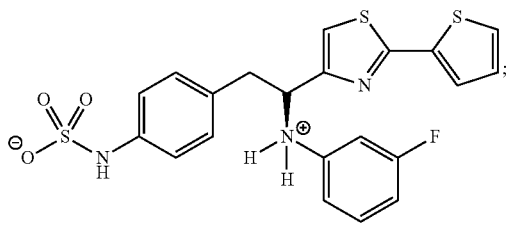

as a salt of a strong acid, for example:

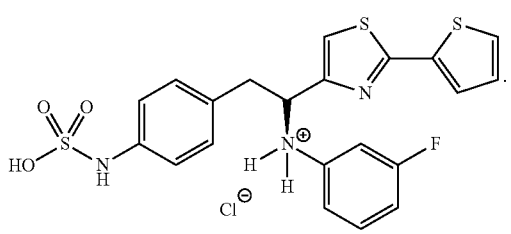

The first aspect of Category I of the present disclosure relates to compounds wherein R is a substituted or unsubstituted thiazol-2-yl unit having the formula:

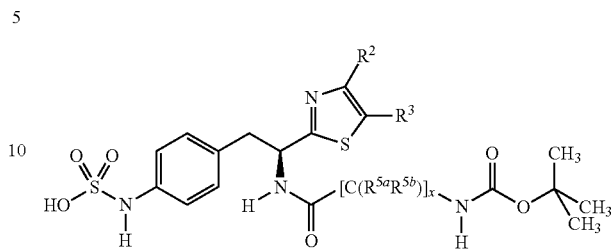

one embodiment of which relates to inhibitors having the formula:

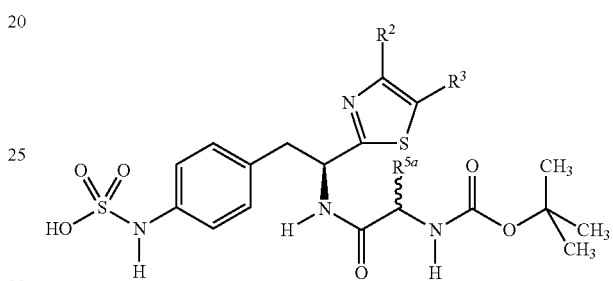

wherein R units are thiazol-2-yl units, that when substituted, are substituted with $R^2$ and $R^3$ units. R and $R^{5a}$ units are further described in Table I.

TABLE I

| No. | R | $R^{5a}$ |
|-----|---|----------|
| A1 | thiazol-2-yl | (S)-benzyl |
| A2 | 4-methylthiazol-2-yl | (S)-benzyl |
| A3 | 4-ethylthiazol-2-yl | (S)-benzyl |
| A4 | 4-propylthiazol-2-yl | (S)-benzyl |
| A5 | 4-iso-propylthiazol-2-yl | (S)-benzyl |
| A6 | 4-cyclopropylthiazol-2-yl | (S)-benzyl |
| A7 | 4-butylthiazol-2-yl | (S)-benzyl |
| A8 | 4-tert-butylthiazol-2-yl | (S)-benzyl |
| A9 | 4-cyclohexylthiazol-2-yl | (S)-benzyl |
| A10 | 4-(2,2,2-trifluoroethyl)thiazol-2-yl | (S)-benzyl |
| A11 | 4-(3,3,3-trifluoropropyl)thiazol-2-yl | (S)-benzyl |
| A12 | 4-(2,2-difluorocyclopropyl)thiazol-2-yl | (S)-benzyl |
| A13 | 4-(methoxymethyl)thiazol-2-yl | (S)-benzyl |
| A14 | 4-(carboxylic acid ethyl ester)thiazol-2-yl | (S)-benzyl |
| A15 | 4,5-dimethylthiazol-2-yl | (S)-benzyl |
| A16 | 4-methyl-5-ethylthiazol-2-yl | (S)-benzyl |
| A17 | 4-phenylthiazol-2-yl | (S)-benzyl |
| A18 | 4-(4-chlorophenyl)thiazol-2-yl | (S)-benzyl |
| A19 | 4-(3,4-dimethylphenyl)thiazol-2-yl | (S)-benzyl |
| A20 | 4-methyl-5-phenylthiazol-2-yl | (S)-benzyl |
| A21 | 4-(thiophen-2-yl)thiazol-2-yl | (S)-benzyl |
| A22 | 4-(thiophen-3-yl)thiazol-2-yl | (S)-benzyl |
| A23 | 4-(5-chlorothiophen-2-yl)thiazol-2-yl | (S)-benzyl |
| A24 | 5,6-dihydro-4H-cyclopenta[d]thiazol-2-yl | (S)-benzyl |
| A25 | 4,5,6,7-tetrahydrobenzo[d]thiazol-2-yl | (S)-benzyl |

The compounds encompassed within the first aspect of Category I of the present disclosure can be prepared by the procedure outlined in Scheme I and described in Example 1 herein below.

Scheme I
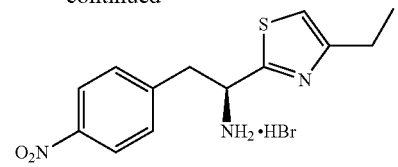
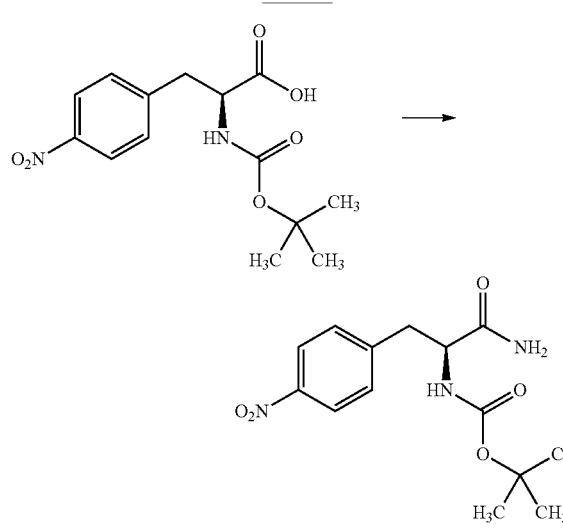
Reagents and conditions: (a)(i) (iso-butyl)OCOCl, NMM, DMF; 0° C., 20 min. (ii) NH₃; 0° C. for 30 min.
Reagents and conditions: (b) Lawesson's reagent, THF; rt, 3 hr.
Reagents and conditions: (c) CH₃CN; reflux, 3 hr.
Reagents and conditions: (d) Boc-Phe, EDCI, HOBt, DIPEA, DMF; rt, 18 hr.
Reagents and conditions: (e) (i) H₂:Pd/C, MeOH; (ii) SO₃-pyridine, NH₄OH; rt, 2 hr.

Example 1

4-{(S)-2-[(S)-2-(tert-Butoxycarbonylamino)-3-phenylpropanamido]-2-(4-ethylthiazol-2-yl)ethyl}phenylsulfamic acid (5)

Preparation of [1-(S)-carbamoyl-2-(4-nitrophenyl)ethyl-carbamic acid tert-butyl ester (1): To a 0° C. solution of 2-(S)-tert-butoxycarbonylamino-3-(4-nitrophenyl)-propionic acid and N-methylmorpholine (1.1 mL, 9.65 mmol) in DMF (10 mL) is added dropwise iso-butyl chloroformate (1.25 mL, 9.65 mmol). The mixture is stirred at 0° C. for 20 minutes after which $NH_3$ (g) is passed through the reaction mixture for 30 minutes at 0° C. The reaction mixture is concentrated and the residue dissolved in EtOAc, washed successively with 5% citric acid, water, 5% $NaHCO_3$, water and brine, dried ($Na_2SO_4$), filtered and concentrated in vacuo to a residue that is triturated with a mixture of EtOAc/petroleum ether to provide 2.2 g (74%) of the desired product as a white solid.

Preparation of [2-(4-nitrophenyl)-1-(S)-thiocarbamoyl-ethyl]carbamic acid tert-butyl ester (2): To a solution of [1-(S)-carbamoyl-2-(4-nitrophenyl)ethyl-carbamic acid tert-butyl ester, 1, (0.400 g, 1.29 mmol) in THF (10 mL) is added Lawesson's reagent (0.262 g. 0.65 mmol). The reaction mixture is stirred for 3 hours and concentrated to a residue which is purified over silica to provide 0.350 g (83%) of the desired product. $^1$H NMR (300 MHz, $CDCl_3$) δ 8.29 (s, 1H), 8.10 (d. J=8.4 Hz, 2H), 8.01 (s, 1H), 7.42 (d, J=8.4 Hz, 2H), 5.70 (d, J=7.2 Hz, 1H), 4.85 (d, J=7.2 Hz, 1H), 3.11-3.30 (m, 1H), 1.21 (s, 9H).

Preparation of 1-(S)-(4-ethylthiazol-2-yl)-2-(4-nitrophenyl)ethyl amine (3): A mixture of [2-(4-nitrophenyl)-1-(S)-thiocarbamoylethyl]-carbamic acid tert-butyl ester, 2, (0.245 g, 0.753 mmol), 1-bromo-2-butanone (0.125 g, 0.828 mmol) in $CH_3CN$ (5 mL) is refluxed 3 hours. The reaction mixture is cooled to room temperature and diethyl ether is added to the solution and the precipitate which forms is removed by filtration. The solid is dried under vacuum to afford 0.242 g (90% yield) of the desired product. ESI+ MS 278 (M+1).

Preparation of {1-[1-(4-ethylthiazol-2-yl)-2-(4-nitrophenyl)ethylcarbamoyl]-2-phenylethyl}carbamic acid tert-butyl ester (4): To a solution of 1-(S)-(4-ethylthiazol-2-yl)-2-(4-nitrophenyl)ethyl amine hydrobromide, 3, (0.393 g, 1.1 mmol), (S)-(2-tert-butoxycarbonylamino)-3-phenylpropionic acid (0.220 g, 0.828 mmol) and 1-hydroxybenzotriazole (HOBt) (0.127 g, 0.828 mmol) in DMF (10 mL) at 0° C., is added 1-(3-dimethylaminopropyl)-3-ethylcarbodiimide (EDCI) (0.159 g, 0.828 mmol) followed by diisopropylamine (0.204 g, 1.58 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous $NaHCO_3$, water and brine, and dried over $Na_2SO_4$. The solvent is removed in vacuo to afford 0.345 g of the desired product which is used without further purification. LC/MS ESI+ 525 (M+1).

Preparation of 4-{(S)-2-[(S)-2-(tert-butoxycarbonylamino)-3-phenylpropanamido]-2-(4-ethylthiazol-2-yl)ethyl}phenylsulfamic acid ammonium salt (5): {1-[1-(4-ethylthiazol-2-yl)-2-(4-nitrophenyl)ethylcarbamoyl]-2-phenylethyl}carbamic acid tert-butyl ester, 4, (0.345 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with $SO_3$-pyridine (0.314 g). The reaction is stirred at room temperature for 5 minutes after which a 7% solution of $NH_4OH$ (50 mL) is added. The mixture is then concentrated and the resulting residue is purified by reverse phase chromatography to afford 0.222 g of the desired product as the ammonium salt. $^1$H NMR ($CD_3OD$): δ 7.50-6.72 (m, 10H), 5.44-5.42 (d, 1H, J=6.0 Hz), 4.34 (s, 1H), 3.34-2.79 (m, 4H), 2.83-2.76 (q, 2H, J=7.2 Hz), 1.40 (s, 9H), 1.31 (t, 3H, J=7.5 Hz).

The disclosed inhibitors can also be isolated as the free acid. A non-limiting example of this procedure is described herein below in Example 4.

The following is a non-limiting example of compounds encompassed within this embodiment of the first aspect of Category I of the present disclosure.

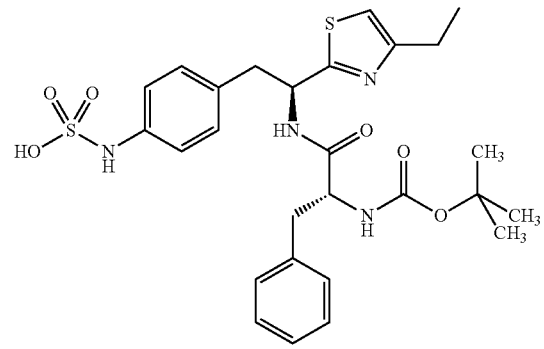 [SMILES: CCc1csc([C@H](Cc2ccc(NS(=O)(=O)O)cc2)NC(=O)[C@@H](Cc2ccccc2)NC(=O)OC(C)(C)C)n1]

4-{(S)-2-[(R)-2-(tert-butoxycarbonylamino)-3-phenyl-propanamido]-2-(4-ethylthiazol-2-yl)ethyl}phenylsulfamic acid: $^1$H NMR ($CD_3OD$): δ 7.22-7.02 (m, 10H), 5.39 (s, 1H), 4.34 (s, 1H), 3.24-2.68 (m, 6H), 1.37 (s, 9H), 1.30 (t, 3H, J=7.5 Hz).

Another embodiment of this aspect of Category I relates to inhibitors having the formula:

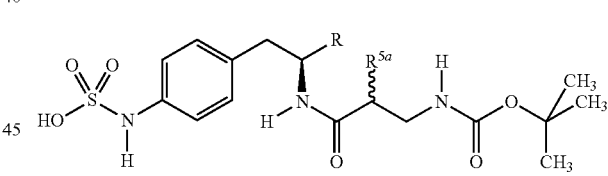

wherein R units and $R^{5a}$ units further described in Table II.

TABLE II

| No. | R | $R^{5a}$ |
| --- | --- | --- |
| B26 | thiazol-2-yl | (S)-benzyl |
| B27 | 4-methylthiazol-2-yl | (S)-benzyl |
| B28 | 4-ethylthiazol-2-yl | (S)-benzyl |
| B29 | 4-propylthiazol-2-yl | (S)-benzyl |
| B30 | 4-iso-propylthiazol-2-yl | (S)-benzyl |
| B31 | 4-cyclopropylthiazol-2-yl | (S)-benzyl |
| B32 | 4-butylthiazol-2-yl | (S)-benzyl |
| B33 | 4-tert-butylthiazol-2-yl | (S)-benzyl |
| B34 | 4-cyclohexylthiazol-2-yl | (S)-benzyl |
| B35 | 4-(2,2,2-trifluoroethyl)thiazol-2-yl | (S)-benzyl |
| B36 | 4-(3,3,3-trifluoropropyl)thiazol-2-yl | (S)-benzyl |
| B37 | 4-(2,2-difluorocyclopropyl)thiazol-2-yl | (S)-benzyl |
| B38 | 4-(methoxymethyl)thiazol-2-yl | (S)-benzyl |
| B39 | 4-(carboxylic acid ethyl ester)thiazol-2-yl | (S)-benzyl |
| B40 | 4,5-dimethylthiazol-2-yl | (S)-benzyl |
| B41 | 4-methyl-5-ethylthiazol-2-yl | (S)-benzyl |

TABLE II-continued

| No. | R | $R^{5a}$ |
|---|---|---|
| B42 | 4-phenylthiazol-2-yl | (S)-benzyl |
| B43 | 4-(4-chlorophenyl)thiazol-2-yl | (S)-benzyl |
| B44 | 4-(3,4-dimethylphenyl)thiazol-2-yl | (S)-benzyl |
| B45 | 4-methyl-5-phenylthiazol-2-yl | (S)-benzyl |
| B46 | 4-(thiophen-2-yl)thiazol-2-yl | (S)-benzyl |
| B47 | 4-(thiophen-3-yl)thiazol-2-yl | (S)-benzyl |
| B48 | 4-(5-chlorothiophen-2-yl)thiazol-2-yl | (S)-benzyl |
| B49 | 5,6-dihydro-4H-cyclopenta[d]thiazol-2-yl | (S)-benzyl |
| B50 | 4,5,6,7-tetrahydrobenzo[d]thiazol-2-yl | (S)-benzyl |

The compounds of this embodiment can be prepared according to the procedure outlined above in Scheme I and described in Example 1 by substituting the appropriate Boc-β-amino acid for (S)-(2-tert-butoxycarbonylamino)-3-phenylpropionic acid in step (d).

The following are non-limiting examples of compounds according to this embodiment.

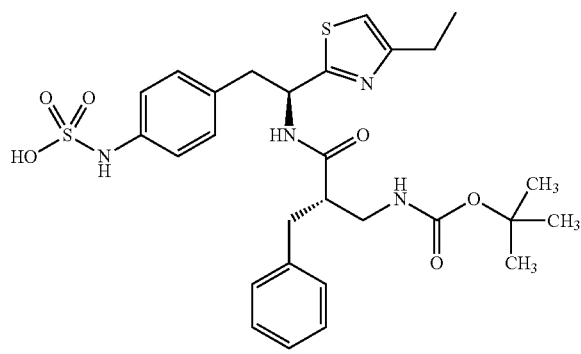 [SMILES: CCc1csc([C@H](Cc2ccc(NS(=O)(=O)O)cc2)NC(=O)[C@H](CNC(=O)OC(C)(C)C)Cc2ccccc2)n1]

{1-[1-(4-Ethylthiazol-2-yl)-(S)-2-(4-sulfoaminophenyl)ethylcarbamoyl]-(S)-2-phenylethyl}methyl carbamic acid tert-butyl ester: $^1$H NMR (300 MHz, MeOH-d$_4$) δ 8.36 (d, J=8.1 Hz, 1H), 7.04-7.22 (m, 9H), 5.45 (s, 1H), 3.01-3.26 (m, 2H), 2.60-2.88 (m, 4H), 2.33 (s, 3H), 1.30 (s, 9H).

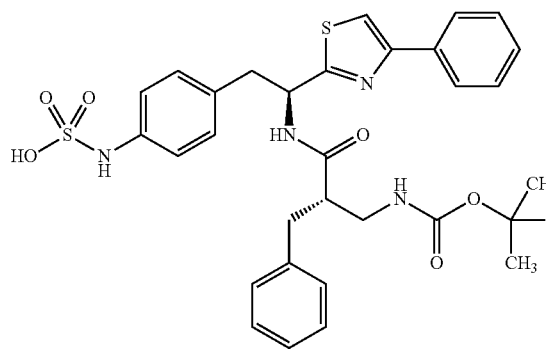

{1-[1-(4-Phenylthiazol-2-yl)-(S)-2-(4-sulfoaminophenyl)ethylcarbamoyl]-(S)-2-phenylethyl}methyl carbamic acid tert-butyl ester: $^1$H NMR (300 MHz, MeOH-d$_4$) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

The second aspect of Category I of the present disclosure relates to compounds wherein R is a substituted or unsubstituted thiazol-4-yl having the formula:

one embodiment of which relates to inhibitors having the formula:

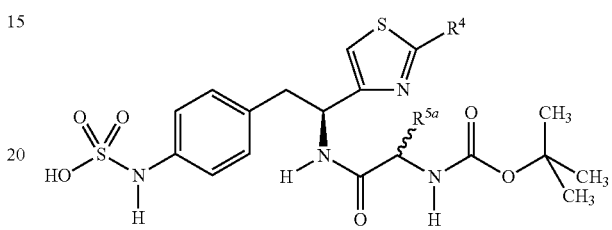

wherein R units and $R^{5a}$ units further described in Table III.

TABLE III

| No. | R | $R^{5a}$ |
|---|---|---|
| C51 | thiazol-4-yl | (S)-benzyl |
| C52 | 2-methylthiazol-4-yl | (S)-benzyl |
| C53 | 2-ethylthiazol-4-yl | (S)-benzyl |
| C54 | 2-propylthiazol-4-yl | (S)-benzyl |
| C55 | 2-iso-propylthiazol-4-yl | (S)-benzyl |
| C56 | 2-cyclopropylthiazol-4-yl | (S)-benzyl |
| C57 | 2-butylthiazol-4-yl | (S)-benzyl |
| C58 | 2-tert-butylthiazol-4-yl | (S)-benzyl |
| C59 | 2-cyclohexylthiazol-4-yl | (S)-benzyl |
| C60 | 2-(2,2,2-trifluoroethyl)thiazol-4-yl | (S)-benzyl |
| C61 | 2-(3,3,3-trifluoropropyl)thiazol-4-yl | (S)-benzyl |
| C62 | 2-(2,2-difluorocyclopropyl)thiazol-4-yl | (S)-benzyl |
| C63 | 2-phenylthiazol-4-yl | (S)-benzyl |
| C64 | 2-(4-chlorophenyl)thiazol-4-yl | (S)-benzyl |
| C65 | 2-(3,4-dimethylphenyl)thiazol-4-yl | (S)-benzyl |
| C66 | 2-(thiophen-2-yl)thiazol-4-yl | (S)-benzyl |
| C67 | 2-(thiophen-3-yl)thiazol-4-yl | (S)-benzyl |
| C68 | 2-(3-chlorothiophen-2-yl)thiazol-4-yl | (S)-benzyl |
| C69 | 2-(3-methylthiophen-2-yl)thiazol-4-yl | (S)-benzyl |
| C70 | 2-(2-methylthiazol-4-yl)thiazol-4-yl | (S)-benzyl |
| C71 | 2-(furan-2-yl)thiazol-4-yl | (S)-benzyl |
| C72 | 2-(pyrazin-2-yl)thiazol-4-yl | (S)-benzyl |
| C73 | 2-[(methyl)pyridin-5-yl]thiazol-4-yl | (S)-benzyl |
| C74 | 2-(4-chlorobenzenesulfonylmethyl)thiazol-4-yl | (S)-benzyl |
| C75 | 2-(tert-butylsulfonylmethyl)thiazol-4-yl | (S)-benzyl |

The compounds encompassed within the second aspect of Category I of the present disclosure can be prepared by the procedure outlined in Scheme II and described in Example 2 herein below.

Scheme II

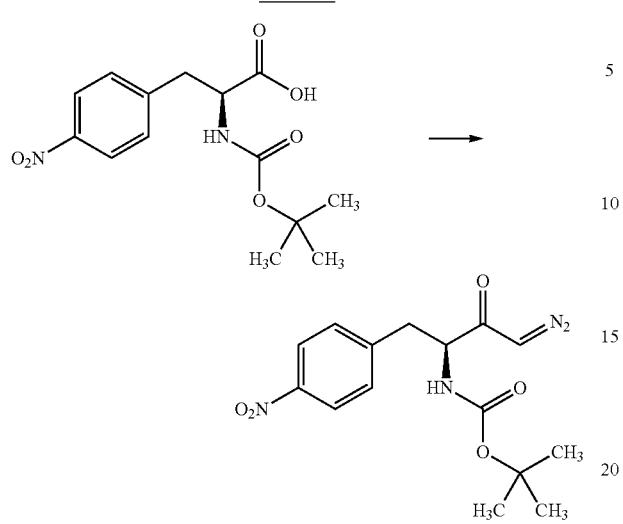

Reagents and conditions: (a)(i) (iso-butyl)OCOCl, Et₃N, THF; 0° C., 20 min. (ii) CH₂N₂; room temp for 3 hours.

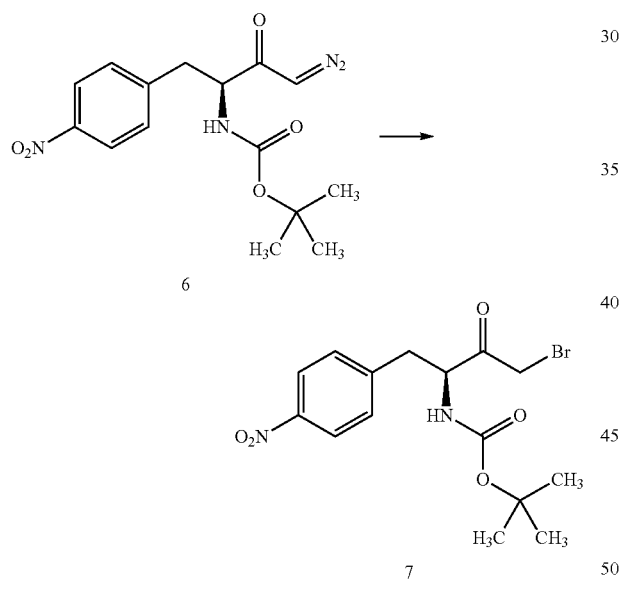

Reagents and conditions: (b) 48% HBr, THF; 0° C., 1.5 hr.

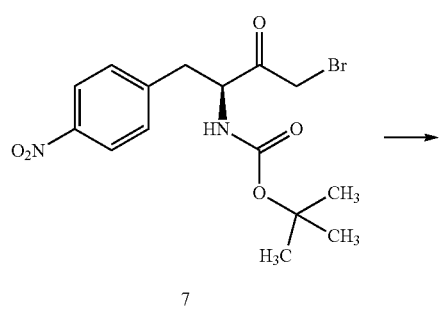

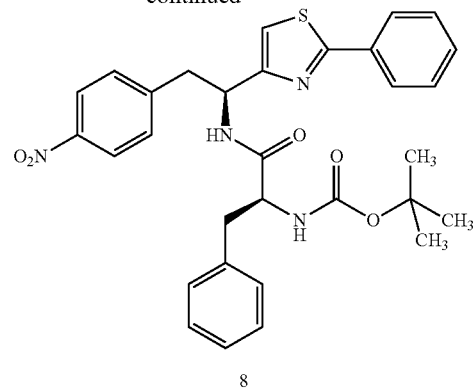

Reagents and conditions: (c)(i) thiobenzamide, CH₃CN; reflux, 2 hr. (ii) Boc-Phe, HOBt, DIPEA, DMF; rt, 18 hr.

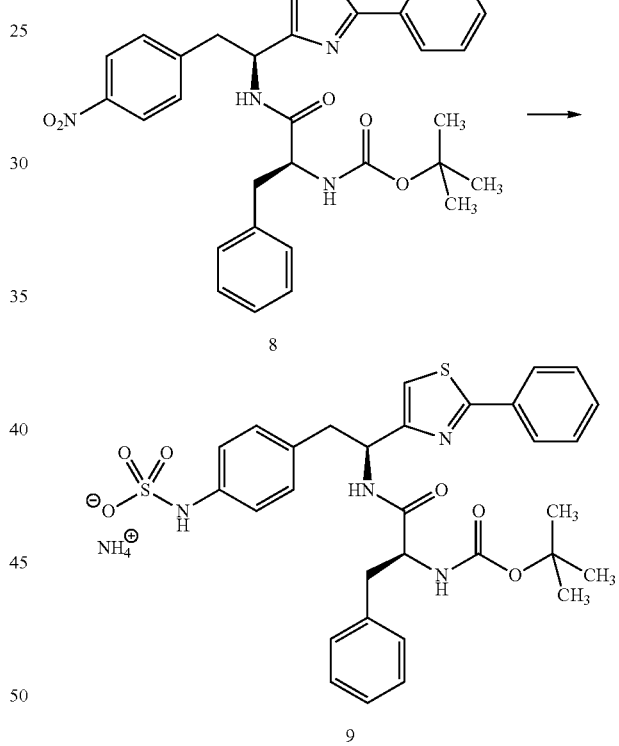

Reagents and conditions: (d) (i) H₂:Pd/C, MeOH; (ii) SO₃-pyridine, NH₄OH; rt, 12 hr.

Example 2

4-{(S)-2-(S)-2-(tert-Butoxycarbonylamino)-3-phenylpropanamido-2-(2-phenylthiazol-4-yl)}phenylsulfamic acid (9)

Preparation of (S)-[3-diazo-1-(4-nitrobenzyl)-2-oxo-propyl]-carbamic acid tert-butyl ester (6): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by iso-butyl chloroformate (0.57 mL, 4.4 mmol). The reaction mixture is stirred at 0° C. for 20 minutes and filtered. The filtrate is treated with an ether solution of diazomethane (~16 mmol) at 0° C. The reaction mixture is stirred at room temperature for 3 hours then concentrated in vacuo. The resulting residue is dissolved in EtOAc and washed successively with water and brine, dried (Na$_2$SO$_4$), filtered and concentrated. The residue is purified over silica (hexane/EtOAc 2:1) to afford 1.1 g (82% yield) of the desired product as a slightly yellow solid. $^1$H NMR (300 MHz, CDCl$_3$) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of (S)-tert-butyl 4-bromo-1-(4-nitrophenyl)-3-oxobutan-2-ylcarbamate (7): To a 0° C. solution of (S)-[3-diazo-1-(4-nitrobenzyl)-2-oxo-propyl]-carbamic acid tert-butyl ester, 6, (0.350 g, 1.04 mmol) in THF (5 mL) is added dropwise 48% aq. HBr (0.14 mL, 1.25 mmol). The reaction mixture is stirred at 0° C. for 1.5 hours then the reaction is quenched at 0° C. with sat. Na$_2$CO$_3$. The mixture is extracted with EtOAc (3×25 mL) and the combined organic extracts are washed with brine, dried (Na$_2$SO$_4$), filtered and concentrated to obtain 0.400 g of the product which is used in the next step without further purification. $^1$H NMR (300 MHz, CDCl$_3$) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of tert-butyl (S)-1-(S)-2-(4-nitrophenyl)-1-(2-phenylthiazole-4-yl)ethylamino-1-oxo-3-phenylpropan-2-ylcarbamate (8): A mixture of thiobenzamide (0.117 g, 0.85 mmol) and (S)-tert-butyl 4-bromo-1-(4-nitrophenyl)-3-oxobutan-2-ylcarbamate, 7, (0.300 g, 0.77 mmol) in CH$_3$CN (4 mL) is refluxed 2 hours. The reaction mixture is cooled to room temperature and diethyl ether is added to precipitate the intermediate 2-(nitrophenyl)-(S)-1-(4-phenylthiazol-2-yl)ethylamine which is isolated by filtration as the hydrobromide salt. The hydrobromide salt is dissolved in DMF (3 mL) together with diisoproylethylamine (0.42 mL, 2.31 mmol), 1-hydroxybenzotriazole (0.118 g, 0.79 mmol) and (S)-(2-tert-butoxycarbonyl-amino)-3-phenylpropionic acid (0.212 g, 0.80 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.395 g (90% yield) of the desired product which is used without further purification. LC/MS ESI+ 573 (M+1).

Preparation of (4-((S)-2-((S)-2-((tert-Butoxycarbonyl)amino)-3-phenylpropanamido)-2-(2-phenylthiazol-4-yl)ethyl)phenyl)sulfamic acid (9): tert-butyl (S)-1-(S)-2-(4-nitrophenyl)-1-(2-phenylthiazole-4-yl)ethylamino-1-oxo-3-phenylpropan-2-ylcarbamate, 8, (0.360 g) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with SO$_3$-pyridine (0.296 g). The reaction is stirred at room temperature for 5 minutes after which a 7% solution of NH$_4$OH (10 mL) is added. The mixture is then concentrated and the resulting residue is purified by reverse phase chromatography to afford 0.050 g of the desired product as the ammonium salt. $^1$H NMR (300 MHz, MeOH-d$_4$) δ 8.20 (d, J=8.1 Hz, 1H), 7.96-7.99 (m, 2H), 7.48-7.52 (m, 3H), 7.00-7.23 (m, 7H), 6.89 (s, 1H), 5.28 (q, J=7.5 Hz, 1H), 4.33 (t, J=6.6 Hz, 1H), 3.09-3.26 (m, 2H), 3.34 (dd, J=13.2 and 8.4 Hz, 1H), 2.82 (dd, J=13.2 and 8.4 Hz, 1H), 1.38 (s, 9H).

The first aspect of Category II of the present disclosure relates to compounds wherein R is a substituted or unsubstituted thiazol-4-yl unit having the formula:

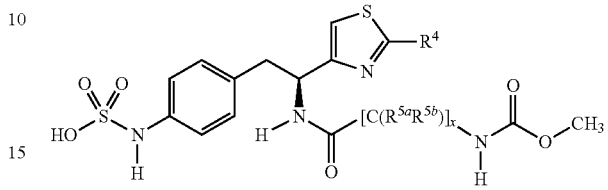

one embodiment of which relates to inhibitors having the formula:

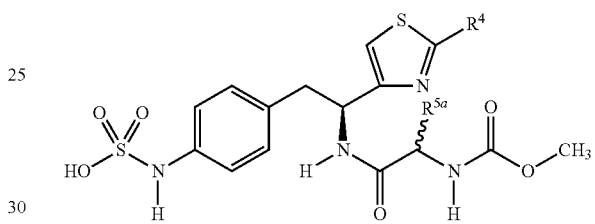

wherein R units are thiazol-4-yl units, that when substituted, are substituted with R$^4$ units. R and R$^{5a}$ units are further described in Table IV.

TABLE IV

| No. | R | R$^{5a}$ |
|---|---|---|
| D76 | thiazol-4-yl | (S)-benzyl |
| D77 | 2-methylthiazol-4-yl | (S)-benzyl |
| D78 | 2-ethylthiazol-4-yl | (S)-benzyl |
| D79 | 2-propylthiazol-4-yl | (S)-benzyl |
| D80 | 2-iso-propylthiazol-4-yl | (S)-benzyl |
| D81 | 2-cyclopropylthiazol-4-yl | (S)-benzyl |
| D82 | 2-butylthiazol-4-yl | (S)-benzyl |
| D83 | 2-tert-butylthiazol-4-yl | (S)-benzyl |
| D84 | 2-cyclohexylthiazol-4-yl | (S)-benzyl |
| D85 | 2-(2,2,2-trifluoroethyl)thiazol-4-yl | (S)-benzyl |
| D86 | 2-(3,3,3-trifluoropropyl)thiazol-4-yl | (S)-benzyl |
| D87 | 2-(2,2-difluorocyclopropyl)thiazol-4-yl | (S)-benzyl |
| D88 | 2-phenylthiazol-4-yl | (S)-benzyl |
| D89 | 2-(4-chlorophenyl)thiazol-4-yl | (S)-benzyl |
| D90 | 2-(3,4-dimethylphenyl)thiazol-4-yl | (S)-benzyl |
| D91 | 2-(thiophen-2-yl)thiazol-4-yl | (S)-benzyl |
| D92 | 2-(thiophen-3-yl)thiazol-4-yl | (S)-benzyl |
| D93 | 2-(3-chlorothiophen-2-yl)thiazol-4-yl | (S)-benzyl |
| D94 | 2-(3-methylthiophen-2-yl)thiazol-4-yl | (S)-benzyl |
| D95 | 2-(2-methylthiazol-4-yl)thiazol-4-yl | (S)-benzyl |
| D96 | 2-(furan-2-yl)thiazol-4-yl | (S)-benzyl |
| D97 | 2-(pyrazin-2-yl)thiazol-4-yl | (S)-benzyl |
| D98 | 2-[(2-methyl)pyridin-5-yl]thiazol-4-yl | (S)-benzyl |
| D99 | 2-(4-chlorobenzenesulfonylmethyl)thiazol-4-yl | (S)-benzyl |
| D100 | 2-(tert-butylsulfonylmethyl)thiazol-4-yl | (S)-benzyl |

The compounds encompassed within the second aspect of Category II of the present disclosure can be prepared by the procedure outlined in Scheme III and described in Example 3 herein below.

Scheme III

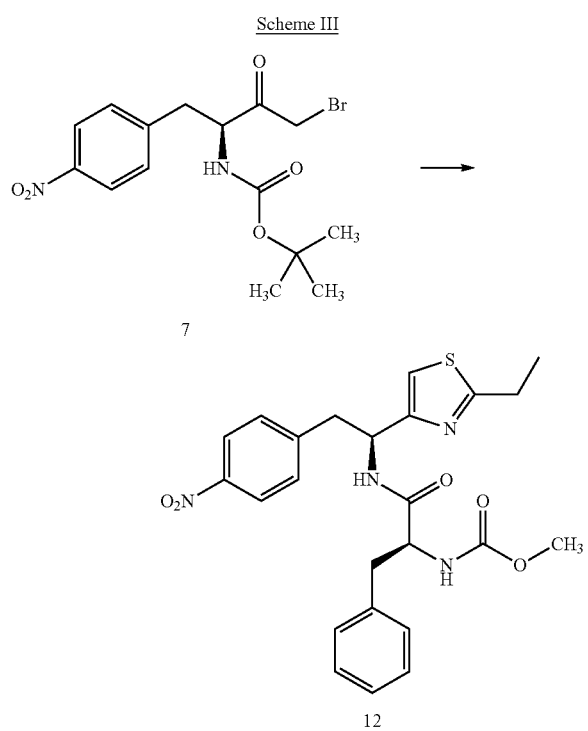

Reagents and conditions: (a)(i) propanethioamide, CH$_3$CN; reflux, 2 hr. (ii) Boc-Phe, HOBt, DIPEA, DMF; rt, 18 hr.

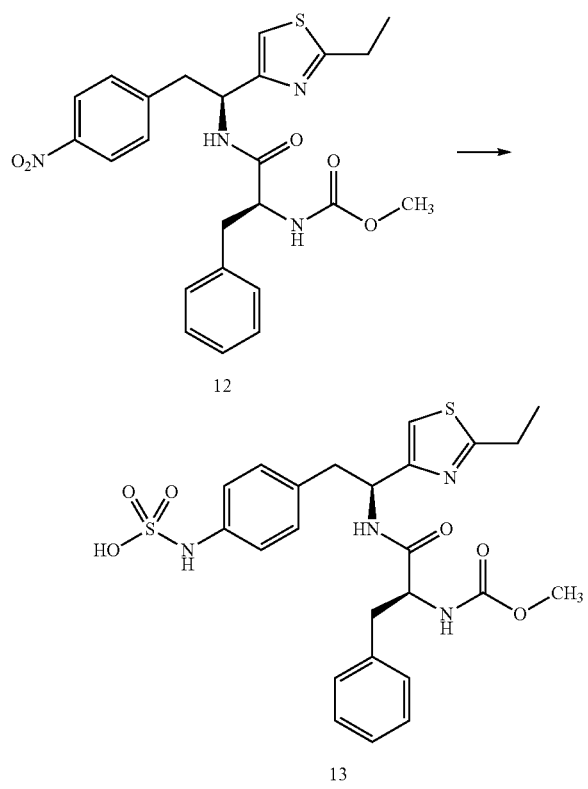

Reagents and conditions: (b) (i) H$_2$:Pd/C, MeOH; (ii) SO$_3$-pyridine, NH$_4$OH; rt, 18 hr.

Example 3

4-{(S)-2-[(S)-2-(Methoxycarbonylamino)-3-phenyl-propanamido]-2-(2-ethylthiazol-4-yl) ethyl}phenylsulfamic acid (13)

Preparation of methyl (S)-1-[(S)-1-(2-ethylthiazole-4-yl)-2-(4-nitrophenyl)-ethyl]amino-1-oxo-3-phenylpropane-2-ylcarbamate (12): A mixture of propanethioamide (69 mg, 0.78 mmol) and (S)-tert-butyl 4-bromo-1-(4-nitrophenyl)-3-oxobutan-2-ylcarbamate, 7, (0.300 g, 0.77 mmol) in CH$_3$CN (4 mL) is refluxed for 2 hours. The reaction mixture is cooled to room temperature and diethyl ether is added to precipitate the intermediate 2-(nitrophenyl)-(S)-1-(4-ethyl-thiazol-2-yl)ethylamine which is isolated by filtration as the hydrobromide salt. The hydrobromide salt is dissolved in DMF (8 mL) together with diisoproylethylamine (0.38 mL, 2.13 mmol), 1-hydroxybenzotriazole (107 mg, 0.71 mmol) and (S)-(2-methoxycarbonyl-amino)-3-phenylpropionic acid (175 mg, 0.78 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.300 g (81% yield) of the desired product which is used without further purification. LC/MS ESI+ MS 483 (M+1).

Preparation of 4-((S)-2-((S)-2-(methoxycarbonylamino)-3-phenylpropanamido)-2-(2-ethylthiazol-4-yl)ethyl)phenyl-sulfamic acid ammonium salt (13): tert-Butyl (S)-1-(S)-2-(4-nitrophenyl)-1-(2-ethylthiazole-4-yl)ethylamino-1-oxo-3-phenylpropan-2-ylcarbamate, 12, (0.300 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (223 mg, 1.40 mmol). The reaction is stirred at room temperature for 5 minutes after which a 7% solution of NH$_4$OH (12 mL) is added. The mixture is then concentrated and the resulting residue is purified by reverse phase chromatography to afford 25 mg of the desired product as the ammonium salt. $^1$H NMR (300 MHz, MeOH-d$_4$) δ 7.14-7.24 (m, 6H), 6.97-7.0 (m, 4H), 6.62 (s, 1H), 5.10-5.30 (m, 1H), 4.36 (t, J=7.2 Hz, 1H), 3.63 (s, 3H), 3.14 (dd, J=13.5 and 6.3 Hz, 1H), 2.93-3.07 (m, 5H), 2.81 (dd, J=13.5 and 6.3 HZ, 1H), 1.39 (t, J=7.8 Hz, 3H).

In another iteration of the process of the present disclosure, compound 13, as well as the other analogs which comprise the present disclosure, can be isolated as the free acid by adapting the procedure described herein below.

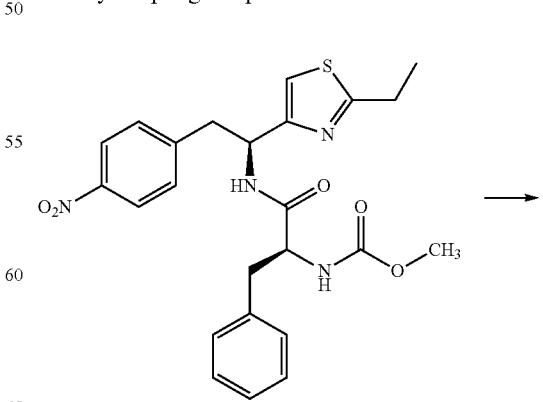

12

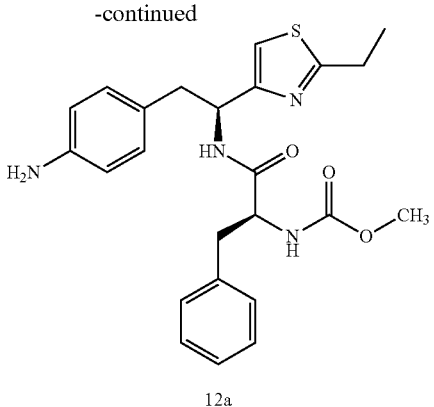

12a

Reagents and conditions: (a) H₂:Pd/C, MeOH; rt, 40 hr.

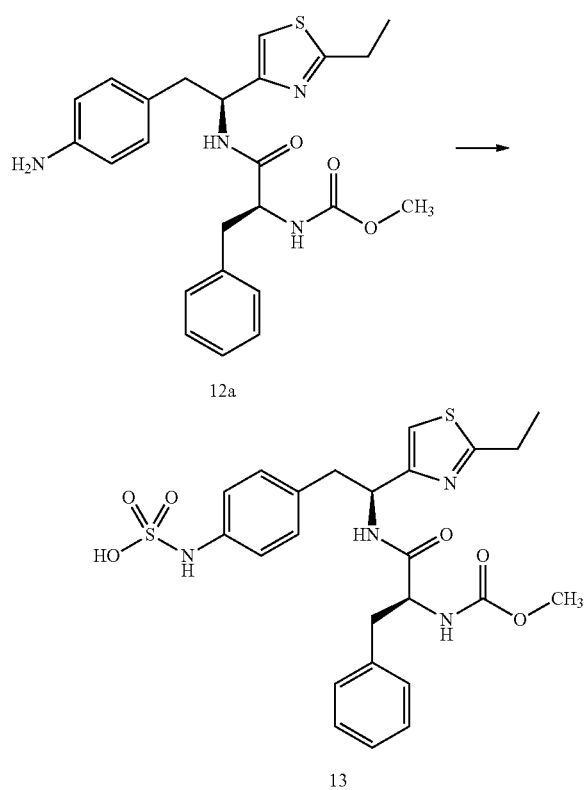

Reagents and conditions: (b) SO₃-pyridine, CH₃CN; heat, 45 min.

Example 4

4-((S)-2-((S)-2-(Methoxycarbonylamino)-3-phenyl-propanamido)-2-(2-ethylthiazol-4-yl)ethyl)phenyl-sulfamic acid [Free Acid Form] (13)

Preparation of {1-[2-(S)-(4-(S)-aminophenyl)-1-(2-ethyl-thiazol-4-yl)ethyl-carbamoyl]-2-phenylethyl}-carbamic acid methyl ester (12a): A Parr hydrogenation vessel is charged with tert-butyl (S)-1-(S)-2-(4-nitrophenyl)-1-(2-ethylthiazole-4-yl)ethylamino-1-oxo-3-phenylpropan-2-yl-carbamate, 12, (18.05 g, 37.4 mmol, 1.0 eq) and Pd/C (10% Pd on C, 50% wet, Degussa-type E101 NE/W, 2.68 g, 15 wt %) as solids. MeOH (270 mL, 15 mL/g) is added to provide a suspension. The vessel is put on a Parr hydrogenation apparatus. The vessel is submitted to a fill/vacuum evacuate process with N₂ (3×20 psi) to inert, followed by the same procedure with H₂ (3×40 psi). The vessel is filled with H₂ and the vessel is shaken under 40 psi H₂ for ~40 hr. The vessel is evacuated and the atmosphere is purged with N₂ (5×20 psi). An aliquot is filtered and analyzed by HPLC to insure complete conversion. The suspension is filtered through a pad of celite to remove the catalyst, and the homogeneous yellow filtrate is concentrated by rotary evaporation to afford 16.06 g (95% yield) of the desired product as a tan solid, which is used without further purification.

Preparation of 4-((S)-2-((S)-2-(methoxycarbonyl)-3-phenylpropanamido)-2-(2-ethylthiazol-4-yl)ethyl)phenylsulfamic acid (13): A 100 mL RBF is charged with {1-[2-(S)-(4-(S)-aminophenyl)-1-(2-ethylthiazol-4-yl)ethyl-carbamoyl]-2-phenylethyl}-carbamic acid methyl ester, 12a, (10.36 g, 22.9 mmol, 1.0 eq) prepared in the step described herein above. Acetonitrile (50 mL, 5 mL/g) is added and the yellow suspension is stirred at room temperature. A second 3-necked 500 mL RBF is charged with SO₃.pyr (5.13 g, 32.2 mmol, 1.4 eq) and acetonitrile (50 mL 5 mL/g) and the white suspension is stirred at room temperature. Both suspensions are gently heated until the reaction solution containing {1-[2-(S)-(4-(S)-aminophenyl)-1-(2-ethylthiazol-4-yl)ethyl-carbamoyl]-2-phenylethyl}-carbamic acid methyl ester becomes red-orange in color (typically for this example about 44° C.). This substrate containing solution is poured in one portion into the stirring suspension of SO₃.pyr at 35° C. The resulting opaque mixture (39° C.) is stirred vigorously while allowed to slowly cool to room temperature. After stirring for 45 min, the reaction is determined to be complete by HPLC. H₂O (200 mL, 20 mL/g) is added to the orange suspension to provide a yellow-orange homogeneous solution having a pH of approximately 2.4. Concentrated H₃PO₄ is added slowly over 12 minutes to lower the pH to approximately 1.4. During this pH adjustment, an off-white precipitate is formed and the solution is stirred at room temperature for 1 hr. The suspension is filtered and the filter cake is washed with the filtrate. The filter cake is air-dried on the filter overnight to afford 10.89 g (89% yield) of the desired product as a tan solid.

The following are further non-limiting examples of the second aspect of Category II of the present disclosure.

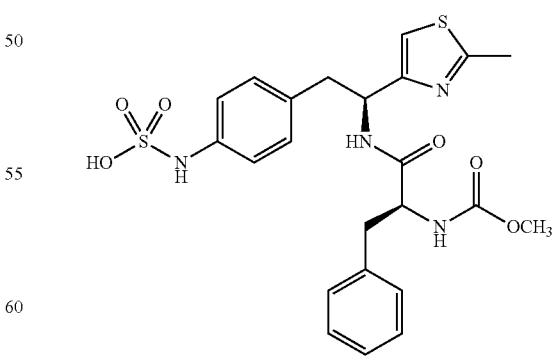

4-{(S)-2-[(S)-2-(Methoxycarbonylamino)-3-phenylpropanamido]-2-(2-methylthiazol-4-yl)ethyl}phenylsulfamic acid: ¹H NMR (300 MHz, MeOH-d₄) δ 8.15 (d, J=8.4 Hz, 1H), 7.16-7.25 (m, 5H), 6.97-7.10 (m, 4H), 6.61 (s, 1H), 5.00-5.24 (m, 1H), 4.36 (t, J=7.2 Hz, 1H), 3.64 (s, 2H), 3.11-3.19 (s, 1H), 2.92-3.04 (s, 2H), 2.81 (dd, J=13.5 and 8.1 Hz, 1H), 2.75 (s, 3H).

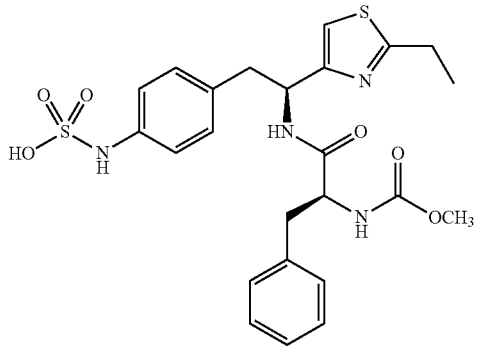 [SMILES: CCc1nc([C@H](Cc2ccc(NS(=O)(=O)O)cc2)NC(=O)[C@H](Cc2ccccc2)NC(=O)OC)cs1]

4-{(S)-2-(2-Ethylthiazole-4-yl)-2-[(S)-2-(methoxycarbonylamino)-3-phenylpropanamido]ethyl}phenylsulfamic acid: ¹H NMR (300 MHz, MeOH-d₄) δ 7.16-7.29 (m, 5H), 7.02-7.12 (m, 4H), 6.83 (s, 1H), 5.10-5.35 (m, 1H), 3.52-3.67 (m, 3H), 3.18-3.25 (m, 2H), 3.05 (q, J=7.5 Hz, 2H), 2.82-2.95 (m, 2H), 2.65 (s 3H), 1.39 (t, J=7.5 Hz, 3H).

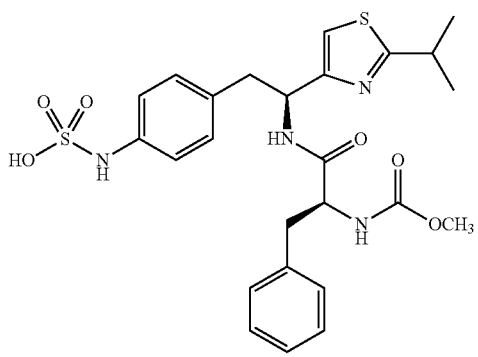 [SMILES: COC(=O)N[C@@H](Cc1ccccc1)C(=O)N[C@@H](Cc1ccc(NS(=O)(=O)O)cc1)c1csc(C(C)C)n1]

4-{(S)-2-(2-Isopropylthiazol-4-yl)-2-[(S)-2-(methoxycarbonylamino)-3-phenylpropan-amido]ethyl}phenylsulfamic acid: ¹H NMR (CD₃OD) δ 8.16 (d, 1H, J=8.7 Hz), 7.22-7.13 (m, 3H), 7.07 (d, 1H, J=8.4 Hz), 6.96 (d, 1H, J=8.1 Hz), 6.62 (s, 1H), 5.19 (t, 1H, J=7.2 Hz), 4.36 (t, 1H, J=7.8 Hz), 3.63 (s, 3H), 3.08 (1H, A of ABX, J=3.6, 14.5 Hz), 2.99 (1H, B of ABX, J=7.2, 13.8 Hz), 2.85-2.78 (m, 1H), 1.41 (d, 6H, J=6.9 Hz).

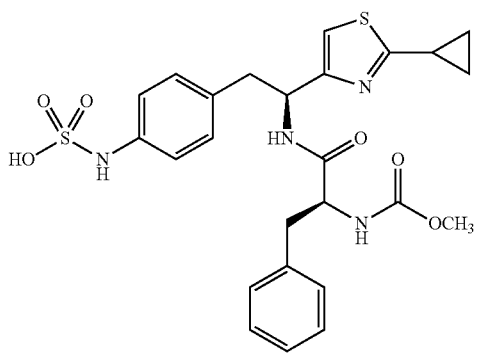 [SMILES: COC(=O)N[C@@H](Cc1ccccc1)C(=O)N[C@@H](Cc1ccc(NS(=O)(=O)O)cc1)c1csc(C2CC2)n1]

4-{(S)-2-(2-Cyclopropylthiazol-4-yl)-2-[(S)-2-(methoxycarbonylamino)-3-phenylpropanamido]ethyl}phenylsulfamic acid: ¹H NMR (CD₃OD): δ 7.15-7.02 (m, 5H), 6.96-6.93 (d, 2H, J=8.4 Hz), 6.86-6.83 (d, 2H, J=8.3 Hz), 6.39 (s, 1H), 5.01 (t, 1H, J=5.0 Hz), 4.22 (t, 1H, J=7.4 Hz), 3.51 (s, 3H), 2.98-2.69 (m, 2H), 2.22-2.21 (m, 1H), 1.06-1.02 (m, 2H), 0.92-0.88 (m, 2H).

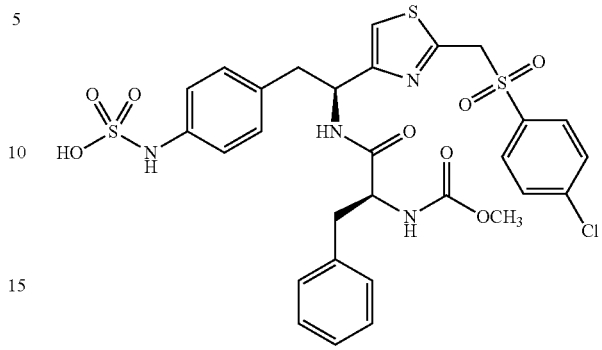

4-{(S)-2-{2-[(4-Chlorophenylsulfonyl)methyl]thiazol-4-yl}-2-[(S)-2-(methoxycarbonylamino)-3-phenylpropanamido]ethyl}phenylsulfamic acid: ¹H NMR (CD₃OD): δ 7.96-7.93 (d, 2H, J=8.6 Hz), 7.83-7.80 (d, 2H, J=8.6 Hz), 7.44-7.34 (m, 5H), 7.29-7.27 (d, 2H, J=8.4 Hz), 7.14-7.11 (d, 2H, J=8.4 Hz), 6.97 (s, 1H), 5.31 (t, 1H, J=6.8 Hz), 5.22-5.15 (m, 2H), 4.55 (t, 1H, J=7.3 Hz), 3.84 (s, 3H), 3.20-2.96 (m, 4H).

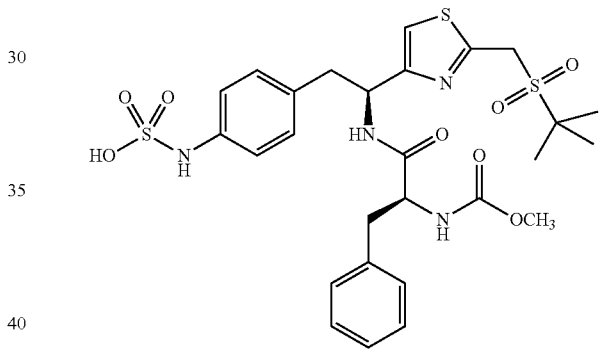

4-{(S)-2-[2-(tert-Butylsulfonylmethyl)thiazol-4-yl]-2-[(S)-2-(methoxycarbonylamino)-3-phenylpropanamido]ethyl}phenylsulfamic acid: ¹H NMR (CD₃OD): δ 7.40-7.30 (m, 5H), 7.21-7.10 (m, 4H), 7.02 (s, 1H), 5.37 (t, 1H, J=6.9 Hz), 5.01-4.98 (m, 2H), 4.51 (t, 1H, J=7.1 Hz), 3.77 (s, 3H), 3.34-2.91 (m, 4H), 1.58 (s, 9H).

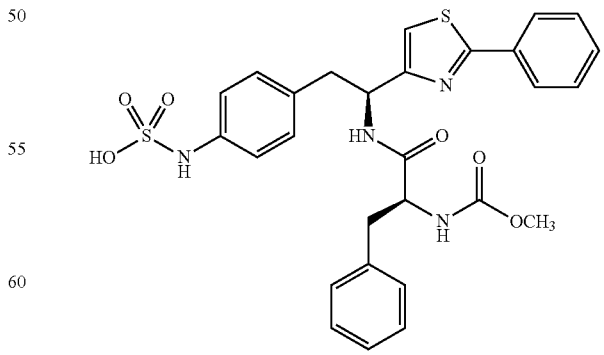

4-{(S)-2-[(S)-2-(Methoxycarbonylamino)-3-phenylpropionamido]-2-(2-phenylthiazol-4-yl)ethyl}phenylsulfamic acid: ¹H NMR (300 MHz, DMSO-d₆) δ 7.96-7.99 (m, 2H), 7.51-7.56 (m, 3H), 7.13-7.38 (m, 6H), 6.92-6.95 (m, 4H), 5.11-5.16 (m, 1H), 4.32-4.35 (m, 1H), 3.51 (s, 3H), 3.39-3.40 (m, 2H), 3.09-3.19 (m, 1H), 2.92-3.02 (m, 2H), 2.75 (dd, J=10.5 Hz and 9.9 Hz, 1H).

ethyl}phenylsulfamic acid: $^1$H NMR (CD$_3$OD): δ 7.38 (d, 1H, J=5.1 Hz), 7.15-6.93 (m, 10H), 6.73 (s, 1H), 5.17 (t, 1H, J=6.9 Hz), 4.31 (t, 1H, J=7.3 Hz), 3.57 (s, 3H), 3.18-3.11 (m, 1H), 3.02-2.94 (m, 2H), 2.80-2.73 (m, 1H), 2.46 (s, 3H).

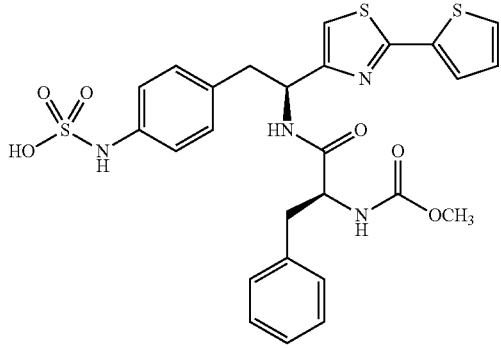 [SMILES: COC(=O)N[C@@H](Cc1ccccc1)C(=O)N[C@@H](Cc1ccc(NS(=O)(=O)O)cc1)c1csc(-c2cccs2)n1]

4-{(S)-2-[(S)-2-(Methoxycarbonylamino)-3-phenylpropanamido]-2-[2-(thiophen-2-yl)thiazol-4-yl] ethyl}phenylsulfamic acid: $^1$H NMR (CD$_3$OD): δ 7.61-7.56 (m, 2H), 7.25-7.01 (m, 10H), 6.75 (s, 1H), 5.24-5.21 (q, 1H, J=7.2 Hz), 4.38 (t, 1H, J=7.2 Hz), 3.60 (s, 3H), 3.23-3.14 (m, 1H), 3.08-3.00 (m, 2H), 2.87-2.80 (m, 1H).

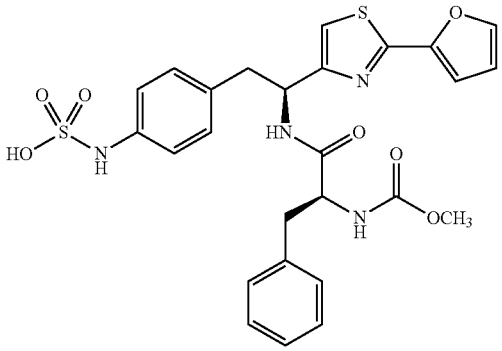

4-{[(S)-2-(2-(Furan-2-yl)thiazol-4-yl]-2-[(S)-2-(methoxycarbonylamino)-3-phenylpropanamido] ethyl}phenylsulfamic acid: $^1$H NMR (CD$_3$OD): δ 7.54-7.46 (m, 1H), 7.02-6.79 (m, 10H), 6.55-6.51 (m, 1H), 6.44-6.41 (m, 1H), 5.02-5.00 (q, 1H, J=6.4 Hz), 4.16-4.14 (q, 1H, J=7.1 Hz), 3.43 (s, 3H), 2.96-2.58 (m, 4H).

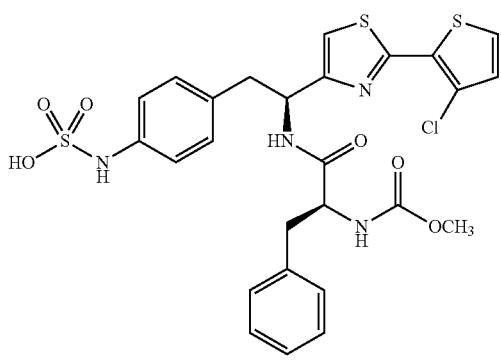 [SMILES: COC(=O)N[C@@H](Cc1ccccc1)C(=O)N[C@@H](Cc1ccc(NS(=O)(=O)O)cc1)c1csc(-c2sccc2Cl)n1]

4-{(S)-2-[2-(3-Chlorothiophen-2-yl)thiazol-4-yl]-2-[(S)-2-(methoxycarbonylamino)-3-phenylpropanamido] ethyl}phenylsulfamic acid: $^1$H NMR (CD$_3$OD): δ 7.78-7.76 (d, 1H, J=5.4 Hz), 7.36-7.14 (m, 10H), 7.03 (s, 1H), 5.39 (t, 1H, J=6.9 Hz), 4.54 (t, 1H, J=7.3 Hz), 3.80 (s, 3H), 3.39-2.98 (m, 4H).

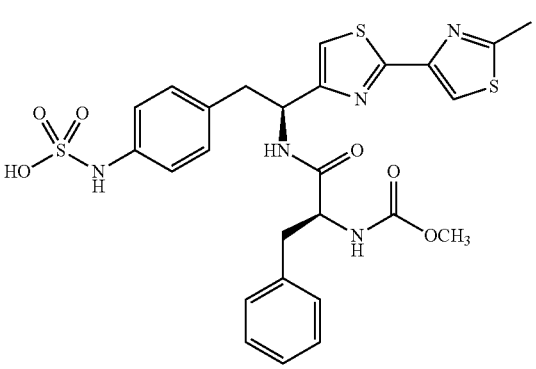

4-{(S)-2-[(S)-2-(Methoxycarbonylamino)-3-phenylpropanamido]-2-[2-(2-methylthiazole-4-yl)thiazole-4yl] ethyl}phenylsulfamic acid: $^1$H NMR (300 MHz, MeOH-d$_4$) δ 8.27 (d, J=5.4 Hz, 1H), 7.97 (s, 1H), 6.99-7.21 (m, 8H), 5.18-5.30 (m, 1H), 4.30-4.39 (m, 1H), 3.64 (s, 3H), 3.20 (dd, J=14.1 and 6.6 Hz, 1H), 2.98-3.08 (m, 2H), 2.84 (dd, J=14.1 and 6.6 Hz, 1H), 2.78 (s, 3H).

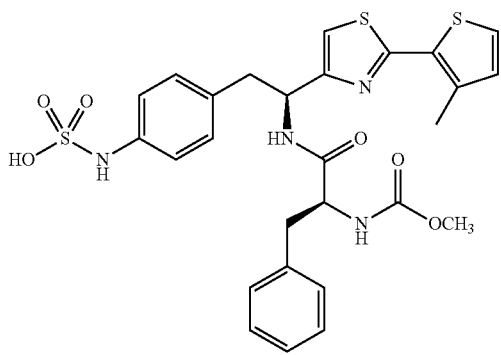 [SMILES: COC(=O)N[C@@H](Cc1ccccc1)C(=O)N[C@@H](Cc1ccc(NS(=O)(=O)O)cc1)c1csc(-c2sccc2C)n1]

4-{(S)-2-[(S)-2-(Methoxycarbonylamino)-3-phenylpropanamido]-2-[2-(3-methylthiophen-2-yl)thiazol-4-yl]

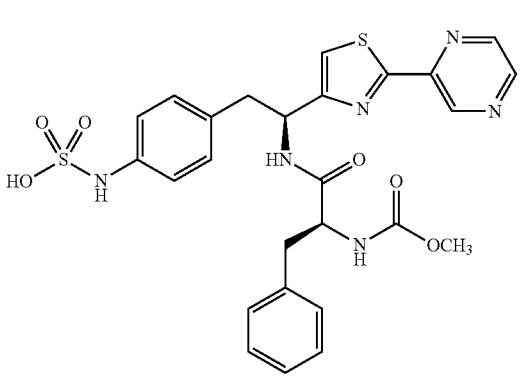 [SMILES: COC(=O)N[C@@H](Cc1ccccc1)C(=O)N[C@@H](Cc1ccc(NS(=O)(=O)O)cc1)c1csc(-c2cnccn2)n1]

4-{(S)-2-[(S)-2-(Methoxycarbonylamino)-3-phenylpropanamido]-2-[(2-pyrazin-2-yl)thiazole-4-yl]

ethyl}phenylsulfamic acid: $^1$H NMR (300 MHz, MeOH-d$_4$) δ 9.34 (s, 1H), 8.65 (s, 2H), 8.34 (d, J=8.1 Hz, 1H), 7.00-5.16 (m. 9H), 5.30 (q, J=7.2 Hz, 1H), 4.41 (t, J=7.2 Hz, 1H), 3.65 (s, 3H), 3.23 (dd, J=13.8 and 6.9 Hz, 1H), 2.98-3.13 (m, 2H), 2.85 (dd, J=13.8 and 6.9 Hz, 1H).

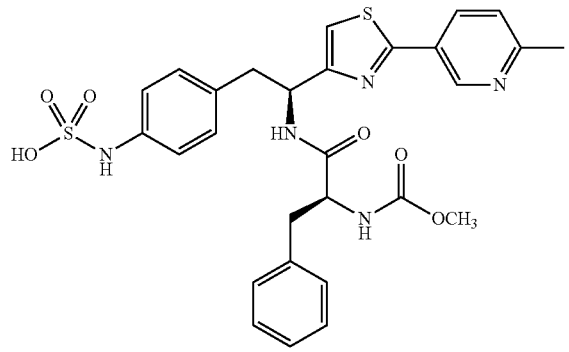 [SMILES: COC(=O)N[C@@H](Cc1ccccc1)C(=O)N[C@@H](Cc1ccc(NS(=O)(=O)O)cc1)c1csc(-c2ccc(C)nc2)n1]

4-{(S)-2-[(S)-2-(Methoxycarbonylamino)-3-phenylpropanamido]-2-[2-(6-methylpyridin-3-yl)thiazol-4-yl]ethyl}phenylsulfamic acid: $^1$H NMR (CD$_3$OD): δ 8.90 (s, 1H), 8.19-8.13 (m, 1H), 7.39-7.36 (d, 1H, J=8.2 Hz), 7.07-6.88 (m, 9H), 6.79 (s, 1H), 5.17 (t, 1H, J=7.0 Hz), 4.29 (t, 1H, J=7.4 Hz), 3.54 (s, 3H), 3.10-2.73 (m, 4H), 2.53 (s, 3H).

Category III of the present disclosure relates to compounds wherein R is a substituted or unsubstituted thiazol-2-yl unit having the formula:

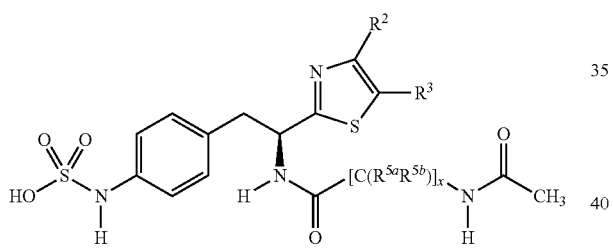

one embodiment of which relates to inhibitors having the formula:

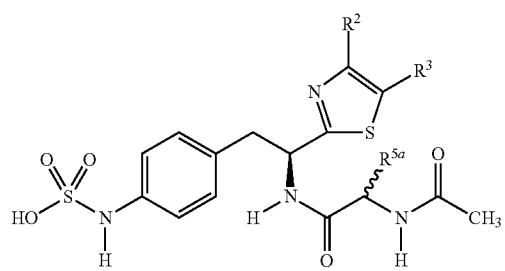

wherein R units are thiazol-2-yl units, that when substituted, are substituted with R$^2$ and R$^3$ units. R and R$^{5a}$ units are further described in Table V.

TABLE V

| No. | R | R$^{5a}$ |
| --- | --- | --- |
| E101 | thiazol-2-yl | (S)-benzyl |
| E102 | 4-methylthiazol-2-yl | (S)-benzyl |
| E103 | 4-ethylthiazol-2-yl | (S)-benzyl |

TABLE V-continued

| No. | R | R$^{5a}$ |
| --- | --- | --- |
| E104 | 4-propylthiazol-2-yl | (S)-benzyl |
| E105 | 4-iso-propylthiazol-2-yl | (S)-benzyl |
| E106 | 4-cyclopropylthiazol-2-yl | (S)-benzyl |
| E107 | 4-butylthiazol-2-yl | (S)-benzyl |
| E108 | 4-tert-butylthiazol-2-yl | (S)-benzyl |
| E109 | 4-cyclohexylthiazol-2-yl | (S)-benzyl |
| E110 | 4-(2,2,2-trifluoroethyl)thiazol-2-yl | (S)-benzyl |
| E111 | 4-(3,3,3-trifluoropropyl)thiazol-2-yl | (S)-benzyl |
| E112 | 4-(2,2-difluorocyclopropyl)thiazol-2-yl | (S)-benzyl |
| E113 | 4-(methoxymethyl)thiazol-2-yl | (S)-benzyl |
| E114 | 4-(carboxylic acid ethyl ester)thiazol-2-yl | (S)-benzyl |
| E115 | 4,5-dimethylthiazol-2-yl | (S)-benzyl |
| E116 | 4-methyl-5-ethylthiazol-2-yl | (S)-benzyl |
| E117 | 4-phenylthiazol-2-yl | (S)-benzyl |
| E118 | 4-(4-chlorophenyl)thiazol-2-yl | (S)-benzyl |
| E119 | 4-(3,4-dimethylphenyl)thiazol-2-yl | (S)-benzyl |
| E120 | 4-methyl-5-phenylthiazol-2-yl | (S)-benzyl |
| E121 | 4-(thiophen-2-yl)thiazol-2-yl | (S)-benzyl |
| E122 | 4-(thiophen-3-yl)thiazol-2-yl | (S)-benzyl |
| E123 | 4-(5-chlorothiophen-2-yl)thiazol-2-yl | (S)-benzyl |
| E124 | 5,6-dihydro-4H-cyclopenta[d]thiazol-2-yl | (S)-benzyl |
| E125 | 4,5,6,7-tetrahydrobenzo[d]thiazol-2-yl | (S)-benzyl |

The compounds encompassed within Category III of the present disclosure can be prepared by the procedure outlined in Scheme IV and described in Example 5 herein below.

Scheme IV

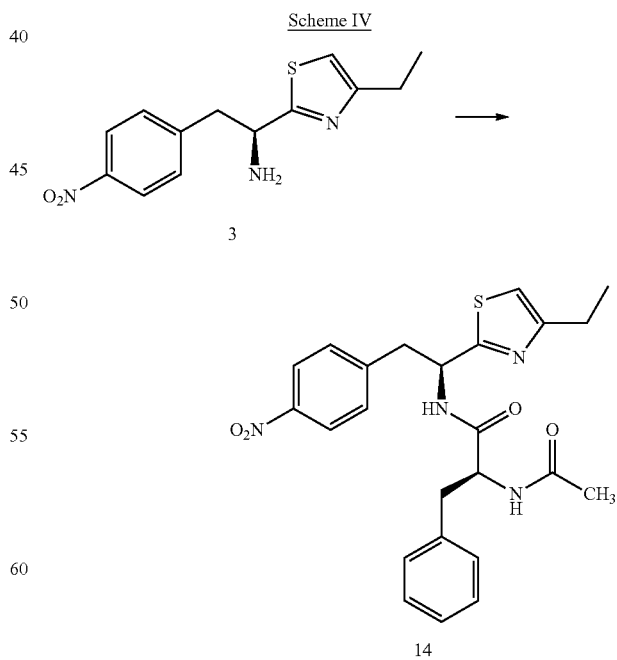

Reagents and conditions: (a) Ac-Phe, EDCI, HOBt, DIPEA, DMF; rt, 18 hr.

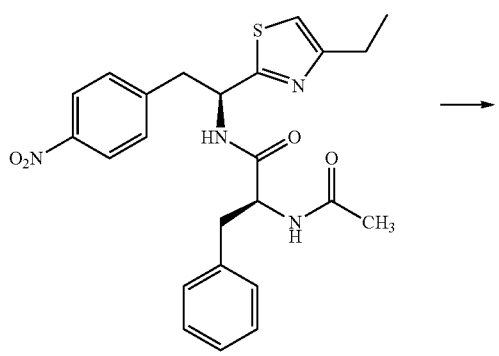

14

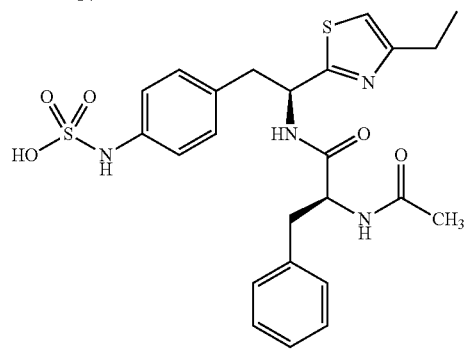

15

Reagents and conditions: (b) (i) H₂:Pd/C, MeOH; (ii) SO₃-pyridine, NH₄OH.

Example 5

4-[(S)-2-((S)-2-Acetamido-3-phenylpropanamido)-2-(4-ethylthiazol-2-yl)ethyl]phenylsulfamic acid (15)

Preparation of (S)-2-acetamido-N—[(S)-1-(4-ethylthiazol-2-yl)-2-(4-nitrophenyl)-ethyl]-3-phenylpropanamide (14): To a solution of 1-(S)-(4-ethylthiazol-2-yl)-2-(4-nitrophenyl)ethyl amine hydrobromide, 3, (0.343 g, 0.957 mmol), N-acetyl-L-phenylalanine (0.218 g), 1-hydroxybenzotriazole (HOBt) (0.161 g), diisopropyl-ethylamine (0.26 g), in DMF (10 mL) at 0°, is added 1-(3-dimethylaminopropyl)-3-ethylcarbodiimide (EDCI) (0.201 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.313 g (70% yield) of the desired product which is used without further purification. LC/MS ESI+ 467 (M+1).

Preparation of 4-((S)-2-((S)-2-acetamido-3-phenylpropanamido)-2-(4-ethylthiazol-2-yl)ethyl)phenylsulfamic acid (15): (S)-2-Acetamido-N—[(S)-1-(4-ethylthiazol-2-yl)-2-(4-nitrophenyl)ethyl]-3-phenylpropanamide, 14, (0.313 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (12 mL) and treated with SO₃-pyridine (0.320 g). The reaction is stirred at room temperature for 5 minutes after which a 7% solution of NH₄OH (30 mL) is added. The mixture is then concentrated and the resulting residue is purified by reverse phase chromatography to afford 0.215 g of the desired product as the ammonium salt. ¹H NMR (CD₃OD): δ 7.23-6.98 (m, 10H), 5.37 (t, 1H), 4.64 (t, 1H, J=6.3 Hz), 3.26-2.74 (m, 6H), 1.91 (s, 3H), 1.29 (t, 3H, J=7.5 Hz).

The following are further non-limiting examples of compounds encompassed within Category III of the present disclosure.

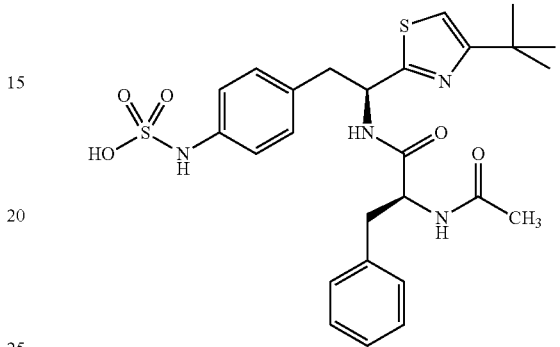

4-[(S)-2-((S)-2-Acetamido-3-phenylpropanamido)-2-(4-tert-butylthiazol-2-yl)ethyl]phenylsulfamic acid: ¹H NMR (300 MHz, CD₃OD): δ 7.22-7.17 (m, 5H), 7.06 (dd, J=14.1, 8.4 Hz, 4H), 6.97 (d, J=0.9 Hz, 1H), 5.39 (dd, J=8.4, 6.0 Hz, 1H), 4.65 (t, J=7.2 Hz, 1H), 3.33-3.26 (m, 1H), 3.13-3.00 (m, 3H), 2.80 (dd, J=13.5, 8.7 Hz, 1H), 1.91 (s, 3H), 1.36 (s, 9H).

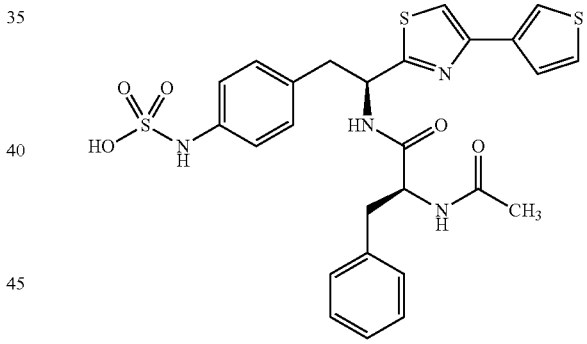

4-{(S)-2-((S)-2-Acetamido-3-phenylpropanamido)-2-[4-(thiophen-3-yl)thiazol-2-yl]ethyl)phenylsulfamic acid: ¹H NMR (300 MHz, CD₃OD): δ 8.58 (d, J=8.1 Hz, 1H), 7.83-7.82 (m, 1H), 7.57-7.46 (m, 3H), 7.28-6.93 (m, 11H), 5.54-5.43 (m, 1H), 4.69-4.55 (m, 2H), 3.41-3.33 (m, 1H), 3.14-3.06 (3H), 2.86-2.79 (m, 1H), 1.93 (s, 3H).

The first aspect of Category IV of the present disclosure relates to compounds wherein R is a substituted or unsubstituted thiazol-2-yl unit having the formula:

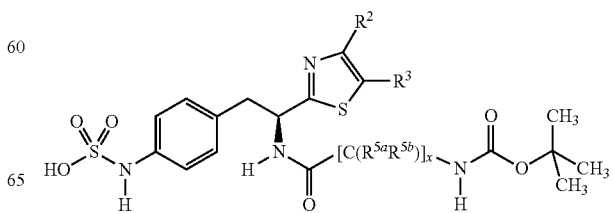

one embodiment of which relates to inhibitors having the formula:

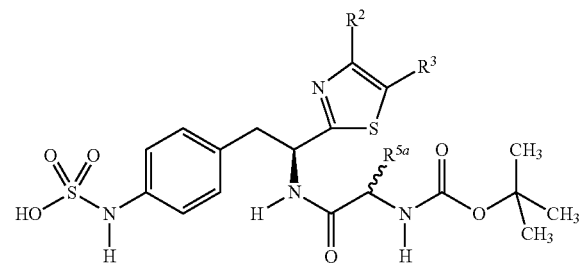

wherein R units and $R^{5a}$ units further described in Table VI.

TABLE VI

| No. | R | $R^{5a}$ |
| --- | --- | --- |
| F126 | thiazol-2-yl | hydrogen |
| F127 | 4-methylthiazol-2-yl | hydrogen |
| F128 | 4-ethylthiazol-2-yl | hydrogen |
| F129 | 4-propylthiazol-2-yl | hydrogen |
| F130 | 4-iso-propylthiazol-2-yl | hydrogen |
| F131 | 4-cyclopropylthiazol-2-yl | hydrogen |
| F132 | 4-butylthiazol-2-yl | hydrogen |
| F133 | 4-tert-butylthiazol-2-yl | hydrogen |
| F134 | 4-cyclohexylthiazol-2-yl | hydrogen |
| F135 | 4,5-dimethylthiazol-2-yl | hydrogen |
| F136 | 4-methyl-5-ethylthiazol-2-yl | hydrogen |
| F137 | 4-phenylthiazol-2-yl | hydrogen |
| F138 | thiazol-2-yl | (S)-iso-propyl |
| F139 | 4-methylthiazol-2-yl | (S)-iso-propyl |
| F140 | 4-ethylthiazol-2-yl | (S)-iso-propyl |
| F141 | 4-propylthiazol-2-yl | (S)-iso-propyl |
| F142 | 4-iso-propylthiazol-2-yl | (S)-iso-propyl |
| F143 | 4-cyclopropylthiazol-2-yl | (S)-iso-propyl |
| F144 | 4-butylthiazol-2-yl | (S)-iso-propyl |
| F145 | 4-tert-butylthiazol-2-yl | (S)-iso-propyl |
| F146 | 4-cyclohexylthiazol-2-yl | (S)-iso-propyl |
| F147 | 4,5-dimethylthiazol-2-yl | (S)-iso-propyl |
| F148 | 4-methyl-5-ethylthiazol-2-yl | (S)-iso-propyl |
| F149 | 4-phenylthiazol-2-yl | (S)-iso-propyl |
| F150 | 4-(thiophen-2-yl)thiazol-2-yl | (S)-iso-propyl |

The compounds encompassed within Category IV of the present disclosure can be prepared by the procedure outlined in Scheme V and described in Example 6 herein below.

Scheme V

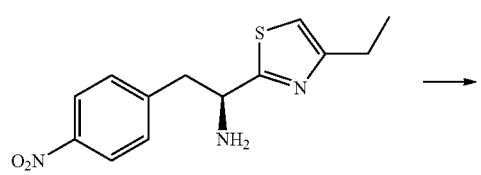

3

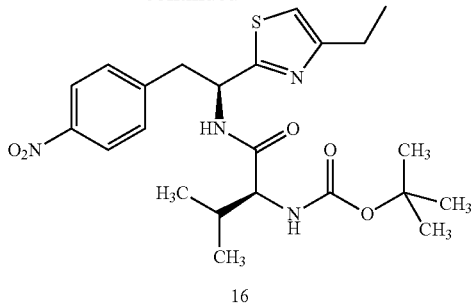

16

Reagents and conditions: (a) Boc-Val; EDCI, HOBt, DIPEA, DMF; rt, 18 hr.

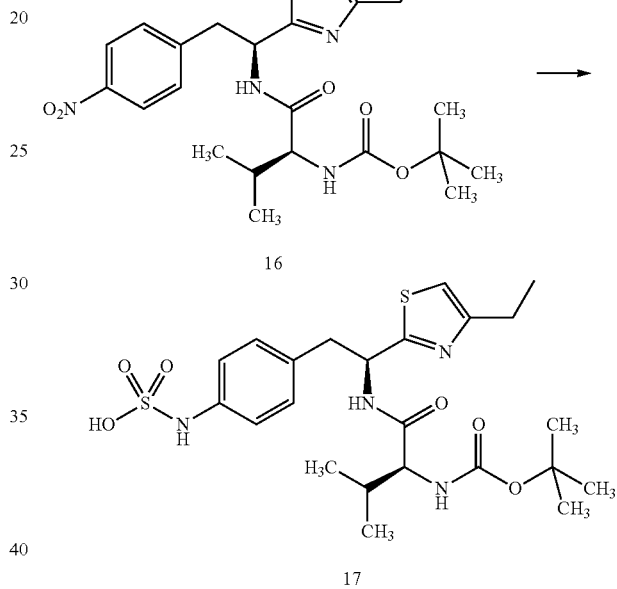

Reagents and conditions: (b) (i) $H_2$:Pd/C, MeOH; (ii) $SO_3$-pyridine, $NH_4OH$, rt, 2 hr.

Example 6

4-{(S)-2-[(S)-2-(tert-Butoxycarbonylamino)-3-methylbutanamido]-2-(4-ethylthiazol-2-yl)ethyl}phenylsulfamic acid (17)

Preparation of tert-butyl (S)-1-[(S)-(4-ethylthiazol-2-yl)-2-(4-nitrophenyl)ethylamino]-3-methyl-1-oxobutan-2-ylcarbamate (16): To a solution of 1-(S)-(4-ethylthiazol-2-yl)-2-(4-nitrophenyl)ethyl amine hydrobromide, 3, (0.200 g, 0.558 mmol), (S)-(2-tert-butoxycarbonylamino)-3-methylbutyric acid (0.133 g) and 1-hydroxybenzotriazole (HOBt) (0.094 g) in DMF (5 mL) at 0°, is added 1-(3-dimethylaminopropyl)-3-ethylcarbodiimide (EDCI) (0.118 g) followed by diisopropylamine (0.151 g). The mixture is stirred at 0° C. for 30 minutes then at room temperature overnight. The reaction mixture is diluted with water and extracted with EtOAc. The combined organic phase is washed with 1 N aqueous HCl, 5% aqueous $NaHCO_3$, water and brine, and dried over $Na_2SO_4$. The solvent is removed in vacuo to afford 0.219 g (82% yield) of the desired product which is used without further purification. LC/MS ESI+ 477 (M+1).

Preparation of 4-{(S)-2-[(S)-2-(tert-butoxycarbonylamino)-3-methylbutanamido]-2-(4-ethylthiazol-2-yl)ethyl}phenylsulfamic acid (17): tert-Butyl (S)-1-[(S)-(4-ethylthiazol-2-yl)-2-(4-nitrophenyl)ethylamino]-3-methyl-1-oxobutan-2-ylcarbamate, 16, (0.219 g) is dissolved in MeOH (4 mL). A catalytic amount of Pd/C (10% w/w) is added and the mixture is stirred under a hydrogen atmosphere 2 hours. The reaction mixture is filtered through a bed of CELITE™ and the solvent is removed under reduced pressure. The crude product is dissolved in pyridine (5 mL) and treated with SO$_3$-pyridine (0.146 g). The reaction is stirred at room temperature for 5 minutes after which a 7% solution of NH$_4$OH (30 mL) is added. The mixture is then concentrated and the resulting residue is purified by reverse phase chromatography to afford 0.148 g of the desired product as the ammonium salt. $^1$H NMR (CD$_3$OD): δ 7.08 (s, 4H), 7.02 (s, 1H), 5.43 (s, 1H), 3.85 (s, 1H), 3.28-2.77 (m, 4H), 1.94 (s, 1H), 1.46 (s, 9H), 1.29 (s, 3H, J=7.3 Hz), 0.83 (s, 6H).

The following are further non-limiting examples of the second aspect of Category IV of the present disclosure.

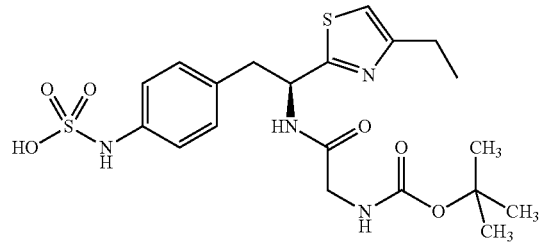 [SMILES: CCc1csc([C@H](Cc2ccc(NS(=O)(=O)O)cc2)NC(=O)CNC(=O)OC(C)(C)C)n1]

(S)-4-{2-[2-(tert-Butoxycarbonyl)acetamide]-2-(4-ethylthiazol-2-yl)ethyl}-phenylsulfamic acid: $^1$H NMR (CD$_3$OD): δ 7.09-6.91 (m, 5H), 5.30 (t, 1H, J=8.4 Hz), 3.60-2.64 (m, 6H), 1.34 (s, 9H), 1.16 (t, 3H, J=7.5 Hz).

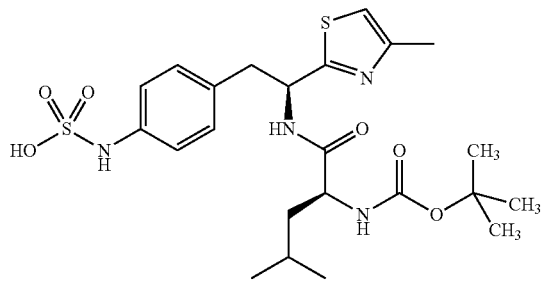 [SMILES: Cc1csc([C@H](Cc2ccc(NS(=O)(=O)O)cc2)NC(=O)[C@H](CC(C)C)NC(=O)OC(C)(C)C)n1]

4-{(S)-2-[(S)-2-(tert-Butoxycarbonylamino)-4-methylpentanamido]-2-(4-ethylthiazol-2-yl)ethyl}phenylsulfamic acid: $^1$H NMR (CD3OD) δ 7.19-7.00 (m, 4H), 5.50-5.40 (m, 1H), 4.13-4.06 (m, 1H), 3.32 (1H, A of ABX, J=7.5, 18 Hz), 3.12 (1H, B of ABX, J=8.1, 13.8 Hz), 2.79 (q, 2H, J=7.8, 14.7 Hz), 1.70-1.55 (m, 1H), 1.46 (s, 9H), 1.33 (t, 3H, J=2.7 Hz), 0.92 (q, 6H, J=6, 10.8 Hz).

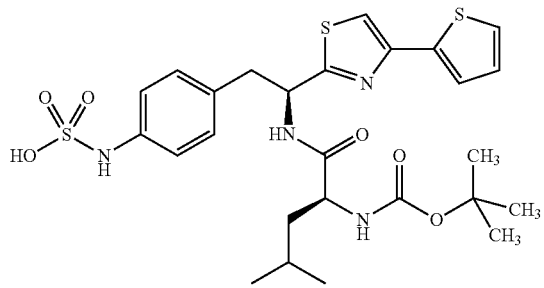 [SMILES: CC(C)C[C@H](NC(=O)OC(C)(C)C)C(=O)N[C@@H](Cc1ccc(NS(=O)(=O)O)cc1)c1nc(-c2cccs2)cs1]

4-{(S)-2-[(S)-2-(tert-Butoxycarbonylamino)-4-methylpentanamido]-2-[2-(thiophen-2-yl)thiazol-4-yl]ethyl}phenylsulfamic acid: $^1$H NMR (CD3OD) δ 8.06 (d, 1H, J=8.4 Hz), 7.61-7.58 (m, 1H), 7.57 (s, 1H), 7.15 (t, 1H, J=0.6 Hz), 7.09-6.98 (m, 6H), 5.30-5.20 (m, 1H), 4.10-4.00 (m, 1H), 3.19-3.13 (m, 2H), 1.63-1.55 (m, 2H), 1.48-1.33 (m, 10H), 0.95-0.89 (m, 6H).

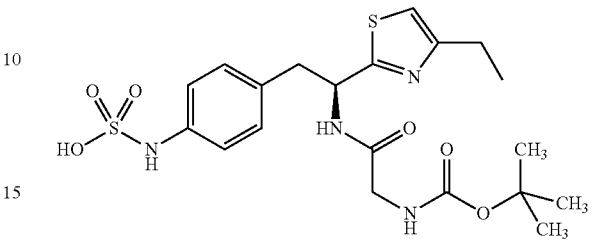

(S)-4-{2-[2-(tert-Butoxycarbonyl)amino]acetamido-2-(4-ethylthiazol-2-yl)ethyl}-phenylsulfamic acid: $^1$H NMR (CD$_3$OD): δ 7.09-6.91 (m, 5H), 5.30 (t, 1H, J=8.4 Hz), 3.60-2.64 (m, 6H), 1.34 (s, 9H), 1.16 (t, 3H, J=7.5 Hz).

A further embodiment of Category IV relates to inhibitors having the formula:

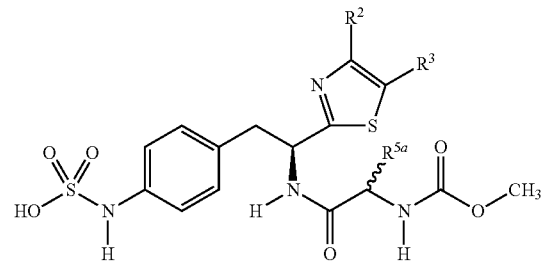

wherein R units and R$^{5a}$ units further described in Table VII.

TABLE VII

| No. | R | R$^{5a}$ |
|---|---|---|
| G151 | thiazol-2-yl | hydrogen |
| G152 | 4-methylthiazol-2-yl | hydrogen |
| G153 | 4-ethylthiazol-2-yl | hydrogen |
| G154 | 4-propylthiazol-2-yl | hydrogen |
| G155 | 4-iso-propylthiazol-2-yl | hydrogen |
| G156 | 4-cyclopropylthiazol-2-yl | hydrogen |
| G157 | 4-butylthiazol-2-yl | hydrogen |
| G158 | 4-tert-butylthiazol-2-yl | hydrogen |
| G159 | 4-cyclohexylthiazol-2-yl | hydrogen |
| G160 | 4,5-dimethylthiazol-2-yl | hydrogen |
| G161 | 4-methyl-5-ethylthiazol-2-yl | hydrogen |
| G162 | 4-phenylthiazol-2-yl | hydrogen |
| G163 | thiazol-2-yl | (S)-iso-propyl |
| G164 | 4-methylthiazol-2-yl | (S)-iso-propyl |
| G165 | 4-ethylthiazol-2-yl | (S)-iso-propyl |
| G166 | 4-propylthiazol-2-yl | (S)-iso-propyl |
| G167 | 4-iso-propylthiazol-2-yl | (S)-iso-propyl |
| G168 | 4-cyclopropylthiazol-2-yl | (S)-iso-propyl |
| G169 | 4-butylthiazol-2-yl | (S)-iso-propyl |
| G170 | 4-tert-butylthiazol-2-yl | (S)-iso-propyl |
| G171 | 4-cyclohexylthiazol-2-yl | (S)-iso-propyl |
| G172 | 4,5-dimethylthiazol-2-yl | (S)-iso-propyl |
| G173 | 4-methyl-5-ethylthiazol-2-yl | (S)-iso-propyl |
| G174 | 4-phenylthiazol-2-yl | (S)-iso-propyl |
| G175 | 4-(thiophen-2-yl)thiazol-2-yl | (S)-iso-propyl |

The compounds encompassed within this embodiment of Category IV can be made according to the procedure outlined in Scheme V and described in Example 6 by substituting the corresponding methylcarbamate for the Boc-protected reagent. The following are non-limiting examples of this embodiment.

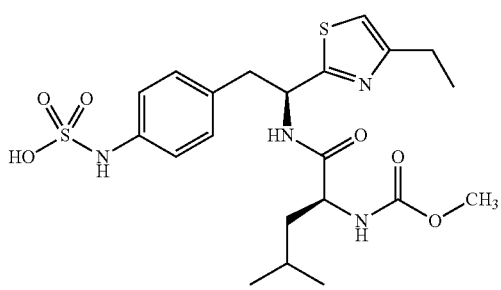 [SMILES: CCc1csc([C@H](Cc2ccc(NS(=O)(=O)O)cc2)NC(=O)[C@H](CC(C)C)NC(=O)OC)n1]

4-{(S)-2-(4-Ethylthiazol-2-yl)-2-[(S)-2-(methoxycarbonylamino)-4-methylpentanamido]ethyl}phenylsulfamic acid: ¹H NMR (CD3OD) δ 7.12-7.03 (m, 5H), 6.84 (d, 1H, J=8.4 Hz), 5.40 (t, 1H, J=5.7 Hz), 4.16 (t, 1H, J=6.3 Hz), 3.69 (s, 3H), 3.61-3.55 (m, 1H), 3.29-3.27 (m, 1H), 3.14-3.07 (m, 1H), 2.81 (q, 2H, J=3.9, 11.2 Hz), 1.66-1.59 (m, 1H), 1.48-1.43 (m, 2H), 1.31 (t, 3H, J=4.5 Hz), 0.96-0.90 (m, 6H).

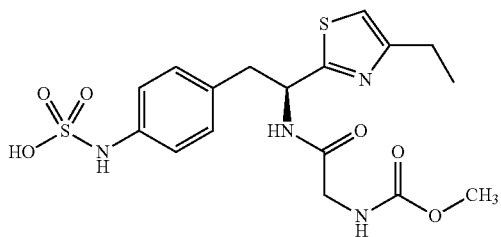 [SMILES: CCc1csc([C@H](Cc2ccc(NS(=O)(=O)O)cc2)NC(=O)CNC(=O)OC)n1]

(S)-4-{2-(4-Ethylthiazol-2-yl)-2-[2-(methoxycarbonylamino)acetamido]-ethyl}phenyl-sulfamic acid: ¹H NMR (CD₃OD): δ 7.12-7.07 (m, 4H), 7.03 (s, 1H), 5.42 (t, 1H, J=5.7 Hz), 3.83-3.68 (q, 2H, J=11.4 Hz), 3.68 (s, 3H), 3.34-3.04 (m, 2H), 2.83-2.76 (q, 2H, J=7.8 Hz), 1.31 (t, 3H, J=7.5 Hz).

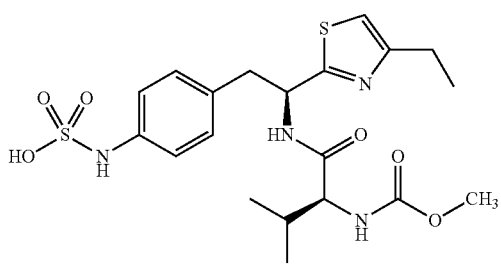 [SMILES: CCc1csc([C@H](Cc2ccc(NS(=O)(=O)O)cc2)NC(=O)[C@@H](NC(=O)OC)C(C)C)n1]

4-{(S)-2-(4-Ethylthiazol-2-yl)-2-[(S)-2-(methoxycarbonylamino)-3-methylbutanamido]-ethyl}phenylsulfamic acid: ¹H NMR (CD₃OD) δ 8.56 (d, 1H, J=7.8 Hz), 7.09 (s, 4H), 7.03 (s, 1H), 5.26-5.20 (m, 1H), 3.90 (d, 1H, J=7.8 Hz), 3.70 (s, 3H), 3.30 (1H, A of ABX, obscured by solvent), 3.08 (1H, B of ABX, J=9.9, 9 Hz), 2.79 (q, 2H, J=11.1, 7.2 Hz), 2.05-1.97 (m, 1H), 1.31 (t, 3H, J=7.5 Hz), 0.88 (s, 3H), 0.85 (s, 3H), 0.79-0.75 (m, 1H).

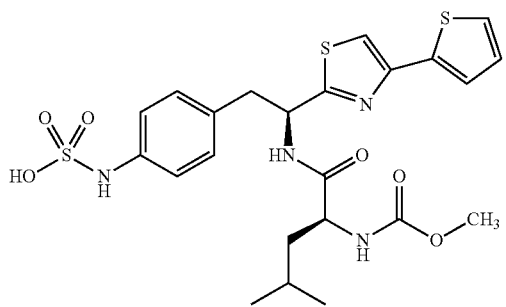 [SMILES: COC(=O)N[C@@H](CC(C)C)C(=O)N[C@@H](Cc1ccc(NS(=O)(=O)O)cc1)c1nc(-c2cccs2)cs1]

4-{(S)-2-[(S)-2-(Methoxycarbonylamino)-4-methylpentanamido]-2-[2-(thiophen-2-yl)thiazol-4-yl]ethyl}phenylsulfamic acid: ¹H NMR (CD3OD) δ 8.22 (d, 1H, J=9 Hz), 7.62-7.57 (m, H), 7.15 (t, 1H, J=0.6 Hz), 7.10-6.97 (m, 4H), 5.30-5.20 (m, 1H), 4.16-4.11 (m, 1H), 3.67 (s, 2H), 3.22 (1H, A of ABX, J=6.9, 13.5 Hz), 3.11 (1H, B of ABX, J=7.8, 13.6 Hz), 1.65-1.58 (m, 1H), 1.50-1.45 (m, 2H), 0.95-0.88 (m, 6H).

Category IV of the present disclosure relates to compounds having the formula:

wherein R is a substituted or unsubstituted thiophen-2-yl or thiophen-4-yl unit and non-limiting examples of R² are further described in Table VIII.

TABLE VIII

| No. | R | R⁸ |
| --- | --- | --- |
| H176 | thiazol-2-yl | —OC(CH₃)₃ |
| H177 | 4-methylthiazol-2-yl | —OC(CH₃)₃ |
| H178 | 4-ethylthiazol-2-yl | —OC(CH₃)₃ |
| H179 | 4-cyclopropylthiazol-2-yl | —OC(CH₃)₃ |
| H180 | 4-tert-butylthiazol-2-yl | —OC(CH₃)₃ |
| H181 | 4-cyclohexylthiazol-2-yl | —OC(CH₃)₃ |
| H182 | 4-(2,2,2-trifluoroethyl)thiazol-2-yl | —OC(CH₃)₃ |
| H183 | 4-(3,3,3-trifluoropropyl)thiazol-2-yl | —OC(CH₃)₃ |
| H184 | 4-(2,2-difluorocyclopropyl)thiazol-2-yl | —OC(CH₃)₃ |
| H185 | 4,5-dimethylthiazol-2-yl | —OC(CH₃)₃ |
| H186 | 4-methyl-5-ethylthiazol-2-yl | —OC(CH₃)₃ |
| H187 | 4-phenylthiazol-2-yl | —OC(CH₃)₃ |
| H188 | 4-(4-chlorophenyl)thiazol-2-yl | —OC(CH₃)₃ |
| H189 | 4-(3,4-dimethylphenyl)thiazol-2-yl | —OC(CH₃)₃ |
| H190 | 4-methyl-5-phenylthiazol-2-yl | —OC(CH₃)₃ |
| H191 | 4-(thiophen-2-yl)thiazol-2-yl | —OC(CH₃)₃ |
| H192 | thiazol-4-yl | —OC(CH₃)₃ |
| H193 | 4-methylthiazol-4-yl | —OC(CH₃)₃ |
| H194 | 4-ethylthiazol-4-yl | —OC(CH₃)₃ |
| H195 | 4-cyclopropylthiazol-4-yl | —OC(CH₃)₃ |
| H196 | 4-tert-butylthiazol-4-yl | —OC(CH₃)₃ |
| H197 | 4-cyclohexylthiazol-4-yl | —OC(CH₃)₃ |
| H198 | 4-(2,2,2-trifluoroethyl)thiazol-4-yl | —OC(CH₃)₃ |
| H199 | 4-(3,3,3-trifluoropropyl)thiazol-4-yl | —OC(CH₃)₃ |
| H200 | 4-(2,2-difluorocyclopropyl)thiazol-4-yl | —OC(CH₃)₃ |
| H201 | 4,5-dimethylthiazol-4-yl | —OC(CH₃)₃ |
| H202 | 4-methyl-5-ethylthiazol-4-yl | —OC(CH₃)₃ |
| H203 | 4-phenylthiazol-4-yl | —OC(CH₃)₃ |
| H204 | 4-(4-chlorophenyl)thiazol-4-yl | —OC(CH₃)₃ |
| H205 | 4-(3,4-dimethylphenyl)thiazol-4-yl | —OC(CH₃)₃ |
| H206 | 4-methyl-5-phenylthiazol-4-yl | —OC(CH₃)₃ |
| H207 | 4-(thiophen-2-yl)thiazol-4-yl | —OC(CH₃)₃ |

TABLE VIII-continued

| No. | R | R[8] |
|---|---|---|
| H208 | thiazol-2-yl | —OCH₃ |
| H209 | 4-methylthiazol-2-yl | —OCH₃ |
| H210 | 4-ethylthiazol-2-yl | —OCH₃ |
| H211 | 4-cyclopropylthiazol-2-yl | —OCH₃ |
| H212 | 4-tert-butylthiazol-2-yl | —OCH₃ |
| H213 | 4-cyclohexylthiazol-2-yl | —OCH₃ |
| H214 | 4-(2,2,2-trifluoroethyl)thiazol-2-yl | —OCH₃ |
| H215 | 4-(3,3,3-trifluoropropyl)thiazol-2-yl | —OCH₃ |
| H216 | 4-(2,2-difluorocyclopropyl)thiazol-2-yl | —OCH₃ |
| H217 | 4,5-dimethylthiazol-2-yl | —OCH₃ |
| H218 | 4-methyl-5-ethylthiazol-2-yl | —OCH₃ |
| H219 | 4-phenylthiazol-2-yl | —OCH₃ |
| H220 | 4-(4-chlorophenyl)thiazol-2-yl | —OCH₃ |
| H221 | 4-(3,4-dimethylphenyl)thiazol-2-yl | —OCH₃ |
| H222 | 4-methyl-5-phenylthiazol-2-yl | —OCH₃ |
| H223 | 4-(thiophen-2-yl)thiazol-2-yl | —OCH₃ |
| H224 | thiazol-4-yl | —OCH₃ |
| H225 | 4-methylthiazol-4-yl | —OCH₃ |
| H226 | 4-ethylthiazol-4-yl | —OCH₃ |
| H227 | 4-cyclopropylthiazol-4-yl | —OCH₃ |
| H228 | 4-tert-butylthiazol-4-yl | —OCH₃ |
| H229 | 4-cyclohexylthiazol-4-yl | —OCH₃ |
| H230 | 4-(2,2,2-trifluoroethyl)thiazol-4-yl | —OCH₃ |
| H231 | 4-(3,3,3-trifluoropropyl)thiazol-4-yl | —OCH₃ |
| H232 | 4-(2,2-difluorocyclopropyl)thiazol-4-yl | —OCH₃ |
| H233 | 4,5-dimethylthiazol-4-yl | —OCH₃ |
| H234 | 4-methyl-5-ethylthiazol-4-yl | —OCH₃ |
| H235 | 4-phenylthiazol-4-yl | —OCH₃ |
| H236 | 4-(4-chlorophenyl)thiazol-4-yl | —OCH₃ |
| H237 | 4-(3,4-dimethylphenyl)thiazol-4-yl | —OCH₃ |
| H238 | 4-methyl-5-phenylthiazol-4-yl | —OCH₃ |
| H239 | 4-(thiophen-2-yl)thiazol-4-yl | —OCH₃ |
| H240 | thiazol-2-yl | —CH₃ |
| H241 | 4-methylthiazol-2-yl | —CH₃ |
| H242 | 4-ethylthiazol-2-yl | —CH₃ |
| H243 | 4-cyclopropylthiazol-2-yl | —CH₃ |
| H244 | 4-tert-butylthiazol-2-yl | —CH₃ |
| H245 | 4-cyclohexylthiazol-2-yl | —CH₃ |
| H246 | 4-(2,2,2-trifluoroethyl)thiazol-2-yl | —CH₃ |
| H247 | 4-(3,3,3-trifluoropropyl)thiazol-2-yl | —CH₃ |
| H248 | 4-(2,2-difluorocyclopropyl)thiazol-2-yl | —CH₃ |
| H249 | 4,5-dimethylthiazol-2-yl | —CH₃ |
| H250 | 4-methyl-5-ethylthiazol-2-yl | —CH₃ |
| H251 | 4-phenylthiazol-2-yl | —CH₃ |
| H252 | 4-(4-chlorophenyl)thiazol-2-yl | —CH₃ |
| H253 | 4-(3,4-dimethylphenyl)thiazol-2-yl | —CH₃ |
| H254 | 4-methyl-5-phenylthiazol-2-yl | —CH₃ |
| H255 | 4-(thiophen-2-yl)thiazol-2-yl | —CH₃ |
| H256 | thiazol-4-yl | —CH₃ |
| H257 | 4-methylthiazol-4-yl | —CH₃ |
| H258 | 4-ethylthiazol-4-yl | —CH₃ |
| H259 | 4-cyclopropylthiazol-4-yl | —CH₃ |
| H260 | 4-tert-butylthiazol-4-yl | —CH₃ |
| H261 | 4-cyclohexylthiazol-4-yl | —CH₃ |
| H262 | 4-(2,2,2-trifluoroethyl)thiazol-4-yl | —CH₃ |
| H263 | 4-(3,3,3-trifluoropropyl)thiazol-4-yl | —CH₃ |
| H264 | 4-(2,2-difluorocyclopropyl)thiazol-4-yl | —CH₃ |
| H265 | 4,5-dimethylthiazol-4-yl | —CH₃ |
| H266 | 4-methyl-5-ethylthiazol-4-yl | —CH₃ |
| H267 | 4-phenylthiazol-4-yl | —CH₃ |
| H268 | 4-(4-chlorophenyl)thiazol-4-yl | —CH₃ |
| H269 | 4-(3,4-dimethylphenyl)thiazol-4-yl | —CH₃ |
| H270 | 4-methyl-5-phenylthiazol-4-yl | —CH₃ |
| H271 | 4-(thiophen-2-yl)thiazol-4-yl | —CH₃ |

The compounds encompassed within Category IV of the present disclosure can be prepared by the procedure outlined in VI and described in Example 7 herein below.

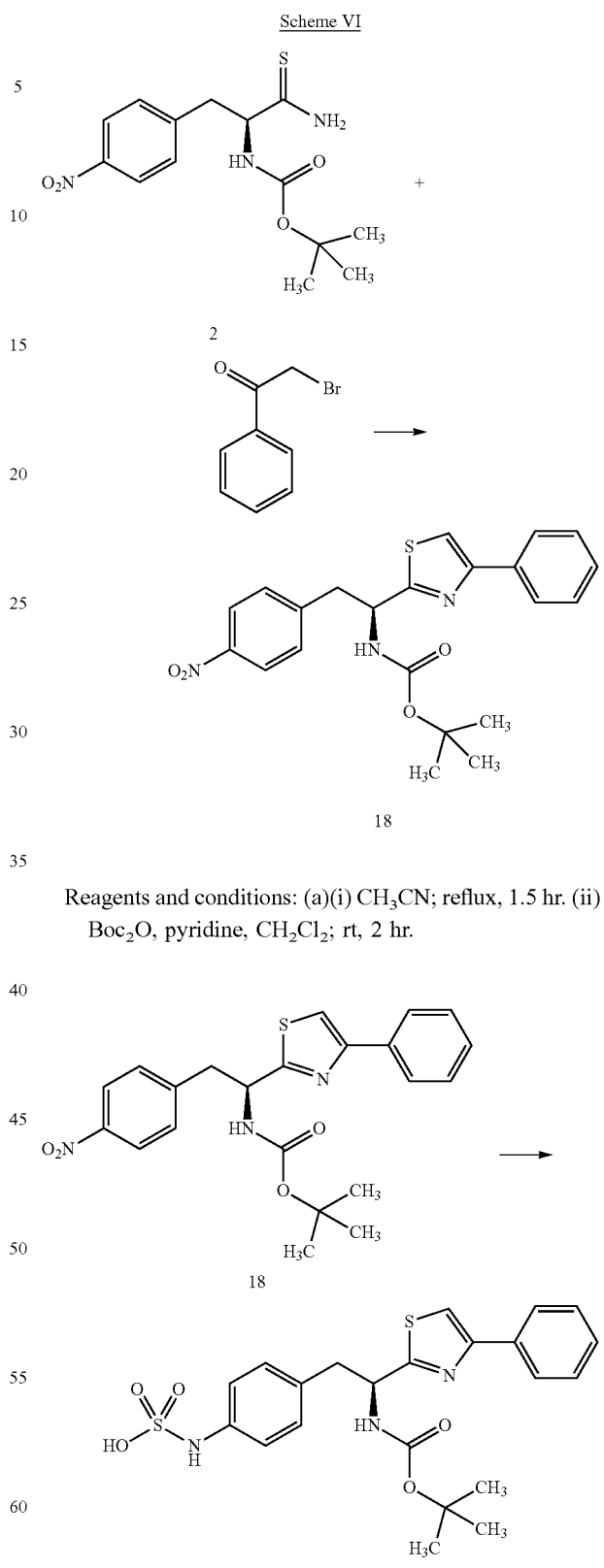

Scheme VI

Reagents and conditions: (a)(i) CH₃CN; reflux, 1.5 hr. (ii) Boc₂O, pyridine, CH₂Cl₂; rt, 2 hr.

Reagents and conditions: (b)(i) H₂:Pd/C, MeOH; reflux (ii) SO₃-pyridine, NH₄OH; rt, 12 hr.

Example 7

[1-(S)-(Phenylthiazol-2-yl)-2-(4-sulfoaminophenyl)ethyl]-carbamic acid tert-butyl ester (19)

Preparation of [2-(4-nitrophenyl)-1-(S)-(4-phenylthiazol-2-yl)ethyl]-carbamic acid tert-butyl ester (18): A mixture of [2-(4-nitrophenyl)-1-(S)-thiocarbamoylethyl]-carbamic acid tert-butyl ester, 2, (0.343 g, 1.05 mmol), 2-bromoacetophenone (0.231 g, 1.15 mmol), in CH₃CN (5 mL) is refluxed 1.5 hour. The solvent is removed under reduced pressure and the residue re-dissolved in CH₂Cl₂ then pyridine (0.24 mL, 3.0 mmol) and Boc₂O (0.24 mL, 1.1 mmol) are added. The reaction is stirred for 2 hours and diethyl ether is added to the solution and the precipitate which forms is removed by filtration. The organic layer is dried (Na₂SO₄), filtered, and concentrated to a residue which is purified over silica to afford 0.176 g (39%) of the desired product ESI+ MS 426 (M+1).

Preparation of [1-(S)-(phenylthiazol-2-yl)-2-(4-sulfoaminophenyl)ethyl]-carbamic acid tert-butyl ester (19): [2-(4-nitrophenyl)-1-(S)-(4-phenylthiazol-2-yl)ethyl]-carbamic acid tert-butyl ester, 18, (0.176 g, 0.41 mmol) is dissolved in MeOH (4 mL). A catalytic amount of Pd/C (10% w/w) is added and the mixture is stirred under a hydrogen atmosphere 12 hours. The reaction mixture is filtered through a bed of CELITE™ and the solvent is removed under reduced pressure. The crude product is dissolved in pyridine (12 mL) and treated with SO₃-pyridine (0.195 g, 1.23 mmol). The reaction is stirred at room temperature for 5 minutes after which a 7% solution of NH₄OH (10 mL) is added. The mixture is then concentrated and the resulting residue is purified by reverse phase chromatography to afford 0.080 g of the desired product as the ammonium salt. ¹H NMR (300 MHz, MeOH-d₄) δ 7.93 (d, J=6.0 Hz, 2H), 7.68 (s, 1H), 7.46-7.42 (m, 3H), 7.37-7.32 (m, 1H), 7.14-7.18 (m, 3H), 5.13-5.18 (m, 1H), 3.40 (dd, J=4.5 and 15.0 Hz, 1H), 3.04 (dd, J=9.6 and 14.1 Hz, 1H), 1.43 (s, 9H).

The following are further non-limiting examples of Category IV of the present disclosure.

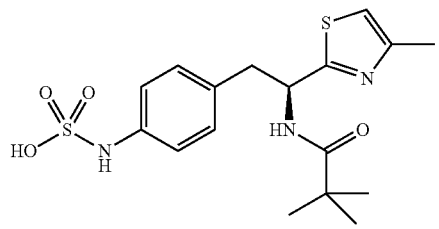 [SMILES: Cc1csc([C@H](Cc2ccc(NS(=O)(=O)O)cc2)NC(=O)C(C)(C)C)n1]

(S)-4-(2-(4-Methylthiazol-2-yl)-2-pivalamidoethyl)phenylsulfamic acid: ¹H NMR (CD₃OD): δ 7.31 (s, 4H), 7.20 (s, 1H), 5.61-5.56 (m, 1H), 3.57-3.22 (m, 2H), 2.62 (s, 3H), 1.31 (s, 3H).

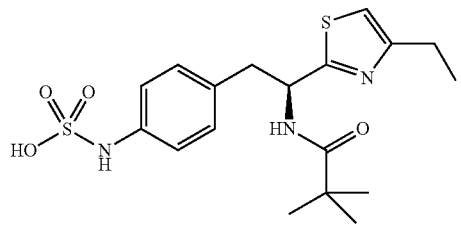 [SMILES: CCc1csc([C@H](Cc2ccc(NS(=O)(=O)O)cc2)NC(=O)C(C)(C)C)n1]

(S)-4-(2-(4-Ethylthiazol-2-yl)-2-pivalamidoethyl)phenylsulfamic acid: ¹H NMR (300 MHz, MeOH-d₄) δ 7.92 (d, J=8.1 Hz, 1H), 7.12-7.14 (m, 4H), 7.03 (s, 1H), 5.38-5.46 (m, 1H), 3.3-3.4 (m, 1H), 3.08 (dd, J=10.2 and 13.8 Hz, 1H), 2.79 (q, J=7.2 Hz, 2H), 1.30 (t, J=7.2 Hz, 3H), 1.13 (s, 9H).

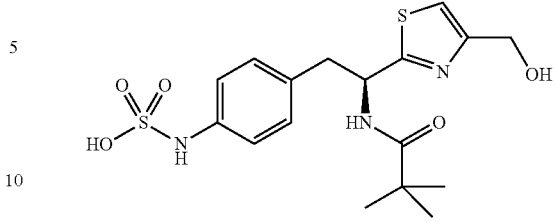

(S)-4-(2-(4-(Hydroxymethyl)thiazol-2-yl)-2-pivalamidoethyl)phenylsulfamic acid: ¹H NMR (300 MHz, MeOH-d₄) δ 7.92 (d, J=8.1 Hz, 1H), 7.24 (s, 1H), 7.08 (d, J=8.7 Hz, 2H), 7.00 (d, J=8.7 Hz, 2H), 5.29-5.37 (m, 1H), 4.55 (s, 2H), 3.30 (dd, J=4.8 and 13.5 Hz, 1H), 2.99 (dd, J=10.5 and 13.5 Hz, 1H), 0.93 (s, 9H).

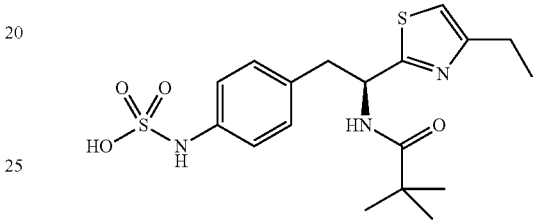

(S)-4-(2-(4-(Ethoxycarbonyl)thiazol-2-yl)-2-pivalamidoethyl)phenylsulfamic acid: ¹H NMR (300 MHz, MeOH-d₄) δ 8.30 (s, 1H), 8.04 (d, J=8.1 Hz, 1H), 7.13 (s, 4H), 5.41-5.49 (m, 1H), 4.41 (q, J=7.2 Hz, 2H), 3.43 (dd, J=5.1 and 13.8 Hz, 1H), 3.14 (dd, J=5.7 and 9.9 Hz, 1H), 1.42 (t, J=7.2 Hz, 3H), 1.14 (s, 9H).

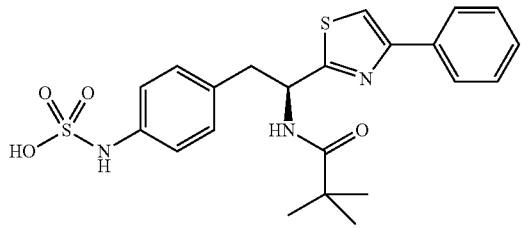 [SMILES: CC(C)(C)C(=O)N[C@@H](Cc1ccc(NS(=O)(=O)O)cc1)c1nc(-c2ccccc2)cs1]

(S)-4-(2-(4-Phenylthiazol-2-yl)-2-pivalamidoethyl)phenylsulfamic acid: ¹H NMR (300 MHz, MeOH-d₄) δ 7.94-8.01 (m, 3H), 7.70 (s, 1H), 7.42-7.47 (m, 2H), 7.32-7.47 (m, 1H), 7.13-7.20 (m, 3H), 5.48-5.55 (m, 1H), 3.50 (dd, J=5.1 and 14.1 Hz, 1H), 3.18 (dd, J=10.2 and 14.1 Hz, 1H), 1.17 (s, 9H).

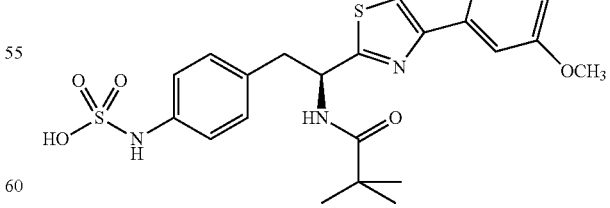

4-((S)-2-(4-(3-Methoxyphenyl)thiazol-2-yl)-2-pivalamidoethyl)phenylsulfamic acid: ¹H NMR (CD₃OD): δ 7.96-7.93 (d, 1H, J=8.1 Hz), 7.69 (s, 1H), 7.51-7.49 (d, 2H, J=7.9 Hz), 7.33 (t, 1H, J=8.0 Hz), 7.14 (s, 4H), 6.92-6.90 (d, 1H, J=7.8 Hz), 5.50 (t, 1H, J=5.1 Hz), 3.87 (s, 3H), 3.50-3.13 (m, 2H), 1.15 (s, 9H).

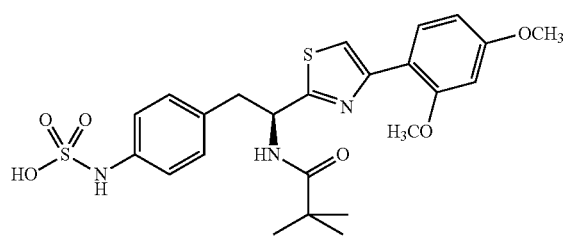 [SMILES: COc1ccc(-c2csc([C@H](Cc3ccc(NS(=O)(=O)O)cc3)NC(=O)C(C)(C)C)n2)c(OC)c1]

4-((S)-2-(4-(2,4-Dimethoxyphenyl)thiazol-2-yl)-2-pivalamidoethyl)phenylsulfamic acid: $^1$H NMR (CD$_3$OD): δ 8.11-8.09 (d, 1H, J=7.8 Hz), 7.96-7.93 (d, 1H, J=8.4 Hz), 7.74 (s, 1H), 7.18-7.16 (m, 4H), 6.67-6.64 (d, 2H, J=9.0 Hz), 5.55-5.47 (m, 1H), 3.95 (s, 3H), 3.87 (s, 3H), 3.52-3.13 (m, 2H), 1.17 (s, 9H).

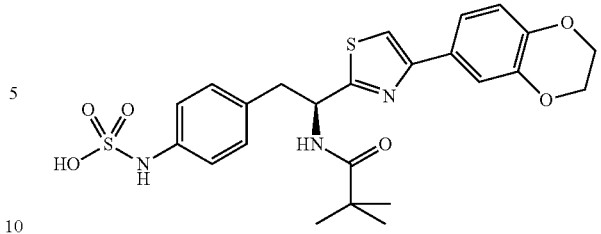

4-((S)-2-(4-(2,3-Dihydrobenzo[b][1,4]dioxin-6-yl)thiazol-2-yl)-2-pivalamidoethyl)-phenylsulfamic acid: $^1$H (CD$_3$OD): δ 7.53 (s, 1H), 7.45 (s, 1H), 7.42-7.40 (d, 1H, J=8.4 Hz), 7.19-7.15 (m, 4H), 6.91-6.88 (d, 2H, J=8.4 Hz), 5.51-5.46 (m, 1H), 4.30 (s, 4H), 3.51-3.12 (m, 2H), 1.16 (s, 9H).

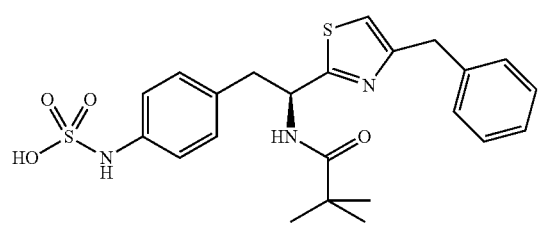 [SMILES: CC(C)(C)C(=O)N[C@@H](Cc1ccc(NS(=O)(=O)O)cc1)c1nc(Cc2ccccc2)cs1]

(S)-4-(2-(4-Benzylthiazol-2-yl)-2-pivalamidoethyl)phenylsulfamic acid $^1$H NMR (CD$_3$OD) δ 7.85 (d, 1H, J=8.4 Hz), 7.38-7.20 (m, 4H), 7.11-7.02 (m, 1H), 7.00 (s, 1H), 5.42-5.37 (m, 1H), 4.13 (s, 2H), 3.13-3.08 (m, 2H), 1.13 (s, 9H).

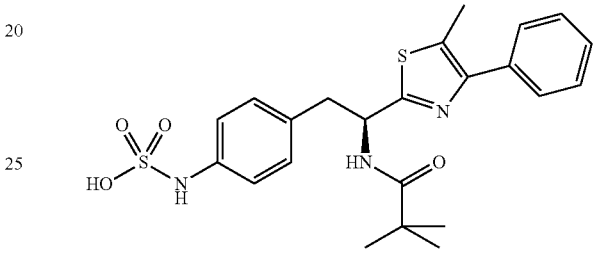

(S)-4-(2-(5-Methyl-4-phenylthiazol-2-yl)-2-pivalamidoethyl)phenylsulfamic acid: $^1$H NMR (CD$_3$OD): δ 7.63-7.60 (d, 2H, J=7.1 Hz), 7.49-7.35 (m, 3H), 7.14 (s, 4H), 5.43-5.38 (m, 1H), 3.42-3.09 (m, 2H), 2.49 (s, 3H), 1.14 (s, 9H).

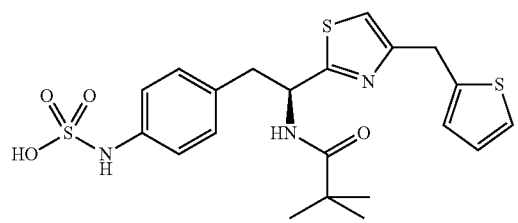 [SMILES: CC(C)(C)C(=O)N[C@@H](Cc1ccc(NS(=O)(=O)O)cc1)c1nc(Cc2cccs2)cs1]

(S)-4-(2-Pivalamido-2-(4-(thiophen-2-ylmethyl)thiazol-2-yl)ethyl)phenylsulfamic acid: $^1$H NMR (CD$_3$OD) δ 7.88-7.85 (d, 1H), 7.38-7.35 (m, 1H), 7.10-7.01 (m, 4H), 7.02 (s, 1H), 5.45-5.38 (m, 1H), 4.13 (s, 2H), 3.13-3.05 (m, 2H), 1.13 (2, 9H).

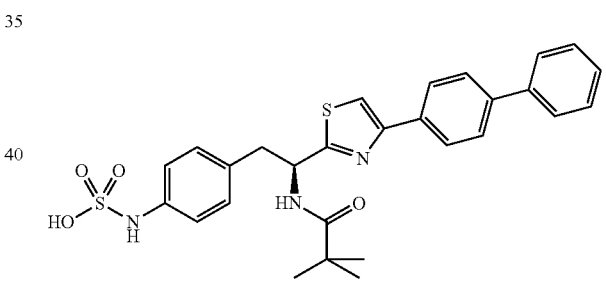

(S)-4-(2-(4-(Biphen-4-yl)thiazol-2-yl)-2-pivalamidoethyl)phenylsulfamic acid: $^1$H NMR (CD$_3$OD): δ 8.04-8.01 (m, 2H), 7.72-7.66 (m, 5H), 7.48-7.35 (m, 3H), 7.15 (s, 4H), 5.50 (t, 1H, J=5.0 Hz), 3.57-3.15 (d, 2H), 1.16 (s, 9H).

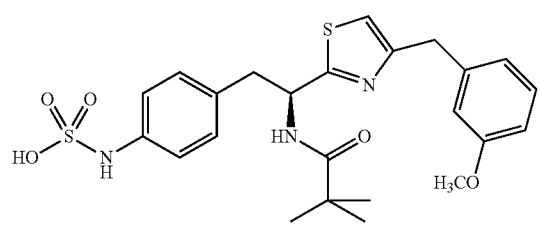 [SMILES: COc1cccc(Cc2csc([C@H](Cc3ccc(NS(=O)(=O)O)cc3)NC(=O)C(C)(C)C)n2)c1]

(S)-4-(2-(4-(3-Methoxybenzyl)thiazol-2-yl)-2-pivalamidoethyl)phenylsulfamic acid: $^1$H NMR (CD$_3$OD) δ 7.85 (d, 1H, J=8.4 Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

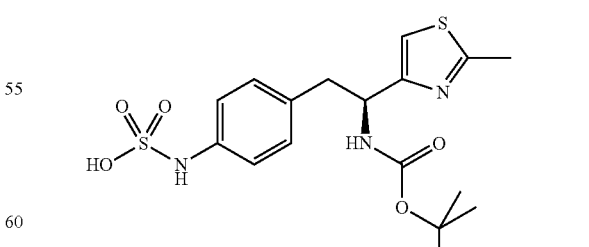

(S)-4-(2-tert-Butoxycarbonyl-2-(2-methylthiazol-4-yl)-phenylsulfamic acid $^1$H NMR (300 MHz, D$_2$O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

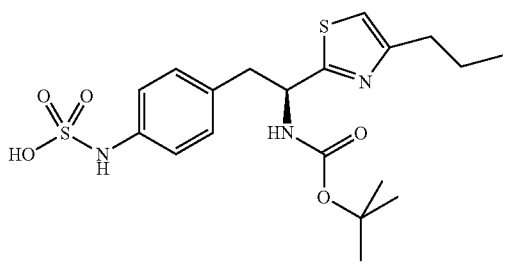 [SMILES: CCCc1csc([C@H](Cc2ccc(NS(=O)(=O)O)cc2)NC(=O)OC(C)(C)C)n1]

(S)-4-(2-(tert-Butoxycarbonyl)-2-(4-propylthiazol-2-yl)ethyl)-phenyl sulfamic acid: $^1$H NMR (300 MHz, CD₃OD): δ 7.18-7.02 (m, 5H), 5.06-5.03 (m, 1H), 3.26 (dd, J=13.8, 4.8 Hz, 1H), 2.95 (dd, J=13.8, 9.3 Hz, 1H), 2.74 (dd, J=15.0, 7.2 Hz, 2H), 1.81-1.71 (m, 2H), 1.40 (s, 7H), 1.33 (bs, 2H), 0.988 (t, J=7.5 Hz 3H).

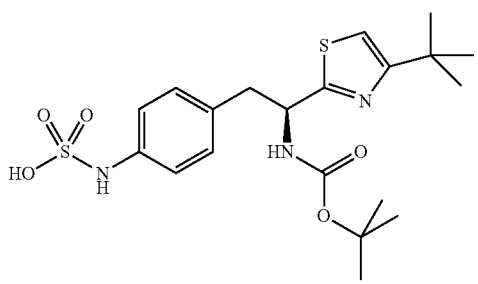 [SMILES: CC(C)(C)OC(=O)N[C@@H](Cc1ccc(NS(=O)(=O)O)cc1)c1nc(C(C)(C)C)cs1]

(S)-4-(2-(tert-Butoxycarbonyl)-2-(4-tert-butylthiazol-2-yl)ethyl)-phenyl sulfamic acid: $^1$H NMR (300 MHz, CD₃OD): δ 7.12 (s, 4H), 7.01 (s, 1H), 5.11-5.06 (m, 1H), 3.32-3.25 (m, 1H), 2.96 (m, 1H), 1.42 (s, 8H), 1.38 (s, 9H), 1.32 (s, 1H).

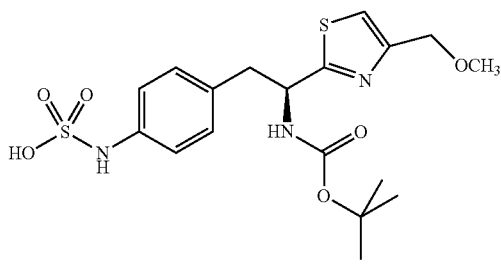 [SMILES: COCc1csc([C@H](Cc2ccc(NS(=O)(=O)O)cc2)NC(=O)OC(C)(C)C)n1]

(S)-4-(2-(tert-Butoxycarbonylamino)-2-(4-(methoxymethyl)thiazol-2-yl)ethyl)-phenyl sulfamic acid: $^1$H NMR (300 MHz, CD₃OD): δ 7.36 (s, 1H), 7.14-7.05 (m, 4H), 5.06 (dd, J=9.0, 5.1 Hz, 1H), 4.55 (s, 2H), 3.42 (s, 3H), 3.31-3.24 (m, 1H), 2.97 (dd, J=13.8, 9.9 Hz, 1H), 1.47-1.31 (m, 9H).

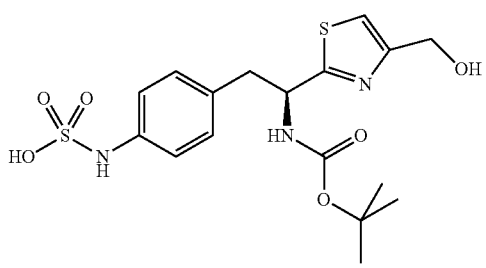 [SMILES: CC(C)(C)OC(=O)N[C@@H](Cc1ccc(NS(=O)(=O)O)cc1)c1nc(CO)cs1]

(S)-4-(2-tert-Butoxycarbonylamino)-2-(4-(2-hydroxymethyl)thiazol-2 yl)ethyl)phenylsulfamic acid: $^1$H NMR (300 MHz, MeOH-d₄) δ 7.22-7.25 (m, 1H), 7.09-7.15 (m, 4H), 5.00-5.09 (m, 1H), 4.32-4.35 (m, 1H), 3.87 (t, J=6.6 Hz, 2H), 3.23-3.29 (m, 1H), 3.09-3.18 (m, 1H), 2.98 (t, J=6.6 Hz, 2H), 1.41 (s, 9H).

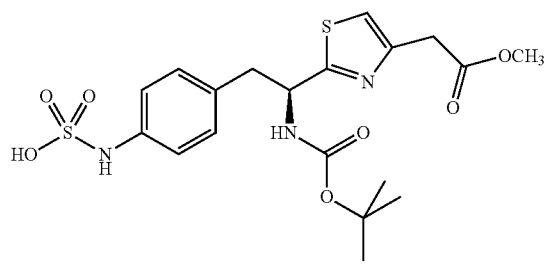 [SMILES: COC(=O)Cc1csc([C@H](Cc2ccc(NS(=O)(=O)O)cc2)NC(=O)OC(C)(C)C)n1]

(S)-(4-(2-tert-Butoxycarbonylamino)-2-(4-(2-ethoxy-2-oxoethyl)-thiazole-2-yl)-ethyl)phenylsulfamic acid: $^1$H NMR (300 MHz, MeOH-d₄) δ 7.29 (s, 1H), 7.09-7.16 (m, 4H), 5.04-5.09 (m, 1H), 4.20 (q, J=6.9 Hz, 2H), 3.84 (s, 2H), 3.30 (dd, J=4.8 and 14.1 HZ, 1H), 2.97 (dd, J=9.6 Hz and 13.8 Hz, 1H), 1.41 (s, 9H), 1.29 (t, J=7.2 Hz, 3H).

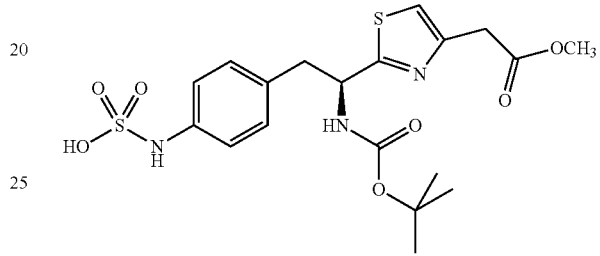

(S)-4-(2-(tert-Butoxycarbonylamino)-2-(4-(2-methoxy-2-oxoethyl)thiazol-2-yl)ethyl)phenylsulfamic acid: $^1$H NMR (300 MHz, MeOH-d₄) δ 7.31 (s, 1H), 7.01-7.16 (m, 4H), 5.04-5.09 (m, 1H), 4.01 (s, 2H), 3.78 (s, 2H), 3.74 (s, 3H), 3.29 (dd, J=5.1 and 13.8 Hz, 1H), 2.99 (dd, J=9.3 and 13.8 Hz, 1H), 1.41 (s, 9H).

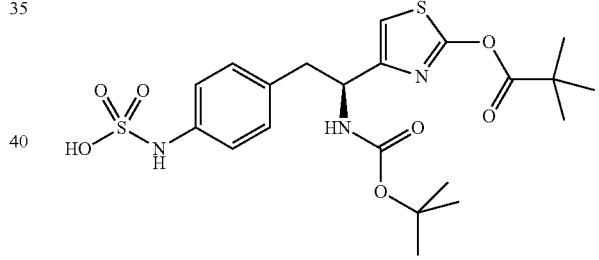

(S)-4-(2-(tert-Butoxycarbonylamino)-2-(2-(pivaloyloxy)thiazol-4-yl)ethyl)phenylsulfamic acid: $^1$H NMR (300 MHz, D₂O) δ 6.95 (s, 4H), 6.63 (s, 1H), 2.94 (dd, J=13.5 and 4.8 Hz, 1H), 2.75 (dd, J=13.5 and 4.8 Hz, 1H), 1.16 (s, 9H), 1.13 (s, 9H).

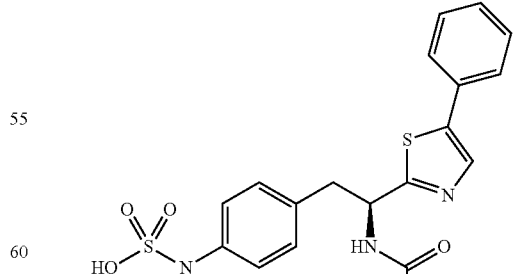

(S)-4-(2-(tert-Butoxycarbonylamino)-2-(5-phenylthiazol-2-yl)ethyl)-phenyl sulfamic acid: $^1$H NMR (300 MHz, CD₃OD): δ 7.98 (s, 1H), 7.62 (d, J=7.2 Hz, 2H), 7.46-7.35 (m, 4H), 7.14 (s, 4H), 5.09 (bs, 1H), 3.07-2.99 (m, 2H), 1.43 (s, 9H).

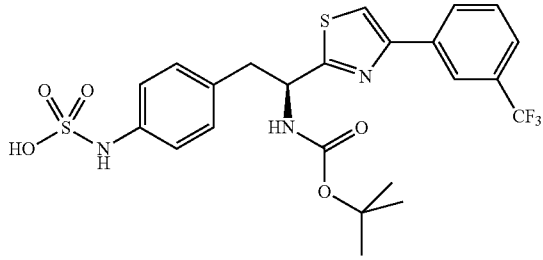 [SMILES: CC(C)(C)OC(=O)N[C@@H](Cc1ccc(NS(=O)(=O)O)cc1)c1nc(-c2cccc(C(F)(F)F)c2)cs1]

4-((S)-2-(tert-Butoxycarbonylamino)-2-(4-(3-(trifluoromethyl)phenyl)thiazol-2-yl)ethyl)-phenyl sulfamic acid: ¹H NMR (300 MHz, CD₃OD): δ 8.28 (s, 1H), 8.22-8.19 (m, 1H), 7.89 (s, 1H), 7.65 (d, J=5.1 Hz, 2H), 7.45 (d, J=8.1 Hz, 1H), 7.15 (s, 4H), 5.17-5.14 (m, 1H), 3.43-3.32 (m, 1H), 3.05 (dd, J=14.1, 9.6 Hz, 1H), 1.42 (s, 9H).

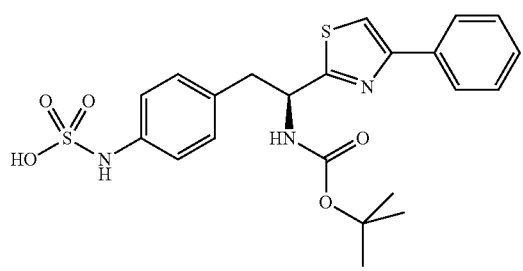 [SMILES: CC(C)(C)OC(=O)N[C@@H](Cc1ccc(NS(=O)(=O)O)cc1)c1nc(-c2ccccc2)cs1]

(S)-4-(2-(tert-Butoxycarbonylamino)-2-(4-phenylthiazol-2-yl)ethyl)-phenyl sulfamic acid: ¹H NMR (300 MHz, CD₃OD): δ 7.98 (s, 1H), 7.94 (d, J=7.2 Hz, 2H), 7.46-7.35 (m, 4H), 7.14 (s, 4H), 5.09 (bs, 1H), 3.07-2.99 (m, 2H), 1.43 (s, 9H).

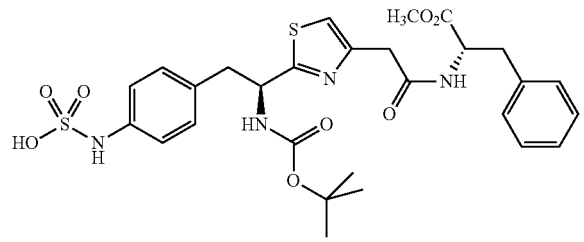 [SMILES: COC(=O)[C@H](Cc1ccccc1)NC(=O)Cc1csc([C@H](Cc2ccc(NS(=O)(=O)O)cc2)NC(=O)OC(C)(C)C)n1]

(S,S)-2-(2-{2-[2-tert-Butoxycarbonylamino-2-(4-sulfoaminophenyl)ethyl]thiazol-4-yl}acetylamido)-3-phenylpropionic acid methyl ester: ¹H NMR (300 MHz, MeOH-d₄) δ 6.85-6.94 (m, 9H), 6.64 (s, 1H), 4.83 (s, 1H), 4.54-4.58 (m, 1H), 3.49 (s, 3H), 3.39 (s, 2H), 2.80-2.97 (m, 1H), 2.64-2.78 (m, 1H), 1.12 (s, 9H).

(S)-[1-{1-Oxo-4-[2-(1-phenyl-1H-tetrazol-5-sulfonyl)ethyl]-1H-1λ⁴-thiazol-2-yl}-2-(4-sulfamino-phenyl)-ethyl]-carbamic acid tert-butyl ester: ¹H NMR (300 MHz, MeOH-d₄) δ 7.22-7.75 (m, 2H), 7.62-7.69 (m, 2H), 7.55 (s, 1H), 7.10-7.20 (m, 5H), 5.25 (m, 1H), 4.27-4.36 (m, 1H), 4.11-4.21 (m, 1H), 3.33-3.44 (m, 4H), 2.84-2.90 (m, 1H), 1.33 (s, 9H).

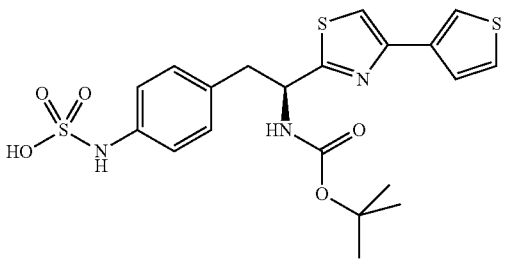 [SMILES: CC(C)(C)OC(=O)N[C@@H](Cc1ccc(NS(=O)(=O)O)cc1)c1nc(-c2ccsc2)cs1]

4-((S)-2-(tert-Butoxycarbonylamino)-2-(4-(thiophen-3-yl)thiazol-2-yl)ethyl)phenyl sulfamic acid: ¹H NMR (300 MHz, CD₃OD): δ 7.84 (dd, J=3.0, 1.5 Hz, 1H), 7.57-7.55 (m, 2H), 7.47 (dd, J=4.8, 3.0 Hz, 1H), 7.15 (s, 4H), 5.15-5.10 (m, 1H), 3.39-3.34 (m, 1H), 3.01 (dd, J=14.1, 9.6 Hz, 1H), 1.42 (s, 8H), 1.32 (s, 1H).

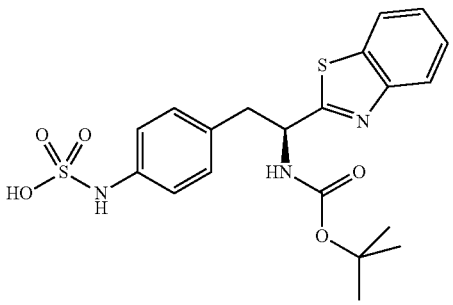 [SMILES: CC(C)(C)OC(=O)N[C@@H](Cc1ccc(NS(=O)(=O)O)cc1)c1nc2ccccc2s1]

(S)-4-(2-(Benzo[d]thiazol-2-ylamino)-2-(tert-butoxycarbonyl)ethyl)phenylsulfamic acid: ¹H NMR (CD₃OD) δ 7.86-7.82 (m, 2H), 7.42 (t, 2H, J=7.1 Hz), 7.33 (t, 1H, J=8.2 Hz), 7.02 (s, 4H), 5.10-5.05 (m, 1H), 2.99-2.91 (m, 2H), 1.29 (s, 9H).

(S)-4-(2-tert-Butoxycarbonylamino)-2-(2-methylthiazol-4-yl)-phenylsulfamic acid ¹H NMR (300 MHz, D₂O) δ 6.99-7.002 (m, 4H), 6.82 (s, 1H), 2.26 (dd, J=13.8 and 7.2 Hz, 1H), 2.76 (dd, J=13.8 and 7.2 Hz, 1H), 2.48 (s, 3H), 1.17 (s, 9H).

The first aspect of Category V of the present disclosure relates to 2-(thiazol-2-yl) compounds having the formula:

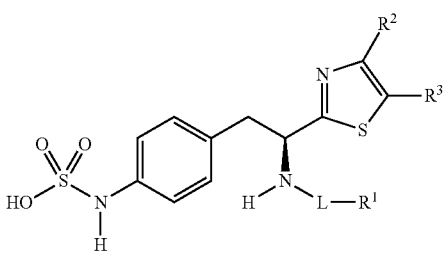

wherein R¹, R², R³, and L are further defined herein in Table IX herein below.

TABLE IX

| No. | L | R¹ | R² | R³ |
|---|---|---|---|---|
| I272 | —C(O)CH₂— | phenyl | —CH₃ | —H |
| I273 | —C(O)CH₂— | 2-fluorophenyl | —CH₃ | —H |
| I274 | —C(O)CH₂— | 3-fluorophenyl | —CH₃ | —H |
| I275 | —C(O)CH₂— | 4-fluorophenyl | —CH₃ | —H |
| I276 | —C(O)CH₂— | 2,3-difluorophenyl | —CH₃ | —H |
| I277 | —C(O)CH₂— | 3,4-difluorophenyl | —CH₃ | —H |
| I278 | —C(O)CH₂— | 3,5-difluorophenyl | —CH₃ | —H |

TABLE IX-continued

| No. | L | R¹ | R² | R³ |
|---|---|---|---|---|
| I279 | —C(O)CH₂— | 2-chlorophenyl | —CH₃ | —H |
| I280 | —C(O)CH₂— | 3-chlorophenyl | —CH₃ | —H |
| I281 | —C(O)CH₂— | 4-chlorophenyl | —CH₃ | —H |
| I282 | —C(O)CH₂— | 2,3-dichlorophenyl | —CH₃ | —H |
| I283 | —C(O)CH₂— | 3,4-dichlorophenyl | —CH₃ | —H |
| I284 | —C(O)CH₂— | 3,5-dichlorophenyl | —CH₃ | —H |
| I285 | —C(O)CH₂— | 2-hydroxyphenyl | —CH₃ | —H |
| I286 | —C(O)CH₂— | 3-hydroxyphenyl | —CH₃ | —H |
| I287 | —C(O)CH₂— | 4-hydroxyphenyl | —CH₃ | —H |
| I288 | —C(O)CH₂— | 2-methoxyphenyl | —CH₃ | —H |
| I289 | —C(O)CH₂— | 3-methoxyphenyl | —CH₃ | —H |
| I290 | —C(O)CH₂— | 4-methoxyphenyl | —CH₃ | —H |
| I291 | —C(O)CH₂— | 2,3-dimethoxyphenyl | —CH₃ | —H |
| I292 | —C(O)CH₂— | 3,4-dimethoxyphenyl | —CH₃ | —H |
| I293 | —C(O)CH₂— | 3,5-dimethoxyphenyl | —CH₃ | —H |
| I294 | —C(O)CH₂— | phenyl | —CH₂CH₃ | —H |
| I295 | —C(O)CH₂— | 2-fluorophenyl | —CH₂CH₃ | —H |
| I296 | —C(O)CH₂— | 3-fluorophenyl | —CH₂CH₃ | —H |
| I297 | —C(O)CH₂— | 4-fluorophenyl | —CH₂CH₃ | —H |
| I298 | —C(O)CH₂— | 2,3-difluorophenyl | —CH₂CH₃ | —H |
| I299 | —C(O)CH₂— | 3,4-difluorophenyl | —CH₂CH₃ | —H |
| I300 | —C(O)CH₂— | 3,5-difluorophenyl | —CH₂CH₃ | —H |
| I301 | —C(O)CH₂— | 2-chlorophenyl | —CH₂CH₃ | —H |
| I302 | —C(O)CH₂— | 3-chlorophenyl | —CH₂CH₃ | —H |
| I303 | —C(O)CH₂— | 4-chlorophenyl | —CH₂CH₃ | —H |
| I304 | —C(O)CH₂— | 2,3-dichlorophenyl | —CH₂CH₃ | —H |
| I305 | —C(O)CH₂— | 3,4-dichlorophenyl | —CH₂CH₃ | —H |
| I306 | —C(O)CH₂— | 3,5-dichlorophenyl | —CH₂CH₃ | —H |
| I307 | —C(O)CH₂— | 2-hydroxyphenyl | —CH₂CH₃ | —H |
| I308 | —C(O)CH₂— | 3-hydroxyphenyl | —CH₂CH₃ | —H |
| I309 | —C(O)CH₂— | 4-hydroxyphenyl | —CH₂CH₃ | —H |
| I310 | —C(O)CH₂— | 2-methoxyphenyl | —CH₂CH₃ | —H |
| I311 | —C(O)CH₂— | 3-methoxyphenyl | —CH₂CH₃ | —H |
| I312 | —C(O)CH₂— | 4-methoxyphenyl | —CH₂CH₃ | —H |
| I313 | —C(O)CH₂— | 2,3-dimethoxyphenyl | —CH₂CH₃ | —H |
| I314 | —C(O)CH₂— | 3,4-dimethoxyphenyl | —CH₂CH₃ | —H |
| I315 | —C(O)CH₂— | 3,5-dimethoxyphenyl | —CH₂CH₃ | —H |
| I316 | —C(O)CH₂CH₂— | phenyl | —CH₃ | —H |
| I317 | —C(O)CH₂CH₂— | 2-fluorophenyl | —CH₃ | —H |
| I318 | —C(O)CH₂CH₂— | 3-fluorophenyl | —CH₃ | —H |
| I319 | —C(O)CH₂CH₂— | 4-fluorophenyl | —CH₃ | —H |
| I320 | —C(O)CH₂CH₂— | 2,3-difluorophenyl | —CH₃ | —H |
| I321 | —C(O)CH₂CH₂— | 3,4-difluorophenyl | —CH₃ | —H |
| I322 | —C(O)CH₂CH₂— | 3,5-difluorophenyl | —CH₃ | —H |
| I323 | —C(O)CH₂CH₂— | 2-chlorophenyl | —CH₃ | —H |
| I324 | —C(O)CH₂CH₂— | 3-chlorophenyl | —CH₃ | —H |
| I325 | —C(O)CH₂CH₂— | 4-chlorophenyl | —CH₃ | —H |
| I326 | —C(O)CH₂CH₂— | 2,3-dichlorophenyl | —CH₃ | —H |
| I327 | —C(O)CH₂CH₂— | 3,4-dichlorophenyl | —CH₃ | —H |
| I328 | —C(O)CH₂CH₂— | 3,5-dichlorophenyl | —CH₃ | —H |
| I329 | —C(O)CH₂CH₂— | 2-hydroxyphenyl | —CH₃ | —H |
| I330 | —C(O)CH₂CH₂— | 3-hydroxyphenyl | —CH₃ | —H |
| I331 | —C(O)CH₂CH₂— | 4-hydroxyphenyl | —CH₃ | —H |
| I332 | —C(O)CH₂CH₂— | 2-methoxyphenyl | —CH₃ | —H |
| I333 | —C(O)CH₂CH₂— | 3-methoxyphenyl | —CH₃ | —H |
| I334 | —C(O)CH₂CH₂— | 4-methoxyphenyl | —CH₃ | —H |
| I335 | —C(O)CH₂CH₂— | 2,3-dimethoxyphenyl | —CH₃ | —H |
| I336 | —C(O)CH₂CH₂— | 3,4-dimethoxyphenyl | —CH₃ | —H |
| I337 | —C(O)CH₂CH₂— | 3,5-dimethoxyphenyl | —CH₃ | —H |
| I338 | —C(O)CH₂CH₂— | phenyl | —CH₂CH₃ | —H |
| I339 | —C(O)CH₂CH₂— | 2-fluorophenyl | —CH₂CH₃ | —H |
| I340 | —C(O)CH₂CH₂— | 3-fluorophenyl | —CH₂CH₃ | —H |
| I341 | —C(O)CH₂CH₂— | 4-fluorophenyl | —CH₂CH₃ | —H |
| I342 | —C(O)CH₂CH₂— | 2,3-difluorophenyl | —CH₂CH₃ | —H |
| I343 | —C(O)CH₂CH₂— | 3,4-difluorophenyl | —CH₂CH₃ | —H |
| I344 | —C(O)CH₂CH₂— | 3,5-difluorophenyl | —CH₂CH₃ | —H |
| I345 | —C(O)CH₂CH₂— | 2-chlorophenyl | —CH₂CH₃ | —H |
| I346 | —C(O)CH₂CH₂— | 3-chlorophenyl | —CH₂CH₃ | —H |
| I347 | —C(O)CH₂CH₂— | 4-chlorophenyl | —CH₂CH₃ | —H |
| I348 | —C(O)CH₂CH₂— | 2,3-dichlorophenyl | —CH₂CH₃ | —H |
| I349 | —C(O)CH₂CH₂— | 3,4-dichlorophenyl | —CH₂CH₃ | —H |
| I350 | —C(O)CH₂CH₂— | 3,5-dichlorophenyl | —CH₂CH₃ | —H |
| I351 | —C(O)CH₂CH₂— | 2-hydroxyphenyl | —CH₂CH₃ | —H |
| I352 | —C(O)CH₂CH₂— | 3-hydroxyphenyl | —CH₂CH₃ | —H |
| I353 | —C(O)CH₂CH₂— | 4-hydroxyphenyl | —CH₂CH₃ | —H |
| I354 | —C(O)CH₂CH₂— | 2-methoxyphenyl | —CH₂CH₃ | —H |
| I355 | —C(O)CH₂CH₂— | 3-methoxyphenyl | —CH₂CH₃ | —H |
| I356 | —C(O)CH₂CH₂— | 4-methoxyphenyl | —CH₂CH₃ | —H |
| I357 | —C(O)CH₂CH₂— | 2,3-dimethoxyphenyl | —CH₂CH₃ | —H |
| I358 | —C(O)CH₂CH₂— | 3,4-dimethoxyphenyl | —CH₂CH₃ | —H |
| I359 | —C(O)CH₂CH₂— | 3,5-dimethoxyphenyl | —CH₂CH₃ | —H |

The compounds encompassed within the first aspect of Category V of the present disclosure can be prepared by the procedure outlined in Scheme VII and described in Example 8 herein below.

Scheme VII

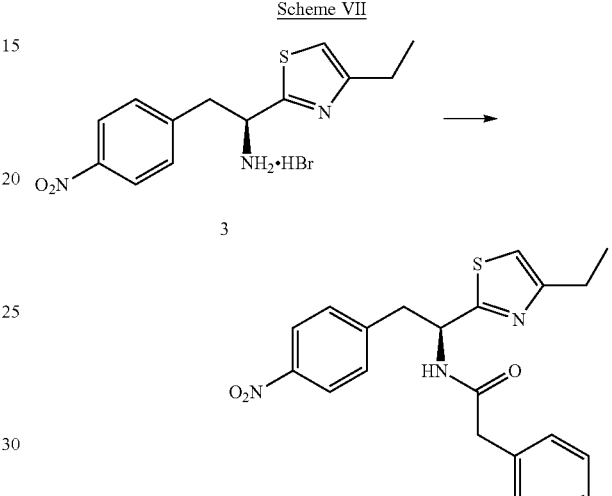

Reagents and conditions: (a) C₆H₄CO₂H, EDCI, HOBt, DIPEA, DMF; rt, 18 hr.

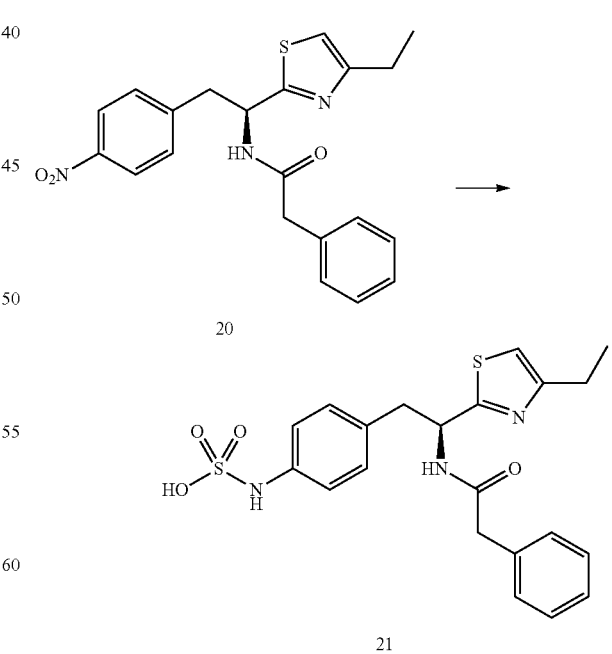

Reagents and conditions: (b) (i) H₂:Pd/C, MeOH; (ii) SO₃-pyridine, NH₄OH, rt, 18 hr.

Example 8

{4-[2-(S)-(4-Ethylthiazol-2-yl)-2-(2-phenylacetylamido)ethyl]phenyl}sulfamic acid (21)

Preparation of N-[1-(4-ethylthiazol-2-yl)-2-(4-nitrophenyl)ethyl]-2-phenyl-acetamide (20): To a solution of 1-(S)-(4-ethylthiazol-2-yl)-2-(4-nitrophenyl)ethyl amine hydrobromide, 3, (0.393 g, 1.1 mmol), phenylacetic acid (0.190 g, 1.4 mmol) and 1-hydroxybenzotriazole (HOBt) (0.094 g, 0.70 mmol) in DMF (10 mL) at 00, is added 1-(3-dimethylaminopropyl)-3-ethylcarbodiimide (EDCI) (0.268 g, 1.4 mmol) followed by triethylamine (0.60 mL, 4.2 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.260 g (60% yield) of the desired product which is used without further purification. ESI+ MS 396 (M+1).

Preparation of {4-[2-(S)-(4-ethylthiazol-2-yl)-2-(2-phenylacetylamido)ethyl]-phenyl}sulfamic acid (21): N-[1-(4-ethylthiazol-2-yl)-2-(4-nitrophenyl)ethyl]-2-phenyl-acetamide, 20, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (0.177 g, 1.23). The reaction is stirred at room temperature for 5 minutes after which a 7% solution of NH$_4$OH (10 mL) is added. The mixture is then concentrated and the resulting residue is purified by reverse phase chromatography to afford 0.136 g of the desired product as the ammonium salt. $^1$H NMR (CD$_3$OD) δ 8.60 (d, 1H, J=8.1 Hz), 7.33-7.23 (m, 3H), 7.16-7.00 (m, 6H), 5.44-5.41 (m, 1H), 3.28 (1H, A of ABX, obscured by solvent), 3.03 (1H, B of ABX, J=14.1, 9.6 Hz), 2.80 (q, 2H, J=10.5, 7.8 Hz) 1.31 (t, 3H, J=4.6 Hz).

The following are non-limiting examples of the first aspect of Category V of the present disclosure.

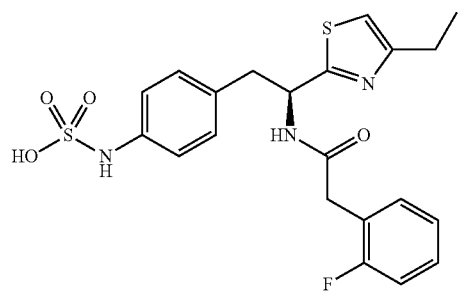 [SMILES: CCc1csc([C@H](Cc2ccc(NS(=O)(=O)O)cc2)NC(=O)Cc2ccccc2F)n1]

(S)-4-(2-(4-Ethylthiazol-2-yl)-2-(2-(2-fluorophenyl)acetamido)ethyl)phenylsulfamic acid: $^1$H NMR (CD$_3$OD) δ 8.65 (d, 1H, J=8.4 Hz), 7.29-7.15 (m, 1H), 7.13-7.03 (m, 7H), 5.46-5.42 (m, 1H), 3.64-3.51 (m, 2H), 3.29 (1H), 3.04 (1H, B of ABX, J=13.8, 9.6 Hz), 2.81 (q, 2H, J=15.6, 3.9 Hz), 1.31 (t, 3H, J=7.8 Hz). $^{19}$F NMR (CD$_3$OD) δ 43.64.

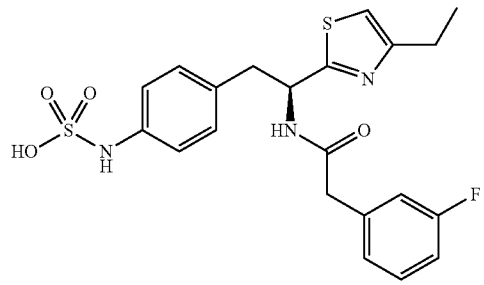 [SMILES: CCc1csc([C@H](Cc2ccc(NS(=O)(=O)O)cc2)NC(=O)Cc2cccc(F)c2)n1]

(S)-4-(2-(4-Ethylthiazol-2-yl)-2-(2-(3-fluorophenyl)acetamido)ethyl)phenylsulfamic acid: $^1$H NMR (CD$_3$OD) δ 8.74 (d, 1H, J=8.4 Hz), 7.32 (q, 1H, J=6.6, 14.2 Hz), 7.10-6.91 (m, 8H), 5.47-5.40 (m, 1H), 3.53 (s, 2H), 3.30 (1H), 3.11 (1H, B of ABX, J=9.6, 14.1 Hz), 2.80 (q, 2H, J=6.6, 15.1 Hz), 1.31 (t, 3H, J=7.8 Hz). 19F NMR δ 47.42.

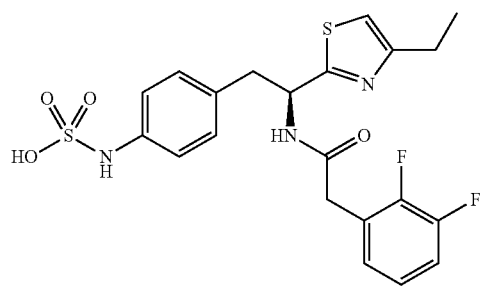 [SMILES: CCc1csc([C@H](Cc2ccc(NS(=O)(=O)O)cc2)NC(=O)Cc2cccc(F)c2F)n1]

(S)-4-(2-(2-(2,3-Difluorophenyl)acetamido)-2-(4-ethylthiazol-2-yl)ethyl)phenyl-sulfamic acid: $^1$H NMR (CD$_3$OD) δ 7.16-7.05 (m, 5H), 6.85-6.80 (m, 1H), 5.48-5.43 (m, 1H), 3.63 (s, 2H), 3.38 (1H, A of ABX, obscured by solvent), 3.03 (1H), 2.80 (q, H, J=15.1, 7.8 Hz), 1.31 (t, 3H, J=7.5 Hz).

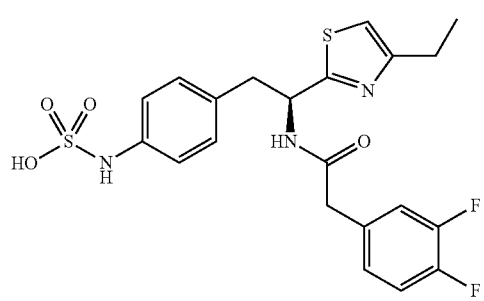 [SMILES: CCc1csc([C@H](Cc2ccc(NS(=O)(=O)O)cc2)NC(=O)Cc2ccc(F)c(F)c2)n1]

(S)-4-(2-(2-(3,4-Difluorophenyl)acetamido)-2-(4-ethylthiazol-2-yl)ethyl)phenyl-sulfamic acid: $^1$H NMR (CD$_3$OD) δ 8.75 (d, 1H, J=7.8 Hz), 7.23-7.04 (m, 6H), 6.88-6.84 (m, 1H), 5.44-5.40 (m, 1H), 3.49 (s, 2H), 3.34 (1H), 3.02 (1H, B of ABX, J=14.1, 9.9 Hz), 2.80 (q, 2H, J=15.1, 7.8 Hz), 1.31 (t, 1H, J=7.5 Hz). 19F NMR (CD$_3$OD) δ 22.18, 19.45.

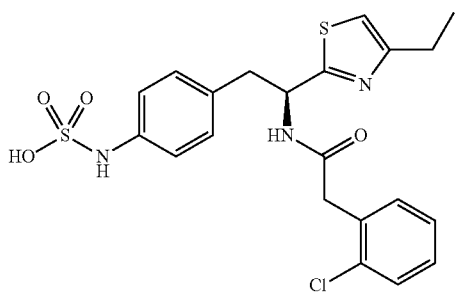 [SMILES: CCc1csc([C@H](Cc2ccc(NS(=O)(=O)O)cc2)NC(=O)Cc2ccccc2Cl)n1]

(S)-4-(2-(2-(2-Chlorophenyl)acetamido)-2-(4-ethylthiazol-2-yl)ethyl)phenylsulfamic acid: ¹H NMR (CD₃OD) δ 7.39-7.36 (m, 1H), 7.27-7.21 (m, 2H), 7.15-6.98 (m, 5H), 5.49-5.44 (m, 1H), 3.69 (d, 2H, J=11.7 Hz), 3.32 (1H), 3.04 (1H, B of ABX, J=9.3, 13.9 Hz), 2.80 (q, 2H, J=7.8, 15.3 Hz), 1.31 (t, 3H, J=7.5 Hz).

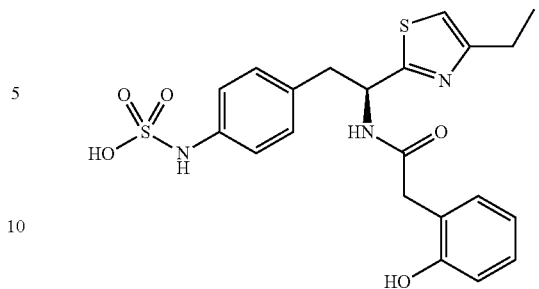

(S)-4-(2-(4-Ethylthiazol-2-yl)-2-(2-(2-methoxyphenyl)acetamido)ethyl)phenyl-sulfamic acid: ¹H NMR (CD₃OD) δ 8.00 (d, 1H, J=7.8 Hz), 7.26 (t, 1H, J=13.2 Hz), 7.09-7.05 (m, 4H), 7.01 (s, 1H), 6.91-6.89 (m, 4H), 5.44-5.39 (m, 1H), 3.71 (s, 3H), 3.52 (s, 2H), 3.26 (1H, A of ABX, J=14.1, 5.1 Hz), 3.06 (1H B of ABX, J=13.8, 8.4 Hz), 2.80 (q, 2H, J=8.1, 15.6 Hz), 1.31 (t, 3H, J=1.2 Hz).

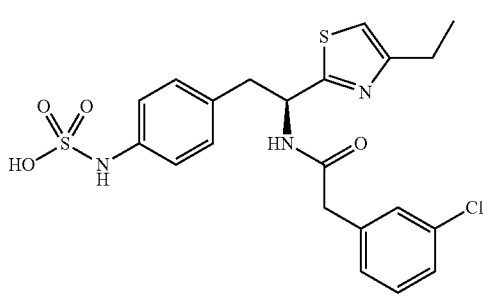 [SMILES: CCc1csc([C@H](Cc2ccc(NS(=O)(=O)O)cc2)NC(=O)Cc2cccc(Cl)c2)n1]

(S)-4-(2-(2-(3-Chlorophenyl)acetamido)-2-(4-ethylthiazol-2-yl)ethyl)phenylsulfamic acid: ¹H NMR (CD3OD) δ 7.33-7.23 (m, 3H), 7.13-7.03 (m, 5H), 5.43 (q, 1H, J=5.1, 9.6 Hz), 3.51 (s, 2H), 3.29 (1H), 3.03 (1H, B of ABX, J=9.9, 14.1 Hz), 2.80 (q, 2H, J=7.5, 15 Hz), 1.31 (t, 3H, J=7.8 Hz).

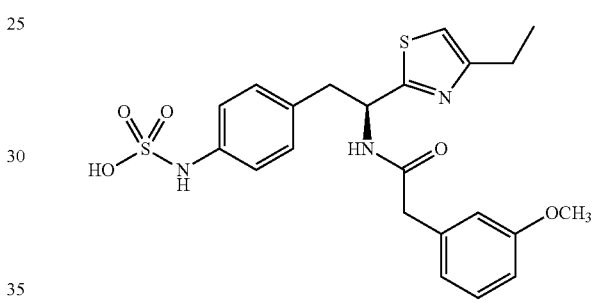

(S)-4-{2-(4-Ethylthiazol-2-yl)-2-[2-(3-methoxyphenyl)acetamido]ethyl}-phenylsulfamic acid: ¹H NMR (CD₃OD) δ 8.58 (d, 1H, J=8.1 Hz), 7.21 (t, 1H, J=7.8 Hz), 7.12-7.02 (m, 4H), 6.81 (s, 2H), 6.72 (d, 1H, J=7.5 Hz), 5.45-5.40 (m, 1H), 3.79 (s, 3H), 3.50 (s, 2H), 3.29 (1H, A of ABX, obscured by solvent), 3.08 (1H, B of ABX, J=11.8, 5.1 Hz), 2.80 (q, 2H, J=15, 7.5 Hz), 1.31 (t, 3H, J=6.6 Hz).

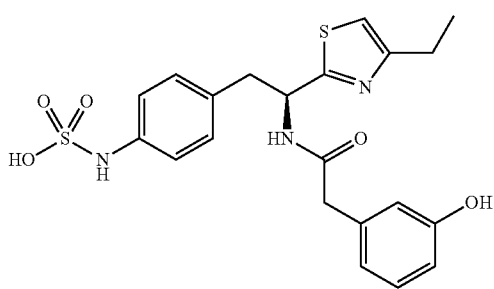 [SMILES: CCc1csc([C@H](Cc2ccc(NS(=O)(=O)O)cc2)NC(=O)Cc2cccc(O)c2)n1]

(S)-4-(2-(4-Ethylthiazol-2-yl)-2-(2-(3-hydroxyphenyl)acetamido)ethyl)phenyl-sulfamic acid: ¹H NMR (CD₃OD) δ 7.16-7.08 (m, 3H), 7.03-7.00 (m, 3H), 6.70-6.63 (m, 2H), 5.42-5.40 (m, 1H), 3.44 (s, 2H), 3.28 (1H, A of ABX, obscured by solvent), 3.04 (B of ABX, J=14.1, 9.6 Hz), 2.89 (q, 2H, J=15, 7.5 Hz), 1.31 (t, 3H, J=7.5 Hz).

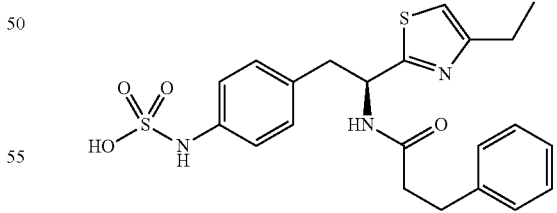

(S)-4-(2-(4-Ethylthiazol-2-yl)-2-(3-phenylpropanamido)ethyl)phenylsulfamic acid: ¹H NMR (CD₃OD) δ 8.56 (d, 1H, J=8.4 Hz), 7.25-6.98 (m, 9H), 5.43-5.38 (m, 1H), 3.26 (1H, A of ABX, J=14.1, 9.6 Hz), 2.97 (1H, B of ABX, J=10.9, 3 Hz), 2.58-2.76 (m, 3H), 2.98 (q, 2H, J=13.8, 7.2 Hz), 1.29 (t, 3H, J=8.7 Hz).

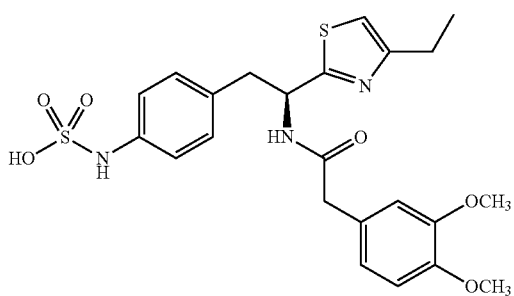 [SMILES: CCc1csc([C@H](Cc2ccc(NS(=O)(=O)O)cc2)NC(=O)Cc2ccc(OC)c(OC)c2)n1]

(S)-4-(2-(2-(3,4-Dimethoxyphenyl)acetamido)-2-(4-ethylthiazol-2-yl)ethyl)-phenylsulfamic acid: ¹H NMR (CD₃OD) δ 7.12-7.03 (m, 3H), 6.91 (d, 1H, J=8.4 Hz), 6.82 (s, 1H), 6.66 (d, 1H, J=2.1 Hz), 6.63 (d, 1H, J=2.1 Hz), 5.43 (m, 1H), 3.84 (s, 3H), 3.80 (s, 3H), 3.45 (s, 2H), 3.30 (1H), 3.03 (1H, B of ABX, J=14.1, 9.6 Hz), 2.79 (q, 2H, J=15.1, 7.2 Hz), 1.30 (t, 3H, J=7.2 Hz).

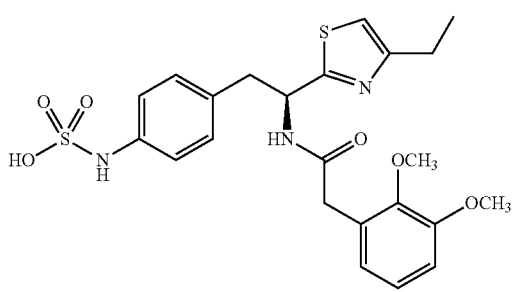 [SMILES: CCc1csc([C@H](Cc2ccc(NS(=O)(=O)O)cc2)NC(=O)Cc2cccc(OC)c2OC)n1]

(S)-4-(2-(2-(2,3-Dimethoxyphenyl)acetamido)-2-(4-ethylthiazol-2-yl)ethyl)-phenylsulfamic acid: ¹H NMR (CD₃OD) δ 8.31 (d, 1H, J=7.8 Hz), 7.11-6.93 (m, 6H), 6.68 (d, 1H, J=7.5 Hz), 5.49-5.40 (m, 1H), 3.87 (s, 3H), 3.70 (s, 3H), 3.55 (s, 2H), 3.26 (1H, A of ABX, obscured by solvent), 3.06 (1H, B of ABX, J=13.9, 9 Hz), 2.80 (q, 2H, J=14.8, 7.5 Hz), 1.31 (t, 3H, J=7.5 Hz).

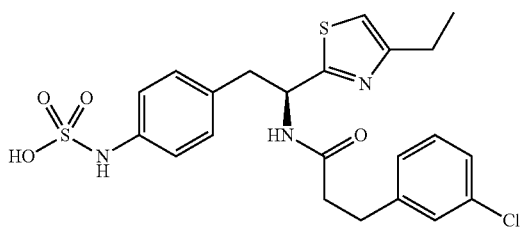 [SMILES: CCc1csc([C@H](Cc2ccc(NS(=O)(=O)O)cc2)NC(=O)CCc2cccc(Cl)c2)n1]

(S)-4-(2-(3-(3-Chlorophenyl)propanamido)-2-(4-ethylthiazol-2-yl)ethyl)phenyl-sulfamic acid: ¹H NMR (CD₃OD) δ 7.27-7.18 (m, 3H), 7.13-7.08 (m, 5H), 7.01 (s, 1H), 5.39 (q, 1H, J=5.1, 9.4 Hz), 3.28 (1H, A of ABX, J=5.1, 14.1 Hz), 2.97 (1H, B of ABX, J=9.3, 13.9 Hz), 2.88-2.76 (m, 4H), 2.50 (t, 2H, J=8.1 Hz), 1.31 (t, 3H, J=7.8 Hz).

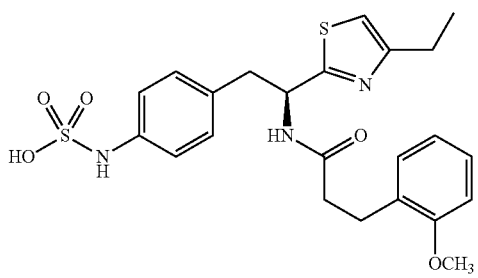 [SMILES: CCc1csc([C@H](Cc2ccc(NS(=O)(=O)O)cc2)NC(=O)CCc2ccccc2OC)n1]

(S)-4-(2-(4-Ethylthiazol-2-yl)-2-(3-(2-methoxyphenyl)propanamido)ethyl)phenyl-sulfamic acid: ¹H NMR (CD₃OD) δ 7.18-7.08 (m, 6H), 6.92 (d, 1H, J=8.1 Hz), 6.82 (t, 1H, J=7.5 Hz), 5.40-5.35 (m, 1H), 3.25 (1H, A of ABX, J=15, 5.4 Hz), 3.00 (1H, B of ABX, J=10.5, 7.5 Hz), 2.88-2.76 m, 4H), 2.47 (q, 2H, J=9.1, 6 Hz), 1.31 (t, 3H, J=7.8 Hz).

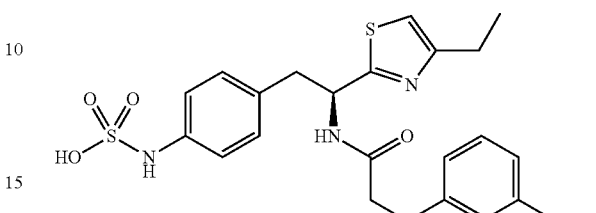

(S)-4-(2-(4-Ethylthiazol-2-yl)-2-(3-(3-methoxyphenyl)propanamido)ethyl)phenyl-sulfamic acid: ¹H NMR (CD₃OD) δ 7.19-7.00 (m, 5H), 6.75 (s, 1H), 6.73 (s, 1H), 5.42-5.37 (m, 1H), 3.76 (s, 3H), 3.25 (1H, A of ABX, J=13.9, 5.4 Hz), 2.98 (1H, B of ABX, J=14.1, 9.6 Hz), 2.86-2.75 (m, 4H), 2.48 (q, 2H, J=11.7, 1.2 Hz), 1.31 (t, 3H, J=7.5 Hz).

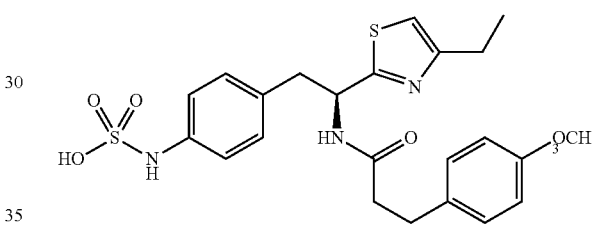

(S)-4-(2-(4-Ethylthiazol-2-yl)-2-(3-(4-methoxyphenyl)propanamido)ethyl)phenyl-sulfamic acid: ¹H NMR (CD₃OD) δ 7.13-6.99 (m, 7H), 6.82-6.78 (m, 2H), 5.42-5.37 (m, 1H), 3.33 (s, 3H), 3.23 (1H), 2.97 (1H, B of ABX, J=13.3, 11.4 Hz), 2.83-2.75 (m, 4H), 2.49 (q, 2H, J=6.4, 3.3 Hz), 1.31 (t, 3H, J=7.5 Hz).

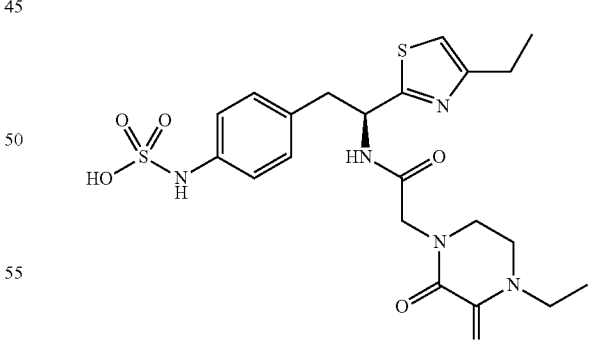

(S)-4-{2-[2-(4-Ethyl-2,3-dioxopiperazin-1-yl)acetamido]-2-(4-ethylthiazol-2-yl)ethyl}phenylsulfamic acid: ¹H NMR (CD₃OD) δ 7.14 (s, 4H), 7.08 (s, 1H), 5.56-5.51 (m, 1H), 4.34 (d, 2H, J=16.2 Hz), 3.88 (d, 2H, J=17.6 Hz), 3.59-3.40 (m, 3H), 3.26-3.14 (m, 3H), 2.98 (1H, B of ABX, J=10.8, 13.9 Hz), 2.82 (q, 2H, J=6.9, 15 Hz), 1.32 (t, 3H, J=7.5 Hz), 1.21 (t, 3H, J=7.2 Hz).

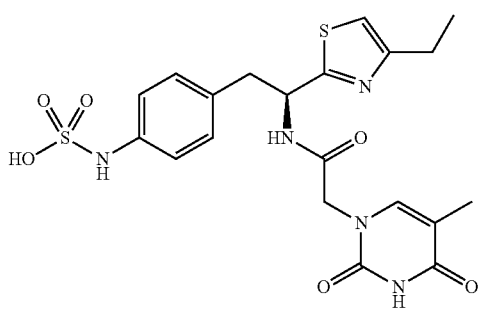 [SMILES: CCc1csc([C@H](Cc2ccc(NS(=O)(=O)O)cc2)NC(=O)Cn2cc(C)c(=O)[nH]c2=O)n1]

(S)-4-{2-(4-Ethylthiazol-2-yl)-2-[2-(5-methyl-2,4-dioxo-3,4-dihydropyrimidin-1(2H)-yl)acetamido]ethyl}phenylsulfamic acid: $^1$H NMR (CD$_3$OD): δ 7.13 (s, 1H), 7.06-7.02 (m, 4H), 6.95 (s, 1H), 5.42-5.31 (m, 1H), 4.43-4.18 (dd, 2H, J=16.5 Hz), 3.24-2.93 (m, 2H), 2.74-2.69 (q, 2H, J=7.3 Hz), 1.79 (s, 3H), 1.22 (t, 3H, J=7.5 Hz).

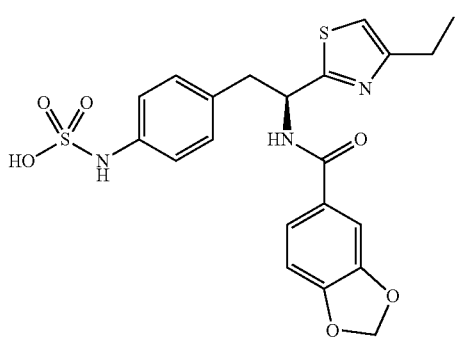 [SMILES: CCc1csc([C@H](Cc2ccc(NS(=O)(=O)O)cc2)NC(=O)c2ccc3c(c2)OCO3)n1]

(S)-4-[2-(benzo[d][1,3]dioxole-5-carboxamido)-2-(4-ethylthiazol-2-yl)ethyl]-phenylsulfamic acid: $^1$H NMR (CD$_3$OD) δ 7.25 (d, 1H, J=6.5 Hz), 7.13 (s, 1H), 7.06 (d, 2H, J=8.5 Hz), 7.00 (d, 2H, J=8.5 Hz), 6.91 (s, 1H), 6.76 (d, 1H, J=8.1 Hz), 5.90 (s, 2H), 5.48 (q, 1H, J=5.0 Hz), 3.32-3.24 (m, 2H), 3.07-2.99 (m, 2H), 2.72 (q, 2H, J=7.5 Hz), 1.21 (t, 3H, J=7.5 Hz).

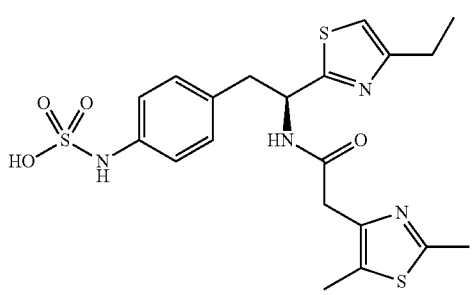 [SMILES: CCc1csc([C@H](Cc2ccc(NS(=O)(=O)O)cc2)NC(=O)Cc2nc(C)sc2C)n1]

(S)-4-{2-[2-(2,5-Dimethylthiazol-4-yl)acetamido]-2-(4-ethylthiazol-2-yl)ethyl}-phenylsulfamic acid: $^1$H NMR (CD$_3$OD): δ 7.10-7.01 (m, 5H), 5.41 (t, 1H, J=6.9 Hz), 3.58 (s, 2H), 3.33-3.01 (m, 2H), 2.82-2.75 (q, 2H, J=7.5 Hz), 2.59 (s, 3H), 2.23 (s, 3H), 1.30 (t, 3H, J=7.5 Hz).

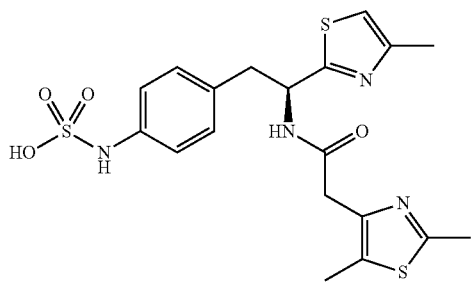 [SMILES: Cc1csc([C@H](Cc2ccc(NS(=O)(=O)O)cc2)NC(=O)Cc2nc(C)sc2C)n1]

(S)-4-{2-[2-(2,4-Dimethylthiazol-5-yl)acetamido]-2-(4-methylthiazol-2-yl)ethyl}-phenylsulfamic acid: $^1$H NMR (CD$_3$OD): δ 8.71-8.68 (d, 1H, J=8.4 Hz), 7.10-7.03 (m, 4H), 7.01 (s, 1H), 5.41 (m, 1H), 3.59 (s, 1H), 3.34-2.96 (m, 2H), 2.59 (s, 3H), 2.40 (s, 3H), 2.23 (s, 3H).

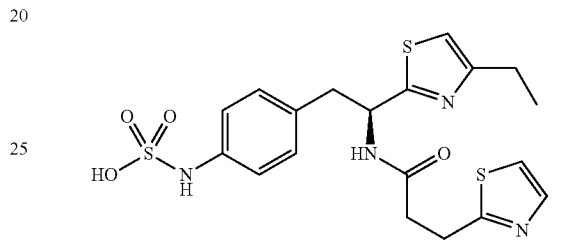

(S)-4-{2-(4-Ethylthiazol-2-yl)-2-[3-(thiazol-2-yl)propanamido]ethyl}phenylsulfamic acid: $^1$H NMR (CD$_3$OD): δ 7.67-7.65 (m, 1H), 7.49-7.47 (m, 1H), 7.14-7.08 (m, 4H), 7.04 (s, 1H), 5.46-5.41 (q, 1H, J=5.1 Hz), 3.58 (s, 2H), 3.30-3.25 (m, 3H), 3.02-2.67 (m, 5H), 1.31 (t, 3H, J=7.5 Hz).

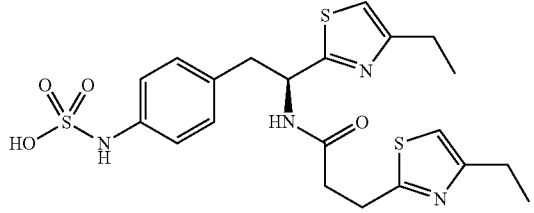 [SMILES: CCc1csc(CCC(=O)N[C@@H](Cc2ccc(NS(=O)(=O)O)cc2)c2nc(CC)cs2)n1]

(S)-4-{2-(4-Ethylthiazol-2-yl)-2-[2-(4-ethylthiazol-2-yl)acetamido]ethyl}phenyl-sulfamic acid: $^1$H NMR (CD$_3$OD): δ 7.04-6.91 (m, 6H), 5.32 (t, 1H, J=5.4 Hz), 3.25-2.90 (m, 2H), 2.71-2.61 (m, 4H) 1.93 (s, 2H) 1.22-1.14 (m, 6H).

The second aspect of Category V of the present disclosure relates to 2-(thiazol-4-yl) compounds having the formula:

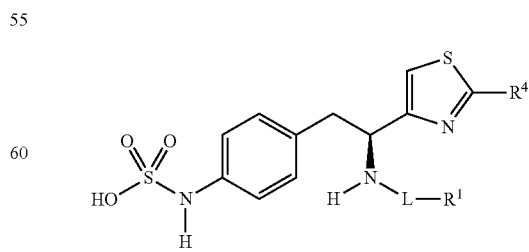

wherein R$^1$, R$^4$, and L are further defined herein in Table X herein below.

TABLE X

| No. | L | R¹ | R⁴ |
|---|---|---|---|
| J360 | —C(O)CH₂— | Phenyl | methyl |
| J361 | —C(O)CH₂— | Phenyl | ethyl |
| J362 | —C(O)CH₂— | Phenyl | phenyl |
| J363 | —C(O)CH₂— | phenyl | thiophen-2-yl |
| J364 | —C(O)CH₂— | phenyl | thiazol-2-yl |
| J365 | —C(O)CH₂— | phenyl | oxazol-2-yl |
| J366 | —C(O)CH₂— | phenyl | isoxazol-3-yl |
| J367 | —C(O)CH₂— | 3-chlorophenyl | methyl |
| J368 | —C(O)CH₂— | 3-chlorophenyl | ethyl |
| J369 | —C(O)CH₂— | 3-chlorophenyl | phenyl |
| J370 | —C(O)CH₂— | 3-chlorophenyl | thiophen-2-yl |
| J371 | —C(O)CH₂— | 3-chlorophenyl | thiazol-2-yl |
| J372 | —C(O)CH₂— | 3-chlorophenyl | oxazol-2-yl |
| J373 | —C(O)CH₂— | 3-chlorophenyl | isoxazol-3-yl |
| J374 | —C(O)CH₂— | 3-methoxyphenyl | methyl |
| J375 | —C(O)CH₂— | 3-methoxyphenyl | ethyl |
| J376 | —C(O)CH₂— | 3-methoxyphenyl | phenyl |
| J377 | —C(O)CH₂— | 3-methoxyphenyl | thiophen-2-yl |
| J378 | —C(O)CH₂— | 3-methoxyphenyl | thiazol-2-yl |
| J379 | —C(O)CH₂— | 3-methoxyphenyl | oxazol-2-yl |
| J380 | —C(O)CH₂— | 3-methoxyphenyl | isoxazol-3-yl |
| J381 | —C(O)CH₂— | 3-fluorophenyl | methyl |
| J382 | —C(O)CH₂— | 3-fluorophenyl | ethyl |
| J383 | —C(O)CH₂— | 3-fluorophenyl | phenyl |
| J384 | —C(O)CH₂— | 3-fluorophenyl | thiophen-2-yl |
| J385 | —C(O)CH₂— | 3-fluorophenyl | thiazol-2-yl |
| J386 | —C(O)CH₂— | 3-fluorophenyl | oxazol-2-yl |
| J387 | —C(O)CH₂— | 3-fluorophenyl | isoxazol-3-yl |
| J388 | —C(O)CH₂— | 2,5-dimethylthiazol-4-yl | methyl |
| J389 | —C(O)CH₂— | 2,5-dimethylthiazol-4-yl | ethyl |
| J390 | —C(O)CH₂— | 2,5-dimethylthiazol-4-yl | phenyl |
| J391 | —C(O)CH₂— | 2,5-dimethylthiazol-4-yl | thiophen-2-yl |
| J392 | —C(O)CH₂— | 2,5-dimethylthiazol-4-yl | thiazol-2-yl |
| J393 | —C(O)CH₂— | 2,5-dimethylthiazol-4-yl | oxazol-2-yl |
| J394 | —C(O)CH₂— | 2,5-dimethylthiazol-4-yl | isoxazol-3-yl |
| J395 | —C(O)CH₂— | 2,4-dimethylthiazol-5-yl | methyl |
| J396 | —C(O)CH₂— | 2,4-dimethylthiazol-5-yl | ethyl |
| J397 | —C(O)CH₂— | 2,4-dimethylthiazol-5-yl | phenyl |
| J398 | —C(O)CH₂— | 2,4-dimethylthiazol-5-yl | thiophen-2-yl |
| J399 | —C(O)CH₂— | 2,4-dimethylthiazol-5-yl | thiazol-2-yl |
| J400 | —C(O)CH₂— | 2,4-dimethylthiazol-5-yl | oxazol-2-yl |
| J401 | —C(O)CH₂— | 2,4-dimethylthiazol-5-yl | isoxazol-3-yl |
| J402 | —C(O)CH₂— | 4-ethylthiazol-2-yl | methyl |
| J403 | —C(O)CH₂— | 4-ethylthiazol-2-yl | ethyl |
| J404 | —C(O)CH₂— | 4-ethylthiazol-2-yl | phenyl |
| J405 | —C(O)CH₂— | 4-ethylthiazol-2-yl | thiophen-2-yl |
| J406 | —C(O)CH₂— | 4-ethylthiazol-2-yl | thiazol-2-yl |
| J407 | —C(O)CH₂— | 4-ethylthiazol-2-yl | oxazol-2-yl |
| J408 | —C(O)CH₂— | 4-ethylthiazol-2-yl | isoxazol-3-yl |
| J409 | —C(O)CH₂— | 3-methyl-1,2,4-oxadiazol-5-yl | methyl |
| J410 | —C(O)CH₂— | 3-methyl-1,2,4-oxadiazol-5-yl | ethyl |
| J411 | —C(O)CH₂— | 3-methyl-1,2,4-oxadiazol-5-yl | phenyl |
| J412 | —C(O)CH₂— | 3-methyl-1,2,4-oxadiazol-5-yl | thiophen-2-yl |
| J413 | —C(O)CH₂— | 3-methyl-1,2,4-oxadiazol-5-yl | thiazol-2-yl |
| J414 | —C(O)CH₂— | 3-methyl-1,2,4-oxadiazol-5-yl | oxazol-2-yl |
| J415 | —C(O)CH₂— | 3-methyl-1,2,4-oxadiazol-5-yl | isoxazol-3-yl |
| J416 | —C(O)CH₂CH₂— | phenyl | methyl |
| J417 | —C(O)CH₂CH₂— | phenyl | ethyl |
| J418 | —C(O)CH₂CH₂— | phenyl | phenyl |
| J419 | —C(O)CH₂CH₂— | phenyl | thiophen-2-yl |
| J420 | —C(O)CH₂CH₂— | phenyl | thiazol-2-yl |
| J421 | —C(O)CH₂CH₂— | phenyl | oxazol-2-yl |
| J422 | —C(O)CH₂CH₂— | phenyl | isoxazol-3-yl |
| J423 | —C(O)CH₂CH₂— | 3-chlorophenyl | methyl |
| J424 | —C(O)CH₂CH₂— | 3-chlorophenyl | ethyl |
| J425 | —C(O)CH₂CH₂— | 3-chlorophenyl | phenyl |
| J426 | —C(O)CH₂CH₂— | 3-chlorophenyl | thiophen-2-yl |
| J427 | —C(O)CH₂CH₂— | 3-chlorophenyl | thiazol-2-yl |
| J428 | —C(O)CH₂CH₂— | 3-chlorophenyl | oxazol-2-yl |
| J429 | —C(O)CH₂CH₂— | 3-chlorophenyl | isoxazol-3-yl |
| J430 | —C(O)CH₂CH₂— | 3-methoxyphenyl | methyl |
| J431 | —C(O)CH₂CH₂— | 3-methoxyphenyl | ethyl |
| J432 | —C(O)CH₂CH₂— | 3-methoxyphenyl | phenyl |
| J433 | —C(O)CH₂CH₂— | 3-methoxyphenyl | thiophen-2-yl |
| J434 | —C(O)CH₂CH₂— | 3-methoxyphenyl | thiazol-2-yl |
| J435 | —C(O)CH₂CH₂— | 3-methoxyphenyl | oxazol-2-yl |
| J436 | —C(O)CH₂CH₂— | 3-methoxyphenyl | isoxazol-3-yl |
| J437 | —C(O)CH₂CH₂— | 3-fluorophenyl | methyl |
| J438 | —C(O)CH₂CH₂— | 3-fluorophenyl | ethyl |
| J439 | —C(O)CH₂CH₂— | 3-fluorophenyl | phenyl |
| J440 | —C(O)CH₂CH₂— | 3-fluorophenyl | thiophen-2-yl |
| J441 | —C(O)CH₂CH₂— | 3-fluorophenyl | thiazol-2-yl |
| J442 | —C(O)CH₂CH₂— | 3-fluorophenyl | oxazol-2-yl |
| J443 | —C(O)CH₂CH₂— | 3-fluorophenyl | isoxazol-3-yl |
| J444 | —C(O)CH₂CH₂— | 2,5-dimethylthiazol-4-yl | methyl |
| J445 | —C(O)CH₂CH₂— | 2,5-dimethylthiazol-4-yl | ethyl |
| J446 | —C(O)CH₂CH₂— | 2,5-dimethylthiazol-4-yl | phenyl |
| J447 | —C(O)CH₂CH₂— | 2,5-dimethylthiazol-4-yl | thiophen-2-yl |
| J448 | —C(O)CH₂CH₂— | 2,5-dimethylthiazol-4-yl | thiazol-2-yl |
| J449 | —C(O)CH₂CH₂— | 2,5-dimethylthiazol-4-yl | oxazol-2-yl |
| J450 | —C(O)CH₂CH₂— | 2,5-dimethylthiazol-4-yl | isoxazol-3-yl |
| J451 | —C(O)CH₂CH₂— | 2,4-dimethylthiazol-5-yl | methyl |
| J452 | —C(O)CH₂CH₂— | 2,4-dimethylthiazol-5-yl | ethyl |
| J453 | —C(O)CH₂CH₂— | 2,4-dimethylthiazol-5-yl | phenyl |
| J454 | —C(O)CH₂CH₂— | 2,4-dimethylthiazol-5-yl | thiophen-2-yl |
| J455 | —C(O)CH₂CH₂— | 2,4-dimethylthiazol-5-yl | thiazol-2-yl |
| J456 | —C(O)CH₂CH₂— | 2,4-dimethylthiazol-5-yl | oxazol-2-yl |
| J457 | —C(O)CH₂CH₂— | 2,4-dimethylthiazol-5-yl | isoxazol-3-yl |
| J458 | —C(O)CH₂CH₂— | 4-ethylthiazol-2-yl | methyl |
| J459 | —C(O)CH₂CH₂— | 4-ethylthiazol-2-yl | ethyl |
| J460 | —C(O)CH₂CH₂— | 4-ethylthiazol-2-yl | phenyl |
| J461 | —C(O)CH₂CH₂— | 4-ethylthiazol-2-yl | thiophen-2-yl |
| J462 | —C(O)CH₂CH₂— | 4-ethylthiazol-2-yl | thiazol-2-yl |
| J463 | —C(O)CH₂CH₂— | 4-ethylthiazol-2-yl | oxazol-2-yl |
| J464 | —C(O)CH₂CH₂— | 4-ethylthiazol-2-yl | isoxazol-3-yl |
| J465 | —C(O)CH₂CH₂— | 3-methyl-1,2,4-oxadiazol-5-yl | methyl |
| J466 | —C(O)CH₂CH₂— | 3-methyl-1,2,4-oxadiazol-5-yl | ethyl |
| J467 | —C(O)CH₂CH₂— | 3-methyl-1,2,4-oxadiazol-5-yl | phenyl |
| J468 | —C(O)CH₂CH₂— | 3-methyl-1,2,4-oxadiazol-5-yl | thiophen-2-yl |
| J469 | —C(O)CH₂CH₂— | 3-methyl-1,2,4-oxadiazol-5-yl | thiazol-2-yl |
| J470 | —C(O)CH₂CH₂— | 3-methyl-1,2,4-oxadiazol-5-yl | oxazol-2-yl |
| J471 | —C(O)CH₂CH₂— | 3-methyl-1,2,4-oxadiazol-5-yl | isoxazol-3-yl |

The compounds encompassed within the second aspect of Category I of the present disclosure can be prepared by the procedure outlined in Scheme II and described in Example 9 herein below.

Scheme VIII

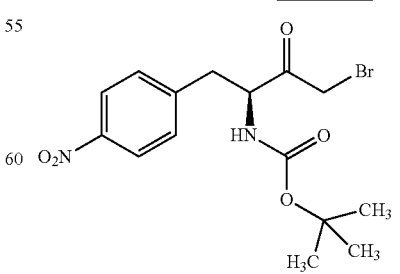

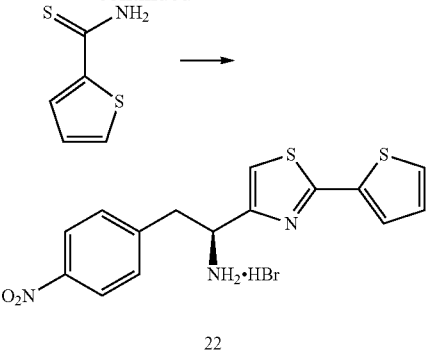

Reagents and conditions: (a) CH₃CN; reflux 5 hr.

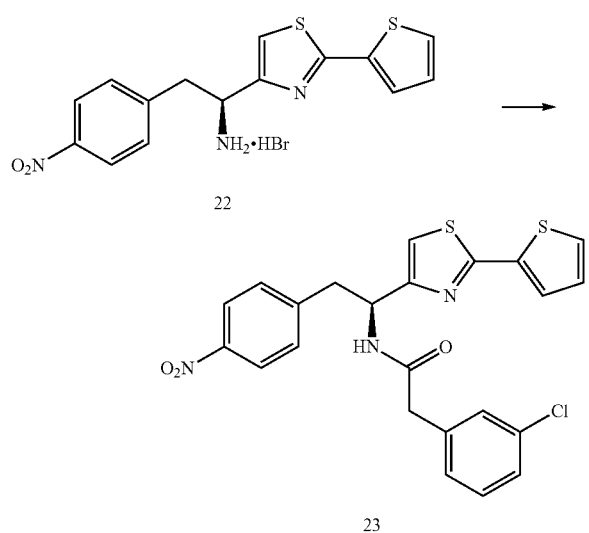

Reagents and conditions: (b) (3-Cl)C₆H₄CO₂H, EDCI, HOBt, DIPEA, DMF; rt, 18 hr.

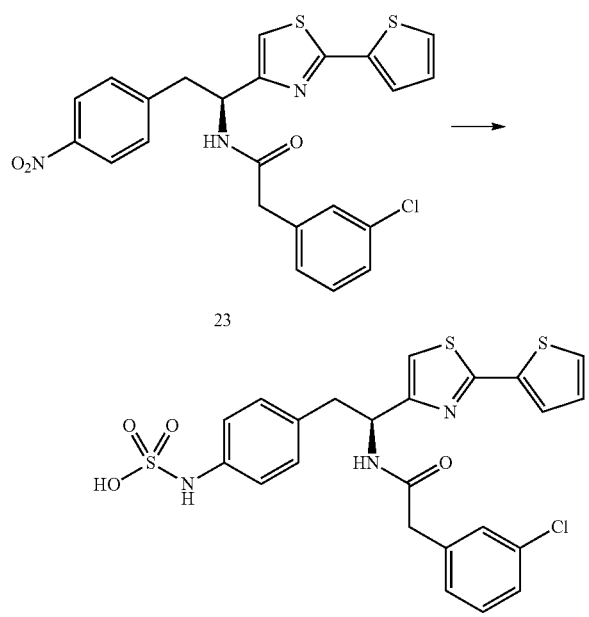

Reagents and conditions: (c) (i) H₂:Pd/C, MeOH; (ii) SO₃-pyridine, NH₄OH, rt, 18 hr.

Example 9

4-((S)-2-(2-(3-chlorophenyl)acetamido)-2-(2-(thiophen-2-yl)thiazol-4-yl)ethyl)phenylsulfamic acid (23)

Preparation of (S)-2-(4-nitrophenyl)-1-[(thiophen-2-yl)thiazol-4-yl]ethanamine hydrobromide salt (22): A mixture of (S)-tert-butyl 4-bromo-1-(4-nitrophenyl)-3-oxobutan-2-ylcarbamate, 7, (7.74 g, 20 mmol), and thiophen-2-carbothioic acid amide (3.14 g, 22 mmol) in CH₃CN (200 mL) is refluxed for 5 hours. The reaction mixture is cooled to room temperature and diethyl ether (50 mL) is added to the solution. The precipitate which forms is collected by filtration. The solid is dried under vacuum to afford 7.14 g (87% yield) of the desired product. ESI+ MS 332 (M+1).

Preparation of 2-(3-chlorophenyl)-N—{(S)-2-(4-nitrophenyl)-1-[2-(thiophen-2-yl)thiazol-4-yl]ethyl}acetamide (23): To a solution of 2-(4-nitrophenyl)-1-(2-thiophene2-ylthiazol-4-yl)ethylamine, 22, (0.41 g, 1 mmol) 3-chlorophenylacetic acid (0.170 g, 1 mmol) and 1-hydroxybenzotriazole (HOBt) (0.070 g, 0.50 mmol) in DMF (5 mL) at 00, is added 1-(3-dimethylaminopropyl)-3-ethylcarbodiimide (EDCI) (0.190 g, 1 mmol) followed by triethylamine (0.42 mL, 3 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.290 g (60% yield) of the desired product which is used without further purification. ESI– MS 482 (M–1).

Preparation of (S)-(4-(2-(2-(3-chlorophenyl)acetylamino]-2-(2-(thiophen-2-ylthiazol-4-yl)ethyl]phenyl)sulfamic acid (24): 2-(3-chlorophenyl)-N—{(S)-2-(4-nitrophenyl)-1-[2-(thiophene2-yl)thiazol-4-yl]ethyl}acetamide, 23, (0.290 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.157 g). The reaction is stirred at room temperature for 5 minutes after which a 7% solution of NH₄OH is added. The mixture is then concentrated and the resulting residue is purified by reverse phase chromatography to afford 0.078 g of the desired product as the ammonium salt. ¹H NMR (CD3OD) δ 7.61 (d, 1H, J=3.6 Hz), 7.58 (d, 1H, J=5.1 Hz), 7.41-7.35 (m, 1H), 7.28-7.22 (m, 2H), 7.18-6.98 (m, 6H), 5.33 (t, 1H, J=6.6 Hz), 3.70 (d, 2H, J=3.9 Hz), 3.23 (1H, A of ABX, J=6.6, 13.8 Hz), 3.07 (1H, B of ABX, J=8.1, 13.5 Hz).

The following are non-limiting examples of compounds encompassed within the second aspect of Category V of the present disclosure.

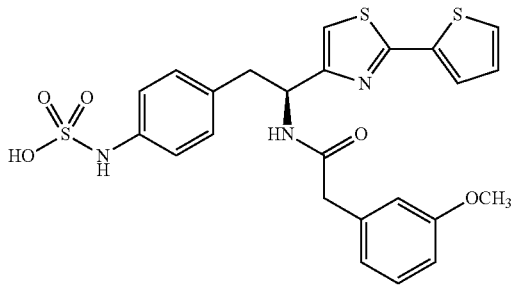 [SMILES: COc1cccc(CC(=O)N[C@@H](Cc2ccc(NS(=O)(=O)O)cc2)c2csc(-c3cccs3)n2)c1]

4-((S)-2-(2-(3-Methoxyphenyl)acetamido)-2-(2-(thiophen-2-yl)thiazol-4-yl)ethyl)-phenylsulfamic acid: ¹H NMR (CD₃OD) δ 8.35 (d, 1H, J=8.7 Hz), 7.61-7.57 (m, 2H), 7.25-7.20 (m, 2H), 7.25-7.20 (m, 2H), 7.09 (s, 1H), 7.05 (d, 2H, J=4.2 Hz), 6.99 (d, 1H, J=8.7 Hz), 6.81 (d, 1H, J=7.8 Hz), 6.77 (s, 1H), 5.30-5.28 (m, 1H), 3.76 (s, 3H), 3.51 (s, 2H), 3.20 (1H, A of ABX, J=6.3, 13.6 Hz), 3.06 (1H, B of ABX, J=8.1, 13.8 Hz).

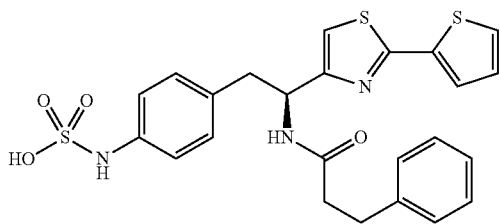 [SMILES: O=C(CCc1ccccc1)N[C@@H](Cc1ccc(NS(=O)(=O)O)cc1)c1csc(-c2cccs2)n1]

4-{(S)-2-(3-Phenylpropanamido)-2-[2-(thiophen-2-yl)thiazol-4-yl]ethyl}-phenylsulfamic acid: ¹H NMR (CD₃OD) δ 8.30 (d, 1H, J=9 Hz), 7.61-7.56 (m, 2H), 7.26-7.14 (m, 7H), 7.12 (d, 1H, J=1.5 Hz), 7.09 (d, 1H, J=2.1 Hz), 6.89 (s, 1H), 5.28-5.26 (m, 1H), 3.18 (1H, A of ABX, J=6.2, 13.8 Hz), 2.96 (1H, B of ABX, J=8.4, 13.6 Hz).

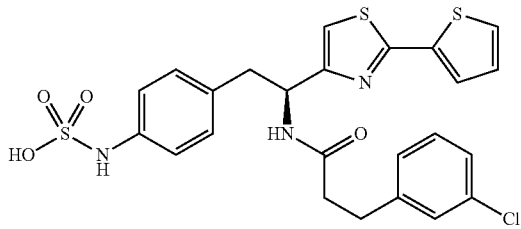 [SMILES: O=C(CCc1cccc(Cl)c1)N[C@@H](Cc1ccc(NS(=O)(=O)O)cc1)c1csc(-c2cccs2)n1]

4-{(S)-2-(3-(3-Chlorophenyl)propanamido)-2-[2-(thiophen-2-yl)thiazol-4-yl]ethyl}phenylsulfamic acid: ¹H NMR (CD₃OD) δ 7.61-7.56 (m, 3H), 7.22-7.14 (m, 6H), 7.08 (d, 1H), 7.00 (d, 1H, J=77.5 Hz), 6.870 (s, 1H), 5.25 (t, 1H, J=7.8 Hz), 3.18 (1H, A of ABX, J=6.6, 13.8 Hz), 2.97 (1H, B of ABX, J=7.8, 13.8 Hz), 2.87 (t, 2H, J=7.5 Hz), 2.51 (t, 2H, J=7.2 Hz).

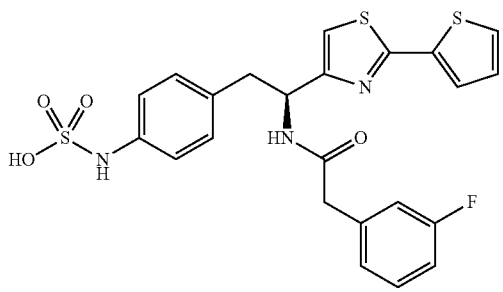 [SMILES: O=C(Cc1cccc(F)c1)N[C@@H](Cc1ccc(NS(=O)(=O)O)cc1)c1csc(-c2cccs2)n1]

4-{(S)-2-[2-(3-Fluorophenyl)acetamido]-2-[2-(thiophen-2-yl)thiazol-4-yl]ethyl}phenylsulfamic acid: ¹H NMR (CD₃OD) δ 7.61-7.57 (m, 2H), 7.32-7.28 (m, 1H), 7.19-7.16 (m, 2H), 7.08 (t, 1H, J=4.5 Hz), 7.02-6.95 (m, 6H), 5.29 (t, 1H, J=8.1 Hz), 3.53 (s, 2H), 3.22 (1H, A of ABX, J=6.6, 13.9 Hz), 3.06 (1H, B of ABX, J=8.4, 13.6 Hz).

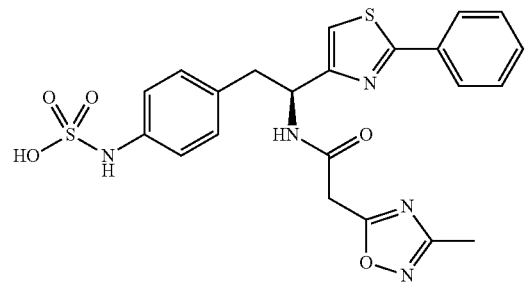 [SMILES: Cc1noc(CC(=O)N[C@@H](Cc2ccc(NS(=O)(=O)O)cc2)c2csc(-c3ccccc3)n2)n1]

(S)-4-{2-[2-(3-Methyl-1,2,4-oxadiazol-5-yl)acetamido]-2-(2-phenylthiazol-4-yl)ethyl}phenylsulfamic acid: ¹H NMR (CD₃OD): δ 7.98-7.95 (m, 2H), 7.48-7.46 (m, 3H), 7.23 (s, 1H), 7.09-7.05 (m, 4H), 5.33 (t, 1H, J=7.2 Hz), 3.33-3.06 (m, 2H), 2.35 (s, 3H).

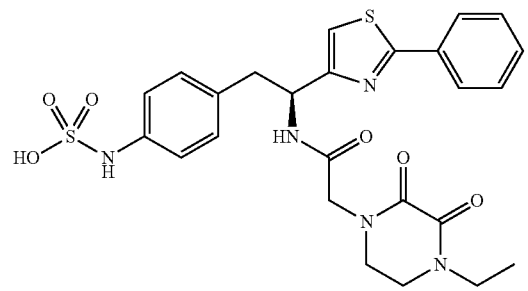 [SMILES: CCN1CCN(CC(=O)N[C@@H](Cc2ccc(NS(=O)(=O)O)cc2)c2csc(-c3ccccc3)n2)C(=O)C1=O]

4-{(S)-2-[2-(4-ethyl-2,3-dioxopiperazin-1-yl)acetamido]-2-[2-(thiophen-2-yl)thiazol-4-yl]ethyl}phenylsulfamic acid: ¹H NMR (CD₃OD) δ 7.62 (d, 1H, J=3 Hz), 7.58 (d, 1H, J=15.6 Hz), 7.27 (s, 1H), 7.16 (t, 1H, J=1.5 Hz), 5.42-5.32 (m, 1H), 4.31 (d, 1H, J=15.6 Hz), 3.91 (d, 1H, J=15.9 Hz), 3.60-3.50 (m, 4H), 3.30-3.23 (m, 2H), 2.98 (1H, B of ABX, J=9.9, 13.8 Hz), 1.21 (t, 3H, J=6.9 Hz).

The third aspect of Category V of the present disclosure relates to compounds having the formula:

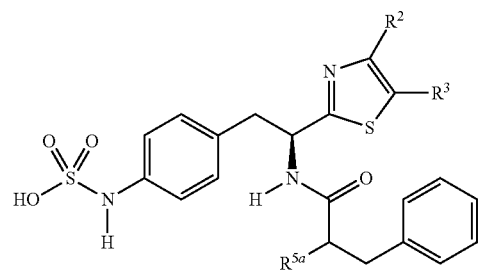

wherein the linking unit L comprises a phenyl unit, said linking group having the formula:

—C(O)[(CR⁵ᵃH)][(CR⁶ᵃH)]—

R¹ is hydrogen, R⁶ᵃ is phenyl, R⁵ᵃ is phenyl or substituted phenyl and non-limiting examples of the units R², R³, and R⁵ᵃ are further exemplified herein below in Table XI.

TABLE XI

| No. | R² | R³ | R⁵ᵃ |
|---|---|---|---|
| K472 | methyl | hydrogen | phenyl |
| K473 | methyl | hydrogen | 2-fluorophenyl |
| K474 | methyl | hydrogen | 3-fluorophenyl |

TABLE XI-continued

| No. | R² | R³ | R⁵ᵃ |
|---|---|---|---|
| K475 | methyl | hydrogen | 4-fluorophenyl |
| K476 | methyl | hydrogen | 3,4-difluorophenyl |
| K477 | methyl | hydrogen | 2-chlorophenyl |
| K478 | methyl | hydrogen | 3-chlorophenyl |
| K479 | methyl | hydrogen | 4-chlorophenyl |
| K480 | methyl | hydrogen | 3,4-dichlorophenyl |
| K481 | methyl | hydrogen | 2-methoxyphenyl |
| K482 | methyl | hydrogen | 3-methoxyphenyl |
| K483 | methyl | hydrogen | 4-methoxyphenyl |
| K484 | ethyl | hydrogen | phenyl |
| K485 | ethyl | hydrogen | 2-fluorophenyl |
| K486 | ethyl | hydrogen | 3-fluorophenyl |
| K487 | ethyl | hydrogen | 4-fluorophenyl |
| K488 | ethyl | hydrogen | 3,4-difluorophenyl |
| K489 | ethyl | hydrogen | 2-chlorophenyl |
| K490 | ethyl | hydrogen | 3-chlorophenyl |
| K491 | ethyl | hydrogen | 4-chlorophenyl |
| K492 | ethyl | hydrogen | 3,4-dichlorophenyl |
| K493 | ethyl | hydrogen | 2-methoxyphenyl |
| K494 | ethyl | hydrogen | 3-methoxyphenyl |
| K495 | ethyl | hydrogen | 4-methoxyphenyl |

The compounds encompassed within the third aspect of Category V of the present disclosure can be prepared by the procedure outlined in Scheme IX and described in Example 10 herein below.

Scheme IX

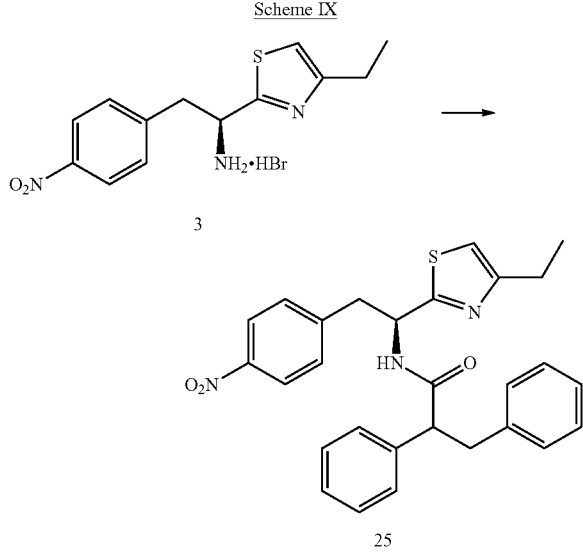

Reagents and conditions: (a) diphenylpropionic acid, EDCI, HOBt, TEA, DMF; 0° C. to rt, 18 hr.

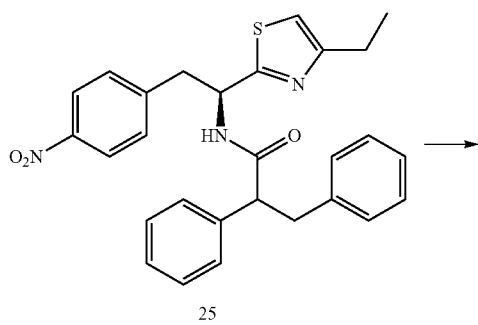

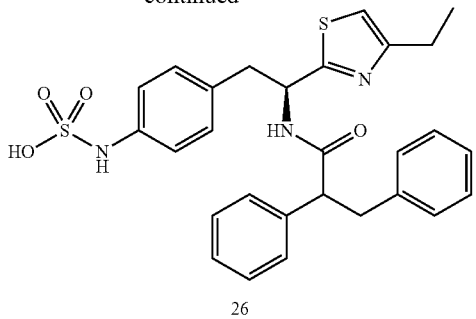

Reagents and conditions: (b) (i) H₂:Pd/C, MeOH; (ii) SO₃-pyridine, NH₄OH; rt, 18 hr.

Example 10

(S)-4-(2-(2,3-Diphenylpropanamido)-2-(4-ethylthiazol-2-yl)ethyl)-phenylsulfamic acid (26)

Preparation of (S)—N-[1-(4-ethylthiazol-2-yl)-2-(4-nitrophenyl)ethyl]-2,3-diphenyl-propanamide (25): To a solution of 1-(S)-(4-ethylthiazol-2-yl)-2-(4-nitrophenyl)ethyl amine hydrobromide, 3, (0.95 g, 2.65 mmol), diphenylpropionic acid (0.60 g, 2.65 mmol) and 1-hydroxybenzotriazole (HOBt) (0.180 g, 1.33 mmol) in DMF (10 mL) at 00, is added 1-(3-dimethylaminopropyl)-3-ethylcarbodiimide (EDCI) (0.502 g, 2.62 mmol) followed by triethylamine (1.1 mL, 7.95 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford 0.903 g (70% yield) of the desired product which is used without further purification.

Preparation of (S)-4-(2-(2,3-diphenylpropanamido)-2-(4-ethylthiazol-2-yl)ethyl)phenylsulfamic acid (26) (S)—N-[1-(4-ethylthiazol-2-yl)-2-(4-nitrophenyl)ethyl]-2,3-diphenyl-propanamide, 25, (0.903 g) is dissolved in MeOH (10 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (30 mL) and treated with SO₃-pyridine (0.621 g). The reaction is stirred at room temperature for 5 minutes after which a 7% solution of NH₄OH is added. The mixture is then concentrated and the resulting residue is purified by reverse phase chromatography to afford 0.415 g of the desired product as the ammonium salt. ¹H NMR (CD₃OD) δ 8.59-8.52 (m, 1H), 7.37-7.04 (m, 9H), 6.97-6.93 (m, 1H), 6.89-6.85 (m, 2H), 5.36-5.32 (m, 1H), 3.91-3.83 (m, 1H), 3.29 (1H, A of ABX, obscured by solvent), 3.15 (1H, B of ABX, J=5.4, 33.8 Hz), 2.99-2.88 (m, 2H), 2.81-2.69 (m, 2H), 1.32-1.25 (m, 3H).

The precursors of many of the Z units which comprise the third aspect of Category V are not readily available. The following procedure illustrates an example of the procedure which can be used to provide different R⁵ᵃ units according to the present disclosure. Using the procedure outlined in Scheme X and described in Example 11 the artisan can make modifications without undue experimentation to achieve the R⁵ᵃ units encompassed by the present disclosure.

Scheme X

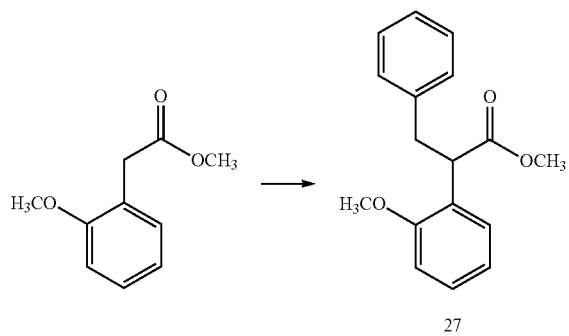

Reagents and conditions: (a) benzyl bromide, LDA, THF; 0° C. to rt 18 hr.

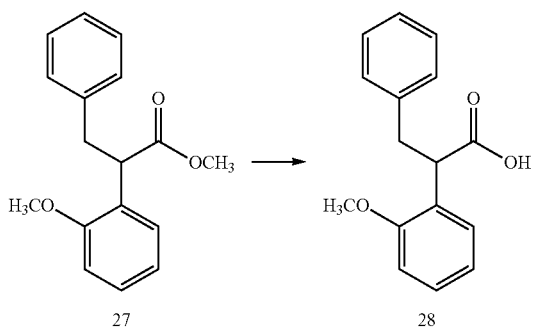 [SMILES: COC(=O)C(Cc1ccccc1)c1ccccc1OC ; COc1ccccc1C(Cc1ccccc1)C(=O)O]

Reagents and conditions: (b) NaOH, THF/MeOH; rt, 18 hr.

Example 11

2-(2-Methoxyphenyl)-3-phenylpropanoic acid (28)

Preparation of methyl 2-(2-methoxyphenyl)-3-phenylpropanoate (27): A 500 mL round-bottom flask is charged with methyl 2-(2-methoxyphenyl)acetate (8.496 g, 47 mmol, 1 eq) and THF (200 mL). The homogeneous mixture is cooled to 0° C. in an ice bath. Lithium diisopropyl amide (23.5 mL of a 2.0M solution in heptane/THF) is added, maintaining a temperature less than 3° C. The reaction is stirred 45 minutes at this reduced temperature. Benzyl bromide (5.6 mL, 47 mmol, 1 eq) is added dropwise. The reaction is allowed to gradually warm to room temperature and is stirred for 18 hours. The reaction is quenched with 1N HCl and extracted 3 times with equal portions of EtOAc. The combined extracts are washed with $H_2O$ and brine, dried over $Na_2SO_4$, filtered, and concentrated. The residue is purified over silica to afford 4.433 g (35%) of the desired compound. ESI+ MS 293 (M+Na).

Preparation of 2-(2-methoxyphenyl)-3-phenylpropanoic acid (28): Methyl 2-(2-methoxyphenyl)-3-phenylpropanoate (4.433 g, 16 mmol, 1 eq) is dissolved in 100 mL of a 1:1 (v:v) mixture of THF and methanol. Sodium hydroxide (3.28 g, 82 mmol, 5 eq) is added and the reaction mixture is stirred 18 hours at room temperature. The reaction is then poured into $H_2O$ and the pH is adjusted to 2 via addition of 1N HCl. A white precipitate forms which is removed by filtration. The resulting solution is extracted with 3 portion of diethyl ether. The extracts are pooled, washed with $H_2O$ and brine, dried over $Na_2SO_4$, filtered, and concentrated in vacuo. The resulting residue is purified over silica to afford 2.107 g (51%) of the desired compound. ESI– MS 255 (M–1), 211 (M-$CO_2H$).

Intermediate 28 can be carried forward according to the procedure outlined in Scheme IX and described in Example 10 to produce the following compound according to the third aspect of Category V.

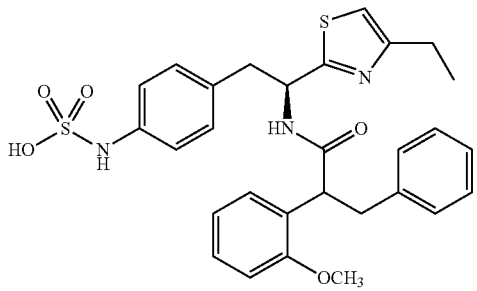 [SMILES: CCc1csc([C@H](Cc2ccc(NS(=O)(=O)O)cc2)NC(=O)C(Cc2ccccc2)c2ccccc2OC)n1]

(S)-4-{2-(4-Ethylthiazol-2-yl)-2-[2-(2-methoxyphenyl)-3-phenylpropanamido]-ethyl}phenylsulfamic acid: $^1$H NMR ($CD_3OD$) δ 7.32-7.12 (m, 7H), 7.05-7.02 (m, 1H), 6.99-6.83 (m, 4H), 6.80-6.75 (m, 2H), 5.35-5.31 (m, 1H), 4.31-4.26 (m, 1H), 3.75 (s, 3H), 3.20-2.90 (m, 4H), 2.79-2.74 (m, 2H), 1.32-1.25 (m, 3H).

The following are further non-limiting examples of compounds according to the third aspect of Category I of the present disclosure.

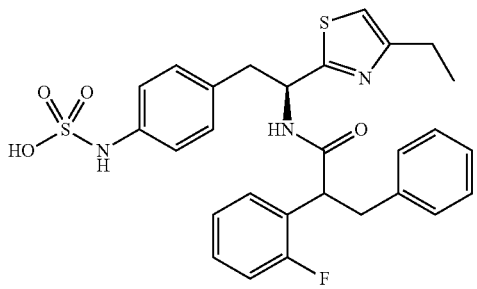 [SMILES: CCc1csc([C@H](Cc2ccc(NS(=O)(=O)O)cc2)NC(=O)C(Cc2ccccc2)c2ccccc2F)n1]

(S)-4-{2-(4-Ethylthiazol-2-yl)-2-[2-(3-fluorophenyl)-3-phenylpropanamido]-ethyl}phenylsulfamic acid: $^1$H NMR ($CD_3OD$) δ 7.33-6.87 (m, 14H), 5.39-5.25 (m, 1H), 3.95-3.83 (m, 1H), 3.31-3.10 (m, 1H), 3.05-2.88 (m, 2H), 2.80-2.70 (m, 2H), 1.32-1.23 (m, 3H). $^{19}$F NMR δ 47.59.

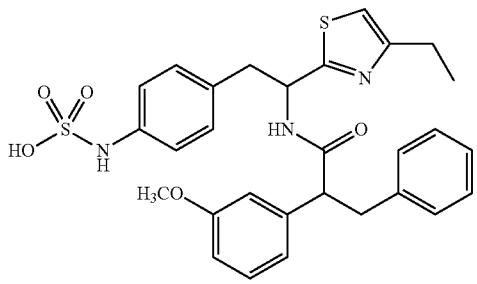 [SMILES: CCc1csc(C(Cc2ccc(NS(=O)(=O)O)cc2)NC(=O)C(Cc2ccccc2)c2cccc(OC)c2)n1]

(S)-4-{2-(4-Ethylthiazol-2-yl)-2-[2-(3-methoxyphenyl)-3-phenylpropanamido]-ethyl}phenylsulfamic acid: $^1$H NMR ($CD_3OD$) δ 7.85 (d, 1H, J=8.4 Hz), 7.25-7.20 (m, 1H), 7.11-7.02 (m, 4H), 7.01 (s, 1H), 6.90-6.79 (m, 2H), 5.45-5.40 (m, 1H), 4.09 (s, 2H), 3.79 (s, 3H), 3.12-3.08 (m, 2H), 1.10 (s, 9H).

The fourth aspect of Category V of the present disclosure relates to compounds having the formula:

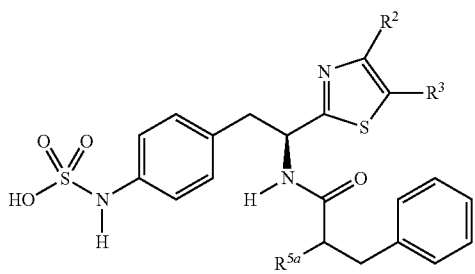

wherein the linking unit L comprises a phenyl unit, said linking group having the formula:

—C(O)[(CR$^{5a}$H)][(CR$^{6a}$H)]—

R$^1$ is hydrogen, R$^{6a}$ is phenyl, R$^{5a}$ is substituted or unsubstituted heteroaryl and the units R$^2$, R$^3$, and R$^{5a}$ are further exemplified herein below in Table XII.

TABLE XII

| No. | R$^2$ | R$^3$ | R$^{5a}$ |
|---|---|---|---|
| L496 | methyl | hydrogen | 3-methyl-1,2,4-oxadiazol-5-yl |
| L497 | methyl | hydrogen | thiophen-2-yl |
| L498 | methyl | hydrogen | thiazol-2-yl |
| L499 | methyl | hydrogen | oxazol-2-yl |
| L500 | methyl | hydrogen | isoxazol-3-yl |
| L501 | ethyl | hydrogen | 3-methyl-1,2,4-oxadiazol-5-yl |
| L502 | ethyl | hydrogen | thiophen-2-yl |
| L503 | ethyl | hydrogen | thiazol-2-yl |
| L504 | ethyl | hydrogen | oxazol-2-yl |
| L505 | ethyl | hydrogen | isoxazol-3-yl |
| L506 | ethyl | methyl | 3-methyl-1,2,4-oxadiazol-5-yl |
| L507 | ethyl | methyl | thiophen-2-yl |
| L508 | ethyl | methyl | thiazol-2-yl |
| L509 | ethyl | methyl | oxazol-2-yl |
| L510 | ethyl | methyl | isoxazol-3-yl |
| L511 | thiophen-2-yl | hydrogen | 3-methyl-1,2,4-oxadiazol-5-yl |
| L512 | thiophen-2-yl | hydrogen | thiophen-2-yl |
| L513 | thiophen-2-yl | hydrogen | thiazol-2-yl |
| L514 | thiophen-2-yl | hydrogen | oxazol-2-yl |
| L515 | thiophen-2-yl | hydrogen | isoxazol-3-yl |
| L516 | isoxazol-3-yl | hydrogen | 3-methyl-1,2,4-oxadiazol-5-yl |
| L517 | isoxazol-3-yl | hydrogen | thiophen-2-yl |
| L518 | isoxazol-3-yl | hydrogen | thiazol-2-yl |
| L519 | isoxazol-3-yl | hydrogen | oxazol-2-yl |
| L520 | isoxazol-3-yl | hydrogen | isoxazol-3-yl |

The compounds encompassed within the fourth aspect of Category V of the present disclosure can be prepared by the procedure outlined in Scheme V and described in Example 5 herein below.

Scheme XI

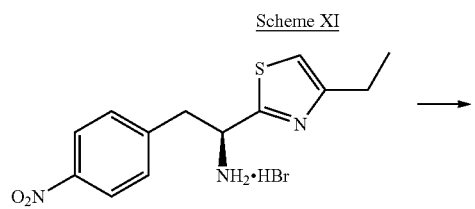

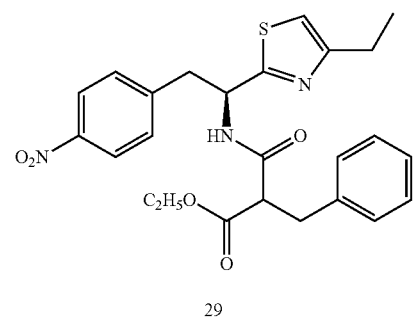

Reagents and conditions: (a) 2-benzyl-3-ethoxy-3-oxopropanoic acid, EDCI, HOBt, DIPEA, DMF; rt, 18 hr.

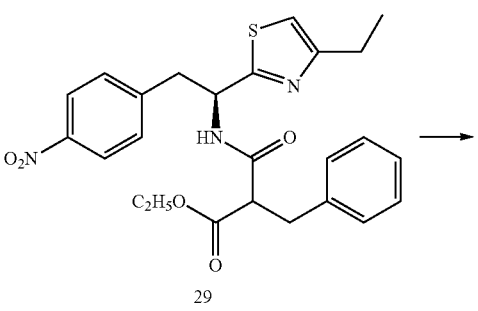

Reagents and conditions: (b) CH$_3$C(=NOH)NH$_2$, K$_2$CO$_3$, toluene; reflux, 18 hr

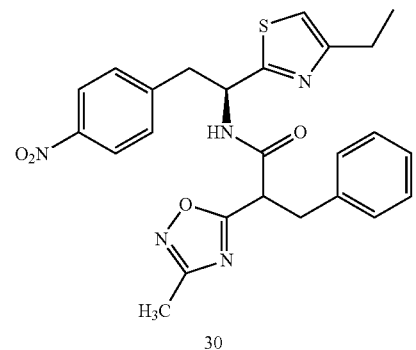

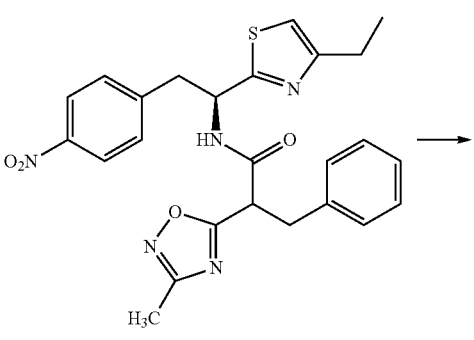

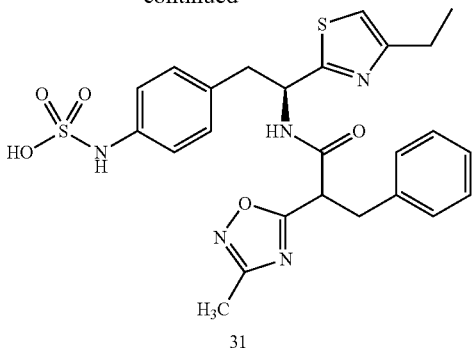

Reagents and conditions: (c) (i) tin (II) chloride, EtOH; (ii) SO$_3$-pyridine, NH$_4$OH; rt, 18 hr.

Example 12

4-{(S)-2-(4-Ethylthiazol-2-yl)-2-[2-(3-methyl-1,2,4-oxadiazol-5-yl)-3-phenylpropanamido]ethyl}phenylsulfamic acid (31)

Preparation of ethyl-2-benzyl-3-[(S)-1-(4-ethylthiazol-2-yl)-2-(4-nitrophenyl)-ethylamino]-3-oxopropanoate (29): To a solution of 1-(S)-(4-ethylthiazol-2-yl)-2-(4-nitrophenyl)ethyl amine hydrobromide, 3, (0.406 g, 1.13 mmol), 2-benzyl-3-ethoxy-3-oxopropanoic acid (0.277 g) and 1-hydroxybenzotriazole (HOBt) (0.191 g, 1.41 mmol) in DMF (10 mL) at 0°, is added 1-(3-dimethylaminopropyl)-3-ethylcarbodiimide (EDCI) (0.240 g, 1.25 mmol) followed by diisopropylethylamine (DIPEA) (0.306 g). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO$_3$, water and brine, and dried over Na$_2$SO$_4$. The solvent is removed in vacuo to afford 0.169 g (31% yield) of the desired product which is used without further purification.

Preparation of N—[(S)-1-(4-ethylthiazol-2-yl)-2-(4-nitrophenyl)ethyl]-2-(3-methyl-1,2,4-oxadiazol-5-yl)-3-phenylpropanamide (30): Ethyl 2-benzyl-3-((S)-1-(4-ethylthiazol-2-yl)-2-(4-nitrophenyl)ethylamino)-3-oxopropanoate is dissolved in toluene (5 mL) and heated to reflux. Potassium carbonate (80 mg) and acetamide oxime (43 mg) are added. and treated with 80 mg potassium carbonate and 43 mg acetamide oxime at reflux. The reaction mixture is cooled to room temperature, filtered and concentrated. The residue is chromatographed over silica to afford 0.221 g (94%) of the desired product as a yellow oil.

Preparation of 4-{(S)-2-(4-ethylthiazol-2-yl)-2-[2-(3-methyl-1,2,4-oxadiazol-5-yl)-3-phenylpropanamido]ethyl}phenylsulfamic acid (31): N—[(S)-1-(4-ethylthiazol-2-yl)-2-(4-nitrophenyl)ethyl]-2-(3-methyl-1,2,4-oxadiazol-5-yl)-3-phenylpropanamide, 30, (0.221 g) and tin (II) chloride (507 mg, 2.2 mmol) are dissolved in EtOH (25 mL) and the solution is brought to reflux 4 hours. The solvent is removed in vacuo and the resulting residue is dissolved in EtOAc. A saturated solution of NaHCO$_3$ (50 mL) is added and the solution is stirred 1 hour. The organic layer is separated and the aqueous layer extracted twice with EtOAc. The combined organic layers are dried (Na$_2$SO$_4$), filtered and concentrated to a residue which is dissolved in pyridine (0.143 g) and treated with SO$_3$-pyridine (0.143 g). The reaction is stirred at room temperature for 5 minutes after which a 7% solution of NH$_4$OH is added. The mixture is then concentrated and the resulting residue is purified by reverse phase chromatography to afford 0.071 g of the desired product as the ammonium salt. $^1$H NMR (CD$_3$OD): δ 7.29-6.87 (m, 10H), 5.38-5.30 (m, 1H), 4.37-4.30 (m, 1H), 3.42-2.74 (m, 6H), 2.38-2.33 (m, 3H), 1.34-1.28 (m, 3H).

Category VI of the present disclosure relates to 2-(thiazol-2-yl) compounds having the formula:

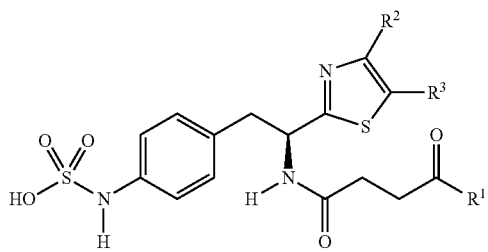

wherein R$^1$, R$^2$, R$^3$, and L are further defined herein in Table XIII herein below.

TABLE XIII

| No. | R$^2$ | R$^3$ | R$^1$ |
|---|---|---|---|
| M521 | ethyl | hydrogen | thiophen-2-yl |
| M522 | ethyl | hydrogen | thiazol-2-yl |
| M523 | ethyl | hydrogen | oxazol-2-yl |
| M524 | ethyl | hydrogen | isoxazol-3-yl |
| M525 | ethyl | hydrogen | imidazol-2-yl |
| M526 | ethyl | hydrogen | isoxazol-3-yl |
| M527 | ethyl | hydrogen | oxazol-4-yl |
| M528 | ethyl | hydrogen | isoxazol-4-yl |
| M529 | ethyl | hydrogen | thiophen-4-yl |
| M530 | ethyl | hydrogen | thiazol-4-yl |
| M531 | ethyl | methyl | methyl |
| M532 | ethyl | methyl | ethyl |
| M533 | ethyl | methyl | propyl |
| M534 | ethyl | methyl | iso-propyl |
| M535 | ethyl | methyl | butyl |
| M536 | ethyl | methyl | phenyl |
| M537 | ethyl | methyl | benzyl |
| M538 | ethyl | methyl | 2-fluorophenyl |
| M539 | ethyl | methyl | 3-fluorophenyl |
| M540 | ethyl | methyl | 4-fluorophenyl |
| M541 | phenyl | hydrogen | methyl |
| M542 | phenyl | hydrogen | ethyl |
| M543 | phenyl | hydrogen | propyl |
| M544 | phenyl | hydrogen | iso-propyl |
| M545 | phenyl | hydrogen | butyl |
| M546 | phenyl | hydrogen | phenyl |
| M547 | phenyl | hydrogen | benzyl |
| M548 | phenyl | hydrogen | 2-fluorophenyl |
| M549 | phenyl | hydrogen | 3-fluorophenyl |
| M550 | phenyl | hydrogen | 4-fluorophenyl |
| M551 | thiophen-2-yl | hydrogen | methyl |
| M552 | thiophen-2-yl | hydrogen | ethyl |
| M553 | thiophen-2-yl | hydrogen | propyl |
| M554 | thiophen-2-yl | hydrogen | iso-propyl |
| M555 | thiophen-2-yl | hydrogen | butyl |
| M556 | thiophen-2-yl | hydrogen | phenyl |
| M557 | thiophen-2-yl | hydrogen | benzyl |
| M558 | thiophen-2-yl | hydrogen | 2-fluorophenyl |
| M559 | thiophen-2-yl | hydrogen | 3-fluorophenyl |
| M560 | thiophen-2-yl | hydrogen | 4-fluorophenyl |

The compounds encompassed within Category VI of the present disclosure can be prepared by the procedure outlined in Scheme XII and described in Example 13 herein below.

Scheme VI

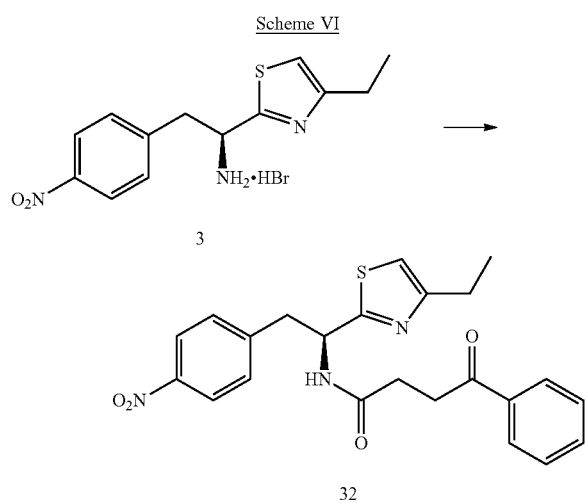

Reagents and conditions: (a) 3-benzoylpropionic acid, SOCl₂, N-methyl imidazole, CH₂Cl₂; rt, 18 hr.

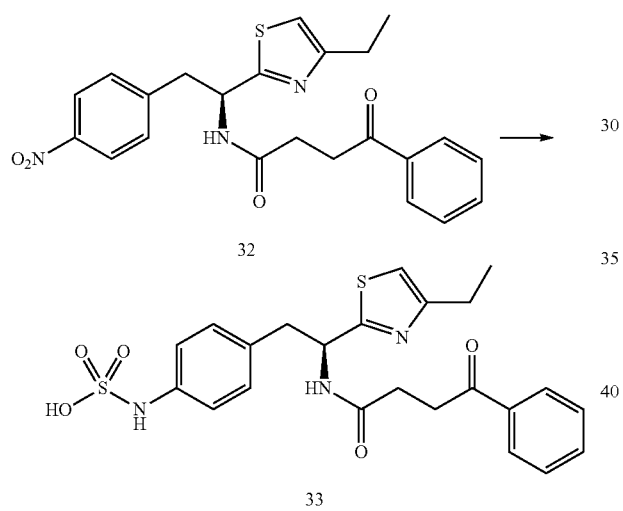

Reagents and conditions: (b) (i) H₂:Pd/C, MeOH; (ii) SO₃-pyridine, NH₄OH.

Example 13

(S)-4-[2-(4-Ethylthiazol-2-yl)-2-(4-oxo-4-phenylbutanamido)ethyl]-phenylsulfamic acid (33)

Preparation of (S)—N-[1-(4-ethylthiazol-2-yl)-2-(4-nitrophenyl)ethyl]-4-oxo-4-phenylbutanamide (32): 3-Benzoylpropionic acid (0.250 g) is dissolved in CH₂Cl₂ (5 mL), N-methyl imidazole (0.333 mL) is added and the resulting solution is cooled to 0° C. after which a solution of thionyl chloride (0.320 g) in CH₂Cl₂ (2 mL) is added dropwise. After 0.5 hours (S)-1-(4-ethylthiazol-2-yl)-2-(4-nitrophenyl)ethanamine, 3, (0.388 g) is added. The reaction is stirred for 18 hours at room temperature and then concentrated in vacuo. The resulting residue is dissolved in EtOAc and washed with 1N HCl and brine. The solution is dried over Na₂SO₄, filtered, and concentrated and the crude material purified over silica to afford 0.415 g of the desired product.

Preparation of (S)-4-[2-(4-ethylthiazol-2-yl)-2-(4-oxo-4-phenylbutanamido)-ethyl]phenylsulfamic acid (33): (S)—N-[1-(4-ethylthiazol-2-yl)-2-(4-nitrophenyl)ethyl]-2,3-diphenyl-propanamide, 32, (0.2 g) is dissolved in MeOH (15 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (5 mL) and treated with SO₃-pyridine (0.153 g). The reaction is stirred at room temperature for 5 minutes after which a 7% solution of NH₄OH is added. The mixture is then concentrated and the resulting residue is purified by reverse phase chromatography to afford 0.090 g of the desired product as the ammonium salt. ¹H NMR (CD₃OD) δ 8.68 (d, 1H, J=8.2 Hz), 8.00 (d, 2H, J=7.2 Hz), 7.80-7.50 (m, 3H), 7.12 (s, 4H), 7.03 (s, 1H), 5.46-5.38 (m, 1H), 3.29-3.14 (m, 2H), 3.06-2.99 (m, 2H), 2.83 (q, 2H, J=7.5 Hz), 2.69-2.54 (m, 2H), 1.33 (t, 3H, J=7.5 Hz).

The following are non-limiting examples of compounds encompassed within Category II of the present disclosure. The intermediate nitro compounds of the following can be prepared by coupling the appropriate 4-oxo-carboxylic acid with intermediate 3 under the conditions described herein above for the formation of intermediate 4 of scheme I.

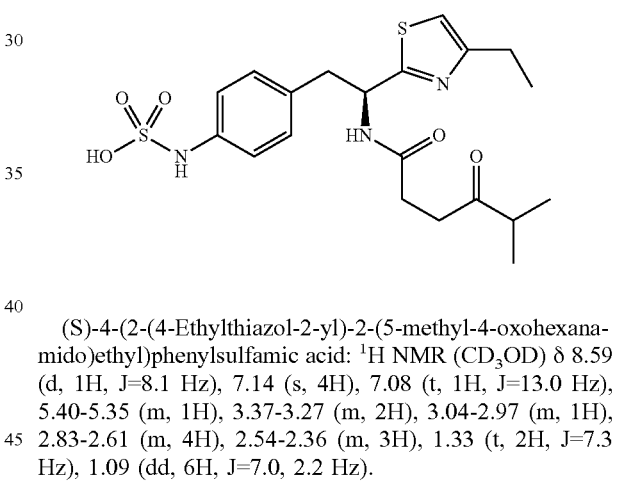

(S)-4-(2-(4-Ethylthiazol-2-yl)-2-(5-methyl-4-oxohexanamido)ethyl)phenylsulfamic acid: ¹H NMR (CD₃OD) δ 8.59 (d, 1H, J=8.1 Hz), 7.14 (s, 4H), 7.08 (t, 1H, J=13.0 Hz), 5.40-5.35 (m, 1H), 3.37-3.27 (m, 2H), 3.04-2.97 (m, 1H), 2.83-2.61 (m, 4H), 2.54-2.36 (m, 3H), 1.33 (t, 2H, J=7.3 Hz), 1.09 (dd, 6H, J=7.0, 2.2 Hz).

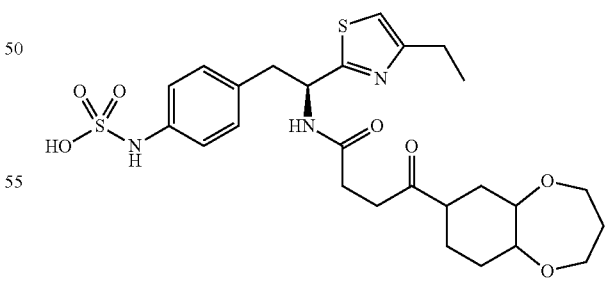

(S)-4-{2-[4-(3,4-Dihydro-2H-benzo[b][1,4]dioxepin-7-yl)-4-oxobutanamido]-2-(4-ethylthiazol-2-yl)ethyl}phenylsulfamic acid: ¹H NMR (CD₃OD) δ 8.64 (d, 1H, J=8.4 Hz), 7.60 (d, 2H, J=10.6 Hz), 7.11 (s, 3H), 7.04 (d, 2H, J=5.5 Hz), 5.42-5.40 (m, 1H), 4.30-4.22 (m, 4H), 3.20-2.98 (m, 4H), 2.82 (q, 2H, J=7.3 Hz), 2.67-2.48 (m, 2H), 2.23 (t, 2H, J=5.5 Hz), 1.32 (t, 3H, J=7.3 Hz).

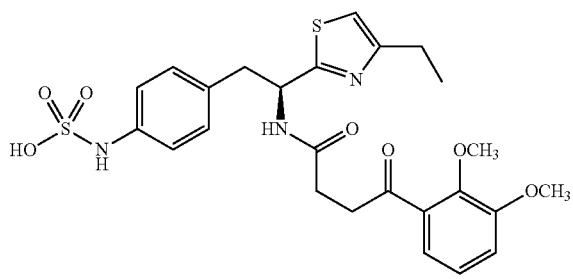 [SMILES: CCc1csc([C@H](Cc2ccc(NS(=O)(=O)O)cc2)NC(=O)CCC(=O)c2cccc(OC)c2OC)n1]

(S)-4-{2-[4-(2,3-Dimethoxyphenyl)-4-oxobutanamido]-2-(4-ethylthiazol-2-yl)ethyl}phenylsulfamic acid: $^1$H NMR (CD$_3$OD), δ 8.64 (d, 1H, J=8.1 Hz), 7.21-7.11 (m, 7H), 7.02 (s, 1H), 5.42 (q, 1H, J=5.9 Hz), 3.90 (d, 3H, J=3.3 Hz), 3.88 (d, 3H, J=2.9 Hz), 3.22-3.18 (m, 2H), 3.07-2.99 (m, 2H), 2.83 (q, 2H, J=7.3 Hz), 2.63-2.54 (m, 2H), 1.34 (t, 3H, J=7.69 Hz).

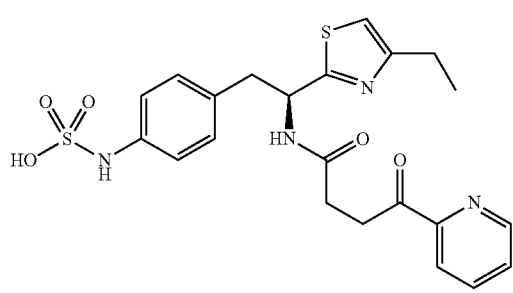 [SMILES: CCc1csc([C@H](Cc2ccc(NS(=O)(=O)O)cc2)NC(=O)CCC(=O)c2ccccn2)n1]

(S)-4-{2-(4-Ethylthiazol-2-yl)-2-[4-oxo-4-(pyridin-2-yl)butanamido]ethyl}-phenylsulfamic acid: $^1$H NMR (CD$_3$OD) δ 8.60 (d, 1H, J=12.8 Hz), 7.91-7.81 (m, 2H), 7.48-7.44 (m, 1H), 7.22-7.21 (m, 1H), 6.99 (s, 3H), 6.91 (s, 1H), 5.30 (q, 1H, J=5.4 Hz), 3.36 (q, 2H, J=7.0 Hz), 3.21-3.15 (m, 1H), 2.91-2.85 (m, 1H), 2.74 (q, 2H, J=10.4 Hz), 2.57-2.50 (m, 2H), 1.20 (t, 3H, J=7.5 Hz).

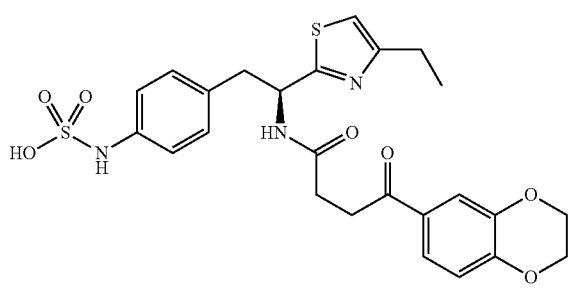 [SMILES: CCc1csc([C@H](Cc2ccc(NS(=O)(=O)O)cc2)NC(=O)CCC(=O)c2ccc3c(c2)OCCO3)n1]

(S)-4-{2-[4-(2,3-dihydrobenzo[b][1,4]dioxin-6-yl)-4-oxobutanamido]-2-(4-ethylthiazol-2-yl)ethyl}phenylsulfamic acid: $^1$H NMR (CD$_3$OD) δ 7.52-7.47 (m, 2H), 7.11 (s, 4H), 7.03 (s, 1H), 6.95 (d, 1H, J=8.4 Hz), 5.41 (q, 1H, J=3.7 Hz), 4.31 (d, 4H, J=5.5 Hz), 3.24-3.12 (m, 2H), 3.06-2.98 (m, 2H), 2.83 (q, 2H, J=7.3 Hz), 2.62-2.53 (m, 2H), 1.33 (t, 3H, J=7.3 Hz).

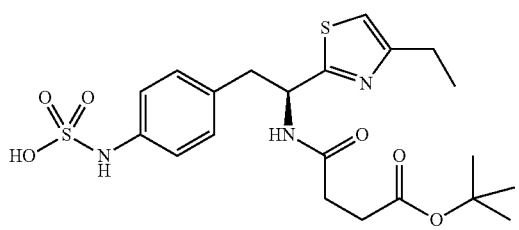 [SMILES: CCc1csc([C@H](Cc2ccc(NS(=O)(=O)O)cc2)NC(=O)CCC(=O)OC(C)(C)C)n1]

(S)-4-[2-(4-tert-butoxy-4-oxobutanamido)-2-(4-ethylthiazol-2-yl)ethyl]phenylsulfamic acid: $^1$H NMR (CD$_3$OD), δ 7.10 (s 4H), 7.02 (s, 1H), 5.41 (q, 1H, J=3.7 Hz), 3.30-3.25 (m, 1H), 3.06-2.99 (m, 1H), 2.83 (q, 2H, J=7.3 Hz), 2.52-2.40 (m, 4H), 1.42 (s, 9H), 1.33 (t, 3H, J=7.3 Hz).

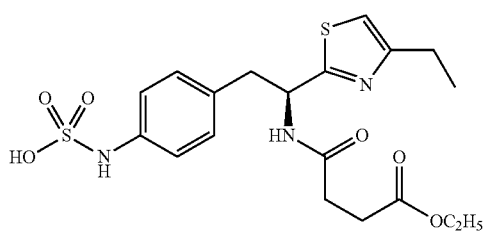 [SMILES: CCOC(=O)CCC(=O)N[C@@H](Cc1ccc(NS(=O)(=O)O)cc1)c1nc(CC)cs1]

(S)-4-[2-(4-ethoxy-4-oxobutanamido)-2-(4-ethylthiazol-2-yl)ethyl]phenylsulfamic acid: $^1$H NMR (CD$_3$OD) δ 8.62 (d, 1H, J=8.4 Hz), 7.10 (s, 4H), 7.02 (s, 1H), 5.40 (q, 1H, 3.7 Hz), 4.15 (q, 2H, J=7.3 Hz), 3.28-3.25 (m, 1H), 3.05-3.02 (m, 1H), 2.82 (q, 2H, J=4.4 Hz), 2.54-2.48 (m, 2H), 1.33 (t, 3H, J=7.3 Hz), 1.24 (t, 3H, J=7.0 Hz).

The first aspect of Category VII of the present disclosure relates to 2-(thiazol-2-yl) compounds having the formula:

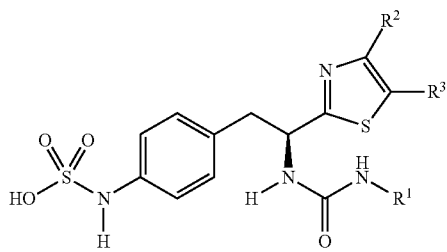

wherein non-limiting examples of R$^1$, R$^2$, and R$^3$ are further described herein below in Table XIV.

TABLE XIV

| No. | R$^2$ | R$^3$ | R$^1$ |
|---|---|---|---|
| N561 | methyl | hydrogen | phenyl |
| N562 | methyl | hydrogen | benzyl |
| N563 | methyl | hydrogen | 2-fluorophenyl |
| N564 | methyl | hydrogen | 3-fluorophenyl |
| N565 | methyl | hydrogen | 4-fluorophenyl |
| N566 | methyl | hydrogen | 2-chlorophenyl |
| N567 | methyl | hydrogen | 3-chlorophenyl |
| N568 | methyl | hydrogen | 4-chlorophenyl |
| N569 | ethyl | hydrogen | phenyl |
| N570 | ethyl | hydrogen | benzyl |
| N571 | ethyl | hydrogen | 2-fluorophenyl |
| N572 | ethyl | hydrogen | 3-fluorophenyl |
| N573 | ethyl | hydrogen | 4-fluorophenyl |
| N574 | ethyl | hydrogen | 2-chlorophenyl |

TABLE XIV-continued

| No. | R² | R³ | R¹ |
|-----|-----|-----|-----|
| N575 | ethyl | hydrogen | 3-chlorophenyl |
| N576 | ethyl | hydrogen | 4-chlorophenyl |
| N577 | thiene-2-yl | hydrogen | phenyl |
| N578 | thiene-2-yl | hydrogen | benzyl |
| N579 | thiene-2-yl | hydrogen | 2-fluorophenyl |
| N580 | thiene-2-yl | hydrogen | 3-fluorophenyl |
| N581 | thiene-2-yl | hydrogen | 4-fluorophenyl |
| N582 | thiene-2-yl | hydrogen | 2-chlorophenyl |
| N583 | thiene-2-yl | hydrogen | 3-chlorophenyl |
| N584 | thiene-2-yl | hydrogen | 4-chlorophenyl |

The compounds encompassed within Category VII of the present disclosure can be prepared by the procedure outlined in Scheme XIII and described in Example 14 herein below.

Scheme XIII

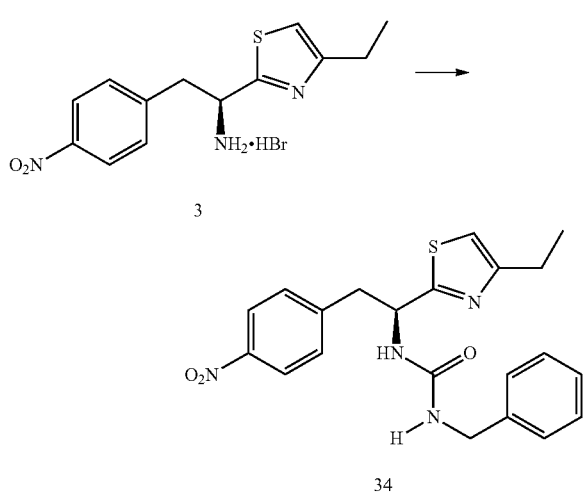

Reagents and conditions: (a) benzyl isocyanate, TEA, CH$_2$Cl$_2$; rt, 18 hr.

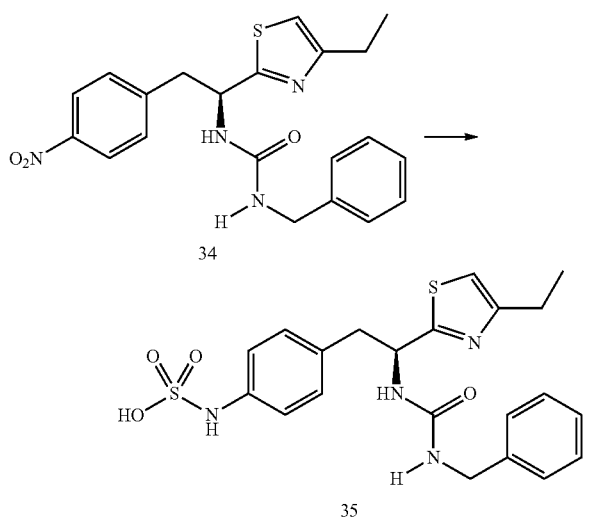

Reagents and conditions: (b) (i) H$_2$:Pd/C, MeOH; (ii) SO$_3$-pyridine, NH$_4$OH.

Example 14

(S)-4-(2-(3-Benzylureido)-2-(4-ethylthiazol-2-yl)ethyl)phenylsulfamic acid (35)

Preparation of (S)-1-benzyl-3-[1-(4-ethylthiazol-2-yl)-2-(4-nitrophenyl)ethyl]urea (34): To a solution of 1-(S)-(4-ethylthiazol-2-yl)-2-(4-nitrophenyl)ethyl amine hydrobromide, 3, (0.360 g, 1 mmol) and Et$_3$N (0.42 mL, 3 mmol) in 10 mL CH$_2$Cl$_2$ is added benzyl isocyanate (0.12 mL, 1 mmol). The mixture is stirred at room temperature for 18 hours. The product is isolated by filtration to afford 0.425 g (96% yield) of the desired product which is used without further purification.

Preparation of (S)-4-(2-(3-benzylureido)-2-(4-ethylthiazol-2-yl)ethyl)phenylsulfamic acid (35): (S)-1-benzyl-3-[1-(4-ethylthiazol-2-yl)-2-(4-nitrophenyl)ethyl]urea, 34, (0.425 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (0.220 g). The reaction is stirred at room temperature for 5 minutes after which a 7% solution of NH$_4$OH is added. The mixture is then concentrated and the resulting residue is purified by reverse phase chromatography to afford 0.143 g of the desired product as the ammonium salt. $^1$H NMR (CD$_3$OD) δ 7.32-7.30 (m, 2H), 7.29-7.22 (m, 3H), 7.12-7.00 (m, 4H), 6.84 (d, 1H, J=8.1 Hz), 5.35-5.30 (m, 1H), 4.29 (s, 2H), 3.27-3.22 (m, 3H), 3.11-3.04 (m, 3H), 2.81 (q, 2H, J=10.2, 13.0 Hz), 1.31 (t, 3H, J=4.5 Hz).

The following is a non-limiting examples of compounds encompassed within the first aspect of Category VII of the present disclosure.

4-{[(S)-2-(2-Ethylthiazol-4-yl)-2-(3-(R)-methoxy-1-oxo-3-phenylpropan-2-yl)ureido]ethyl}phenylsulfamic acid: $^1$H NMR (CD$_3$OD) δ 7.36-7.26 (m, 3H), 7.19-7.17 (m, 2H), 7.10-7.06 (m, 2H), 6.90-6.86 (m, 3H), 5.12-5.06 (m, 1H), 4.60-4.55 (m, 1H), 3.69 (s, 3H) 3.12-2.98 (m, 6H), 1.44-1.38 (m, 3H).

The second aspect of Category VII of the present disclosure relates to 2-(thiazol-4-yl) compounds having the formula:

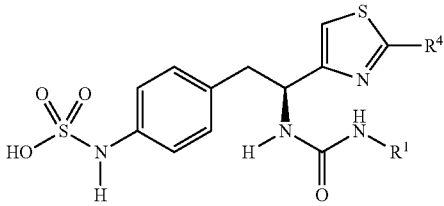

wherein non-limiting examples of R¹ and R⁴ are further described herein below in Table XV.

TABLE XV

| No. | R¹ | R⁴ |
|-----|-----|-----|
| O585 | Methyl | methyl |
| O586 | Ethyl | methyl |
| O587 | n-propyl | methyl |
| O588 | iso-propyl | methyl |
| O589 | Phenyl | methyl |

TABLE XV-continued

| No. | R¹ | R⁴ |
|---|---|---|
| O590 | Benzyl | methyl |
| O591 | 2-fluorophenyl | methyl |
| O592 | 2-chlorophenyl | methyl |
| O593 | thiophen-2-yl | methyl |
| O594 | thiazol-2-yl | methyl |
| O595 | oxazol-2-yl | methyl |
| O596 | isoxazol-3-yl | methyl |
| O597 | methyl | ethyl |
| O598 | ethyl | ethyl |
| O599 | n-propyl | ethyl |
| O600 | iso-propyl | ethyl |
| O601 | phenyl | ethyl |
| O602 | benzyl | ethyl |
| O603 | 2-fluorophenyl | ethyl |
| O604 | 2-chlorophenyl | ethyl |
| O605 | thiophen-2-yl | ethyl |
| O606 | thiazol-2-yl | ethyl |
| O607 | oxazol-2-yl | ethyl |
| O608 | isoxazol-3-yl | ethyl |
| O609 | methyl | thiophen-2-yl |
| O610 | ethyl | thiophen-2-yl |
| O611 | n-propyl | thiophen-2-yl |
| O612 | iso-propyl | thiophen-2-yl |
| O613 | phenyl | thiophen-2-yl |
| O614 | benzyl | thiophen-2-yl |
| O615 | 2-fluorophenyl | thiophen-2-yl |
| O616 | 2-chlorophenyl | thiophen-2-yl |
| O617 | thiophen-2-yl | thiophen-2-yl |
| O618 | thiazol-2-yl | thiophen-2-yl |
| O619 | oxazol-2-yl | thiophen-2-yl |
| O620 | isoxazol-3-yl | thiophen-2-yl |
| O621 | methyl | thiazol-2-yl |
| O622 | ethyl | thiazol-2-yl |
| O623 | n-propyl | thiazol-2-yl |
| O624 | iso-propyl | thiazol-2-yl |
| O625 | phenyl | thiazol-2-yl |
| O626 | benzyl | thiazol-2-yl |
| O627 | 2-fluorophenyl | thiazol-2-yl |
| O628 | 2-chlorophenyl | thiazol-2-yl |
| O629 | thiophen-2-yl | thiazol-2-yl |
| O630 | thiazol-2-yl | thiazol-2-yl |
| O631 | oxazol-2-yl | thiazol-2-yl |
| O632 | isoxazol-3-yl | thiazol-2-yl |
| O633 | methyl | oxazol-2-yl |
| O634 | ethyl | oxazol-2-yl |
| O635 | n-propyl | oxazol-2-yl |
| O636 | iso-propyl | oxazol-2-yl |
| O637 | phenyl | oxazol-2-yl |
| O638 | benzyl | oxazol-2-yl |
| O639 | 2-fluorophenyl | oxazol-2-yl |
| O640 | 2-chlorophenyl | oxazol-2-yl |
| O641 | thiophen-2-yl | oxazol-2-yl |
| O642 | thiazol-2-yl | oxazol-2-yl |
| O643 | oxazol-2-yl | oxazol-2-yl |
| O644 | isoxazol-3-yl | oxazol-2-yl |

The compounds encompassed within the second aspect of Category VII of the present disclosure can be prepared by the procedure outlined in Scheme XIV and described in Example 14 herein below.

Scheme XIV

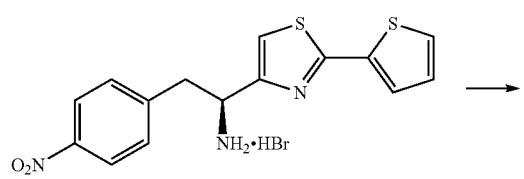

22

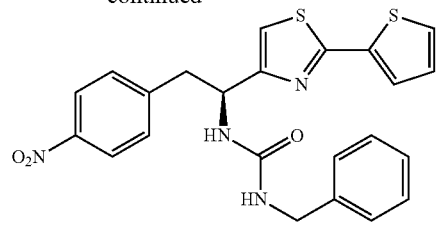

36

Reagents and conditions (a) benzyl isocyanate, TEA, CH₂Cl₂; rt, 18 hr.

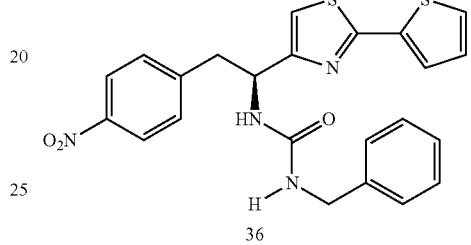

36

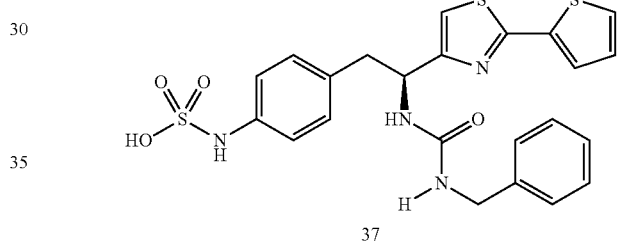

37

Reagents and conditions: (b) (i) H₂:Pd/C, MeOH; (ii) SO₃-pyridine, NH₄OH.

Example 15

4-{(S)-2-(3-Benzylureido)-2-[2-(thiophen-2-yl)thiazol-4-yl]ethyl}-phenylsulfamic acid (37)

Preparation of 1-benzyl-3-{(S)-2-(4-nitrophenyl)-1-[2-(thiophen-2-yl)thiazol-4-yl]ethyl}urea (36): To a solution of (S)-2-(4-nitrophenyl)-1-[(2-thiophen-2-yl)thiazol-4-yl) ethan-amine hydrobromide salt, 8, and Et₃N (0.42 mL, 3 mmol) in 10 mL DCM is added benzyl isocyanate (0.12 mL, 1 mmol). The mixture is stirred at room temperature for 18 hours. The product is isolated by filtration to afford 0.445 g (96% yield) of the desired product which is used without further purification.

Preparation of 4-{(S)-2-(3-benzylureido)-2-[2-(thiophen-2-yl)thiazol-4-yl]ethyl}phenylsulfamic acid (37): 1-Benzyl-3-{(S)-2-(4-nitrophenyl)-1-[2-(thiophen-2-yl)thiazol-4-yl] ethyl}urea, 36, (0.445 g) is dissolved in MeOH (10 mL) and CH₂Cl₂ (5 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO$_3$-pyridine (0.110 g). The reaction is stirred at room temperature for 5 minutes after which a 7% solution of NH$_4$OH is added. The mixture is then concentrated and the resulting residue is purified by reverse phase chromatography to afford 0.080 g of the desired product as the ammonium salt. $^1$H NMR (CD$_3$OD) δ 7.61 (d, 1H, J=2.1 Hz), 7.58 (d, 1H, J=6 Hz), 7.33-7.22 (m, 4H), 7.17-7.14 (m, 1H), 7.09-6.94 (m, 6H), 5.16 (t, 1H, J=6.6 Hz), 4.13 (s, 2H), 3.14-3.11 (m, 2H).

Category VIII of the present disclosure relates to 2-(thiazol-4-yl) compounds having the formula:

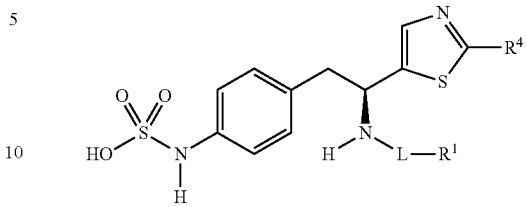

wherein $R^1$, $R^4$, and L are further defined herein in Table XVI herein below.

TABLE XVI

| No. | $R^4$ | L | $R^1$ |
|---|---|---|---|
| P645 | methyl | —SO$_2$— | methyl |
| P646 | ethyl | —SO$_2$— | methyl |
| P647 | phenyl | —SO$_2$— | methyl |
| P648 | thiophen-2-yl | —SO$_2$— | methyl |
| P649 | methyl | —SO$_2$— | trifluoromethyl |
| P650 | ethyl | —SO$_2$— | trifluoromethyl |
| P651 | phenyl | —SO$_2$— | trifluoromethyl |
| P652 | thiophen-2-yl | —SO$_2$— | trifluoromethyl |
| P653 | methyl | —SO$_2$— | ethyl |
| P654 | ethyl | —SO$_2$— | ethyl |
| P655 | phenyl | —SO$_2$— | ethyl |
| P656 | thiophen-2-yl | —SO$_2$— | ethyl |
| P657 | methyl | —SO$_2$— | 2,2,2-trifluoroethyl |
| P658 | ethyl | —SO$_2$— | 2,2,2-trifluoroethyl |
| P659 | phenyl | —SO$_2$— | 2,2,2-trifluoroethyl |
| P660 | thiophen-2-yl | —SO$_2$— | 2,2,2-trifluoroethyl |
| P661 | methyl | —SO$_2$— | phenyl |
| P662 | ethyl | —SO$_2$— | phenyl |
| P663 | phenyl | —SO$_2$— | phenyl |
| P664 | thiophen-2-yl | —SO$_2$— | phenyl |
| P665 | methyl | —SO$_2$— | 4-fluorophenyl |
| P666 | ethyl | —SO$_2$— | 4-fluorophenyl |
| P667 | phenyl | —SO$_2$— | 4-fluorophenyl |
| P668 | thiophen-2-yl | —SO$_2$— | 4-fluorophenyl |
| P669 | methyl | —SO$_2$— | 3,4-dihydro-2H-benzo[b][1,4]oxazin-7-yl |
| P670 | ethyl | —SO$_2$— | 3,4-dihydro-2H-benzo[b][1,4]oxazin-7-yl |
| P671 | phenyl | —SO$_2$— | 3,4-dihydro-2H-benzo[b][1,4]oxazin-7-yl |
| P672 | thiophen-2-yl | —SO$_2$— | 3,4-dihydro-2H-benzo[b][1,4]oxazin-7-yl |
| P673 | methyl | —SO$_2$— | 1-methyl-1H-imidazol-4-yl |
| P674 | ethyl | —SO$_2$— | 1-methyl-1H-imidazol-4-yl |
| P675 | phenyl | —SO$_2$— | 1-methyl-1H-imidazol-4-yl |
| P676 | thiophen-2-yl | —SO$_2$— | 1-methyl-1H-imidazol-4-yl |
| P678 | methyl | —SO$_2$— | 4-acetamidophenyl |
| P679 | ethyl | —SO$_2$— | 4-acetamidophenyl |
| P680 | phenyl | —SO$_2$— | 4-acetamidophenyl |
| P681 | thiophen-2-yl | —SO$_2$— | 4-acetamidophenyl |
| P682 | methyl | —SO$_2$CH$_2$— | phenyl |
| P683 | ethyl | —SO$_2$CH$_2$— | phenyl |
| P684 | phenyl | —SO$_2$CH$_2$— | phenyl |
| P685 | thiophen-2-yl | —SO$_2$CH$_2$— | phenyl |
| P686 | methyl | —SO$_2$CH$_2$— | (4-methylcarboxyphenyl)methyl |
| P687 | ethyl | —SO$_2$CH$_2$— | (4-methylcarboxyphenyl)methyl |
| P688 | phenyl | —SO$_2$CH$_2$— | (4-methylcarboxyphenyl)methyl |
| P689 | thiophen-2-yl | —SO$_2$CH$_2$— | (4-methylcarboxyphenyl)methyl |
| P690 | methyl | —SO$_2$CH$_2$— | (2-methylthiazol-4-yl)methyl |
| P691 | ethyl | —SO$_2$CH$_2$— | (2-methylthiazol-4-yl)methyl |
| P692 | phenyl | —SO$_2$CH$_2$— | (2-methylthiazol-4-yl)methyl |
| P693 | thiophen-2-yl | —SO$_2$CH$_2$— | (2-methylthiazol-4-yl)methyl |
| P694 | methyl | —SO$_2$CH$_2$CH$_2$— | phenyl |
| P695 | ethyl | —SO$_2$CH$_2$CH$_2$— | phenyl |
| P696 | phenyl | —SO$_2$CH$_2$CH$_2$— | phenyl |
| P697 | thiophen-2-yl | —SO$_2$CH$_2$CH$_2$— | phenyl |

The compounds encompassed within Category VIII of the present disclosure can be prepared by the procedure outlined in Scheme XV and described in Example 16 herein below.

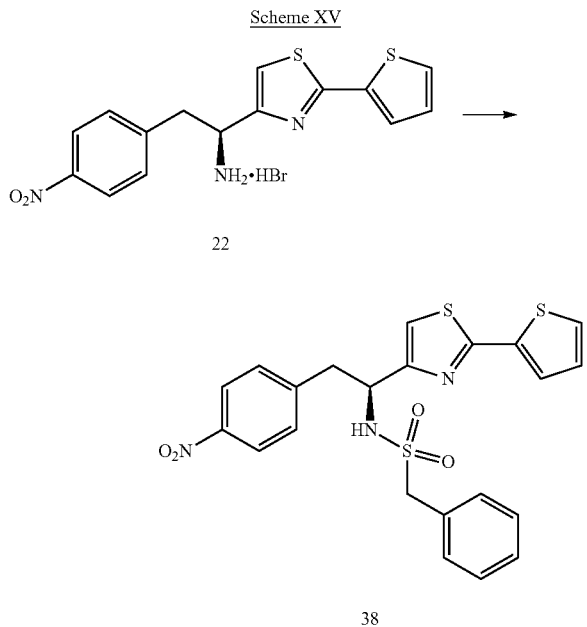

Scheme XV

22

38

Reagents and conditions: (a) C₆H₄CH₂SO₂Cl, DIPEA, CH₂Cl₂; 0° C. to rt, 14 hr.

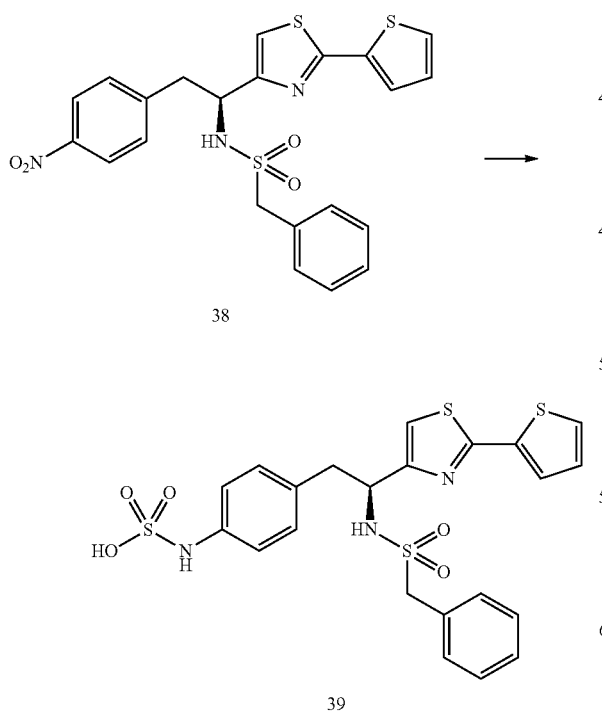

38

39

Reagents and conditions: (b) (i) H₂:Pd/C, MeOH; (ii) SO₃-pyridine, NH₄OH.

Example 16

{4-(S)-[2-Phenylmethanesulfonylamino-2-(2-thiophen-2-ylthiazol-4-yl)ethyl]phenyl}sulfamic acid (39)

Preparation of (S)—N-{2-(4-nitrophenyl)-1-[2-(thiophen-2-yl)thiazol-4-yl]ethyl}-1-phenylmethanesulfonamide (38): To a suspension of 2-(4-nitrophenyl)-1-(2-thiophene2-ylthiazol-4-yl)ethylamine, 8, (330 mg, 0.80 mmol) in CH₂Cl₂ (6 mL) at 0° C. is added diisopropylethylamine (0.30 mL, 1.6 mmol) followed by phenylmethanesulfonyl chloride (167 mg, 0.88 mmol). The reaction mixture is stirred at room temperature for 14 hours. The mixture is diluted with CH₂Cl₂ and washed with sat. NaHCO₃ followed by brine, dried (Na₂SO₄), filtered and concentrated in vacuo. The resulting residue is purified over silica to afford 210 mg of the desired product as a white solid.

Preparation of {4-(S)-[2-phenylmethanesulfonylamino-2-(2-thiophen-2-ylthiazol-4-yl)ethyl]phenyl}sulfamic acid (39): (S)—N-{2-(4-nitrophenyl)-1-[2-(thiophen-2-yl)thiazol-4-yl]ethyl}-1-phenylmethanesulfonamide, 38, (210 mg, 0.41 mmol) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (197 mg, 1.23 mmol). The reaction is stirred at room temperature for 5 minutes after which a 7% solution of NH₄OH is added. The mixture is then concentrated and the resulting residue is purified by reverse phase chromatography to afford 0.060 g of the desired product as the ammonium salt. $^1$H NMR (300 MHz, MeOH-d₄) δ 7.52-7.63 (m, 6.70-7.28 (m, 11H), 4.75 (t, J=7.2 Hz, 1H), 3.95-4.09 (m, 2H), 3.20 (dd, J=13.5 and 7.8 Hz, 1H), 3.05 (dd, J=13.5 and 7.8 Hz, 1H).

Intermediates for use in Step (a) of Scheme XV can be conveniently prepared by the procedure outlined herein below in Scheme XVI and described in Example 17.

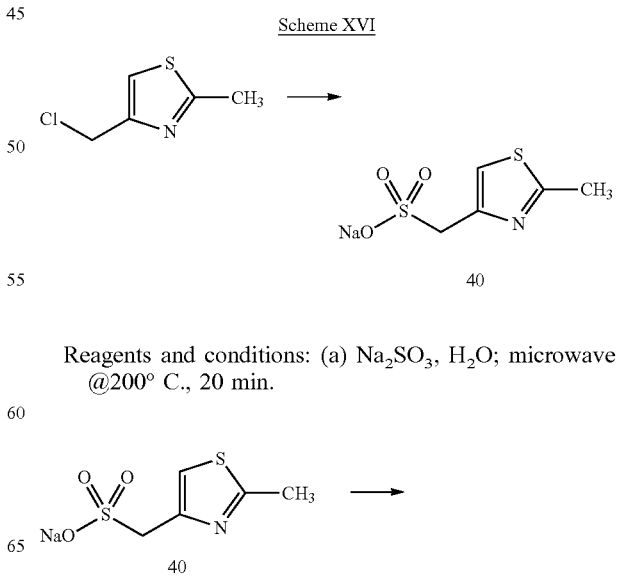

Scheme XVI

40

Reagents and conditions: (a) Na₂SO₃, H₂O; microwave @200° C., 20 min.

40

-continued

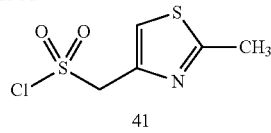

41

Reagents and conditions: (b) PCl₅, POCl₃; 50° C., 3 hrs.

Example 17

(2-Methylthiazol-4-yl)methanesulfonyl chloride (41)

Preparation of sodium (2-methylthiazol-4-yl)methanesulfonate (40): 4-Chloromethyl-2-methylthiazole (250 mg, 1.69 mmol) is dissolved in H₂O (2 mL) and treated with sodium sulfite (224 mg, 1.78 mmol). The reaction mixture is subjected to microwave irradiation for 20 minutes at 200° C. The reaction mixture is diluted with H₂O (30 mL) and washed with EtOAc (2×25 mL). The aqueous layer is concentrated to afford 0.368 g of the desired product as a yellow solid. LC/MS ESI+ 194 (M+1, free acid).

Preparation of (2-methylthiazol-4-yl)methanesulfonyl chloride (41): Sodium (2-methylthiazol-4-yl)methanesulfonate, 40, (357 mg, 1.66 mmol) is dissolved in phosphorous oxychloride (6 mL) and is treated with phosphorous pentachloride (345 mg, 1.66 mmol). The reaction mixture is stirred at 50° C. for 3 hours, then allowed to cool to room temperature. The solvent is removed under reduced pressure and the residue is re-dissolved in CH₂Cl₂ (40 mL) and is washed with sat. NaHCO₃ and brine. The organic layer is dried over MgSO₄, filtered, and the solvent removed in vacuo to afford 0.095 g of the desired product as a brown oil. LC/MS ESI+ 211 (M+1). Intermediates are obtained in sufficient purity to be carried forward according to Scheme IX without the need for further purification.

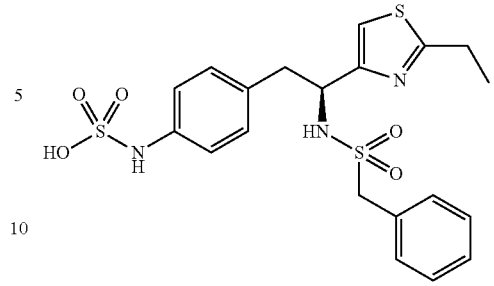

{4-(S)-[2-Phenylmethanesulfonylamino-2-(2-ethylthiazol-4-yl)ethyl]phenyl}-sulfamic acid: ¹H NMR (300 MHz, MeOH-d₄) δ 7.27-7.32 (m, 3H), 7.16-7.20 (m, 3H), 7.05-7.6 (m, 2H), 6.96 (d, J=8.4 Hz, 2H), 4.70 (t, J=9.0 Hz, 1H), 3.91-4.02 (m, 2H), 2.95-3.18 (m, 4H), 1.41 (t, J=7.5 Hz, 3H).

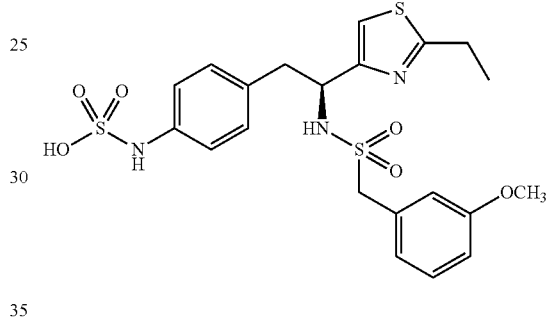

(S)-(4-(2-(2-Ethylthiazol-4-yl)-2-((3-methoxyphenyl)methylsulfonamido)ethyl)-phenyl)sulfamic acid: ¹H NMR (300 MHz, MeOH-d₄) δ 7.20 (t, J=8.1 Hz. 1H), 6.94-7.08 (m, 4H), 6.88-6.94 (m, 3H), 6.75-6.80 (m, 1H), 4.67 (t, J=7.2 Hz, 1H), 3.90-4.0 (m, 2H), 3.76 (s, 3H), 2.95-3.16 (m, 4H), 1.40 (t, J=7.5 HZ, 3H).

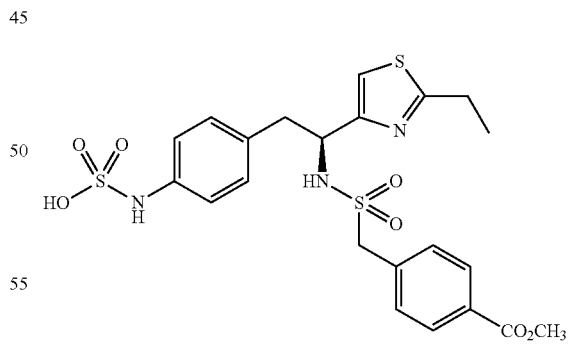

(S)-(4-(2-((2-Methylthiazol-4-yl)methylsulfonamido)-2-(2-(thiophen-2-yl)thiazol-4-yl)ethyl)phenyl)sulfamic acid: ¹H NMR (CD₃OD): δ 7.71-7.66 (m, 2H), 7.27-7.10 (m, 7H), 4.87 (t, 1H, J=7.3 Hz), 4.30-4.16 (q, 2H, J=13.2 Hz), 3.34-3.13 (m, 2H), 2.70 (s, 3H).

The following are non-limiting examples of compounds encompassed within Category VIII of the present disclosure.

(S)-4-{[1-(2-Ethylthiazol-4-yl)-2-(4-sulfoaminophenyl)ethylsulfamoyl]methyl}-benzoic acid methyl ester: ¹H NMR (300 MHz, MeOH-d₄) δ 7.90-7.94- (m, 2H), 7.27-7.30 (m, 2H), 7.06-7.11 (m, 3H), 6.97-7.00 (m, 2H), 4.71 (t, J=7.2 Hz, 1H), 3.95-4.08 (4, 2H), 3.92 (s, 3H), 2.80-3.50 (m, 4H), 1.38-1.44 (m, 3H).

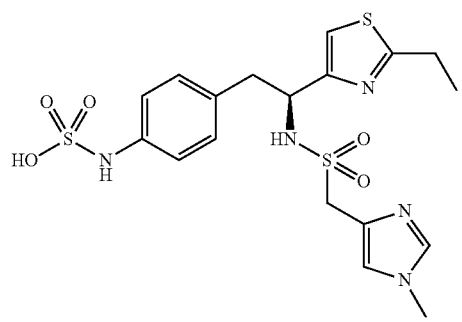 [SMILES: CCc1nc([C@H](Cc2ccc(NS(=O)(=O)O)cc2)NS(=O)(=O)Cc2cn(C)cn2)cs1]

(S)-4-[2-(2-Ethylthiazol-4-yl)-2-(1-methyl-1H-imidazol-4-sulfonamido)ethyl]-phenylsulfamic acid: $^1$H NMR (300 MHz, MeOH-d$_4$) δ 7.54 (s, 1H, 7.20 (s, 1H), 7.09 (s, 1H), 6.92-7.00 (m, 4H), 4.62 (t, J=5.4 Hz, 1H), 3.70 (s, 3H), 2.98-3.14 (m, 3H), 2.79 (dd, J=9.3 and 15.0 Hz, 1H), 1.39 (q, J=7.5 Hz, 3H).

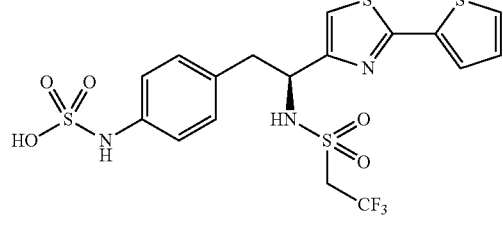

4-{(S)-2-[2-(Thiophen-2-yl)thiazol-4-yl]-2-(2,2,2-trifluoroethylsulfonamido)-ethyl}phenylsulfamic acid: $^1$H NMR (CD$_3$OD): δ 7.62-7.56 (m, 2H), 7.22 (s, 1H), 7.16-7.06 (m, 5H), 4.84 (t, 1H, J=7.6 Hz), 3.71-3.62 (m, 2H), 3.32-3.03 (m, 2H).

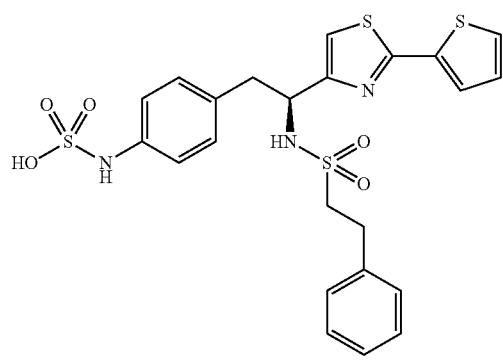 [SMILES: O=S(=O)(O)Nc1ccc(C[C@H](NS(=O)(=O)CCc2ccccc2)c2csc(-c3cccs3)n2)cc1]

{4-(S)-[2-(Phenylethanesulfonylamino)-2-(2thiophen-2-ylthiazol-4-yl)ethyl]-phenyl}sulfamic acid: $^1$H NMR (300 MHz, MeOH-d$_4$) δ 7.56-7.62 (m, 2H), 7.04-7.19 (m, 9H), 6.94-6.97 (m, 2H), 4.78 (t, J=7.8 Hz, 1H), 3.22-3.30 (m, 2H)), 3.11 (dd, J=13.5 and 7.8 Hz, 1H), 2.78-2.87 (m, 4H).

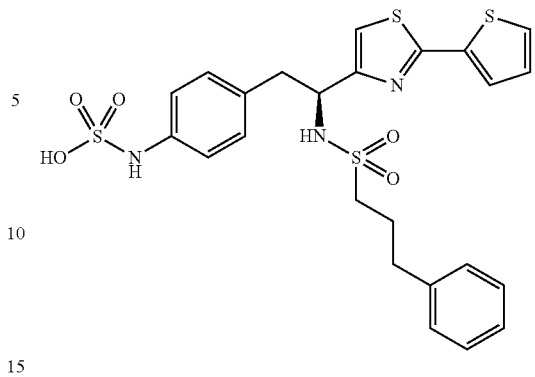

{4-(S)-[3-(Phenylpropanesulfonylamino)-2-(2thiophen-2-ylthiazol-4-yl)ethyl]-phenyl}sulfamic acid: $^1$H NMR (300 MHz, MeOH-d$_4$) δ 7.56-7.62 (m, 2H), 6.99-7.17 (m, 10H), 4.72 (t, J=7.8 Hz, 1H), 3.21 (dd, J=13.5 and 7.2 Hz, 1H), 3.02 (dd, J=13.5 and 7.2 Hz, 1H), 2.39-2.64 (m, 4H), 1.65-1.86 (m, 2H).

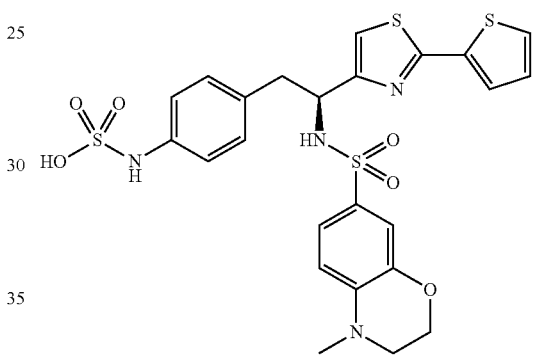

(S)-{4-[2-(4-Methyl-3,4-dihydro-2H-benzo[1,4]oxazine-7-sulfonylamino)-2-(2-thiophen-2-ylthiazol-4-yl)ethyl]phenyl}sulfamic acid: $^1$H NMR (300 MHz, MeOH-d$_4$) δ 7.53 (d, J=5.1 Hz, 1H) 7.48 (d, J=5.1 Hz, 1H), 7.13-7.10 (m, 1H), 7.04 (d, J=8.4 Hz, 2H), 6.93-6.88 (m, 3H), 6.75 (d, J=8.1 Hz, 1H), 6.54 (d, J=8.1 Hz, 1H), 4.61 (t, J=7.5 Hz, 1H), 4.20-4.08 (m, 2H), 3.14-3.00 (m, 4H), 2.69 (s, 3H).

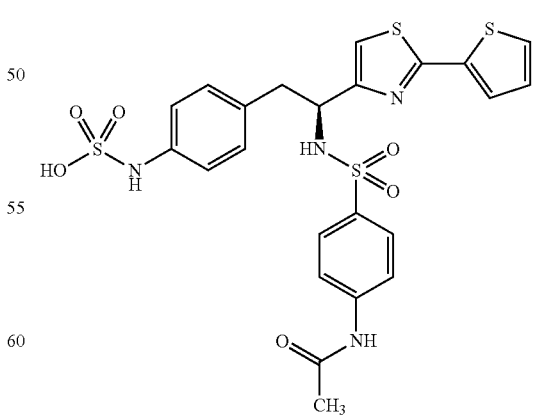

4-{(S)-2-(4-acetamidophenylsulfonamido)-2-[2-(thiophen-2-yl)thiazol-4-yl]ethyl}phenylsulfamic acid: $^1$H NMR (CD$_3$OD): δ 7.67-7.52 (m, 6H), 7.24-7.23 (m, 1H), 7.12-

7.09 (m, 3H), 7.02-6.99 (m, 2H), 4.70 (t, 1H, J=7.3 Hz), 3.25-3.00 (m, 2H), 2.24 (s, 3H).

The first aspect of Category IX of the present disclosure relates to compounds having the formula:

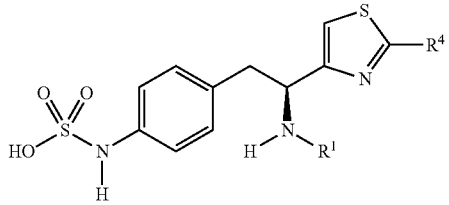

wherein $R^1$ is a substituted or unsubstituted heteroaryl and $R^4$ is $C_1$-$C_6$ linear, branched, or cyclic alkyl as further described herein below in Table XVII.

TABLE XVII

| No. | $R^4$ | $R^1$ |
|---|---|---|
| Q698 | —CH₃ | 4-(methoxycarbonyl)thiazol-5-yl |
| Q699 | —CH₃ | 4-[(2-methoxy-2-oxoethyl)carbamoyl]thiazol-5-yl |
| Q700 | —CH₃ | 5-[1-N-(2-methoxy-2-oxoethyl)-1-H-indol-3-yl]oxazol-2-yl |
| Q701 | —CH₃ | 5-(2-methoxyphenyl)oxazol-2-yl |
| Q702 | —CH₃ | 5-[(S)-1-(tert-butoxycarbonyl)-2-phenylethyl]oxazol-2-yl |
| Q703 | —CH₃ | 5-[4-(methylcarboxy)phenyl]oxazol-2-yl |
| Q704 | —CH₃ | 5-(3-methoxybenzyl)oxazol-2-yl |
| Q705 | —CH₃ | 5-(4-phenyl)oxazol-2-yl |
| Q706 | —CH₃ | 5-(2-methoxyphenyl)thiazol-2-yl |
| Q707 | —CH₃ | 5-(3-methoxyphenyl)thiazol-2-yl |
| Q708 | —CH₃ | 5-(4-fluorophenyl)thiazol-2-yl |
| Q709 | —CH₃ | 5-(2,4-difluorophenyl)thiazol-2-yl |
| Q710 | —CH₃ | 5-(3-methoxybenzyl)thiazol-2-yl |
| Q711 | —CH₃ | 4-(3-methoxyphenyl)thiazol-2-yl |
| Q712 | —CH₃ | 4-(4-fluorophenyl)thiazol-2-yl |
| Q713 | —CH₂CH₃ | 4-(methoxycarbonyl)thiazol-5-yl |
| Q714 | —CH₂CH₃ | 4-[(2-methoxy-2-oxoethyl)carbamoyl]thiazol-5-yl |
| Q715 | —CH₂CH₃ | 5-[1-N-(2-methoxy-2-oxoethyl)-1-H-indol-3-yl]oxazol-2-yl |
| Q716 | —CH₂CH₃ | 5-(2-methoxyphenyl)oxazol-2-yl |
| Q717 | —CH₂CH₃ | 5-[(S)-1-(tert-butoxycarbonyl)-2-phenylethyl]oxazol-2-yl |
| Q718 | —CH₂CH₃ | 5-[4-(methylcarboxy)phenyl]oxazol-2-yl |
| Q719 | —CH₂CH₃ | 5-(3-methoxybenzyl)oxazol-2-yl |
| Q720 | —CH₂CH₃ | 5-(4-phenyl)oxazol-2-yl |
| Q721 | —CH₂CH₃ | 5-(2-methoxyphenyl)thiazol-2-yl |
| Q722 | —CH₂CH₃ | 5-(3-methoxyphenyl)thiazol-2-yl |
| Q723 | —CH₂CH₃ | 5-(4-fluorophenyl)thiazol-2-yl |
| Q724 | —CH₂CH₃ | 5-(2,4-difluorophenyl)thiazol-2-yl |
| Q725 | —CH₂CH₃ | 5-(3-methoxybenzyl)thiazol-2-yl |
| Q726 | —CH₂CH₃ | 4-(3-methoxyphenyl)thiazol-2-yl |
| Q727 | —CH₂CH₃ | 4-(4-fluorophenyl)thiazol-2-yl |
| Q728 | cyclopropyl | 4-(methoxycarbonyl)thiazol-5-yl |
| Q729 | cyclopropyl | 4-[(2-methoxy-2-oxoethyl)carbamoyl]thiazol-5-yl |
| Q730 | cyclopropyl | 5-[1-N-(2-methoxy-2-oxoethyl)-1-H-indol-3-yl]oxazol-2-yl |
| Q731 | cyclopropyl | 5-(2-methoxyphenyl)oxazol-2-yl |
| Q732 | cyclopropyl | 5-[(S)-1-(tert-butoxycarbonyl)-2-phenylethyl]oxazol-2-yl |
| Q733 | cyclopropyl | 5-[4-(methylcarboxy)phenyl]oxazol-2-yl |
| Q734 | cyclopropyl | 5-(3-methoxybenzyl)oxazol-2-yl |
| Q735 | cyclopropyl | 5-(4-phenyl)oxazol-2-yl |
| Q736 | cyclopropyl | 5-(2-methoxyphenyl)thiazol-2-yl |
| Q737 | cyclopropyl | 5-(3-methoxyphenyl)thiazol-2-yl |
| Q738 | cyclopropyl | 5-(4-fluorophenyl)thiazol-2-yl |
| Q739 | cyclopropyl | 5-(2,4-difluorophenyl)thiazol-2-yl |
| Q740 | cyclopropyl | 5-(3-methoxybenzyl)thiazol-2-yl |
| Q741 | cyclopropyl | 4-(3-methoxyphenyl)thiazol-2-yl |
| Q742 | cyclopropyl | 4-(4-fluorophenyl)thiazol-2-yl |

Compounds according to the first aspect of Category IX which comprise a substituted or unsubstituted thiazol-4-yl unit for $R^1$ can be prepared by the procedure outlined in Scheme XVII and described herein below in Example 18.

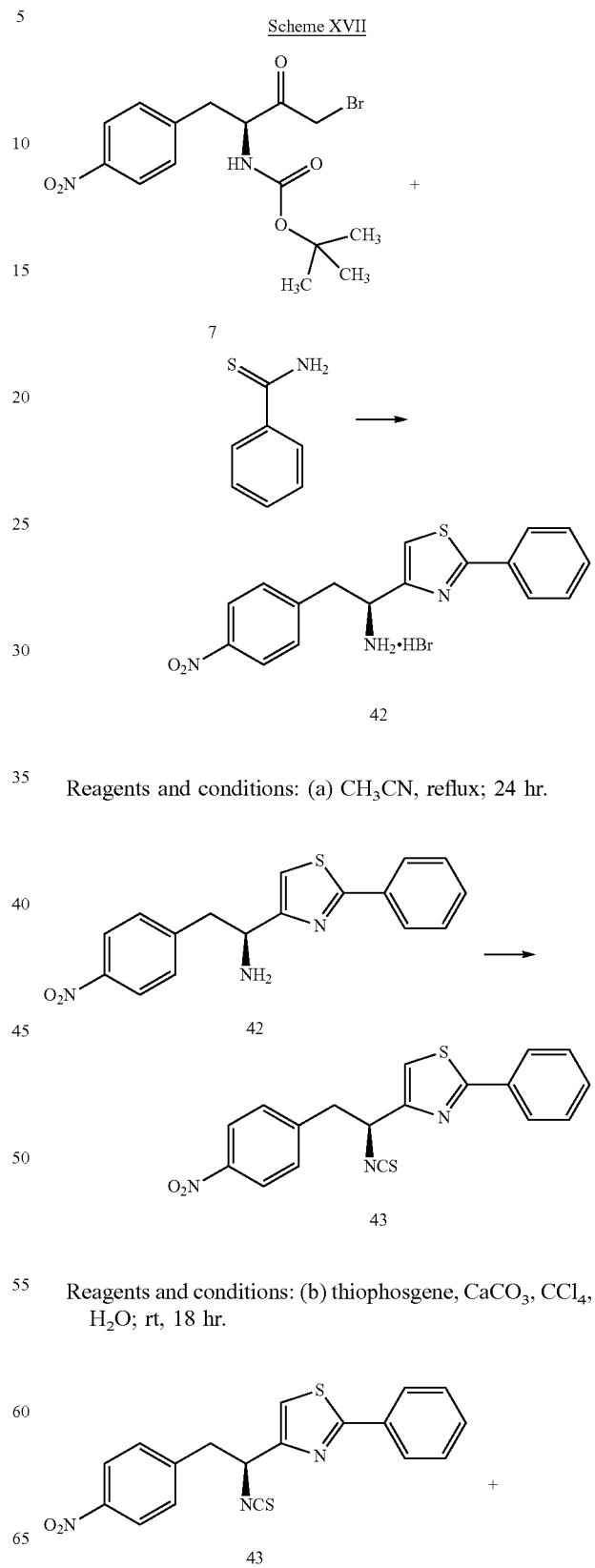

Scheme XVII

Reagents and conditions: (a) CH₃CN, reflux; 24 hr.

Reagents and conditions: (b) thiophosgene, CaCO₃, CCl₄, H₂O; rt, 18 hr.

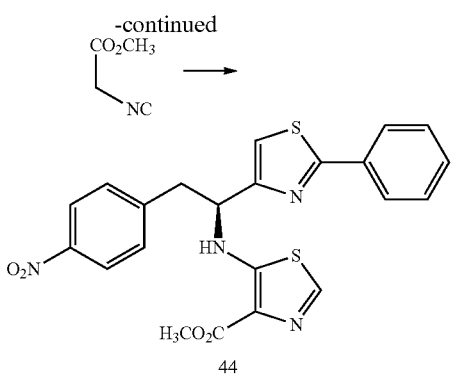

Reagents and conditions: (c) KOtBu, THF; rt, 2 hr.

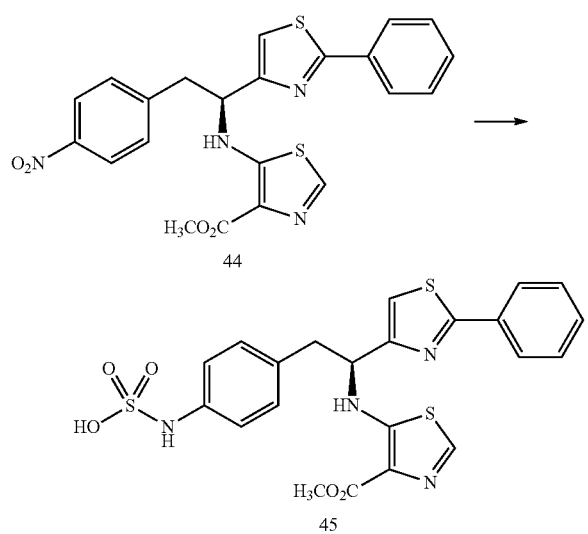

Reagents and conditions: (d) (i) SnCl₂·2H₂O, EtOH; reflux, 4 hours (ii) SO₃-pyridine, NH₄OH.

Example 18

(S)-4-(2-(2-Phenylthiazol-4-yl)2-(4-(methoxycarbonyl)thiazole-5-ylamino)ethyl)phenylsulfamic acid (45)

Preparation of (S)-2-(4-nitrophenyl)-1-(2-phenylthiazol-4-yl)ethanamine hydrobromide salt (42): A mixture of (S)-tert-butyl 4-bromo-1-(4-nitrophenyl)-3-oxobutan-2-ylcarbamate, 7, (1.62 g, 4.17 mmol) and thiobenzamide (0.63 g, 4.60 mmol) in CH₃CN (5 mL) is refluxed for 24 hours. The reaction mixture is cooled to room temperature and diethyl ether (50 mL) is added to the solution. The precipitate which forms is collected by filtration. The solid is dried under vacuum to afford 1.2 g (67% yield) of the desired product. LC/MS ESI+ 326 (M+1).

Preparation of (S)-4-(1-isothiocyanato-2-(4-nitrophenyl)ethyl)-2-phenylthiazole (43): To a solution of (S)-2-(4-nitrophenyl)-1-(2-phenylthiazol-4-yl)ethanamine hydrobromide salt, 42, (726 mg, 1.79 mmol) and CaCO₃ (716 mg, 7.16 mmol) in H₂O (2 mL) is added CCl₄ (3 mL) followed by thiophosgene (0.28 mL, 3.58 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue which is purified over silica (CH₂Cl₂) to afford 480 mg (73%) of the desired product as a yellow solid. ¹H NMR (300 MHz, CDCl₃) δ 8.15 (d, J=8.7 Hz, 2H), 7.97-7.99 (m, 2H), 7.43-7.50 (m, 3H), 7.34 (d, J=8.7 Hz, 2H), 7.15 (d, J=0.9 Hz, 1H), 5.40-5.95 (m, 1H), 3.60 (dd, J=13.8 and 6.0 Hz, 1H), 3.46 (dd, J=13.8 and 6.0 Hz).

Preparation of (S)-methyl 5-[1-(2-phenylthiazol-4-yl)-2-(4-nitrophenyl)-ethylamino]thiazole-4-carboxylate (44): To a suspension of potassium tert-butoxide (89 mg, 0.75 mmol) in THF (3 mL) is added methyl isocyanoacetate (65 μL, 0.68 mmol) followed by (S)-2-phenyl-4-(1-isothiocyanato-2-(4-nitrophenyl)ethyl)thiazole, 43, (250 mg, 0.68 mmol). The reaction mixture is stirred at room temperature for 2 hours then poured into sat. NaHCO₃. The mixture is extracted with EtOAc (3×25 mL) and the combined organic layers are washed with brine and dried (Na₂SO₄) and concentrated in vacuo. The crude residue is purified over silica to afford 323 mg (~100% yield) of the desired product as a slightly yellow solid. ¹H NMR (300 MHz, CDCl₃) δ 8.09-8.13 (m, 2H), 7.95-7.98 (m, 3H), 7.84 (d, J=1.2 Hz, 1H), 7.44-7.50 (m, 3H), 7.28-7.31 (m, 2H), 7.96 (d, J=0.6 Hz, 1H), 4.71-4.78 (m, 1H), 3.92 (s, 3H), 3.60 (dd, J=13.8 and 6.0 Hz, 1H), 3.45 (dd, J=13.8 and 6.0 Hz, 1H).

Preparation of (S)-4-(2-(2-phenylthiazol-4-yl)2-(4-(methoxycarbonyl)thiazole-5-ylamino)ethyl)phenylsulfamic acid (45): (S)-methyl 5-[1-(2-phenylthiazol-4-yl)-2-(4-nitrophenyl)-ethylamino]thiazole-4-carboxylate, 44, (323 mg, 0.68 mmol) and tin (II) chloride (612 mg, 2.72 mmol) are dissolved in EtOH and the solution is brought to reflux. The solvent is removed in vacuo and the resulting residue is dissolved in EtOAc. A saturated solution of NaHCO₃ is added and the solution is stirred 1 hour. The organic layer is separated and the aqueous layer extracted twice with EtOAc. The combined organic layers are dried (Na₂SO₄), filtered and concentrated to a residue which is dissolved in pyridine (10 mL) and treated with SO₃-pyridine (130 mg, 0.82 mmol). The reaction is stirred at room temperature for 5 minutes after which a 7% solution of NH₄OH is added. The mixture is then concentrated and the resulting residue is purified by reverse phase chromatography to afford 0.071 g of the desired product as the ammonium salt ¹H NMR (300 MHz, MeOH-d₄) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

Compounds according to the first aspect of Category IX which comprise a substituted or unsubstituted thiazol-2-yl unit for R¹ can be prepared by the procedure outlined in Scheme XVIII and described herein below in Example 19. Intermediate 46 can be prepared according to Scheme II and Example 2 by substituting cyclopropane-carbothioic acid amide for thiophen-2-carbothioic acid amide.

Scheme XVIII

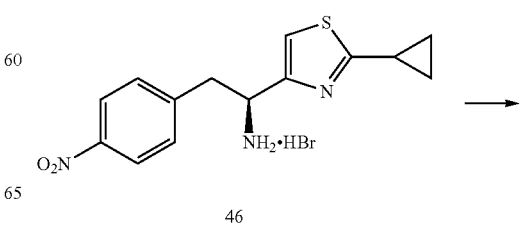

46

111
-continued

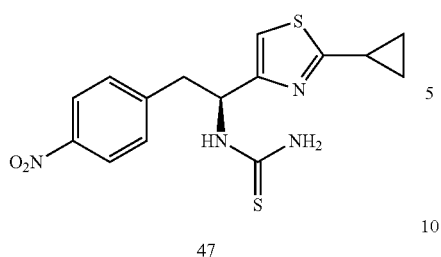
47

Reagents and conditions: (a) thiophosgene, CaCO₃, CCl₄/H₂O; rt, 18 hr.

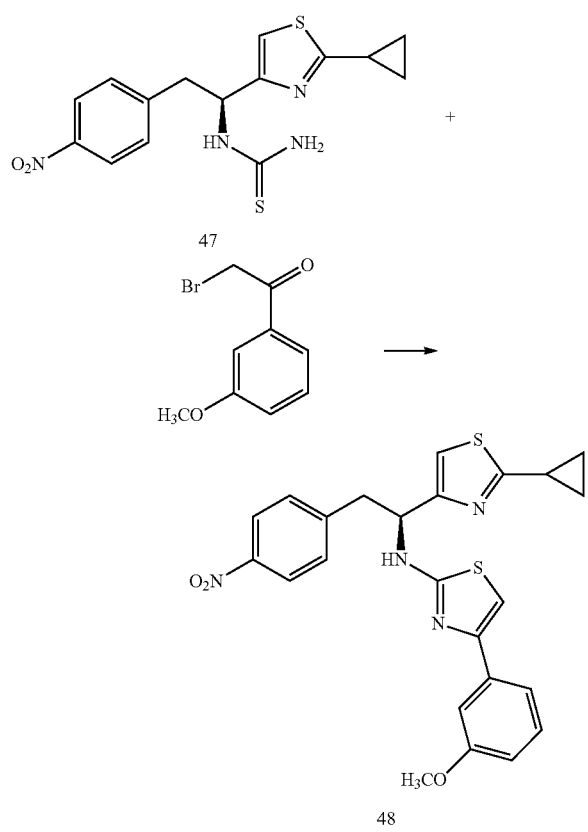

Reagents and conditions: (b) CH₃CN, reflux, 24 hr.

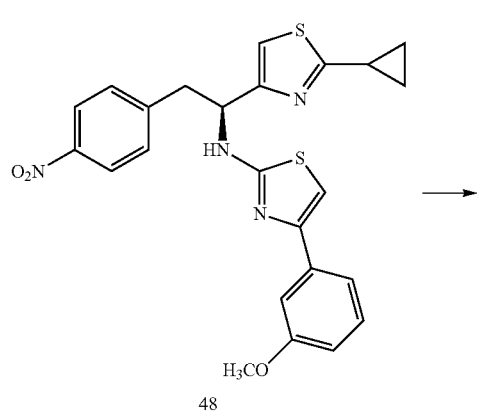
48

112
-continued

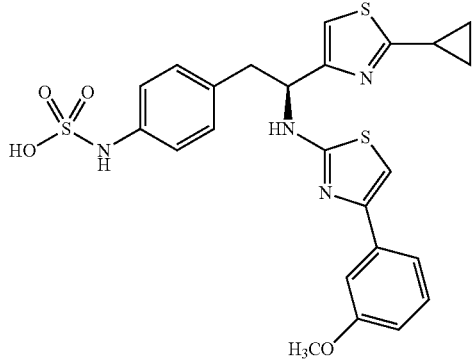
49

Reagents and conditions: (c) (i) H₂:Pd/C, MeOH; (ii) SO₃-pyridine, NH₄OH.

Example 19

4-{(S)-2-(2-Cyclopropylthiazol-4-yl)-2-[4-(3-methoxyphenyl)thiazol-2-ylamino]ethyl}phenylsulfamic acid (50)

Preparation of (S)-1-(1-(2-cyclopropylthiazol-4-yl)-2-(4-nitrophenyl)ethyl)-thiourea (47): To a solution of (S)-1-(2-cyclopropylthiazol-4-yl)-2-(4-nitrophenyl)ethan-amine hydrobromide salt, 32, (4.04 g, 10.9 mmol) and CaCO₃ (2.18 g, 21.8 mmol) in CCl₄/water (25 mL/20 mL) is added thiophosgene (1.5 g, 13.1 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue which is subsequently treated with ammonia (0.5M in 1,4-dioxane, 120 mL) which is purified over silica to afford 2.90 g of the desired product as a red-brown solid. LC/MS ESI-347 (M-1).

Preparation of (S)-4-(3-methoxybenzyl)-N-(1-(2-cyclopropylthiazol-4-yl)-2-(4-nitrophenyl)ethyl)thiazol-2-amine (48): (S)-1-(1-(2-Cyclopropylthiazol-4-yl)-2-(4-nitrophenyl)ethyl)-thiourea, 47, (350 mg, 1.00 mmol) and 2-bromo-3'-methoxyacetophenone (253 mg, 1.10 mmol) are combined in 3 mL CH₃CN and heated to reflux for 24 hours. The mixture is concentrated and chromatographed to afford 0.172 g of the product as a yellow solid. LC/MS ESI+ 479 (M+1).

Preparation of 4-{(S)-2-(2-cyclopropylthiazol-4-yl)-2-[4-(3-methoxyphenyl)-thiazol-2-ylamino]ethyl}phenylsulfamic acid (49): (S)-4-(3-methoxybenzyl)-N-(1-(2-cyclopropylthiazol-4-yl)-2-(4-nitrophenyl)ethyl)thiazol-2-amine, 48, (0.172 g) is dissolved in 10 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 5 mL pyridine and treated with SO₃-pyridine (114 mg). The reaction is stirred at room temperature for 5 minutes after which 10 mL of a 7% solution of NH₄OH is added. The mixture is then concentrated and the resulting residue is purified by reverse-phase chromatography to afford 0.033 g of the desired product as the ammonium salt. ¹H NMR (CD₃OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

The following are non-limiting examples of compounds encompassed within the first aspect of Category IX.

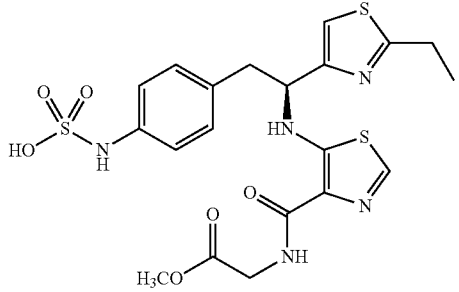 [SMILES: CCc1nc([C@H](Cc2ccc(NS(=O)(=O)O)cc2)Nc2scnc2C(=O)NCC(=O)OC)cs1]

(S)-4-(2-(4-((2-Methoxy-2-oxoethyl)carbamoyl)thiazole-5-ylamino)₂-(2-ethylthiazole-4-yl)ethyl)phenylsulfamic acid: ¹H NMR (300 MHz, MeOH-d₄) δ 7.91 (s, 1H), 7.08-7.10 (m, 3H), 6.99 (d, J=8.7 Hz, 2H), 4.58 (t, J=6.9 Hz, 1H), 4.11 (d, J=2.7 Hz, 2H), 3.78 (s, 3H), 3.14-3.28 (m, 2H), 3.06 (q, J=7.5 Hz, 2H), 1.41 (t, J=7.5 Hz, 3H).

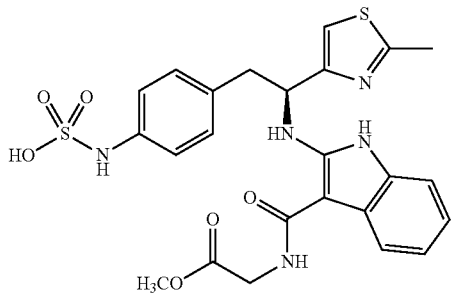 [SMILES: COC(=O)CNC(=O)c1c(N[C@@H](Cc2ccc(NS(=O)(=O)O)cc2)c2csc(C)n2)[nH]c2ccccc12]

(S)-4-(2-{5-[1-N-(2-Methoxy-2-oxoethylcarbamoyl)-1-H-indol-3-yl]oxazol-2-ylamino}-2-(2-methylthiazol-4-yl)ethyl)phenylsulfamic acid: ¹H NMR (300 MHz, MeOH-d₄) δ 7.63 (d, J=7.8 Hz, 1H), 7.37 (s, 1H), 7.18-7.29 (m, 4H), 7.02-7.16 (m, 4H), 6.85 (s, 1H), 5.04-5.09 (m, 1H), 4.85 (s, 3H), 3.27 (dd, J=13.5 and 8.1 Hz, 1H), 3.10 (m, J=13.5 and 8.1 Hz, 1H), 2.69 (s, 3H).

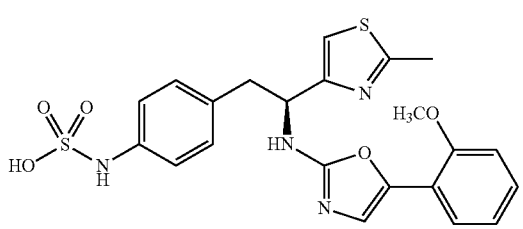 [SMILES: COc1ccccc1-c1cnc(N[C@@H](Cc2ccc(NS(=O)(=O)O)cc2)c2csc(C)n2)o1]

4-((S)-2-(5-(2-Methoxyphenyl)oxazol-2-ylamino)-2-(2-methylthiazol-4-yl)ethyl)phenylsulfamic acid: ¹H NMR (300 MHz, MeOH-d₄) δ 7.52 (dd, J=7.5 and 1.2 Hz, 1H), 6.95-7.24 (m, 10H), 5.04-5.09 (m, 1H), 3.92 (s, 3H), 3.26 (dd, J=13.8 and 8.4 Hz, 1H), 3.10 (dd, J=13.8 and 8.4 Hz, 1H), 2.72 (s, 3H).

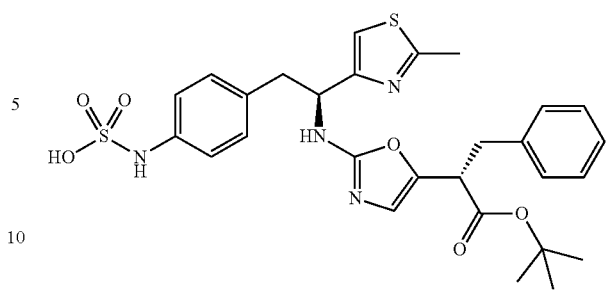

4-((S)-2-(5-((S)-1-(tert-Butoxycarbonyl)-2-phenylethyl)oxazole-2-ylamino)-2-(2-methylthiazole-4-yl)ethyl)phenylsulfamic acid: ¹H NMR (300 MHz, MeOH-d₄) δ 7.03-7.27 (m, 10H), 6.50 (s, 1H), 4.95-5.00 (m, 1H), 4.76 (t, J=6.9 Hz, 1H), 3.22 (dd, J=14.1 and 6.9 Hz, 1H), 3.00-3.10 (m, 2H), 2.90 (dd, J=14.1 and 6.9 Hz, 1H), 2.72 (s, 3H), 1.37 (s, 9H).

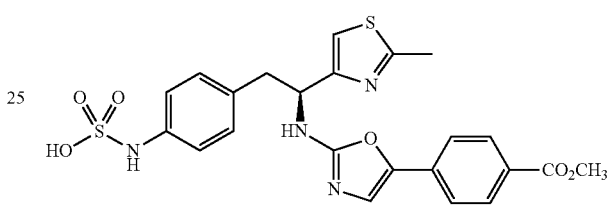

(S)-{4-{2-[5-(4-Methoxycarbonyl)phenyl]oxazol-2-ylamino}-2-(2-methylthiazol-4-yl)ethyl}phenylsulfamic acid: ¹H NMR (300 MHz, MeOH-d₄) δ 7.99 (d, J=7.5 Hz, 2H), 7.56-7.59 (m, 2H), 7.23-7.24 (m, 1H), 7.08-7.14 (m, 4H), 6.83 (d, J=10.2 Hz, 1H), 5.08 (t, J=6.0 Hz, 1H), 3.91 (s, 3H), 3.25-3.35 (m, 1H), 3.09-3.13 (m, 1H), 2.73 (s, 3H).

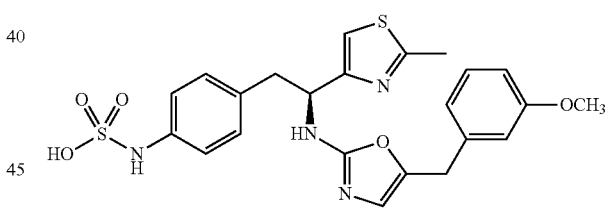

(S)-4-(2-(5-(3-Methoxybenzyl)oxazole-2-ylamino)-2-(2-methylthiazole-4-yl)ethyl)phenylsulfamic acid: ¹H NMR (300 MHz, MeOH-d₄) δ 7.03-7.28 (m, 8H), 6.79-6.83 (m, 1H), 5.70 (s, 1H), 4.99-5.06 (m, 2H), 4.41 (d, J=2.1 Hz, 2H), 3.80 (s, 3H), 3.27-3.37 (m, 1H), 3.03-3.15 (m, 1H), 2.71 (s, 3H).

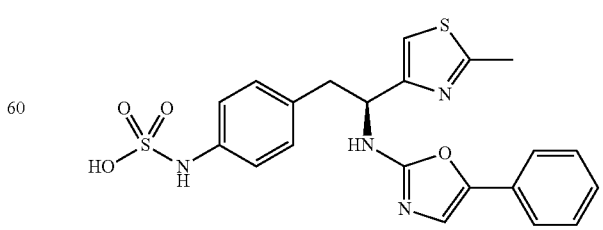

(S)-4-(2-(2-Methylthiazole-4-yl)2-(5-phenyloxazole-2-ylamino)ethyl)phenylsulfamic acid: ¹H NMR (300 MHz, MeOH-d₄) δ 7.45 (d, J=8.7 Hz, 2H), 7.33 (t, J=7.8 Hz, 2H), 7.18-7.22 (m, 1H), 7.10-7.14 (m, 6H), 7.04 (s, 1H), 5.04-5.09 (m, 1H), 3.26 (dd, J=13.8 and 6.3 Hz, 1H), 3.10 (dd, J=13.8 and 6.3 Hz, 1H), 2.70 (s, 3H).

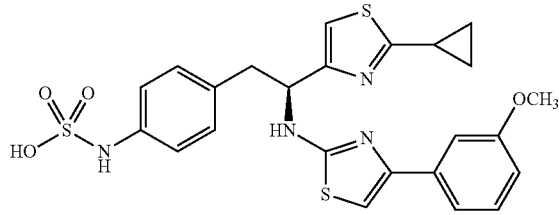 [SMILES: COc1cccc(-c2csc(N[C@@H](Cc3ccc(NS(=O)(=O)O)cc3)c3csc(C4CC4)n3)n2)c1]

4-((S)-2-(2-Cyclopropylthiazol-4-yl)-2-(4-(3-methoxyphenyl)thiazol-2-ylamino)ethyl)phenylsulfamic acid: ¹H NMR (CD₃OD): δ 7.33-7.22 (m, 3H), 7.10-6.97 (m, 5H), 6.84-6.80 (m, 2H), 5.02 (t, 1H, J=6.9 Hz), 3.82 (s, 1H), 3.18 (q, 2H, J=7.1 Hz), 2.36 (q, 1H, J=4.6 Hz), 1.20-1.13 (m, 2H), 1.04-0.99 (m, 2H).

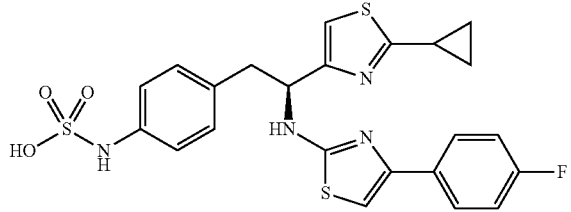 [SMILES: O=S(=O)(O)Nc1ccc(C[C@H](Nc2nc(-c3ccc(F)cc3)cs2)c2csc(C3CC3)n2)cc1]

(S)-4-(2-(2-cyclopropylthiazol-4-yl)-2-(4-(4-fluorophenyl)thiazol-2-ylamino)ethyl)phenylsulfamic acid: ¹H NMR (CD₃OD): δ 7.79-7.74 (m, 2H), 7.14-7.03 (m, 7H), 7.21 (s, 1H), 6.79 (s, 1H), 5.08 (t, 1H, J=6.6 Hz), 3.29-3.12 (m, 2H), 2.40 (q, 2.40, J=5.1 Hz), 1.23-1.18 (m, 2H), 1.08-1.02 (m, 2H).

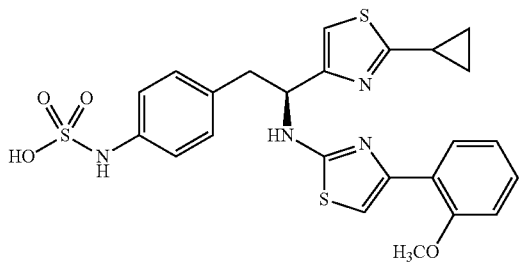 [SMILES: COc1ccccc1-c1csc(N[C@@H](Cc2ccc(NS(=O)(=O)O)cc2)c2csc(C3CC3)n2)n1]

4-((S)-2-(2-cyclopropylthiazol-4-yl)-2-(4-(2-methoxyphenyl)thiazol-2-ylamino)ethyl)phenylsulfamic acid: ¹H NMR (CD₃OD): δ 7.89-7.87 (d, 1H, J=7.6 Hz), 7.28 (t, 1H, J=7.0 Hz), 7.10-6.96 (m, 8H), 5.03 (t, 1H, J=6.9 Hz), 3.90 (s, 1H), 3.19 (q, 2H, J=6.6 Hz), 2.38 (q, 1H, J=4.8 Hz), 1.21-1.14 (m, 2H), 1.06-1.00 (m, 2H).

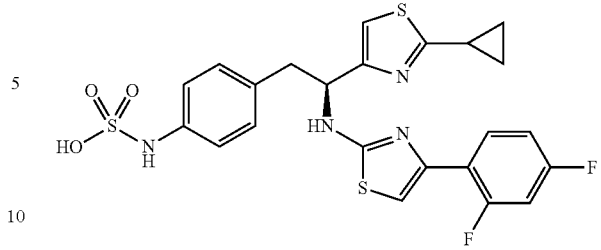

4-((S)-2-(2-cyclopropylthiazol-4-yl)-2-(4-(2,4-difluorophenyl)thiazol-2-ylamino)ethyl)phenylsulfamic acid: ¹H NMR (CD₃OD): δ 8.06-8.02 (q, 2H, J=6.9 Hz), 7.12-6.95 (m, 7H), 6.88 (s, 1H), 5.11 (t, 1H, J=6.9 Hz), 3.22-3.15 (m, 2H), 2.38 (q, 1H, J=4.8 Hz), 1.22-1.15 (m, 2H), 1.06-1.02 (m, 2H).

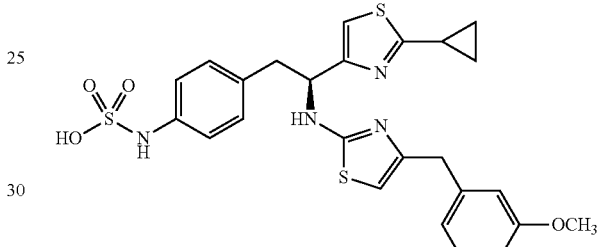

(S)-4-(2-(4-(3-methoxybenzyl)thiazol-2-ylamino)-2-(2-cyclopropylthiazol-4-yl)ethyl)phenylsulfamic acid: ¹H NMR (CD₃OD): δ 7.22-7.17 (m, 3H), 7.09-6.97 (m, 5H), 6.78-6.66 (m, 3H), 3.77 (s, 2H), 3.75 (s, 3H), 3.20-3.07 (m, 2H), 2.35 (q, 1H, J=4.8 Hz), 1.19-1.13 (m, 2H), 1.03-1.00 (m, 2H).

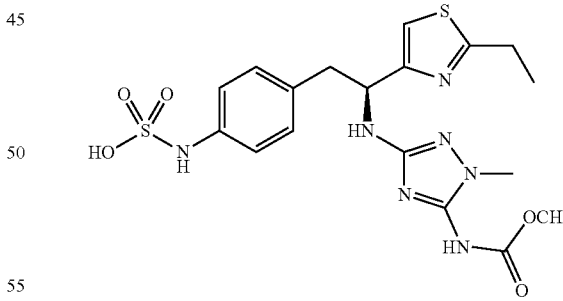

(S)-{5-[1-(2-Ethylthiazol-4-yl)-2-(4-sulfoaminophenyl)ethylamino]-2-methyl-2H-[1,2,4]triazole-3-yl}carbamic acid methyl ester: ¹H NMR (300 MHz, MeOH-d₄) δ 6.97-7.08 (m, 5H), 3.71 (s, 3H), 3.51 (s, 3H), 3.15 (dd, J=13.5 and 6.3 Hz, 1H), 3.02-3.07 (m, 3H), 1.40 (t, J=6.6 Hz, 3H).

The second aspect of Category V of the present disclosure relates to compounds having the formula:

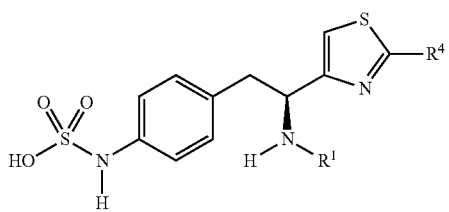

wherein R¹ is a substituted or unsubstituted heteroaryl and R⁴ is substituted or unsubstituted phenyl and substituted or unsubstituted heteroaryl as further described herein below in Table XVIII.

TABLE XVIII

| No. | R⁴ | R¹ |
|---|---|---|
| R743 | phenyl | 4-(methoxycarbonyl)thiazol-5-yl |
| R744 | phenyl | 4-[(2-methoxy-2-oxoethyl)carbamoyl]thiazol-5-yl |
| R745 | phenyl | 5-[1-N-(2-methoxy-2-oxoethyl)-1-H-indol-3-yl]oxazol-2-yl |
| R746 | phenyl | 5-(2-methoxyphenyl)oxazol-2-yl |
| R747 | phenyl | 5-[(S)-1-(tert-butoxycarbonyl)-2-phenylethyl]oxazol-2-yl |
| R748 | phenyl | 5-[4-(methylcarboxy)phenyl]oxazol-2-yl |
| R749 | phenyl | 5-(3-methoxybenzyl)oxazol-2-yl |
| R750 | phenyl | 5-(4-phenyl)oxazol-2-yl |
| R751 | phenyl | 5-(2-methoxyphenyl)thiazol-2-yl |
| R752 | phenyl | 5-(3-methoxyphenyl)thiazol-2-yl |
| R753 | phenyl | 5-(4-fluorophenyl)thiazol-2-yl |
| R754 | phenyl | 5-(2,4-difluorophenyl)thiazol-2-yl |
| R755 | phenyl | 5-(3-methoxybenzyl)thiazol-2-yl |
| R756 | phenyl | 4-(3-methoxyphenyl)thiazol-2-yl |
| R757 | phenyl | 4-(4-fluorophenyl)thiazol-2-yl |
| R758 | thiophen-2-yl | 4-(methoxycarbonyl)thiazol-5-yl |
| R759 | thiophen-2-yl | 4-[(2-methoxy-2-oxoethyl)carbamoyl]thiazol-5-yl |
| R760 | thiophen-2-yl | 5-[1-N-(2-methoxy-2-oxoethyl)-1-H-indol-3-yl]oxazol-2-yl |
| R761 | thiophen-2-yl | 5-(2-methoxyphenyl)oxazol-2-yl |
| R762 | thiophen-2-yl | 5-[(S)-1-(tert-butoxycarbonyl)-2-phenylethyl]oxazol-2-yl |
| R763 | thiophen-2-yl | 5-[4-(methylcarboxy)phenyl]oxazol-2-yl |
| R764 | thiophen-2-yl | 5-(3-methoxybenzyl)oxazol-2-yl |
| R765 | thiophen-2-yl | 5-(4-phenyl)oxazol-2-yl |
| R766 | thiophen-2-yl | 5-(2-methoxyphenyl)thiazol-2-yl |
| R767 | thiophen-2-yl | 5-(3-methoxyphenyl)thiazol-2-yl |
| R768 | thiophen-2-yl | 5-(4-fluorophenyl)thiazol-2-yl |
| R769 | thiophen-2-yl | 5-(2,4-difluorophenyl)thiazol-2-yl |
| R770 | thiophen-2-yl | 5-(3-methoxybenzyl)thiazol-2-yl |
| R771 | thiophen-2-yl | 4-(3-methoxyphenyl)thiazol-2-yl |
| R772 | thiophen-2-yl | 4-(4-fluorophenyl)thiazol-2-yl |
| R773 | cyclopropyl | 4-(methoxycarbonyl)thiazol-5-yl |
| R774 | cyclopropyl | 4-[(2-methoxy-2-oxoethyl)carbamoyl]thiazol-5-yl |
| R775 | cyclopropyl | 5-[1-N-(2-methoxy-2-oxoethyl)-1-H-indol-3-yl]oxazol-2-yl |
| R776 | cyclopropyl | 5-(2-methoxyphenyl)oxazol-2-yl |
| R777 | cyclopropyl | 5-[(S)-1-(tert-butoxycarbonyl)-2-phenylethyl]oxazol-2-yl |
| R778 | cyclopropyl | 5-[4-(methylcarboxy)phenyl]oxazol-2-yl |
| R779 | cyclopropyl | 5-(3-methoxybenzyl)oxazol-2-yl |
| R780 | cyclopropyl | 5-(4-phenyl)oxazol-2-yl |
| R781 | cyclopropyl | 5-(2-methoxyphenyl)thiazol-2-yl |
| R782 | cyclopropyl | 5-(3-methoxyphenyl)thiazol-2-yl |
| R783 | cyclopropyl | 5-(4-fluorophenyl)thiazol-2-yl |
| R784 | cyclopropyl | 5-(2,4-difluorophenyl)thiazol-2-yl |
| R785 | cyclopropyl | 5-(3-methoxybenzyl)thiazol-2-yl |
| R786 | cyclopropyl | 4-(3-methoxyphenyl)thiazol-2-yl |
| R787 | cyclopropyl | 4-(4-fluorophenyl)thiazol-2-yl |

Compounds according to the second aspect of Category IX which comprise a substituted or unsubstituted thiazol-4-yl unit for R¹ can be prepared by the procedure outlined in Schemes XIX, XX, and XXI and described herein below in Examples 20, 21, and 22.

Scheme XIX

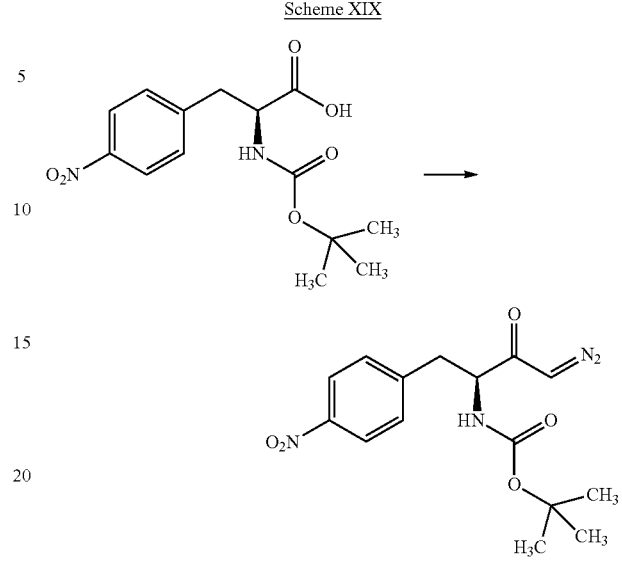

Reagents and conditions: (a)(i) (iso-butyl)OCOCl, Et₃N, THF; 0° C., 20 min. (ii) CH₂N₂; 0° C. to room temp for 3 hours.

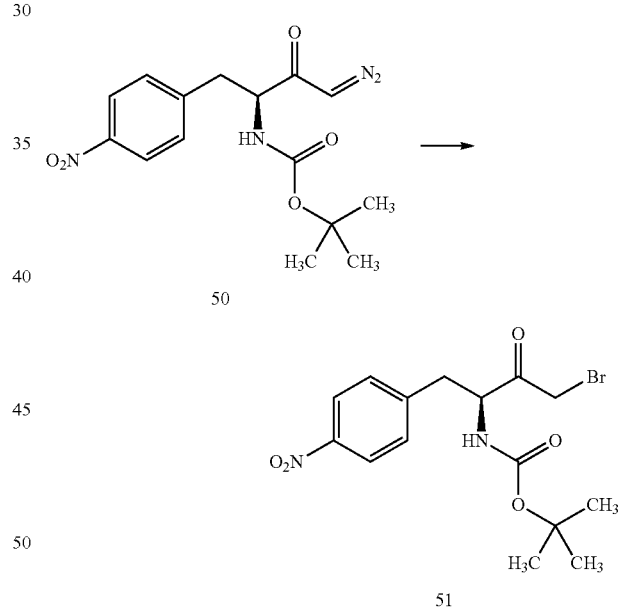

Reagents and conditions: (b) 48% HBr, THF; 0° C., 1.5 hr.

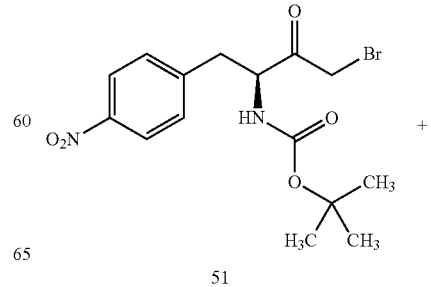

51

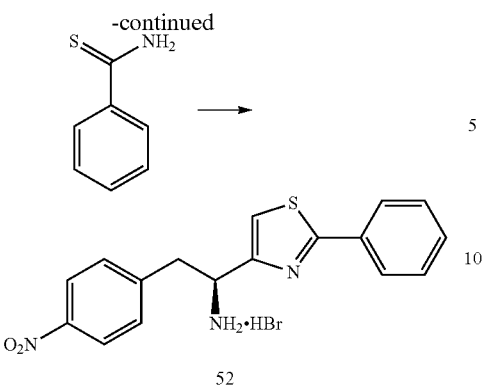

52

Reagents and conditions: (c) CH₃CN; reflux 2 hr.

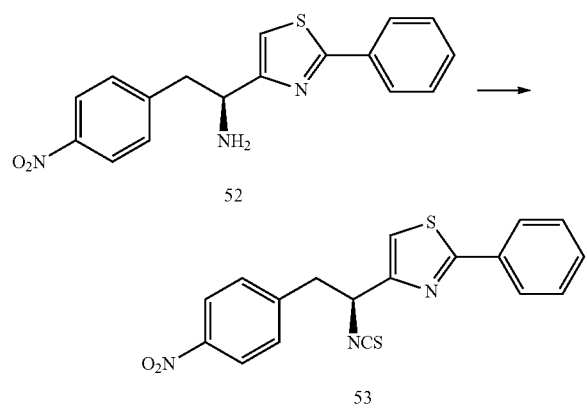

Reagents and conditions: (d) thiophosgene, CaCO₃, CCl₄, H₂O; rt, 18 hr.

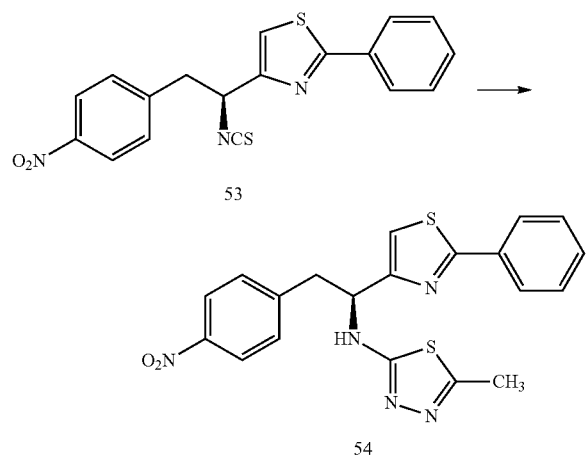

Reagents and conditions: (e)(i) CH₃C(O)NHNH₂, EtOH; reflux, 2 hr. (ii) POCl₃, rt 18 hr; 50° C. 2 hr.

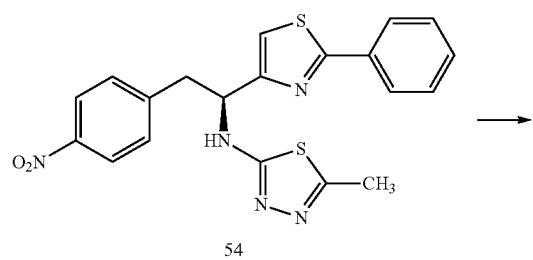

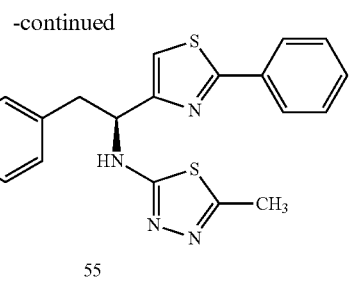

55

Reagents and conditions: (f) (i) H₂:Pd/C, MeOH; (ii) SO₃-pyridine, NH₄OH.

Example 20

(S)-4-(2-(5-Methyl-1,3,4-thiadiazol-2-ylamino)-2-(2-phenylthiazol-4-yl)ethyl)phenylsulfamic acid (55)

Preparation of [3-diazo-1-(4-nitrobenzyl)-2-oxo-propyl]-carbamic acid tert-butyl ester (50): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by iso-butyl chloroformate (0.57 mL, 4.4 mmol). The reaction mixture is stirred at 0° C. for 20 minutes then filtered. The filtrate is treated with an ether solution of diazomethane (~16 mmol) at 0° C. The reaction mixture is stirred at room temperature for 3 hours and concentrated. The residue is dissolved in EtOAc and washed successively with water and brine, dried (Na₂SO₄), filtered and concentrated in vacuo. The resulting residue is purified over silica (hexane/EtOAc 2:1) to afford 1.1 g (82% yield) of the desired product as a slightly yellow solid. ¹H NMR (300 MHz, CDCl₃) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of [3-bromo-1-(4-nitro-benzyl)-2-oxo-propyl]-carbamic acid tert-butyl ester (51): To a 0° C. solution of [3-diazo-1-(4-nitrobenzyl)-2-oxo-propyl]-carbamic acid tert-butyl ester, 50, (0.350 g, 1.04 mmol) in THF (5 mL) is added dropwise 48% aq. HBr (0.14 mL, 1.25 mmol). The reaction mixture is stirred at 0° C. for 1.5 hours and quenched at 0° C. with saturated aqueous Na₂CO₃. The mixture is extracted with EtOAc (3×25 mL) and the combined organic extracts are washed with brine, dried (Na₂SO₄), filtered and concentrated in vacuo to afford 0.400 g of the desired product that is used in the next step without further purification. ¹H NMR (300 MHz, CDCl₃) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of (S)-2-(4-nitrophenyl)-1-(2-phenylthiazol-4-yl)ethanamine hydrobromide salt (52): A mixture of [3-bromo-1-(4-nitro-benzyl)-2-oxo-propyl]-carbamic acid tert-butyl ester, 51, (1.62 g, 4.17 mmol) and benzothioamide (0.630 g, 4.59 mmol), in CH₃CN (5 mL) is refluxed for 24 hours. The reaction mixture is cooled to room temperature and diethyl ether (50 mL) is added to the solution and the precipitate that forms is collected by filtration. The solid is dried under vacuum to afford 1.059 g (63%) of the desired product. ESI+ MS 326 (M+1).

Preparation of (S)-4-[1-isothiocyanato-2-(4-nitrophenyl)-ethyl]-2-phenylthiazole (53): To a solution of (S)-2-(4-nitrophenyl)-1-(2-phenylthiazol-4-yl)ethanamine hydrobromide salt, 52, (2.03 g, 5 mmol) and CaCO₃ (1 g, 10 mmol) in CCl₄/water (10:7.5 mL) is added thiophosgene (0.46 mL, 6 mmol). The reaction is stirred at room temperature for 18 hours then diluted with CH₂Cl₂ and water. The layers are separated and the aqueous layer extracted with CH₂Cl₂. The combined organic layers are washed with brine, dried (Na₂SO₄) and concentrated in vacuo to a residue that is purified over silica (CH₂Cl₂) to afford 1.71 g (93% yield) of the desired product. ESI+ MS 368 (M+1).

Preparation of (S)-5-methyl-N-[2-(4-nitrophenyl)-1-(2-phenylthiazol-4-yl)ethyl]-1,3,4-thiadiazol-2-amine (54): A solution of (S)-4-[1-isothiocyanato-2-(4-nitrophenyl)-ethyl]-2-phenylthiazole, 53, (332 mg, 0.876 mmol) and acetic hydrazide (65 mg, 0.876 mmol) in EtOH (5 mL) is refluxed for 2 hours. The solvent is removed under reduced pressure, the residue is dissolved in POCl₃ (3 mL) and the resulting solution is stirred at room temperature for 18 hours after which the solution is heated to 50° C. for 2 hours. The solvent is removed in vacuo and the residue is dissolved in EtOAc (40 mL) and the resulting solution is treated with 1N NaOH until the pH remains approximately 8. The solution is extracted with EtOAc. The combined aqueous layers are washed with EtOAc, the organic layers combined, washed with brine, dried over MgSO₄, filtered, and concentrated in vacuo to afford 0.345 g (93% yield) of the desired product as a yellow solid. ¹H NMR (CDCl₃) 8.09 (d, J=8.4 Hz, 2H), 7.91 (m, 2H), 7.46 (m, 4H), 7.44 (s, 1H), 5.23 (m, 1H), 3.59 (m, 2H), 2.49 (s, 3H). ESI+ MS 424 (M+1).

Preparation of (S)-4-[2-(5-methyl-1,3,4-thiadiazol-2-ylamino)-2-(2-phenylthiazol-4-yl)ethyl]phenylsulfamic acid (55): (S)-5-Methyl-N-[2-(4-nitrophenyl)-1-(2-phenylthiazol-4-yl)ethyl]-1,3,4-thiadiazol-2-amine, 54, (0.404 g, 0.954 mmol) is dissolved in MeOH (5 mL). Pd/C (50 mg, 10% w/w) is added and the mixture is stirred under a hydrogen atmosphere until the reaction is judged to be complete. The reaction mixture is filtered through a bed of CELITE™ and the solvent removed under reduced pressure. The crude product is dissolved in pyridine (4 mL) and treated with SO₃-pyridine (0.304 g, 1.91 mmol). The reaction is stirred at room temperature for 5 minutes after which a 7% solution of NH₄OH (50 mL) is added. The mixture is then concentrated and the resulting residue is purified by reverse phase preparative HPLC to afford 0.052 g (11% yield) of the desired product as the ammonium salt. ¹H NMR (CD₃OD): δ 8.00-7.97 (m, 2H), 7.51-7.47 (m, 3H), 7.23 (s, 1H), 7.11-7.04 (q, 4H, J=9.0 Hz), 5.18 (t, 1H, J=7.2 Hz), 3.34-3.22 (m, 2H), 2.50 (s, 3H). ESI– MS 472 (M–1).

Scheme XX

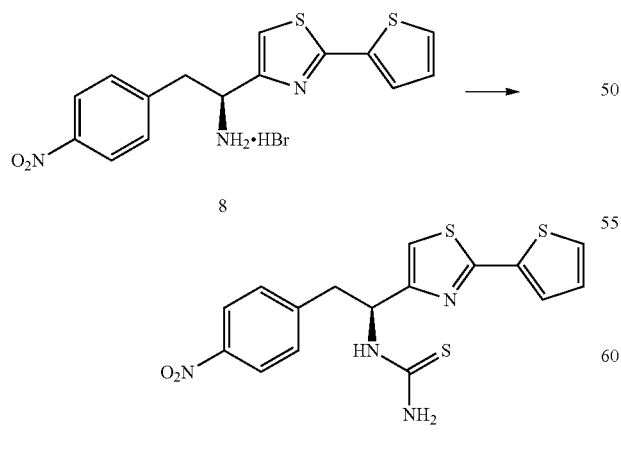

Reagents and conditions: (a) thiophosgene, CaCO₃, CCl₄/H₂O; rt, 18 hr.

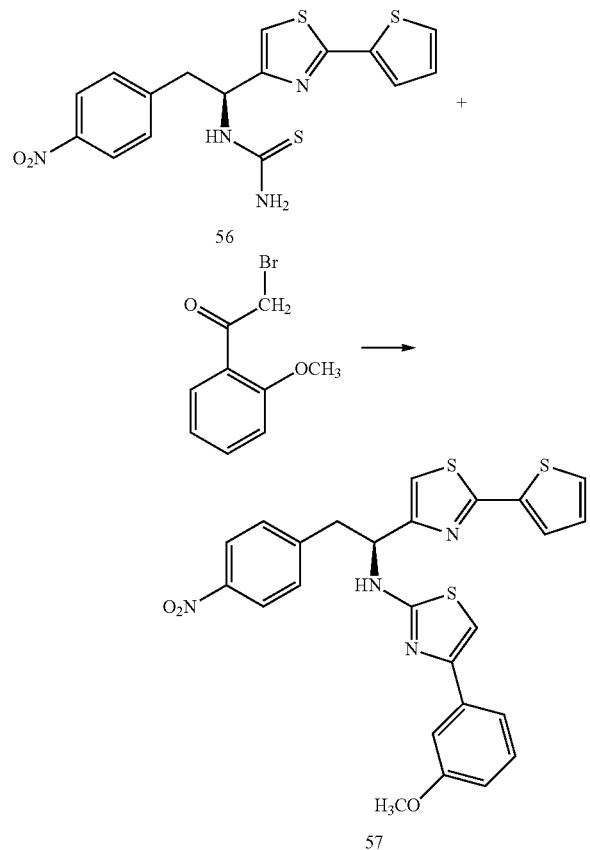

Reagents and conditions: (b) CH₃CN, reflux, 5 hours

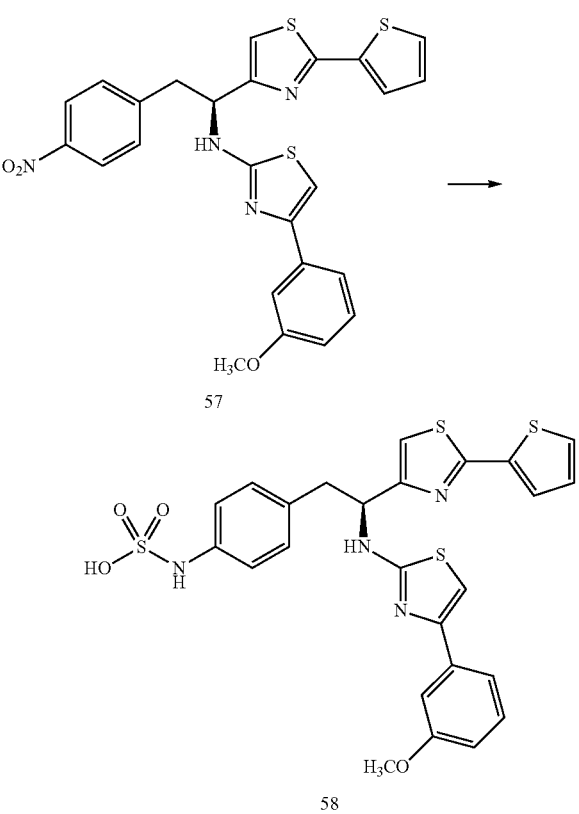

Reagents and conditions: (c) (i) H$_2$:Pd/C, MeOH; (ii) SO$_3$-pyridine, NH$_4$OH; rt, 18 hr.

Example 21

4-{(S)-2-[4-(2-Methoxyphenyl)thiazol-2-ylamino)-2-[2-(thiophen-2-yl)thiazol-4-yl]ethyl}phenylsulfamic acid (58)

Preparation of (S)-1-[1-(thiophen-2-ylthiazol-4-yl)-2-(4-nitrophenyl)ethyl]-thiourea (56): To a solution of (S)-2-(4-nitrophenyl)-1-(thiophen-2-ylthiazol-4-yl)ethanamine hydrobromide salt, 8, (1.23 g, 2.98 mmol) and CaCO$_3$ (0.597 g, 5.96 mmol) in CCl$_4$/water (10 mL/5 mL) is added thiophosgene (0.412 g, 3.58 mmol). The reaction is stirred at room temperature for 18 hours then diluted with CH$_2$Cl$_2$ and water. The layers are separated and the aqueous layer extracted with CH$_2$Cl$_2$. The combined organic layers are washed with brine, dried (Na$_2$SO$_4$) and concentrated in vacuo to a residue which is subsequently treated with ammonia (0.5M in 1,4-dioxane, 29.4 mL, 14.7 mmol) which is purified over silica to afford 0.490 g of the desired product as a red-brown solid. ESI+ MS 399 (M+1).

Preparation of 4-(2-methoxyphenyl)-N—{(S)-2-(4-nitrophenyl)-1-[2-(thiophen-2-yl)thiazol-4-yl]ethyl}thiazol-2-amine (57): (S)-1-[1-(thiophen-2-ylthiazol-4-yl)-2-(4-nitrophenyl)ethyl]-thiourea, 56, (265 mg, 0.679 mmol) is treated with bromo-2'-methoxyacetophenone (171 mg, 0.746 mmol) to afford 0.221 g of the product as a yellow solid. ESI+ MS 521 (M+1).

Preparation on 4-{(S)-2-[4-(2-methoxyphenyl)thiazol-2-ylamino)-2-[2-(thiophen-2-yl)thiazol-4-yl]ethyl}phenylsulfamic acid (58): 4-(2-methoxyphenyl)-N—{(S)-2-(4-nitrophenyl)-1-[2-(thiophen-2-yl)thiazol-4-yl]ethyl}thiazol-2-amine, 57, (0.229 g) is dissolved in 12 mL MeOH. A catalytic amount of Pd/C (10% w/w) is added and the mixture is stirred under a hydrogen atmosphere for 18 hours. The reaction mixture is filtered through a bed of CELITE™ and the solvent is removed under reduced pressure. The crude product is dissolved in 6 mL pyridine and treated with SO$_3$-pyridine (140 mg). The reaction is stirred at room temperature for 5 minutes after which 10 mL of a 7% solution of NH$_4$OH is added. The mixture is then concentrated and the resulting residue is purified by reverse-phase chromatography to afford 0.033 g of the desired product as the ammonium salt. $^1$H NMR (CD$_3$OD): δ 7.96-7.93 (m, 1H), 7.60-7.55 (m, 2H), 7.29-7.23 (m, 1H), 7.18-6.95 (m, 9H), 5.15 (t, 1H, J=6.9 Hz), 3.90 (s, 3H), 3.35-3.24 (m, 2H).

Compounds according to the second aspect of Category IX which comprise a substituted or unsubstituted oxazol-2-yl unit for R$^1$ can be prepared by the procedure outlined in Scheme XXI and described herein below in Example 22. Intermediate 39 can be prepared according to Scheme XVII and Example 18.

Scheme XXI

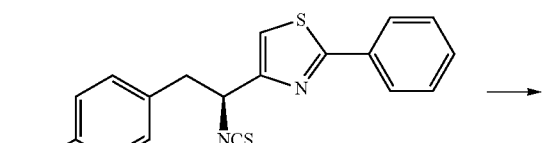

53

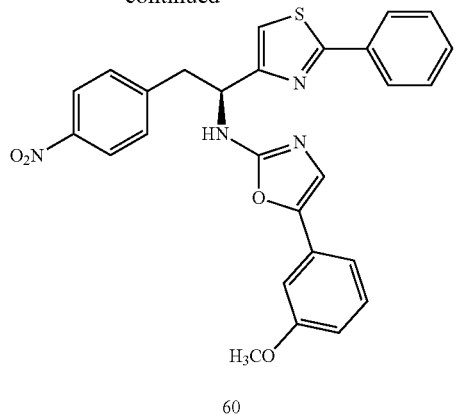

60

Reagents and conditions: (a) 1-azido-1-(3-methoxyphenyl)ethanone, PPh$_3$, dioxane, 90° C. 20 minutes.

60

61

Reagents and conditions: (b) (i) H$_2$:Pd/C, MeOH; (ii) SO$_3$-pyridine, NH$_4$OH; rt, 18 hr.

Example 22

4-{(S)-2-[5-(3-Methoxyphenyl)oxazole-2-ylamino]-2-(2-phenylthiazole-4-yl)ethyl}phenylsulfamic acid (61)

Preparation of [5-(3-methoxyphenyl)oxazol-2-yl]-[2-(4-nitrophenyl)-1-(2-phenylthiazole-4-yl)ethyl]amine (60): A mixture of (S)-4-(isothiocyanato-2-(4-nitrophenyl)ethyl)-2-phenylthiazole, 53, (300 mg, 0.81 mmol), 1-azido-1-(3- methoxyphenyl)ethanone (382 mg, 2.0 mmol) and PPh₃ (0.8 g, polymer bound, ~3 mmol/g) in dioxane (6 mL) is heated at 90° C. for 20 minutes. The reaction solution is cooled to room temperature and the solvent removed in vacuo and the resulting residue is purified over silica to afford 300 mg (74% yield) of the desired product as a yellow solid. ¹H NMR (300 MHz, MeOH-d₄) δ 8.02 (d, J=7.2 Hz, 2H), 7.92-7.99 (m, 2H), 7.42-7.47 (m, 3H), 7.22-7.27 (m, 3H), 6.69-7.03 (m, 4H), 6.75-6.78 (m, 1H), 5.26 (t, J=6.3 Hz, 1H), 3.83 (s, 4H), 3.42-3.45 (m, 2H).

Preparation of 4-{(S)-2-[5-(3-methoxyphenyl)oxazole-2-ylamino]-2-(2-phenylthiazole-4-yl)ethyl}phenylsulfamic acid (61): [5-(3-methoxyphenyl)oxazol-2-yl]-[2-(4-nitrophenyl)-1-(2-phenylthiazole-4-yl)ethyl]amine, 60, (300 mg, 0.60 mmol) is dissolved in MeOH (15 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (10 mL) and treated with SO₃-pyridine (190 mg, 1.2 mmol). The reaction is stirred at room temperature for 5 minutes after which a 7% solution of NH₄OH is added. The mixture is then concentrated and the resulting residue is purified by reverse-phase chromatography to afford 0.042 g of the desired product as the ammonium salt. ¹H NMR (300 MHz, MeOH-d₄) δ 7.99 (d, J=7.5 Hz, 2H), 7.46-7.50 (m, 3H), 7.23-7.29 (m, 3H), 7.04-7.12 (m, 6H), 6.78 (dd, J=8.4 and 2.4 Hz, 1H), 5.16 (t, J=6.6 Hz, 1H), 3.81 (s, 3H), 3.29-3.39 (m, 1H), 3.17 (dd, J=13.8 and 8.1 Hz, 1H).

The following are non-limiting examples of the second aspect of Category IX of the present disclosure.

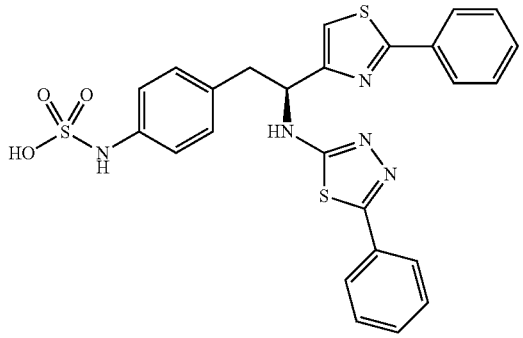 [SMILES: O=S(=O)(O)Nc1ccc(C[C@H](Nc2nnc(-c3ccccc3)s2)c2csc(-c3ccccc3)n2)cc1]

(S)-4-(2-(5-Phenyl-1,3,4-thiadiazol-2-ylamino)-2-(2-phenylthiazol-4-yl)ethyl)-phenylsulfamic acid: ¹H NMR (CD₃OD): δ 7.97-7.94 (m, 2H), 7.73-7.70 (m, 2H), 7.44-7.39 (m, 6H), 7.25 (s, 1H), 7.12 (s, 4H), 5.29 (t, 1H, J=6.9 Hz), 3.35-3.26 (m, 2H).

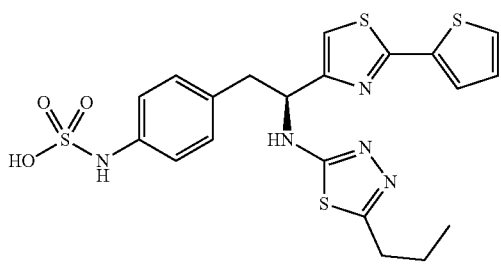 [SMILES: CCCc1nnc(N[C@@H](Cc2ccc(NS(=O)(=O)O)cc2)c2csc(-c3cccs3)n2)s1]

4-((S)-2-(5-Propyl-1,3,4-thiadiazol-2-ylamino)-2-(2-(thiophen-2-yl)thiazol-4-yl)ethyl)phenylsulfamic acid: ¹H NMR (CD₃OD): δ 7.59-7.54 (m, 2H), 7.17-7.03 (m, 6H), 5.13 (t, 1H, J=7.2 Hz), 3.32-3.13 (m, 2H), 2.81 (t, 2H, J=7.4 Hz), 1.76-1.63 (h, 6H, J=7.4 Hz), 0.97 (t, 3H, J=7.3 Hz).

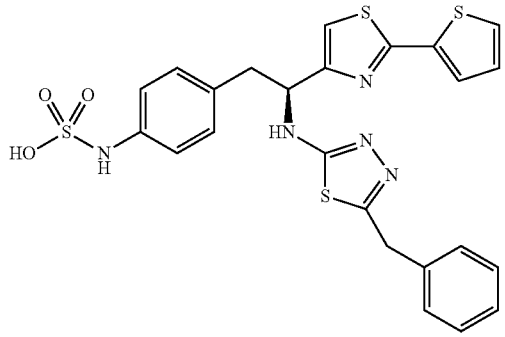 [SMILES: O=S(=O)(O)Nc1ccc(C[C@H](Nc2nnc(Cc3ccccc3)s2)c2csc(-c3cccs3)n2)cc1]

4-((S)-2-(5-Benzyl-1,3,4-thiadiazol-2-ylamino)-2-(2-(thiophen-2-yl)thiazol-4-yl)ethyl)phenylsulfamic acid: ¹H NMR (CD₃OD): δ (m, 2H), 7.49-7.45 (m, 2H), 7.26-7.16 (m, 5H), 7.05-6.94 (m, 6H), 5.04 (t, 1H, J=7.1 Hz), 4.07 (s, 2H), 3.22-3.04 (m, 2H).

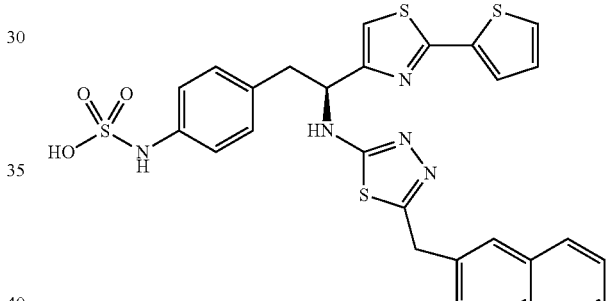

4-((S)-2-(5-(Naphthalen-1-ylmethyl)-1,3,4-thiadiazol-2-ylamino)-2-(2-(thiophen-2-yl)thiazol-4-yl)ethyl)phenylsulfamic acid: ¹H NMR (CD₃OD): δ 8.08-8.05 (m, 1H), 7.89-7.80 (m, 2H), 7.55-7.43 (m, 6H), 7.11-7.00 (m, 6H), 5.08 (t, 1H, J=7.1 Hz), 4.63 (s, 2H), 3.26-3.08 (m, 2H).

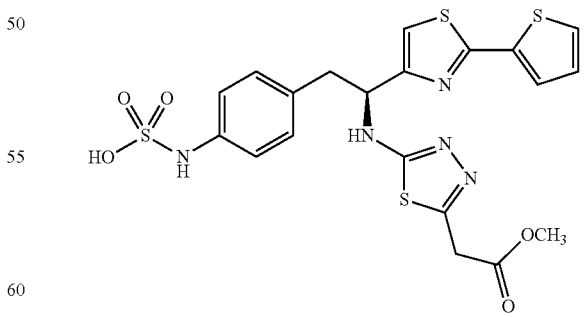

4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid: ¹H NMR (CD₃OD): δ 7.48-7.44 (m, 2H), 7.03-6.92 (m, 6H), 5.02 (t, 1H, J=7.2 Hz), 4.30 (s, 2H), 3.55 (s, 3H), 3.22-3.02 (m, 2H).

7.10-7.04 (m, 4H), 6.37 (s, 1H), 5.09 (t, 1H, J=6.9 Hz), 4.17-4.10 (q, 2H, J=7.1 Hz), 3.54 (s, 2H), 3.35-3.14 (m, 2H), 1.22 (t, 3H, J=7.1 Hz).

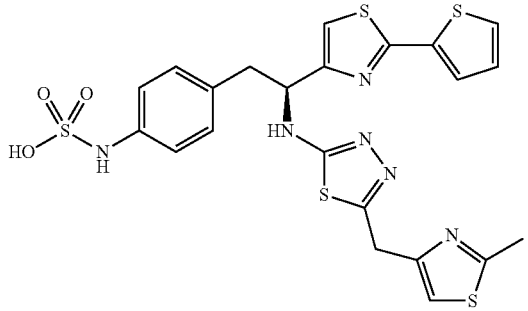 [SMILES: Cc1nc(Cc2nnc(N[C@@H](Cc3ccc(NS(=O)(=O)O)cc3)c3csc(-c4cccs4)n3)s2)cs1]

4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid: $^1$H(CD$_3$OD): δ 7.60-7.56 (m, 2H), 7.19 (s, 1H), 7.15-7.12 (m, 2H), 7.09-7.03 (q, 4H, J=8.7 Hz), 5.14 (t, 1H, J=7.2 Hz), 4.28 (s, 2H), 3.33-3.14 (m, 2H), 2.67 (s, 3H).

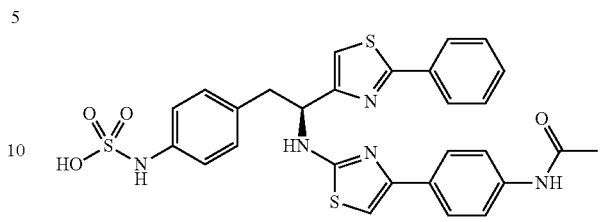

(S)-4-{2-[4-(4-acetamidophenyl)thiazol-2-ylamino]-2-(2-phenylthiazol-4-yl)ethyl}phenylsulfamic acid: $^1$H NMR (CD$_3$OD): δ 8.11 (m, 2H), 7.82-7.80 (m, 2H), 7.71-7.61 (m, 6H), 7.40 (s, 1H), 7.23 (s, 4H), 5.32 (t, 1H, J=7.0 Hz), 3.51-3.35 (m, 2H), 2.28 (s, 3H).

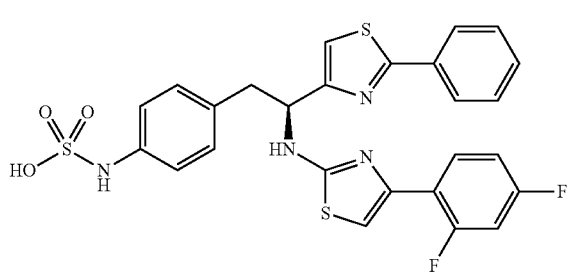 [SMILES: O=S(=O)(O)Nc1ccc(C[C@H](Nc2nc(-c3ccc(F)cc3F)cs2)c2csc(-c3ccccc3)n2)cc1]

4-{(S)-2-[4-(2,4-Difluorophenyl)thiazol-2-ylamino]-2-[2-(thiophen-2-yl)thiazol-4-yl]ethyl}phenylsulfamic acid: $^1$H NMR (CD$_3$OD): δ 8.06-8.02 (q, 1H, J=6.8 Hz), 7.59-7.54 (m, 2H), 7.16-7.08 (m, 6H), 7.01-6.88 (m, 4H), 5.20 (t, 1H, J=7.0 Hz), 3.36-3.17 (m, 2H).

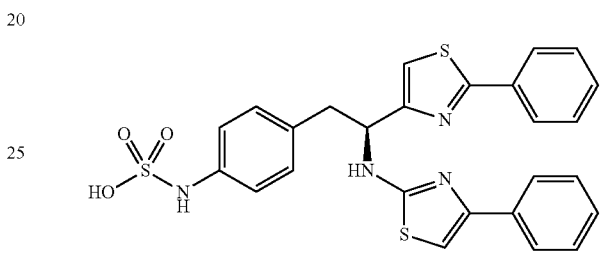

(S)-4-[2-(4-phenylthiazol-2-ylamino)-2-(2-phenylthiazol-4-yl)ethyl]phenylsulfamic acid: $^1$H (CD$_3$OD): δ 8.03-7.99 (m, 2H), 7.75-7.72 (d, 2H, J=8.4 Hz), 7.53-7.48 (m, 3H), 7.42 (m, 4H), 7.12 (s, 4H), 6.86 (s, 1H), 5.23 (t, 1H, J=7.2 Hz), 3.40-3.27 (m, 2H).

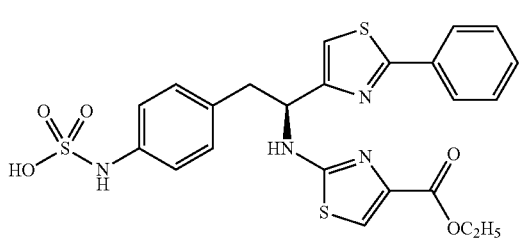 [SMILES: CCOC(=O)c1csc(N[C@@H](Cc2ccc(NS(=O)(=O)O)cc2)c2csc(-c3ccccc3)n2)n1]

(S)-4-{2-[4-(Ethoxycarbonyl)thiazol-2-ylamino]-2-(2-phenylthiazol-4-yl)ethyl}phenylsulfamic acid: $^1$H NMR (CD$_3$OD): δ 8.02-7.99 (m, 2H), 7.54-7.45 (m, 4H), 7.26 (s, 1H), 7.08 (s, 4H), 5.26 (t, 1H, J=6.9 Hz), 4.35-4.28 (q, 2H, J=6.9 Hz), 3.38-3.18 (m, 2H), 1.36 (t, 3H, J=7.2 Hz).

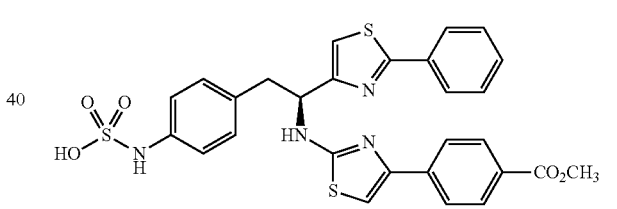

(S)-4-{2-[4-(4-(methoxycarbonyl)phenyl)thiazol-2-ylamino]-2-(2-phenylthiazol-4-yl)ethyl}phenylsulfamic acid: $^1$H NMR (CD$_3$OD): δ 8.04-8.00 (m, 4H), 7.92-7.89 (d, 2H, J=9.0 Hz), 7.53-7.49 (m, 3H), 7.30 (s, 1H), 7.15 (s, 4H), 7.05 (s, 1H), 5.28 (t, 1H, J=6.9 Hz), 3.93 (s, 3H), 3.35-3.24 (2H).

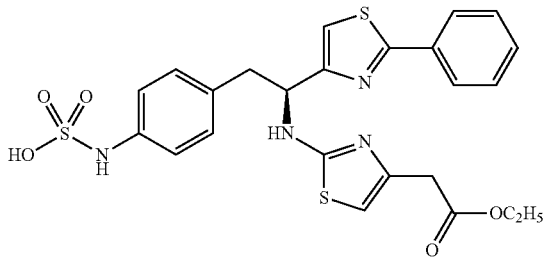 [SMILES: CCOC(=O)Cc1csc(N[C@@H](Cc2ccc(NS(=O)(=O)O)cc2)c2csc(-c3ccccc3)n2)n1]

(S)-4-{2-[4-(2-Ethoxy-2-oxoethyl)thiazol-2-ylamino]-2-(2-phenylthiazol-4-yl)ethyl}phenylsulfamic acid: $^1$H NMR (CD$_3$OD): δ 7.96 (m, 2H), 7.50-7.46 (m, 3H), 7.21 (s, 1H),

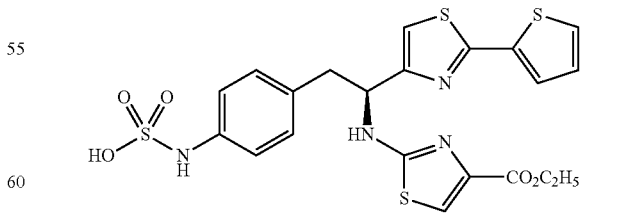

4-{(S)-2-[4-(Ethoxycarbonyl)thiazol-2-ylamino]-2-[2-(thiophen-2-yl)thiazol-4-yl]ethyl}phenylsulfamic acid: $^1$H NMR (CD$_3$OD): δ 7.43-7.38 (m, 2H), 7.26 (s, 1H), 7.00-6.94 (m, 3H), 6.89 (s, 4H), 5.02 (t, 1H, J=7.0 Hz), 4.16-4.09 (q, 2H, J=7.1 Hz), 3.14-2.94 (m, 2H), 1.17 (t, 3H, J=7.1 Hz).

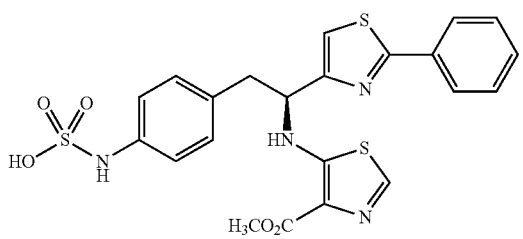 [SMILES: COC(=O)c1ncsc1N[C@@H](Cc1ccc(NS(=O)(=O)O)cc1)c1csc(-c2ccccc2)n1]

(S)-4-[2-(4-(Methoxycarbonyl)thiazol-5-ylamino)-2-(2-phenylthiazole-4-yl)ethyl]phenylsulfamic acid: $^1$H NMR (300 MHz, MeOH-d$_4$) δ 7.97-8.00 (m, 3H), 7.48-7.52 (m, 3H), 7.22 (s, 1H), 7.03-7.13 (m, 4H), 4.74 (t, J=6.6 Hz, 1H), 3.88 (s, 3H), 3.28-3.42 (m, 2H).

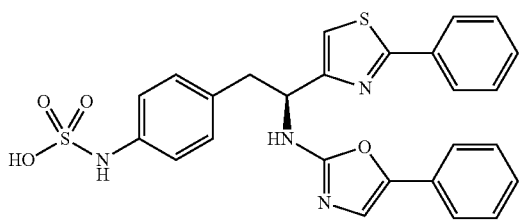 [SMILES: O=S(=O)(O)Nc1ccc(C[C@H](Nc2ncc(-c3ccccc3)o2)c2csc(-c3ccccc3)n2)cc1]

(S)-4-[2-(5-Phenyloxazol-2-ylamino)-2-(2-phenylthiazol-4-yl)ethyl]-phenylsulfamic acid: $^1$H NMR (300 MHz, MeOH-d$_4$) δ 7.94-7.96 (m, 2H), 7.45-7.49 (m, 5H), 7.32 (t, J=7.8 Hz, 2H), 7.12 (s, 1H), 7.19 (t, J=7.2 Hz, 1H), 7.12 (s, 4H), 7.05 (s, 1H), 5.15 (t, J=6.4 Hz, 1H), 3.34 (dd, J=14.1 and 8.4 Hz, 1H), 3.18 (dd, J=14.1 and 8.4 Hz, 1H).

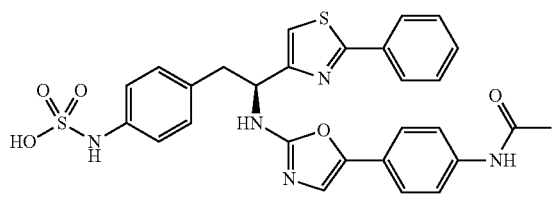 [SMILES: CC(=O)Nc1ccc(-c2cnc(N[C@@H](Cc3ccc(NS(=O)(=O)O)cc3)c3csc(-c4ccccc4)n3)o2)cc1]

(S)-4-{2-[5-(4-Acetamidophenyl)oxazol-2-ylamino]-2-(2-phenylthiazol-4-yl)ethyl}phenylsulfamic acid: $^1$H NMR (300 MHz, MeOH-d$_4$) δ 7.92-7.94 (m, 2H), 7.55-7.58 (m, 2H), 7.39-7.50 (m, 5H), 7.26 (s, 1H), 7.12 (s, 4H), 7.02 (s, 1H0), 5.14 (t, J=7.8 Hz, 1H), 3.13-3.38 (m, 2H), 2.11 (s, 3H).

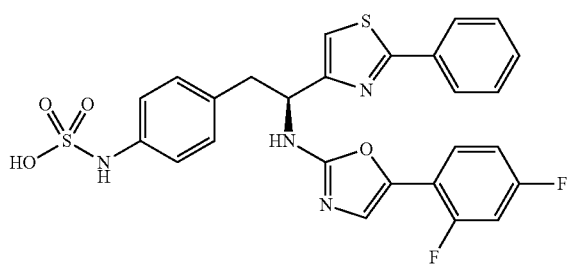 [SMILES: O=S(=O)(O)Nc1ccc(C[C@H](Nc2ncc(-c3ccc(F)cc3F)o2)c2csc(-c3ccccc3)n2)cc1]

4-((S)-2-(5-(2,4-Difluorophenyl)oxazole-2-ylamino)-2-(2-phenylthiazole-4-yl)ethyl)phenylsulfamic acid: $^1$H NMR (300 MHz, MeOH-d$_4$) δ 7.97-7.99 (m, 2H), 7.54-7.62 (m, 1H), 7.45-7.50 (m, 3H), 7.28 (s, 1H), 7.12 (s, 4H), 6.97-7.06 (m, 3H), 5.15-5.20 (m, 1H), 3.28-3.40 (m, 1H), 3.20 (dd, J=13.8 and 8.4 Hz, 1H).

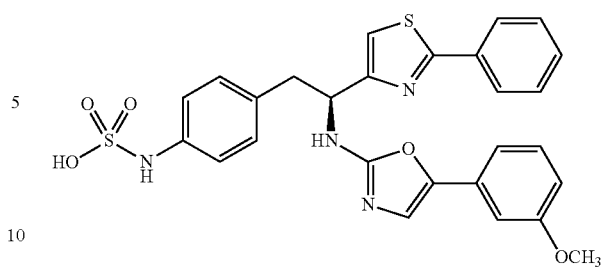

4-{(S)-2-[5-(3-Methoxyphenyl)oxazol-2-ylamino]-2-[(2-thiophen-2-yl)thiazole-4-yl]ethyl}phenylsulfamic acid: $^1$H NMR (300 MHz, MeOH-d$_4$) δ 7.55-7.60 (m, 2H), 7.26 (t, J=8.1 Hz, 1H), 7.21 (s, 1H), 7.04-7.15 (m, 8H), 6.77-6.81 (m, 1H), 5.10 (t, J=6.3 Hz, 1H), 3.81 (s, 3H), 3.29-3.36 (m, 1H), 3.15 (dd, J=14.1 and 8.4 Hz, 1H).

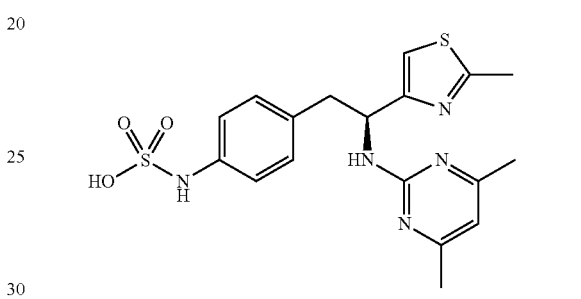

(S)-4-[2-(4,6-Dimethylpyrimidin-2-ylamino)-2-(2-methylthiazole-4-yl)ethyl]phenylsulfamic acid: $^1$H NMR (300 MHz, MeOH-d$_4$) δ 7.00-7.10 (m, 5H), 6.44 (s, 1H), 5.50 (t, J=7.2 Hz, 1H), 3.04-3.22 (m, 2H), 2.73 (s, 3H), 2.27 (s, 6H).

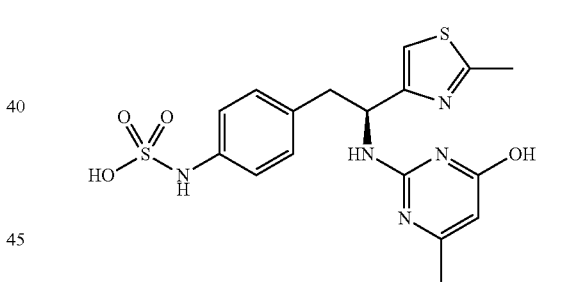

(S)-4-[2-(4-Hydroxy-6-methylpyrimidine-2-ylamino)-2-(2-methylthiazole-4-yl)ethyl]phenylsulfamic acid: $^1$H NMR (300 MHz, MeOH-d4) δ 7.44 (d, J=8.4 Hz, 2H), 6.97-7.10 (m, 4H), 5.61 (s, 1H), 5.40-5.49 (m, 1H), 3.10-3.22 (m, 2H), 2.73 (s, 3H), 2.13 (s, 3H).

The first aspect of Category X of the present disclosure relates to compounds having the formula:

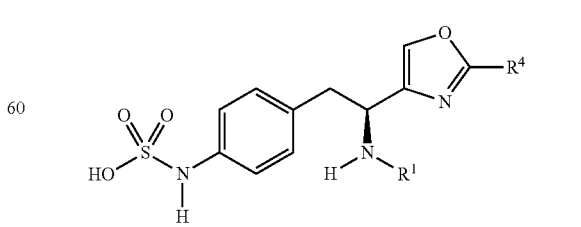

wherein R$^1$ is heteroaryl and R$^4$ is further described herein below in Table XIX.

TABLE XIX

| No. | R⁴ | R¹ |
|---|---|---|
| S788 | phenyl | 4-(methoxycarbonyl)thiazol-5-yl |
| S789 | phenyl | 4-[(2-methoxy-2-oxoethyl)carbamoyl]thiazol-5-yl |
| S790 | phenyl | 5-[1-N-(2-methoxy-2-oxoethyl)-1-H-indol-3-yl]oxazol-2-yl |
| S791 | phenyl | 5-(2-methoxyphenyl)oxazol-2-yl |
| S792 | phenyl | 5-[(S)-1-(tert-butoxycarbonyl)-2-phenylethyl]oxazol-2-yl |
| S793 | phenyl | 5-[4-(methylcarboxy)phenyl]oxazol-2-yl |
| S794 | phenyl | 5-(3-methoxybenzyl)oxazol-2-yl |
| S795 | phenyl | 5-(4-phenyl)oxazol-2-yl |
| S796 | phenyl | 5-(2-methoxyphenyl)thiazol-2-yl |
| S797 | phenyl | 5-(3-methoxyphenyl)thiazol-2-yl |
| S798 | phenyl | 5-(4-fluorophenyl)thiazol-2-yl |
| S799 | phenyl | 5-(2,4-difluorophenyl)thiazol-2-yl |
| S800 | phenyl | 5-(3-methoxybenzyl)thiazol-2-yl |
| S801 | phenyl | 4-(3-methoxyphenyl)thiazol-2-yl |
| S802 | phenyl | 4-(4-fluorophenyl)thiazol-2-yl |
| S803 | thiophen-2-yl | 4-(methoxycarbonyl)thiazol-5-yl |
| S804 | thiophen-2-yl | 4-[(2-methoxy-2-oxoethyl)carbamoyl]thiazol-5-yl |
| S805 | thiophen-2-yl | 5-[1-N-(2-methoxy-2-oxoethyl)-1-H-indol-3-yl]oxazol-2-yl |
| S806 | thiophen-2-yl | 5-(2-methoxyphenyl)oxazol-2-yl |
| S807 | thiophen-2-yl | 5-[(S)-1-(tert-butoxycarbonyl)-2-phenylethyl]oxazol-2-yl |
| S808 | thiophen-2-yl | 5-[4-(methylcarboxy)phenyl]oxazol-2-yl |
| S809 | thiophen-2-yl | 5-(3-methoxybenzyl)oxazol-2-yl |
| S810 | thiophen-2-yl | 5-(4-phenyl)oxazol-2-yl |
| S811 | thiophen-2-yl | 5-(2-methoxyphenyl)thiazol-2-yl |
| S812 | thiophen-2-yl | 5-(3-methoxyphenyl)thiazol-2-yl |
| S813 | thiophen-2-yl | 5-(4-fluorophenyl)thiazol-2-yl |
| S814 | thiophen-2-yl | 5-(2,4-difluorophenyl)thiazol-2-yl |
| S815 | thiophen-2-yl | 5-(3-methoxybenzyl)thiazol-2-yl |
| S816 | thiophen-2-yl | 4-(3-methoxyphenyl)thiazol-2-yl |
| S817 | thiophen-2-yl | 4-(4-fluorophenyl)thiazol-2-yl |
| S818 | cyclopropyl | 4-(methoxycarbonyl)thiazol-5-yl |
| S819 | cyclopropyl | 4-[(2-methoxy-2-oxoethyl)carbamoyl]thiazol-5-yl |
| S820 | cyclopropyl | 5-[1-N-(2-methoxy-2-oxoethyl)-1-H-indol-3-yl]oxazol-2-yl |
| S821 | cyclopropyl | 5-(2-methoxyphenyl)oxazol-2-yl |
| S822 | cyclopropyl | 5-[(S)-1-(tert-butoxycarbonyl)-2-phenylethyl]oxazol-2-yl |
| S823 | cyclopropyl | 5-[4-(methylcarboxy)phenyl]oxazol-2-yl |
| S824 | cyclopropyl | 5-(3-methoxybenzyl)oxazol-2-yl |
| S825 | cyclopropyl | 5-(4-phenyl)oxazol-2-yl |
| S826 | cyclopropyl | 5-(2-methoxyphenyl)thiazol-2-yl |
| S827 | cyclopropyl | 5-(3-methoxyphenyl)thiazol-2-yl |
| S828 | cyclopropyl | 5-(4-fluorophenyl)thiazol-2-yl |
| S829 | cyclopropyl | 5-(2,4-difluorophenyl)thiazol-2-yl |
| S830 | cyclopropyl | 5-(3-methoxybenzyl)thiazol-2-yl |
| S831 | cyclopropyl | 4-(3-methoxyphenyl)thiazol-2-yl |
| S832 | cyclopropyl | 4-(4-fluorophenyl)thiazol-2-yl |

Compounds according to the first aspect of Category X can be prepared by the procedure outlined in Scheme XXII and described herein below in Example 23.

Scheme XXII

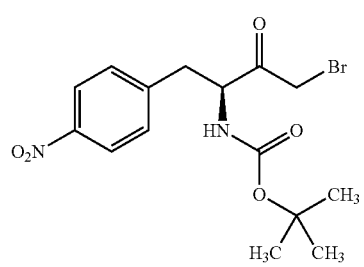

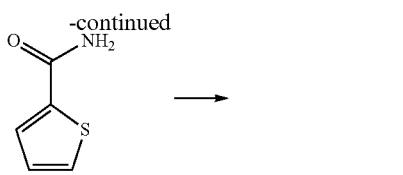

Reagents and conditions: (a) CH₃CN; reflux 2 hr.

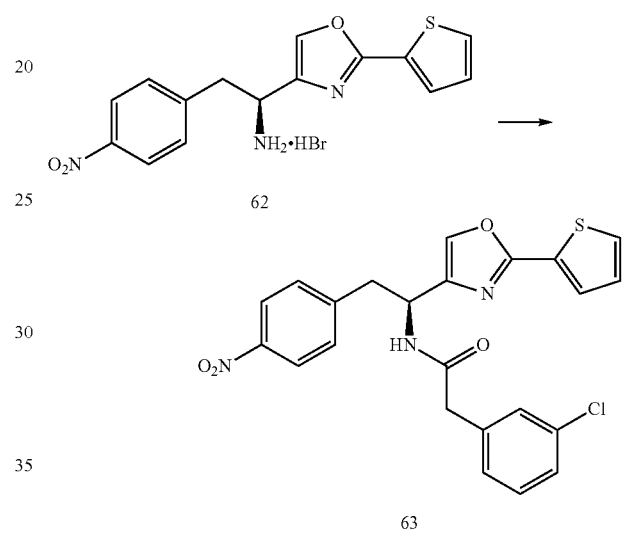

Reagents and conditions: (b) (3-Cl)C₆H₄CO₂H, EDCI, HOBt, DIPEA, DMF; rt, 18 hr.

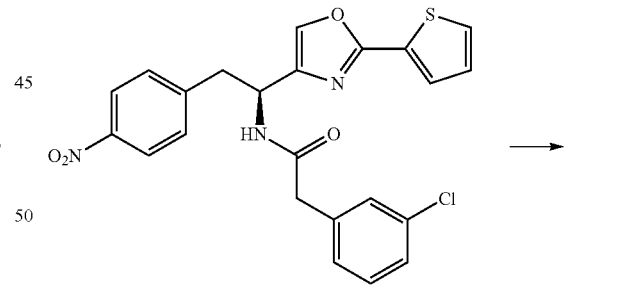

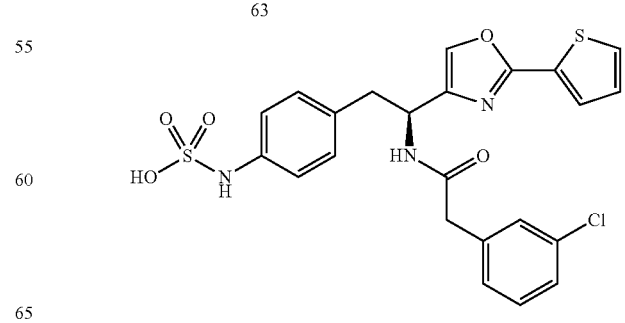

Reagents and conditions: (c) (i) H₂:Pd/C, MeOH; (ii) SO₃-pyridine, NH₄OH, rt, 18 hr.

Example 23

4-((S)-2-(2-(3-Chlorophenyl)acetamido)-2-(2-(thiophen-2-yl)oxazol-4-yl)ethyl)phenylsulfamic acid (64)

Preparation of (S)-2-(4-nitrophenyl)-1-[(thiophen-2-yl)oxazol-4-yl]ethanamine hydrobromide salt (62): A mixture of (S)-tert-butyl 4-bromo-1-(4-nitrophenyl)-3-oxobutan-2-ylcarbamate, 7, (38.7 g, 100 mmol), and thiophen-2-carboxamide (14 g, 110 mmol) (available from Alfa Aesar) in CH₃CN (500 mL) is refluxed for 5 hours. The reaction mixture is cooled to room temperature and diethyl ether (200 mL) is added to the solution. The precipitate which forms is collected by filtration. The solid is dried under vacuum to afford the desired product which can be used for the next step without purification.

Preparation of 2-(3-chlorophenyl)-N—{(S)-2-(4-nitrophenyl)-1-[2-(thiophen-2-yl)oxazol-4-yl]ethyl}acetamide (63): To a solution of (S)-2-(4-nitrophenyl)-1-[(thiophen-2-yl)oxazol-4-yl]ethanamine HBr, 47, (3.15 g, 10 mmol) 3-chlorophenyl-acetic acid (1.70 g, 10 mmol) and 1-hydroxybenzotriazole (HOBt) (0.70 g, 5.0 mmol) in DMF (50 mL) at 0° C., is added 1-(3-dimethylaminopropyl)-3-ethylcarbodiimide (EDCI) (1.90 g, 10 mmol) followed by triethylamine (4.2 mL, 30 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of —((S)-2-(2-(3-chlorophenyl)acetamido)-2-(2-(thiophen-2-yl)oxazol-4-yl)ethyl)phenylsulfamic acid (64): 2-(3-chlorophenyl)-N—{(S)-2-(4-nitrophenyl)-1-[2-(thiophen-2-yl)oxazol-4-yl]ethyl}acetamide, 63, (3 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.157 g). The reaction is stirred at room temperature for 5 minutes after which a 7% solution of NH₄OH is added. The mixture is then concentrated and the resulting residue can be purified by reverse phase chromatography to afford the desired product as the ammonium salt.

The second aspect of Category X of the present disclosure relates to compounds having the formula:

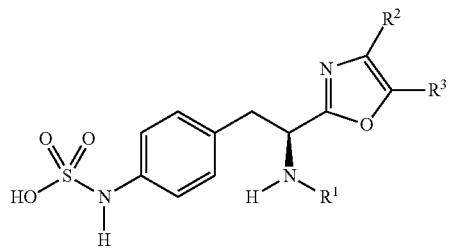

wherein R¹ is aryl and R² and R³ are further described herein below in Table XX.

TABLE XX

| No. | R² | R³ | R¹ |
|---|---|---|---|
| T833 | methyl | hydrogen | phenyl |
| T834 | methyl | hydrogen | benzyl |
| T835 | methyl | hydrogen | 2-fluorophenyl |
| T836 | methyl | hydrogen | 3-fluorophenyl |
| T837 | methyl | hydrogen | 4-fluorophenyl |
| T838 | methyl | hydrogen | 2-chlorophenyl |
| T839 | methyl | hydrogen | 3-chlorophenyl |
| T840 | methyl | hydrogen | 4-chlorophenyl |
| T841 | ethyl | hydrogen | phenyl |
| T842 | ethyl | hydrogen | benzyl |
| T843 | ethyl | hydrogen | 2-fluorophenyl |
| T844 | ethyl | hydrogen | 3-fluorophenyl |
| T845 | ethyl | hydrogen | 4-fluorophenyl |
| T846 | ethyl | hydrogen | 2-chlorophenyl |
| T847 | ethyl | hydrogen | 3-chlorophenyl |
| T848 | ethyl | hydrogen | 4-chlorophenyl |
| T849 | thien-2-yl | hydrogen | phenyl |
| T850 | thien-2-yl | hydrogen | benzyl |
| T851 | thien-2-yl | hydrogen | 2-fluorophenyl |
| T852 | thien-2-yl | hydrogen | 3-fluorophenyl |
| T853 | thien-2-yl | hydrogen | 4-fluorophenyl |
| T854 | thien-2-yl | hydrogen | 2-chlorophenyl |
| T855 | thien-2-yl | hydrogen | 3-chlorophenyl |
| T856 | thiene-2-yl | hydrogen | 4-chlorophenyl |

Compounds according to the second aspect of Category X can be prepared by the procedure outlined in Scheme XXIII and described herein below in Example 24.

Scheme XXIII

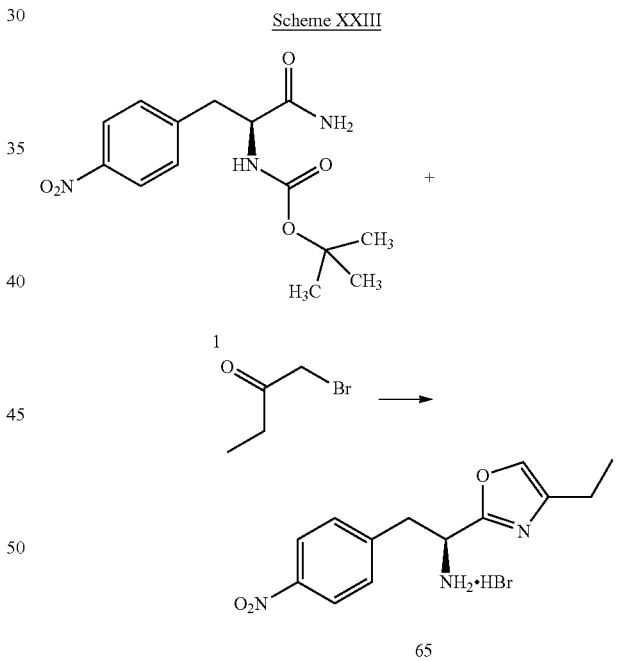

Reagents and conditions: (a) CH₃CN; reflux, 2 hr.

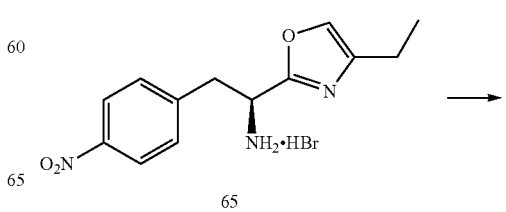

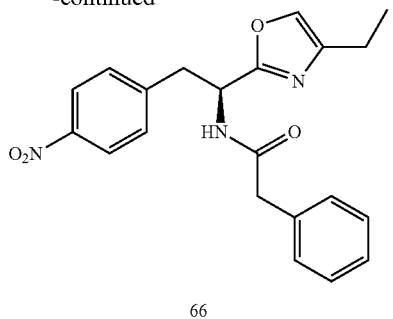

66

Reagents and conditions: (b) C₆H₄CO₂H, EDCI, HOBt, DIPEA, DMF; rt, 18 hr.

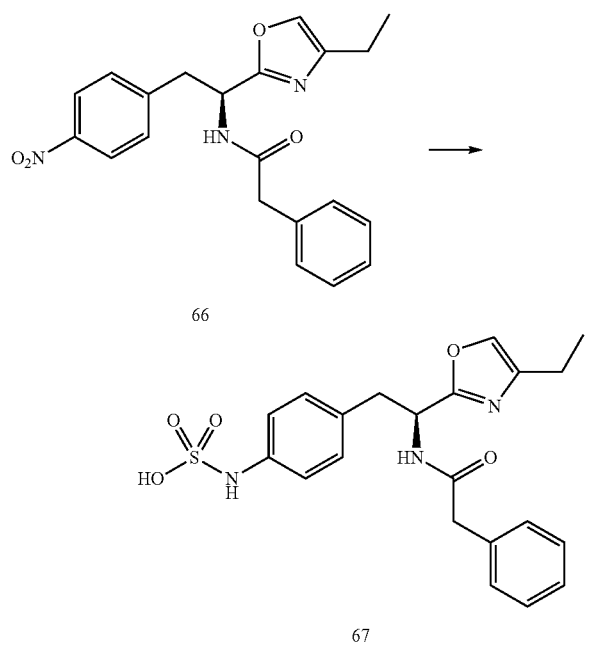

Reagents and conditions: (c) (i) H₂:Pd/C, MeOH; (ii) SO₃-pyridine, NH₄OH, rt, 18 hr.

Example 24

{4-[2-(S)-(4-Ethyloxazol-2-yl)-2-phenylacetylaminoethyl]-phenyl}sulfamic acid (67)

Preparation of (S)-1-(4-ethyloxazol-2-yl)-2-(4-nitrophenyl)ethanamine (65): A mixture of [1-(S)-carbamoyl-2-(4-nitrophenyl)ethyl-carbamic acid tert-butyl ester, 1, (10 g, 32.3 mmol) and 1-bromo-2-butanone (90%, 4.1 mL, 36 mmol) in CH₃CN (500 mL) is refluxed for 18 hours. The reaction mixture is cooled to room temperature and diethyl ether is added to the solution and the precipitate which forms is removed by filtration and is used without further purification.

Preparation of N-[1-(4-ethyloxazol-2-yl)-2-(4-nitrophenyl)ethyl]-2-phenyl-acetamide (66): To a solution of (S)-1-(4-ethyloxazol-2-yl)-2-(4-nitrophenyl)ethanamine, 65, (2.9 g, 11 mmol), phenylacetic acid (1.90 g, 14 mmol) and 1-hydroxybenzotriazole (HOBt) (0.94 g, 7.0 mmol) in DMF (100 mL) at 0° C., is added 1-(3-dimethylaminopropyl)-3-ethylcarbodiimide (EDCI) (2.68 g, 14 mmol) followed by triethylamine (6.0 mL, 42 mmol). The mixture is stirred at 0° C. for 30 minutes then at room temperature overnight. The reaction mixture is diluted with water and extracted with EtOAc. The combined organic phase is washed with 1 N aqueous HCl, 5% aqueous NaHCO₃, water and brine, and dried over Na₂SO₄. The solvent is removed in vacuo to afford the desired product which is used without further purification.

Preparation of {4-[2-(S)-(4-ethyloxazol-2-yl)-2-phenylacetylaminoethyl]-phenyl}sulfamic acid (67): N-[1-(4-ethyloxazol-2-yl)-2-(4-nitrophenyl)ethyl]-2-phenyl-acetamide, 66, (0.260 g) is dissolved in MeOH (4 mL). A catalytic amount of Pd/C (10% w/w) is added and the mixture is stirred under a hydrogen atmosphere 18 hours. The reaction mixture is filtered through a bed of CELITE™ and the solvent is removed under reduced pressure. The crude product is dissolved in pyridine (12 mL) and treated with SO₃-pyridine (0.177 g, 1.23). The reaction is stirred at room temperature for 5 minutes after which a 7% solution of NH₄OH (10 mL) is added. The mixture is then concentrated and the resulting residue is purified by reverse phase chromatography to afford the desired product as the ammonium salt.

Methods

The disclosed compounds can be used to prevent, abate, minimize, control, and/or lessen tumor metastasis in humans and animals. The disclosed compounds can also be used to slow the rate of primary tumor growth. The disclosed compounds when administered to a subject in need of treatment can be used to stop the spread of cancer cells. As such, the compounds disclosed herein can be administered as part of a combination therapy with one or more drugs or other pharmaceutical agents. When used as part of the combination therapy, the decrease in metastasis and reduction in primary tumor growth afforded by the disclosed compounds allows for a more effective and efficient use of any pharmaceutical or drug therapy being used to treat the patient. In addition, control of metastasis by the disclosed compound affords the subject a greater ability to concentrate the disease in one location.

Disclosed herein are methods for preventing metastasis of malignant tumors or other cancerous cells as well as to reduce the rate of tumor growth. The methods comprise administering an effective amount of one or more of the disclosed compounds to a subject diagnosed with a malignant tumor or cancerous cells or to a subject having a tumor or cancerous cells.

Further disclosed herein is the use of the disclosed compounds for making a medicament for preventing metastasis of malignant tumors or other cancerous cells and for slowing tumor growth.

The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytoma/Malignant Glioma; Craniopharyngioma; Ependymoblastoma; Ependymoma; Medulloblastoma; Medulloepithelioma; Pineal Parenchymal Tumors of Intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma; Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; Intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenström; Malignant Fibrous Histiocytoma of Bone and Osteosarcoma; Medulloblastoma; Melanoma; Melanoma, Intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Cell Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sézary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenström Macroglobulinemia; and Wilms Tumor.

In Vivo Anti-Metastasis Study

A total of 50 NCr nu/nu male mice aged 5-6 weeks were selected for the following in vivo test. H460-GFP human tumor cells were grown subcutaneously in NCr nu/nu male mice after which the resulting tumors were harvested. Subsequent to harvesting, recipient NCr nu/nu mice of this study had tumor fragments transplanted by surgical orthotopic implantation (SOI). Each animal was anesthetized is isofurane and the surgical area was sterilized with iodine and alcohol. A transverse incision approximately 1.5 cm long was made in the left chest wall of the mice using a pair of surgical scissors. An intercostal incision was made between the third and the fourth costa and the left lung was exposed. Two pieces of H460-GFP tumor fragments were transplanted to the surface of the lung with 8-0 surgical nylon suture. The chest wall was closed with 6-0 silk suture. The lung was re-inflated by the intrathoracic puncture using 3 cc syringe with 25 G 1½ needle to draw out the remaining air in the chest cavity. The chest wall was closed with 6-0 surgical silk sutures. All procedures of the operation described above were performed with a 7× magnification microscope (Olympus) under HEPA filtered laminar flow hoods.

The treated mice were divided into five groups containing ten mice each. Group I (Control) received 100 µL the drug vehicle twice daily for 15 days. Group II received 15 mg/kg of taxol intravenously at days 6, 9, 12, and 15. Group III received 15 mg/kg of taxol intravenously at days 6, 9, 12, and 15 and 15 mg/kg of 4-{(S)-2-[(S)-2-(methoxycarbonylamino)-3-phenyl-propanamido]-2-[2-(thiophen-2-yl)thiazol-4-yl]ethyl}phenylsulfamic acid, D91, (Test Compound) twice per day from day 3 to day 15. Group IV received 10 mg/kg of taxol intravenously at days 6, 9, 12, and 15 and 15 mg/kg of the Test Compound twice per day from day 3 to day 15. Group V received 15 mg/kg of the Test Compound twice per day from day 3 to day 15. All animals were sacrificed on day 28.

Each animal was checked twice a week for primary tumor and metastasis via GFP open imaging of the mediastinal lymph nodes. No metastasis was found on any other organs. Six mice from the control group died before the end of the study, but were evaluated for tumor and/or cellular metastasis. Table XXI below summarizes the results of this in vivo metastasis study.

TABLE XXI

| Mouse No. | Group I | Group II | Group III | Group IV | Group V |
|---|---|---|---|---|---|
| Evidence of Metastasis | | | | | |
| 1 | Yes | No | No | No | No |
| 2 | Yes | No | No | Yes | Yes |
| 3 | No | Yes | No | No | No |

TABLE XXI-continued

| Mouse No. | Group I | Group II | Group III | Group IV | Group V |
|---|---|---|---|---|---|
| 4 | Yes | No | No | No | No |
| 5 | Yes | No | No | No | No |
| 6 | Yes | No | No | No | Yes |
| 7 | Yes | No | No | No | No |
| 8 | No | No | No | No | No |
| 9 | Yes | No | No | Yes | No |
| 10 | Yes | No | No | No | No |
| # mice with metastases | 8 | 1 | 0 | 2 | 2 |

In Vivo Anticancer Studies
B16 Melanoma

The effectiveness of the disclosed compounds as a treatment for melanoma was studied. C57BL/6 mice (6-8 weeks-old, female, Taconic Farm) were inoculated with B16 melanoma cells ($5 \times 10^4$ cells/site, s.c.). On day 4 post-inoculation, the mice (5/group) were treated (5 day/week, M-F) with vehicle control (bid, i.p.), low dose of IL-2 (100,000 IU/mouse, bid, i.p.), high dose of IL-2 (300,000 IU/mouse, bid, i.p.), or their combinations with D91 (40 mg/kg, bid, s.c., administered 30 minutes prior to IL-2). Tumor volumes were recorded. In a separate experiment, mice similarly inoculated with B16 melanoma cells were treated (5 day/week, M-F) with vehicle control (bid, i.p.), IL-2 (300,000 IU/mouse, bid, i.p.), high dose of D91 (40 mg/kg, bid, s.c.), low dose of D91 (10 mg/kg, bid, s.c.) or the combination of IL-2 (300,000 IU/mouse, bid, i.p.) with low dose of D91 (10 mg/kg, bid, s.c., administered 30 minutes prior to IL-2). Tumor volumes were recorded.

Figure 3:
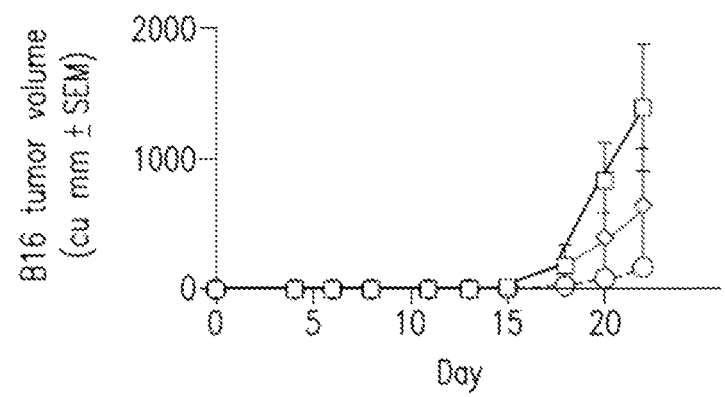
FIG. 3 depicts a graph showing the increase in tumor volume with time of B16 melanoma tumors in mice; vehicle control (□); 300,000 IU/dose of IL-2 twice daily (◇); 300,000 IU/dose of IL-2 and 40 mg/kg of D91 twice daily (○).
Figure 4:
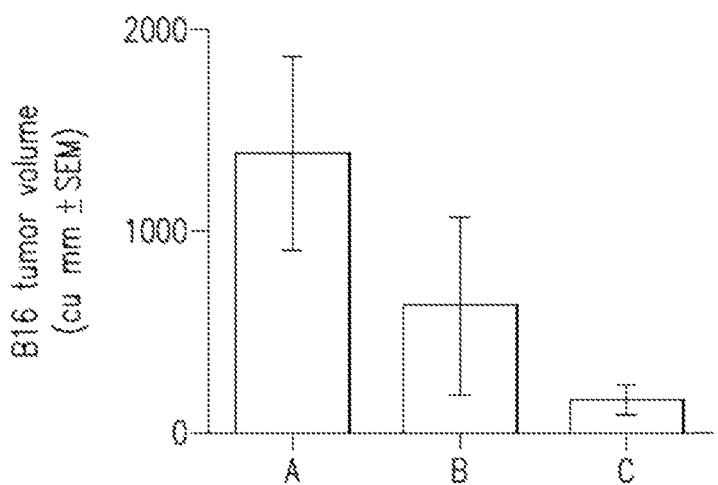
FIG. 4 depicts histogram of the volume of B16 melanoma tumors in mice at day 22; vehicle control (A); 300,000 IU/dose of IL-2 twice daily (B); 300,000 IU/dose of IL-2 and 40 mg/kg of D91 twice daily (C).
Figure 5:
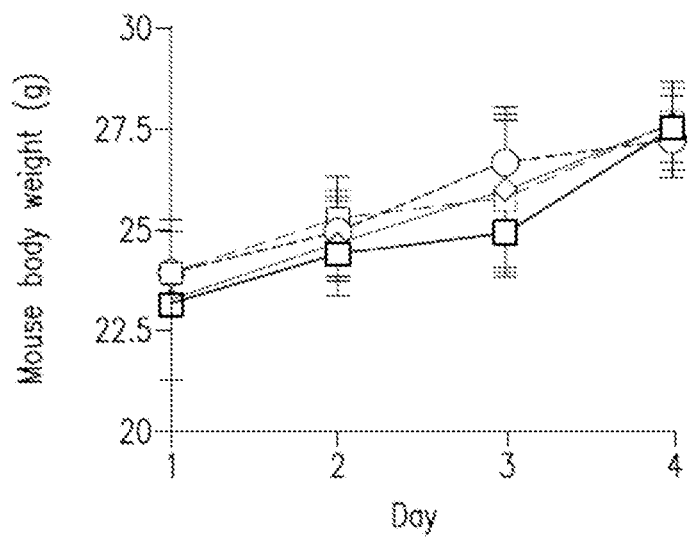
FIG. 5 depicts a graph of the body weight of mice with B16 melanoma tumors; vehicle control (□); 100,000 IU/dose of IL-2 twice daily (◇); 300,000 IU/dose of IL-2 twice daily (Δ); 100,000 IU/dose of IL-2 and 40 mg/kg of D91 twice daily (○); and 300,000 IU/dose of IL-2 and 40 mg/kg of D91 twice daily (■).

As depicted in FIG. 3, although the high dose of IL-2 (◇) reduced tumor volume as expected versus control (□), treatment with high dose of IL-2 in combination with high dose of D91 (○) significantly reduced tumor volume as compared to high dose of IL-2 (◇) alone. FIG. 4 is a histogram representing the tumor volume of animals receiving control (A), high dose IL-2 (B), and high dose IL-2/high dose D91 (C). The data depicted in FIG. 5 indicate that the increase in animal body weights during the study were consistent over each group and did not show any effects due to the choice of treatment.

Figure 6:
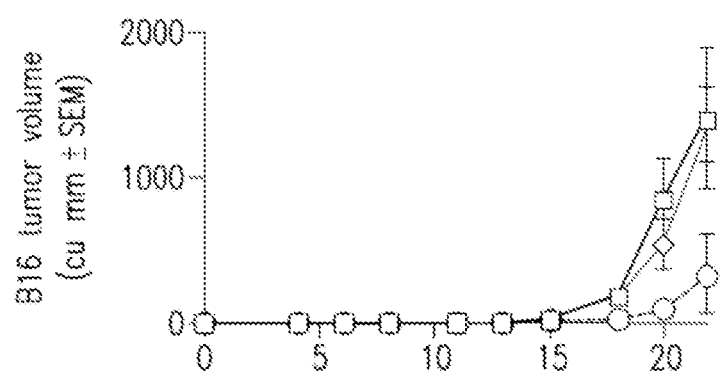
FIG. 6 depicts a graph showing the increase in tumor volume with time of B16 melanoma tumors in mice; vehicle control (□); 100,000 IU/dose of IL-2 twice daily (◇); and 100,000 IU/dose of IL-2 and 40 mg/kg of D91 twice daily (○).
Figure 7:
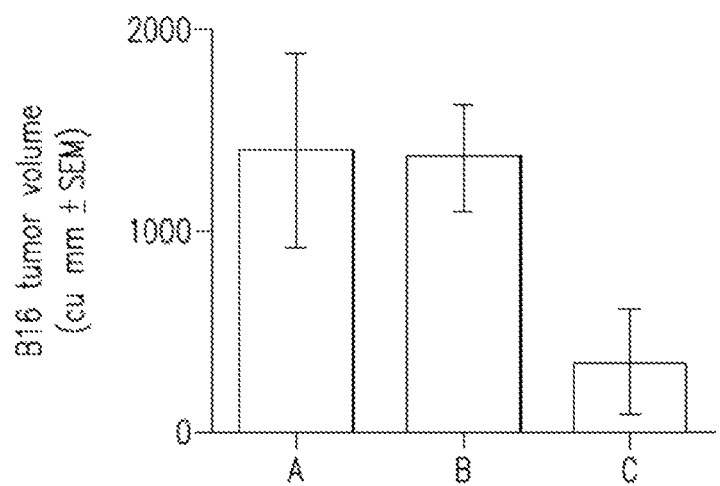
FIG. 7 depicts histogram of the volume of B16 melanoma tumors in mice at day 22; vehicle control (A); 100,000 IU/dose of IL-2 twice daily (B); and 100,000 IU/dose of IL-2 and 40 mg/kg of D91 twice daily (C).
Figure 8:
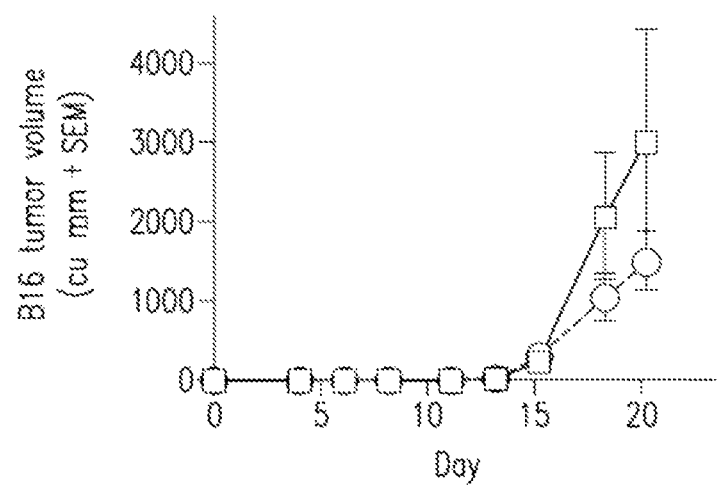
FIG. 8 depicts a graph showing the increase in tumor volume with time of B16 melanoma tumors in mice; vehicle control (□); and 40 mg/kg of D91 twice daily (○).

As depicted in FIG. 6, treatment with a low dose of IL-2 in combination with a high dose of D91 (○) significantly reduced tumor volume versus control (□), whereas low dose of IL-2 (◇) alone did not show measurable tumor volume reduction at the termination of the study on day 22. FIG. 7 is a histogram representing the tumor volume of animals receiving control (A), low dose IL-2 (B), and low dose IL-2/high dose D91 (C). FIG. 8 shows the effectiveness of treatments with 40 mg/kg b.i.d. D91 (○) versus vehicle control (□) on B16 melanoma tumor volume.

Renal Cell Carcinoma

The effectiveness of the disclosed compounds as a treatment against renal cell carcinoma was studied. Balb/c mice (6-8 weeks-old, female, Taconic Farm) were inoculated with Renca renal cancer cells ($5 \times 10^5$ cells/site). On day 4 post-inoculation, the mice were randomly divided into 4 groups (4 mice/group) and treated (5 day/week, M-F) with vehicle control (bid, i.p.), IL-2 (100,000 IU/mouse, bid, i.p.), D91 (40 mg/kg, bid, s.c., administered 30 minutes prior to IL-2) or the combination. Tumor volumes were recorded.

Figure 2:
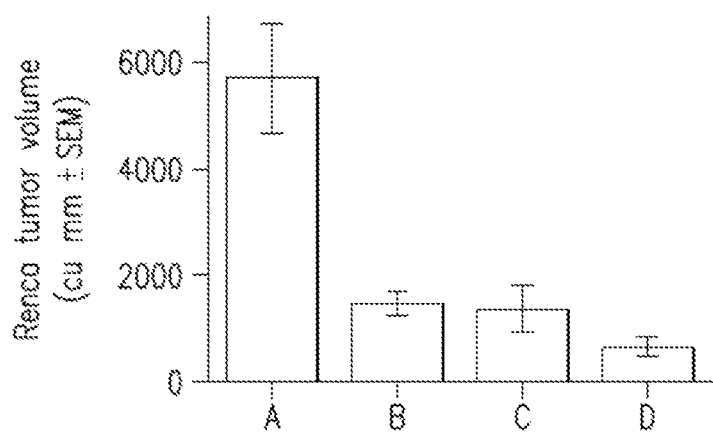
FIG. 2 is a histogram of the volume of renal cell carcinoma tumors (Renca) in mice at day 25; vehicle control (A); 40 mg/kg of D91 twice daily (B); 100,000 IU/dose of IL-2 twice daily (C); 100,000 IU/dose of IL-2 and 40 mg/kg of D91 twice daily (D).

As depicted in FIG. 1 and FIG. 2, 4-{(S)-2-[(S)-2-(methoxycarbonylamino)-3-phenyl-propanamido]-2-[2-(thiophen-2-yl)thiazol-4-yl]ethyl}phenylsulfamic acid, D91, significantly reduced renal tumor growth and was as effective as IL-2 in reducing tumor volume. In addition, the combination of D91 and IL-2 further reduced tumor volume.

Pancreatic Cancer

Pancreatic cancer is a malignant neoplasm of the pancreas. Each year in the United States, about 42,000 individuals are diagnosed with this condition and 35,000 die from the disease ("Pancreatic Cancer—National Cancer Institute, U.S. National Institutes of Health" (2009)). The prognosis is relatively poor but has improved; the three-year survival rate is now about thirty percent, but less than 5 percent of those diagnosed are still alive five years after diagnosis. Complete remission is still rather rare (Ghaneh P et al., (August 2007). "Biology and management of pancreatic cancer". Gut 56 (8): 1134-52).

The effectiveness of the disclosed compounds as a treatment for pancreatic cancer was investigated. 60 NCr nu/nu males, 5-6 weeks old were transplanted by surgical orthotopic implantation (SOI) using MiaPaCa-2-RFP tumor fragments harvested from stock animals. The animals were anesthetized with isoflurane and the surgical area was sterilized using iodine and alcohol. An incision approximately 1.5 cm long was made in the left upper abdomen of the nude mouse using a pair of surgical scissors. The pancreas was exposed, and then two pieces of the MiaPaCa-2-RFP tumor fragments of 2 mm$^3$ were transplanted to the mouse pancreas with 8-0 surgical sutures (nylon) after the capsule of the transplantation site had been stripped. The abdomen was closed with 6-0 surgical sutures (silk). All procedures of the operation described above were performed with a 7× magnification microscope (Olympus) under HEPA filtered laminar flow hoods.

Dosing of the animals began three days following tumor implantation. The high dose of gemcitabine was 150 mg/kg. The low dose of gemcitabine was 100 mg/kg. D91 was given at 20 mg/kg. Gemcitabine was give i.p. whereas D91 was given s.c.

The animals were divided into the following groups often animals each as depicted in Table XXII. As indicated in Table XXII, D91 was administered twice daily whereas

TABLE XXII

| Group | Agent | Dose | Schedule |
|---|---|---|---|
| 1 | vehicle | 100 μL | b.i.d |
| 2 | gemcitabine | 150 mg/kg | Twice weekly |
| 3 | gemcitabine + D91 | 150 mg/kg + 20 mg/kg | Twice weekly + b.i.d. |
| 4 | gemcitabine | 100 mg/kg | Twice weekly |
| 5 | gemcitabine + D91 | 100 mg/kg + 20 mg/kg | Twice weekly + b.i.d. |
| 6 | D91 | 20 mg/kg | b.i.d |

Figure 9:
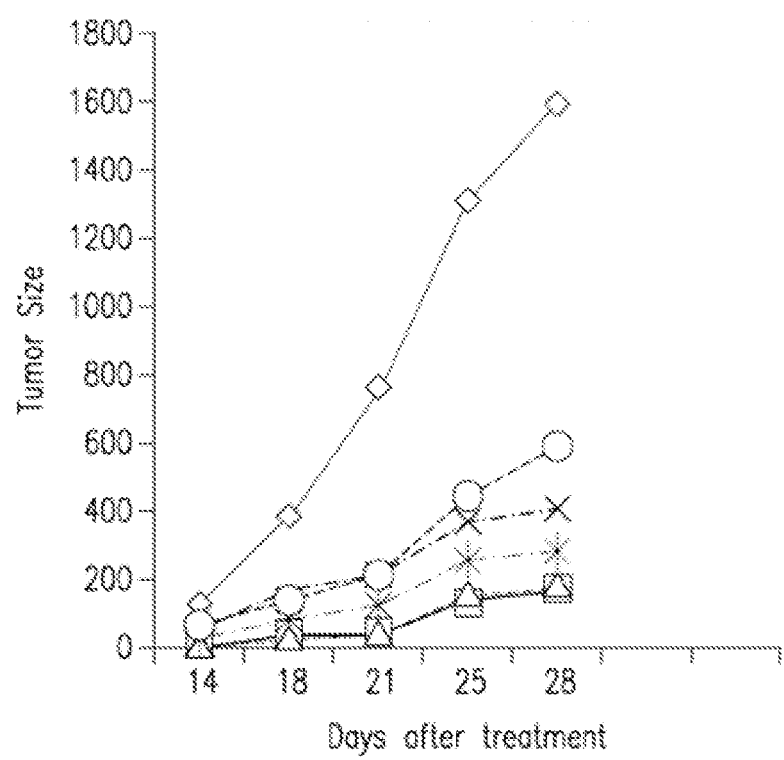
FIG. 9 depicts the size of pancreatic tumors orthotopically implanted in NCr nu/nu mice: vehicle control (◊); 100 mg/kg gemcitabine, i.p. twice weekly (X); 150 mg/kg gemcitabine, i.p. twice weekly (□); 20 mg/kg D91 twice daily (○); 100 mg/kg gemcitabine, i.p. twice weekly and 20 mg/kg D91 twice daily (*); and 150 mg/kg gemcitabine, i.p. twice weekly and 20 mg/kg D91 twice daily (Δ).

As depicted in FIG. 9, D91 given at 20 mg/kg showed a significant reduction in pancreatic tumor volume at day 28 (○). In addition the combination of low dose gemcitabine and 20 mg/kg D91 (*) showed a greater reduction in tumor volume than either low dose gencitabine (X) or D91 alone (○).

Disclosed herein is a method for treating carcinoma in a subject, comprising administering to the subject having a carcinoma an effective amount of one or more of the disclosed compounds.

Also disclosed herein is a method for treating a subject diagnosed with cancer, comprising administering to the subject an effective amount of one or more of the disclosed compounds.

Further disclosed herein is a method for treating carcinoma in a subject, comprising administering to the subject having a carcinoma a composition comprising:
- a) an effective amount of one or more of the disclosed compounds; and
- b) an effective amount of an anticancer drug.

Still further disclosed herein is a method for treating carcinoma in a subject, comprising administering to the subject having a carcinoma a composition comprising:
- a) an effective amount of one or more of the disclosed compounds; and
- b) an effective amount of a compound that inhibits tumor growth.

Yet further disclosed herein is a method for treating a subject diagnosed with cancer, comprising administering to the subject diagnosed with cancer a composition comprising:
- a) an effective amount of one or more of the disclosed compounds; and
- b) an effective amount of an anticancer drug.

Still yet further disclosed herein is a method for treating a subject diagnosed with cancer, comprising administering to the subject diagnosed with cancer a composition comprising:
- a) an effective amount of one or more of the disclosed compounds; and
- b) an effective amount of a compound that inhibits tumor growth.

Compositions

Disclosed herein are compositions which can be used to prevent metastasis of cancer cells in a subject, the compositions comprising an effective amount of one or more of the compounds disclosed herein. Further disclosed herein are compositions that can be used to treat tumors in a human or other mammal.

One aspect relates to a composition comprising:
- a) an effective amount of one or more compounds disclosed herein; and
- b) one or more pharmaceutically acceptable ingredients.

Another aspect relates a composition comprising:
- a) an effective amount of one or more compounds disclosed herein; and
- b) an effective amount of one or chemotherapeutic agents;
- wherein the disclosed compounds and the chemotherapeutic agents can be administered together or in any order.

One embodiment relates to a composition comprising:
- a) an effective amount of one or more compounds disclosed herein; and
- b) an effective amount of taxol;
- wherein the disclosed compounds and taxol can be administered together or in any order.

Another embodiment relates to a composition comprising:
- a) an effective amount of one or more compounds disclosed herein; and
- b) an effective amount of gemcitabine;
- wherein the disclosed compounds and gemcitabine can be administered together or in any order.

A further embodiment relate to a composition comprising:
- a) an effective amount of one or more compounds disclosed herein; and
- b) an effective amount of erlotinib;
- wherein the disclosed compounds and erlotinib can be administered together or in any order.

A yet further embodiment relate to a composition comprising:
- a) an effective amount of one or more compounds disclosed herein; and
- b) an effective amount of doxil;
- wherein the disclosed compounds and doxil can be administered together or in any order.

A still further embodiment relate to a composition comprising:
- a) an effective amount of one or more compounds disclosed herein; and
- b) an effective amount of irinortecan;
- wherein the disclosed compounds and irinortecan can be administered together or in any order.

A still yet further embodiment relate to a composition comprising:
- a) an effective amount of one or more compounds disclosed herein; and
- b) an effective amount of bevacizumab;
- wherein the disclosed compounds and bevacizumab can be administered together or in any order.

A "chemotherapeutic agent" or "chemotherapeutic compound" is a chemical compound useful in the treatment of cancer. Chemotherapeutic cancer agents that can be used in combination with those disclosed herein include, but are not limited to, mitotic inhibitors (vinca alkaloids). These include vincristine, vinblastine, vindesine and Navelbine™ (vinorelbine-5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that may be used in the methods and compositions of the present disclosure are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The present disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions of the present disclosure include antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

The disclosed compounds herein can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

The term "effective amount" as used herein means "an amount of one or more phenylsulfamic acids, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. Thus, it is not possible to specify an exact "effective amount." For example, several divided doses may be administered daily or the dose may be proportionally reduced as indicated by the exigencies of the therapeutic situation. In addition, the compositions of the present disclosure can be administered as frequently as necessary to achieve a therapeutic amount.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for increasing the efficacy of a cancer therapy in a subject in need thereof, the method comprising administering to the subject who has cancer the cancer therapy and an effective amount of a protein tyrosine phosphatase inhibitor, wherein administration of the cancer therapy and the protein tyrosine phosphatase inhibitor provides an efficacy of the cancer therapy that is greater than the efficacy of the cancer therapy in absence of the protein tyrosine phosphatase inhibitor, wherein the efficacy of the cancer therapy and the protein tyrosine phosphatase inhibitor is at least about 10% greater than the efficacy of the cancer therapy in absence of the protein tyrosine phosphatase inhibitor, wherein the protein tyrosine phosphatase inhibitor is a compound of the formula:

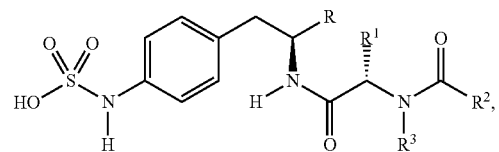

wherein:
R is a thiazolyl group that is substituted or unsubstituted;
R[1] is alkyl, phenyl, or benzyl, any of which is substituted or unsubstituted, or hydrogen;

R² is alkyl or alkoxy, any of which is substituted or unsubstituted; and

R³ is hydrogen or alkyl which is substituted or unsubstituted, or a pharmaceutically-acceptable salt thereof.

2. The method of claim 1, wherein the cancer is glioma.

3. The method of claim 1, wherein the cancer is renal cell carcinoma.

4. The method of claim 1, wherein the cancer is melanoma.

5. The method of claim 1, wherein the cancer is pancreatic cancer.

6. The method of claim 1, wherein the cancer therapy is taxol.

7. The method of claim 1, wherein the cancer therapy is IL-2.

8. The method of claim 1, wherein the cancer therapy is gemcitabine.

9. The method of claim 1, wherein the cancer therapy is erlotinib.

10. The method of claim 1, wherein the cancer therapy is doxil.

11. The method of claim 1, wherein the cancer therapy is irinortecan.

12. The method of claim 1, wherein the cancer therapy is bevacizumab.

13. The method of claim 1, wherein the efficacy of the cancer therapy and the protein tyrosine phosphatase inhibitor is about 50% greater than the efficacy of the cancer therapy in absence of the protein tyrosine phosphatase inhibitor.

14. The method of claim 1, wherein the efficacy of the cancer therapy and the protein tyrosine phosphatase inhibitor is about 80% greater than the efficacy of the cancer therapy in absence of the protein tyrosine phosphatase inhibitor.

15. The method of claim 1, wherein the compound is:

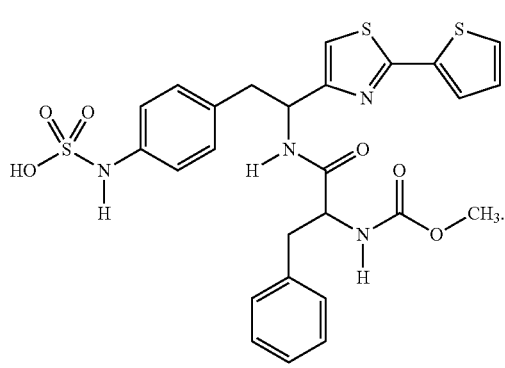 [SMILES: COC(=O)NC(Cc1ccccc1)C(=O)NC(Cc1ccc(NS(=O)(=O)O)cc1)c1csc(-c2cccs2)n1]

16. The method of claim 1, wherein the compound is:

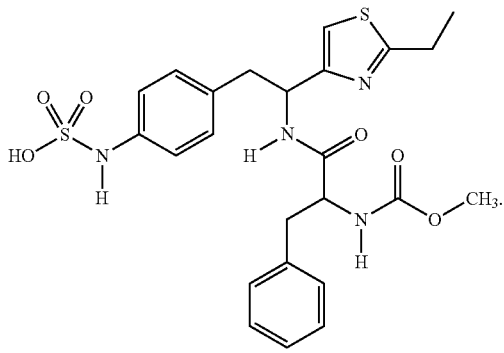 [SMILES: CCc1nc(C(Cc2ccc(NS(=O)(=O)O)cc2)NC(=O)C(Cc2ccccc2)NC(=O)OC)cs1]

17. The method of claim 1, wherein the compound is:

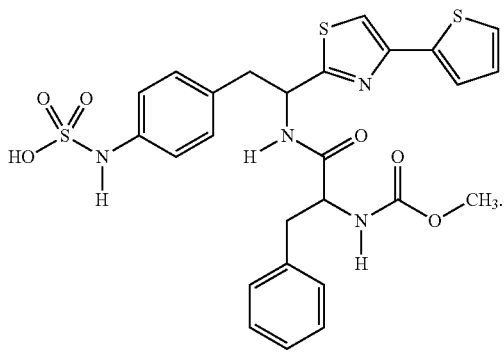 [SMILES: COC(=O)NC(Cc1ccccc1)C(=O)NC(Cc1ccc(NS(=O)(=O)O)cc1)c1nc(-c2cccs2)cs1]

18. The method of claim 1, wherein the compound is:

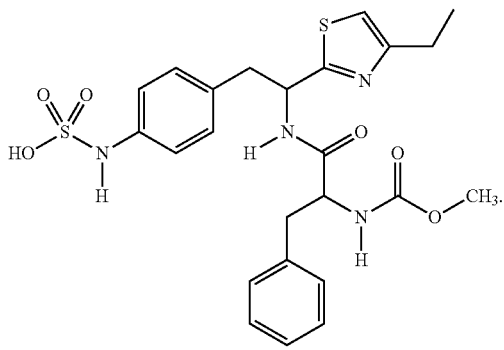 [SMILES: CCc1csc(C(Cc2ccc(NS(=O)(=O)O)cc2)NC(=O)C(Cc2ccccc2)NC(=O)OC)n1]

* * * * *